US008242129B2

(12) United States Patent
Tsuhako et al.

(10) Patent No.: US 8,242,129 B2
(45) Date of Patent: Aug. 14, 2012

(54) 6-PHENYLPYRIMIDINONES AS PIM MODULATORS

(75) Inventors: Amy L. Tsuhako, Milpitas, CA (US); Naing Aay, San Mateo, CA (US); S. David Brown, San Carlos, CA (US); Wai Ki Vicky Chan, San Francisco, CA (US); Hongwang Du, Millbrae, CA (US); Ping Huang, Mountain View, CA (US); Brian Kane, Lynchburg, VA (US); Patrick Kearney, San Francisco, CA (US); Moon Hwan Kim, Palo Alto, CA (US); Elena S. Koltun, Foster City, CA (US); Michael Pack, San Francisco, CA (US); Wei Xu, Danville, CA (US); Peiwen Zhou, Palo Alto, CA (US)

(73) Assignee: Exelixis, Inc., South San Francisco, CA (US)

( * ) Notice: Subject to any disclaimer, the term of this patent is extended or adjusted under 35 U.S.C. 154(b) by 201 days.

(21) Appl. No.: 12/597,275

(22) PCT Filed: Apr. 25, 2008

(86) PCT No.: PCT/US2008/005309
§ 371 (c)(1),
(2), (4) Date: Feb. 8, 2010

(87) PCT Pub. No.: WO2008/133955
PCT Pub. Date: Nov. 6, 2008

(65) Prior Publication Data
US 2010/0135954 A1    Jun. 3, 2010

Related U.S. Application Data

(60) Provisional application No. 60/926,362, filed on Apr. 25, 2007.

(51) Int. Cl.
*A61K 31/505* (2006.01)

(52) U.S. Cl. ........ 514/274; 544/309; 544/310; 544/316; 544/317

(58) Field of Classification Search .................. 544/315, 544/316
See application file for complete search history.

(56) References Cited

U.S. PATENT DOCUMENTS

2009/0215803 A1*  8/2009  Rice et al. ..................... 514/274

FOREIGN PATENT DOCUMENTS

| JP | 2004-049279 A | 2/1992 |
|---|---|---|
| WO | 2004/058769 A | 7/2004 |
| WO | 2007/048065 A2 | 4/2007 |

OTHER PUBLICATIONS

S. Cannistra et al, Ovarian Cancer, Fallopian Tube Carcinoma and Peritoneal Carcinoma in, 2 Cancer Principles & Practice of Oncology 1568 (V.T. DeVita, Jr. et al. eds., 8th ed., 2008).*
M. Kobel et al., PLoS Medicine, 5(12) 1749-1760, 1749 (2008).*
A.J. Tiltman, Best Practice & Research Clinical Obstetrics & Gynaecology, 485-500, 19(4) (2005).*
J. L. Raizer, Journal of Neuro-Oncology, 74(1), 77-86 (2005).*
R.G.W. Verhaak et al., Cancer Cell, 17(1), 1-24 (2010).*
S.K. K Libutti, Colon Cancer in, 1 Cancer Principles & Practice of Oncology 1232, 1243 (V.T. DeVita, Jr. et al. eds., 8th ed., 2008).*
L. Pusztai, Histopathologic and Molecular Markers of Prognosis and Response to Therapy, in Breast Cancer 324, 326-328 (Kelly k. Hunt et al., ed., 2nd ed., 2008).*
A. Kamb, Nature Reviews Drug Discovery 2, 161-165 (2005).*
N.F. Smith, Molecular Cancer Therapeutics, 6, 428-440, 428 (2007).*
N.E. Sharpless et al., Nature Reviews Drug Discovery 5, 741-754, 742 (2006).*
Abad-Zapatero, Drug Discovery Today, 1-8 (2010).*
K.P. Olive et al., Clinical Cancer Research 12, 5277-5287 (2006).*
Y. Song et al., Cancer a Conceptual Framework in, 1 Cancer Principles & Practice of Oncology 1, 5-6 (V.T. DeVita, Jr. et al. eds., 8th ed., 2008).*
B. Hann et al., Current Opinion in Cell Biology, 13, 778-784 (2001).*
W. Schroth et al., Tetrahedron, 38(7), 937-948 (1982).*
Naik et al., "Studies on heterocyclic compounds: part III 4,6-disubstituted 5, 6-dihydro-2-(1H)pyrimidinethiones", Indian Journal of Chemistry, vol. 21B, 1982, 1124-1125.
Grosche et al., "Pyrazole, Pyridine and Pyridone Synthesis on Solid Support", Synthesis, vol. 11, 1999, 1961-1970.
Wang et al., "A Regioselective Tandem Reaction between Chalcones and 2-Acetamido-acetamide Promoted by Cs2CO3 for the Preparation of 3-Unsubstituted 2-Pyridones", Synthesis, 2003, vol. 4, 487-490.
Katritzky et al., "Solid-Phase Synthesis of 4,6-Disubstituted and 3,4,6-Trisubstituted Pyrid-2-ones", Journal of Combinatorial Chemistry, 4(4), 2002, 249-250.
Katritzky et al., "Benzotriazole-Assisted Preparation of 2-(Substituted amino)pyridines and Pyrid-2-ones", Journal of Organic Chemistry, 62(18), 1997, 6210-6214.

* cited by examiner

*Primary Examiner* — James O Wilson
*Assistant Examiner* — Alexander R Pagano
(74) *Attorney, Agent, or Firm* — McDonnell Boehnen Hulbert & Berghoff LLP

(57) ABSTRACT

A compound having Formula I or II (Formula I) or (Formula II), or a pharmaceutically acceptable salt thereof, wherein X, Z, $R_1$, $R_2$, $R_{11}$ and $R_{12}$ are as defined in the specification; pharmaceutical compositions thereof; and methods of use thereof.

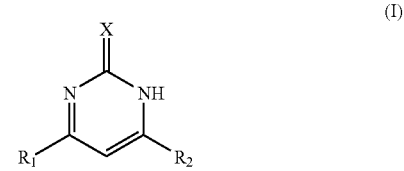

(I)

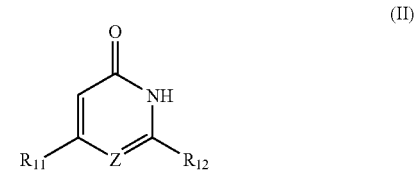

(II)

12 Claims, No Drawings

6-PHENYLPYRIMIDINONES AS PIM MODULATORS

This application is a US national phase of International Application No. PCT/US2008/005309 filed on Apr. 25, 2008, which claims the benefit of priority of U.S. Provisional Application No. 60/926,362 filed on Apr. 25, 2007.

FIELD OF THE INVENTION

The invention relates to compounds for inhibiting PIM, compositions thereof, and methods of use thereof.

BACKGROUND OF THE INVENTION

The PIM protein kinase family which consists of the closely related PIM-1, 2, and 3, have been implicated in diverse biological processes such as cell survival, proliferation, and differentiation. PIM-1 is involved in a number of signaling pathways that are highly relevant to tumorigenesis [reviewed in Bachmann & Moroy, Internat. J. Biochem. Cell Biol., 37, 726-730 (2005)]. Many of these are involved in cell cycle progression and apoptosis. It has been shown that PIM-1 acts as an anti-apoptotic factor via inactivation of the pro-apoptotic factor Bad. This finding suggested a direct role of PIM-1 in preventing cell death since the inactivation of Bad can enhance Bcl-2 activity and thereby promotes cell survival [Aho et al., FEBS Letters, 571, 43-49 (2004)]. PIM-1 has also been recognized as a positive regulator of cell cycle progression. PIM-1 binds and phosphorylates CDC25A, which leads to an increase in its phosphatase activity and promotion of G1/S transition [reviewed in Losman et al., JBC, 278, 4800-4805 (1999)]. In addition, the cyclin kinase inhibitor p21$^{Waf}$ which inhibits G1/S progression was found to be inactivated by PIM-1 [Wang et al., Biochim. Biophys. Act. 1593, 45-55 (2002)]. Furthermore, by means of phosphorylation, Pim-1 inactivates C-TAK1 and activates Cdc25C which results in acceleration of G2/M transition [Bachman et al., JBC, 279, 48319-48 (2004)].

PIM-1 appears to be an essential player in hematopoetic proliferation. Kinase active PIM-1 is required for the gp130-mediated STAT3 proliferation signal [Hirano et al., Oncogene 19, 2548-2556, (2000)]

PIM-1 is overexpressed or even mutated in a number of tumors and different types of tumor cell lines and leads to genomic instability. Examples for a possible involvement of PIM-1 in human tumors are prostate cancer, oral cancer, and Burkitt lymphoma (Gaidano & Dalla Faver, 1993). All these findings point to an important role of PIM-1 in the initiation and progression of human cancer, and it appears that small molecule inhibition of PIM-1 activity is a promising therapeutic strategy. Finally, PIM-2 and PIM-3 have overlapping functions with PIM-1 and inhibition of more than one isoform may provide additional therapeutic benefits.

Accordingly, the identification of compounds that specifically inhibit, regulate and/or modulate the signal transduction of PIM, is desirable as a means to treat or prevent disease states associated with abnormal cell proliferation, such as cancer.

SUMMARY OF THE INVENTION

The invention relates to compounds, pharmaceutically acceptable salts thereof, and pharmaceutical compositions of the compounds for inhibiting PIM (PIM-1, PIM-2 and/or PIM-3).

One aspect of the invention relates to compounds, or pharmaceutically acceptable salts thereof, that inhibit PIM function. The compounds are exemplified by Formula I or II, or a pharmaceutically acceptable salt thereof, as described herein.

Another aspect of the invention relates to a pharmaceutical composition, comprising a compound according to Formula I or II, or a pharmaceutically acceptable salt thereof, and a pharmaceutically acceptable carrier, excipient, or diluent.

Another aspect of the invention relates to a method of inhibiting PIM in a cell, comprising contacting the cell, in which inhibition of PIM is desired, with a compound according to Formula I or II, or a pharmaceutically acceptable salt thereof.

Another aspect of the invention relates to a method of inhibiting PIM in a cell, comprising contacting a cell in which inhibition of PIM is desired with a pharmaceutical composition comprising a compound according to Formula I or II, or a pharmaceutically acceptable salt thereof, and a pharmaceutically acceptable carrier, excipient, or diluent.

Another aspect of the invention relates to a method of treating a disease or condition that involves PIM, comprising administering to a patient, in need of said treatment, a compound according to Formula I or II, or a pharmaceutically acceptable salt thereof.

Another aspect of the invention relates to a method of treating a disease or condition that involves PIM, comprising administering to a patient, in need of said treatment, a pharmaceutical composition comprising a compound according to Formula I or II, or a pharmaceutically acceptable salt thereof, and a pharmaceutically acceptable carrier, excipient, or diluent.

The disease or condition that can be treated by the compounds of Formula I or II, or a pharmaceutically acceptable salt thereof, and the pharmaceutical compositions thereof, include cancer. Non-limiting examples of the types of cancer that can be treated include ovarian cancer, cervical cancer, breast cancer, colorectal cancer, and glioblastomas.

There are many different aspects of the compounds, pharmaceutical compositions thereof, and methods of use thereof, as described hereinbelow, and each aspect is non-limiting in regard to the scope of the invention. The transitional term "comprising" as used herein, which is synonymous with "including," "containing," or "characterized by," is inclusive or open-ended and does not exclude additional, unrecited elements or method steps.

The foregoing only summarizes certain aspects of the invention and is not intended to be limiting in nature. These aspects and other aspects and embodiments are described more fully below.

DETAILED DESCRIPTION OF THE INVENTION

The first aspect of the invention relates to compounds of Formulae I or II:

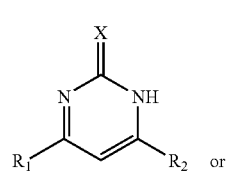

I or

-continued

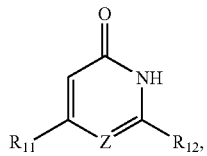

or a pharmaceutically acceptable salt thereof, wherein:

X is O or S;

Z is C(H) or N;

$R_1$ is —$(C_6-C_{10})$aryl, —$(C_6-C_{10})$aryl-$(C_1-C_6)$alkyl, 1,3-benzoxazol-2(3H)-one, thiophenyl optionally substituted with —C(O)NH$_2$, methylisoxazolyl, or isoxazoyl, wherein each of the —$(C_6-C_{10})$aryl or —$(C_6-C_{10})$aryl-$(C_1-C_6)$alkyl is substituted with 1, 2, or 3 groups independently selected from —NHR$^8$, —NR$^8$R$^9$, —OR$^{10}$, -(4-10 membered)heterocycloalkyl, —C(O)-(4-10 membered)heterocycloalkyl, —C(O)—N(E1)$(C_1-C_6)$alkyl-R$^6$, —C(O)N(E7)(4-10 membered)heterocycloalkyl, —C(O)—N(E8)$(C_1-C_6)$alkyl, —C(O)—N(E9)$(C_3-C_{10})$cycloalkyl, —C(O)—N(E10)$(C_1-C_6)$alkyl-O—$(C_6-C_{10})$aryl, —O—$(C_1-C_6)$alkyl-C(O)—N(E11)$(C_1-C_6)$alkyl-O—$(C_6-C_{10})$aryl, —C(O)—N(E12)$(C_1-C_6)$alkyl-CN, —O—$(C_1-C_6)$alkyl-C(O)—OH, and —C(O)—OH, and wherein each of the 1,3-benzoxazol-2(3H)-one or isoxazolyl is substituted with 1, 2, or 3 groups independently selected from —NHR$^8$, —NR$^8$R$^9$, —OR$^{10}$, -(4-10 membered)heterocycloalkyl, —C(O)-(4-10 membered)heterocycloalkyl, —C(O)—N(E1)$(C_1-C_6)$alkyl-R$^6$, —C(O)N(E7)(4-10 membered)heterocycloalkyl, —C(O)—N(E8)$(C_1-C_6)$alkyl, —C(O)—N(E9)$(C_3-C_{10})$cycloalkyl, —C(O)—N(E10)$(C_1-C_6)$alkyl-O—$(C_6-C_{10})$aryl, —O—$(C_1-C_6)$alkyl-C(O)—N(E11)$(C_1-C_6)$alkyl-O—$(C_6-C_{10})$aryl, —C(O)—N(E12)$(C_1-C_6)$alkyl-CN, —O—$(C_1-C_6)$alkyl-C(O)—OH, and —C(O)—OH;

$R_2$ is phenyl optionally substituted with 1, 2 or 3 substitutents selected from hydrogen, halo, —OH, and —$(C_1-C_6)$alkyl;

$R^3$ is —$(C_3-C_{10})$cycloalkyl or -(4-10 membered)heterocycloalkyl;

$R^4$ is -(4-10 membered)heterocycloalkyl, -(5-10 membered)heteroaryl, or —$(C_3-C_{10})$cycloalkyl;

$R^5$ is H or NH$_2$;

$R^6$ is -(4-10 membered)heterocycloalkyl optionally substituted with oxo, -(5-10 membered)heteroaryl, —$(C_3-C_{10})$cycloalkyl, —N[$(C_1-C_6)$alkyl]$_2$ or —$(C_6-C_{10})$aryl;

$R^7$ is -(4-10 membered)heterocycloalkyl optionally substituted with oxo, -(5-10 membered)heteroaryl or —$(C_3-C_{10})$cycloalkyl;

$R^8$ is —$(C_1-C_6)$alkyl-N(H)(4-10 membered)heterocycloalkyl, —$(C_1-C_6)$alkyl-(4-10 membered)heterocycloalkyl, —$(C_1-C_6)$alkyl-NH$_2$, —$(C_1-C_6)$alkyl-(5-6 membered)heteroaryl, or -(4-10 membered)heterocycloalkyl;

$R^9$ is —$(C_1-C_3)$alkyl;

$R^{10}$ is —$(C_1-C_6)$alkyl-C(O)—R$^3$, —$(C_1-C_6)$alkyl-C(O)—N(E14)R$^4$, —$(C_1-C_6)$alkyl-C(O)—N(E2)$(C_1-C_6)$alkyl-R$^5$, —$(C_1-C_6)$alkyl-C(O)—N(E3)$(C_1-C_6)$alkyl-N[$(C_1-C_6)$alkyl]$_2$, —$(C_1-C_6)$alkyl-C(O)N(E4)$(C_1-C_6)$alkyl-R$^7$, —$(C_1-C_6)$alkyl-C(O)N(E4)$(C_1-C_6)$alkyl-aryl substituted at the aryl group with 1 or 2 groups independently selected from halo and —O—$(C_1-C_6)$alkyl, —$(C_1-C_6)$alkyl-(4-10 membered)heterocycloalkyl, —$(C_1-C_6)$alkyl-C(O)—N(E5)$(C_1-C_6)$alkyl-$(C_1-C_6)$alkoxy, —$(C_1-C_6)$alkyl-C(O)—N(E6)$(C_1-C_6)$alkyl-CN, or —$(C_1-C_6)$alkyl-C(O)—N[$(C_1-C_6)$alkyl]$_2$, wherein each of said -(4-10 membered)heterocycloalkyl, -(5-10 membered)heteroaryl, —$(C_3-C_{10})$cycloalkyl, and —$(C_6-C_{10})$aryl within each of R$^1$, R$^3$, R$^4$, R$^6$ or R$^7$ is unsubstituted or independently substituted at any ring position with 1, 2 or 3 substituents independently selected from —$(C_1-C_6)$alkyl, —NH$_2$, -(4-10 membered)heterocycloalkyl optionally substituted with —$(C_1-C_3)$alkyl, —N[$(C_1-C_6)$alkyl]$_2$, —$(C_1-C_6)$alkyl-NH$_2$, —$(C_1-C_6)$alkyl-$(C_1-C_6)$alkoxy, —N(E13)C(O)—$(C_1-C_6)$alkyl, —$(C_6-C_{10})$aryl optionally substituted with —$(C_1-C_3)$alkoxy, halo, —C(O)—$(C_1-C_6)$alkyl, —C(O)-(5-10 membered)heteroaryl, —$(C_1-C_6)$alkyl-OH, —OH, —C(O)O—$(C_1-C_6)$alkyl, —C(O)-(4-10 membered)heterocycloalkyl, —$(C_1-C_3)$alkyl-$(C_6-C_{10})$aryl, —$(C_1-C_6)$alkoxy, and -(5-10 membered)heteroaryl, and wherein the substitutents for each of the -(4-10 membered)heterocycloalkyl, -(5-10 membered)heteroaryl, —$(C_3-C_{10})$cycloalkyl, and —$(C_6-C_{10})$aryl can be the same or different for any one of R$^1$, R$^3$, R$^4$, R$^6$ or R$^7$;

$R_{11}$ is phenyl substituted with 1 or 2 substituents independently selected from halo, —OH, —$(C_1-C_6)$alkyl, and —O—$(C_1-C_6)$alkyl;

$R_{12}$ is phenyl substituted with 1 or 2 substituents independently selected from halo, —$(C_1-C_6)$alkyl, —O—$(C_1-C_6)$alkyl, —NH$_2$, and —N(H)$(C_1-C_6)$alkyl-(4-10 membered)heterocycloalkyl; and each of E1, E2, E3, E4, E5, E6, E7, E8, E9, E10, E11, E12, E13 and E14, which can be the same or different, is hydrogen or —$(C_1-C_3)$alkyl.

In other embodiments, Z is C(H) in the compound of Formula I or II or a pharmaceutically acceptable salt thereof.

In other embodiments, Z is N in the compound of Formula I or II or a pharmaceutically acceptable salt thereof.

In another embodiment of the compound of Formula I or II, or a pharmaceutically acceptable salt thereof, X is O or S;

Z is C(H) or N;

$R_1$ is —$(C_6-C_{10})$aryl, —$(C_6-C_{10})$aryl-$(C_1-C_6)$alkyl, 1,3-benzoxazol-2(3H)-one, thiophenyl optionally substituted with —C(O)NH$_2$, methylisoxazolyl, or isoxazoyl, wherein each of the —$(C_6-C_{10})$aryl or —$(C_6-C_{10})$aryl-$(C_1-C_6)$alkyl is substituted with 1, 2, or 3 groups independently selected from —NHR$^8$, —NR$^8$R$^9$, —OR$^{10}$, -(4-10 membered)heterocycloalkyl, —C(O)-(4-10 membered)heterocycloalkyl, —C(O)—N(E1)$(C_1-C_6)$alkyl-R$^6$, —C(O)N(E7)(4-10 membered)heterocycloalkyl, —C(O)—N(E9)$(C_3-C_{10})$cycloalkyl, —C(O)—N(E10)$(C_1-C_6)$alkyl-O—$(C_6-C_{10})$aryl, —O—$(C_1-C_6)$alkyl-C(O)—N(E11)$(C_1-C_6)$alkyl-O—$(C_6-C_{10})$aryl, —C(O)—N(E12)$(C_1-C_6)$alkyl-CN, —O—$(C_1-C_6)$alkyl-C(O)—OH, and —C(O)—OH, and wherein each of the 1,3-benzoxazol-2(3H)-one or isoxazolyl is substituted with 1, 2, or 3 groups independently selected from —NHR$^8$, —NR$^8$R$^9$, —OR$^{10}$, -(4-10 membered)heterocycloalkyl, —C(O)-(4-10 membered)heterocycloalkyl, —C(O)—N(E1)$(C_1-C_6)$alkyl-R$^6$, —C(O)N(E7)(4-10 membered)heterocycloalkyl, —C(O)—N(E8)$(C_1-C_6)$alkyl, —C(O)—N(E9)$(C_3-C_{10})$cycloalkyl, —C(O)—N(E10)$(C_1-C_6)$alkyl-O—$(C_6-C_{10})$aryl, —O—$(C_1-C_6)$alkyl-C(O)—N(E11)$(C_1-C_6)$alkyl-O—$(C_6-C_{10})$aryl, —C(O)—N(E12)$(C_1-C_6)$alkyl-CN, —O—$(C_1-C_6)$alkyl-C(O)—OH, and —C(O)—OH;

$R_2$ is phenyl optionally substituted with 1, 2 or 3 substitutents selected from hydrogen, halo, —OH, and —$(C_1-C_6)$alkyl;

$R^3$ is —$(C_3-C_{10})$cycloalkyl or -(4-10 membered)heterocycloalkyl;

$R^4$ is -(4-10 membered)heterocycloalkyl, -(5-10 membered)heteroaryl, or —$(C_3-C_{10})$cycloalkyl;

$R^5$ is H or NH$_2$;

$R^6$ is -(4-10 membered)heterocycloalkyl optionally substituted with oxo, -(5-10 membered)heteroaryl, or —($C_3$-$C_{10}$)cycloalkyl;

$R^7$ is -(4-10 membered)heterocycloalkyl optionally substituted with oxo, -(5-10 membered)heteroaryl, —($C_3$-$C_{10}$) cycloalkyl, or —($C_6$-$C_{10}$)aryl;

$R^8$ is —($C_1$-$C_6$)alkyl-N(H)(4-10 membered)heterocycloalkyl, —($C_1$-$C_6$)alkyl-(4-10 membered)heterocycloalkyl, —($C_1$-$C_6$)alkyl-$NH_2$, —($C_1$-$C_6$)alkyl-(5-6 membered)heteroaryl, or -(4-10 membered)heterocycloalkyl;

$R^9$ is —($C_1$-$C_3$)alkyl;

$R^{10}$ is —($C_1$-$C_6$)alkyl-C(O)—$R^3$, —($C_1$-$C_6$)alkyl-C(O)—N(E14)$R^4$, —($C_1$-$C_6$)alkyl-C(O)—N(E2)($C_1$-$C_6$)alkyl-$R^5$, —($C_1$-$C_6$)alkyl-C(O)—N(E3)($C_1$-$C_6$)alkyl-N[($C_1$-$C_6$)alkyl]$_2$, —($C_1$-$C_6$)alkyl-C(O)N(E4)($C_1$-$C_6$)alkyl-$R^7$, —($C_1$-$C_6$)alkyl-C(O)N(E4)($C_1$-$C_6$)alkyl-aryl substituted at the aryl group with 1 or 2 groups independently selected from halo or —O—($C_1$-$C_6$)alkyl; —($C_1$-$C_6$)alkyl-(4-10 membered)heterocycloalkyl, —($C_1$-$C_6$)alkyl-C(O)—N(E5)($C_1$-$C_6$)alkyl-($C_1$-$C_6$)alkoxy, —($C_1$-$C_6$)alkyl-C(O)—N(E6)($C_1$-$C_6$)alkyl-CN, or —($C_1$-$C_6$)alkyl-C(O)—N[($C_1$-$C_6$)alkyl]$_2$; wherein each of said -(4-10 membered)heterocycloalkyl, -(5-10 membered)heteroaryl, —($C_3$-$C_{10}$)cycloalkyl, and —($C_6$-$C_{10}$)aryl within each of $R^1$, $R^3$, $R^4$, $R^6$ or $R^7$ is unsubstituted or independently substituted at any ring position with 1, 2 or 3 substituents independently selected from —($C_1$-$C_6$)alkyl, —$NH_2$, -(4-10 membered)heterocycloalkyl optionally substituted with —($C_1$-$C_3$)alkyl, —N[($C_1$-$C_6$)alkyl]$_2$, —($C_1$-$C_6$)alkyl-$NH_2$, —($C_1$-$C_6$)alkyl-($C_1$-$C_6$)alkoxy, —N(E13)C(O)—($C_1$-$C_6$)alkyl, —($C_6$-$C_{10}$)aryl optionally substituted with —($C_1$-$C_3$)alkoxy, halo, —C(O)—($C_1$-$C_6$)alkyl, —C(O)-(5-10 membered)heteroaryl, —($C_1$-$C_6$)alkyl-OH, —OH, —C(O)O—($C_1$-$C_6$)alkyl, —C(O)-(4-10 membered)heterocycloalkyl, —($C_1$-$C_3$)alkyl-($C_6$-$C_{10}$)aryl, —($C_1$-$C_6$) alkoxy, and -(5-10 membered)heteroaryl, and wherein the substitutents for each of the -(4-10 membered)heterocycloalkyl, -(5-10 membered)heteroaryl, —($C_3$-$C_{10}$)cycloalkyl, and —($C_6$-$C_{10}$)aryl can be the same or different for any one of $R^1$, $R^3$, $R^4$, $R^6$ or $R^7$;

$R_{11}$ is phenyl substituted with 1 or 2 substituents independently selected from halo, —OH, —($C_1$-$C_6$)alkyl, and —O—($C_1$-$C_6$)alkyl;

$R_{12}$ is phenyl substituted with 1 or 2 substituents independently selected from halo, —($C_1$-$C_6$)alkyl, —O—($C_1$-$C_6$) alkyl, —$NH_2$, and —N(H)($C_1$-$C_6$)alkyl-(4-10 membered) heterocycloalkyl; and each of E1, E2, E3, E4, E5, E6, E7, E8, E9, E10, E11, E12, E13 and E14, which can be the same or different, is hydrogen or —($C_1$-$C_3$)alkyl.

In another embodiment, the compound is according to Formula I, or a pharmaceutically acceptable salt thereof.

In another embodiment, the compound is according to Formula II, or a pharmaceutically acceptable salt thereof.

In another embodiment, the compound is according to Formula I, or a pharmaceutically acceptable salt thereof, wherein $R_1$ is phenyl or methylphenyl substituted with —C(O)-(4-10 membered)heterocycloalkyl optionally substituted at any ring position of the —C(O)-(4-10 membered) heterocycloalkyl with 1, 2 or 3 groups independently selected from —($C_1$-$C_3$)alkyl, —($C_6$-$C_{10}$)aryl-O—($C_1$-$C_3$)alkyl, —O—($C_1$-$C_6$)alkyl, -(5-10 membered)heteroaryl, —C(O)-(5-10 membered)heteroaryl, -(4-10 membered)heterocycloalkyl, —C(O)-(4-10 membered)heterocycloalkyl, —OH, —C(O)O—($C_1$-$C_3$)alkyl, —N(H)C(O)—($C_1$-$C_3$)alkyl, —C(O)—($C_1$-$C_3$)alkyl, —($C_1$-$C_3$)alkyl-($C_6$-$C_{10}$)aryl optionally substituted with 1, 2 or 3 halo, —($C_1$-$C_6$)alkyl-O—($C_1$-$C_6$)alkyl, —($C_1$-$C_6$)alkyl-OH, —$NH_2$, and —($C_1$-$C_6$)alkyl-$NH_2$. Non-limiting examples of the heterocycloalkyl group contained within the —C(O)-(4-10 membered)heterocycloalkyl group in this embodiment include piperidinyl, pyrrolidinyl, azepanyl and piperazinyl. Non-limiting examples of the heteroaryl contained within the —C(O)-(5-10 membered)heteroaryl group in this embodiment include furanyl. A non-limiting example of the -(4-10 membered) heterocycloalkyl group includes morpholinyl. A non-limiting example of the -(5-10 membered)heteroaryl group includes pyrazinyl.

In another embodiment, the compound is according to Formula I, or a pharmaceutically acceptable salt thereof, wherein $R_1$ is phenyl or methylphenyl substituted with —C(O)—N(H)($C_1$-$C_6$)alkyl, —C(O)—N[($C_1$-$C_6$)alkyl]$_2$ or —C(O)—N(H)($C_1$-$C_6$)alkyl-N[($C_1$-$C_6$)alkyl]$_2$.

In another embodiment, the compound is according to Formula I, or a pharmaceutically acceptable salt thereof, wherein $R_1$ is phenyl or methylphenyl substituted with —C(O)-piperizinyl-phenyl, wherein the phenyl group is optionally substituted with methoxy or ethoxy.

In another embodiment, the compound is according to Formula I, or a pharmaceutically acceptable salt thereof, wherein $R_1$ is phenyl or methylphenyl substituted with —C(O)N(H)($C_1$-$C_6$)alkyl-($C_3$-$C_6$)cycloalkyl. One non-limiting example of the —($C_3$-$C_6$)cycloalkyl in the —C(O)N(H)($C_1$-$C_6$)alkyl-($C_3$-$C_6$)cycloalkyl group of this embodiment includes cyclohexane.

In another embodiment, the compound is according to Formula I, or a pharmaceutically acceptable salt thereof, wherein $R_1$ is phenyl or methylphenyl substituted with —C(O)-(4-10 membered heterocycloalkyl)-C(O)—(O)—($C_1$-$C_6$)alkyl. One non-limiting example of the -(4-10 membered heterocycloalkyl in the —C(O)-(4-10 membered heterocycloalkyl)-C(O)—(O)—($C_1$-$C_6$)alkyl group of this embodiment includes piperidine.

In another embodiment, the compound is according to Formula I, or a pharmaceutically acceptable salt thereof, wherein $R_1$ is phenyl or methylphenyl substituted with —(O)-alkyl-C(O)-(4-10 membered)heterocycloalkyl optionally substituted at any ring position of the —(O)-alkyl-C(O)-(4-10 membered)heterocycloalkyl group with 1, 2 or 3 groups independently selected from —N(H)C(O)—($C_1$-$C_6$)alkyl, —N[($C_1$-$C_6$)alkyl]-C(O)—($C_1$-$C_6$)alkyl, —C(O)-(5-10 membered)heteroaryl, —($C_1$-$C_6$)alkyl-($C_6$-$C_{10}$)aryl, —($C_1$-$C_6$)alkyl-O—($C_1$-$C_6$)alkyl, —C(O)—($C_1$-$C_6$)alkyl, —OH, -(4-10 membered)heterocycloalkyl, —($C_1$-$C_6$)alkyl-OH, -(5-10 membered)heteroaryl, —C(O)—O—($C_1$-$C_6$)alkyl, —C(O)-(4-10 membered) heterocycloalkyl, —($C_6$-$C_{10}$)aryl optionally substituted with —O—($C_1$-$C_6$)alkyl and —($C_1$-$C_6$)alkyl. Non-limiting examples of the -(4-10 membered) heterocycloalkyl of the —(O)-alkyl-C(O)-(4-10 membered) heterocycloalkyl group in this embodiment include piperazine, piperidine, pyrrolidinyl, morpholinyl and azepanyl.

In another embodiment, the compound is according to Formula I, or a pharmaceutically acceptable salt thereof, wherein $R_1$ is phenyl or methylphenyl substituted with —C(O)—N(H)(4-10 membered)heterocycloalkyl or —C(O)—N[($C_1$-$C_6$)alkyl]-(4-10 membered)heterocycloalkyl, wherein the (4-10 membered)heterocycloalkyl portion is optionally substituted with 1 or 2 groups independently selected from —($C_1$-$C_6$)alkyl and oxo.

In another embodiment, the compound is according to Formula I, or a pharmaceutically acceptable salt thereof, wherein $R_1$ is phenyl or methylphenyl substituted with —C(O)—N(H)($C_3$-$C_7$)cycloalkyl wherein the —($C_3$-$C_7$)cycloalkyl portion of the —C(O)—N(H)(C$_3$-C$_7$)cycloalkyl group in this embodiment is optionally substituted with —(C$_1$-C$_6$)alkyl. A non-limiting example of the —(C$_3$-C$_7$)cycloalkyl portion includes cyclopropyl.

In another embodiment, the compound is according to Formula I, or a pharmaceutically acceptable salt thereof, wherein and R$_1$ is phenyl or methylphenyl substituted with —O—(C$_1$-C$_6$)alkyl-C(O)—N(H)(C$_1$-C$_6$)alkyl-(C$_6$-C$_{10}$)aryl or —O—(C$_1$-C$_6$)alkyl-C(O)—N[(C$_1$-C$_6$)alkyl]-(C$_1$-C$_6$)alkyl-(C$_6$-C$_{10}$)aryl, wherein the (C$_6$-C$_{10}$)aryl portion of the —O—(C$_1$-C$_6$)alkyl-C(O)—N(H)(C$_1$-C$_6$)alkyl-(C$_6$-C$_{10}$)aryl or —O—(C$_1$-C$_6$)alkyl-C(O)—N[(C$_1$-C$_6$)alkyl]-(C$_1$-C$_6$)alkyl-(C$_6$-C$_{10}$)aryl group in this embodiment is optionally substituted with 1, 2 or 3 groups independently selected from halo and —O—(C$_1$-C$_6$)alkyl. Non-limiting examples of the (C$_6$-C$_{10}$)aryl portion of this embodiment include phenyl.

In another embodiment, the compound is according to Formula I, or a pharmaceutically acceptable salt thereof, wherein R$_1$ is phenyl or methylphenyl substituted with —O—(C$_1$-C$_6$)alkyl-C(O)—N(H)(C$_1$-C$_6$)alkyl.

In another embodiment, the compound is according to Formula I, or a pharmaceutically acceptable salt thereof, wherein R$_1$ is phenyl or methylphenyl substituted with —O—(C$_1$-C$_6$)alkyl-C(O)—N(H)(C$_1$-C$_6$)alkyl-CN.

In another embodiment, the compound is according to Formula I, or a pharmaceutically acceptable salt thereof, wherein R$_1$ is phenyl or methylphenyl substituted with —O—(C$_1$-C$_6$)alkyl-C(O)—N(H)(C$_1$-C$_6$)alkyl-O—(C$_1$-C$_6$)alkyl.

In another embodiment, the compound is according to Formula I, or a pharmaceutically acceptable salt thereof, wherein R$_1$ is phenyl or methylphenyl substituted with —O—(C$_1$-C$_6$)alkyl-C(O)—N(H)(C$_1$-C$_6$)alkyl-NH$_2$.

In another embodiment, the compound is according to Formula I, or a pharmaceutically acceptable salt thereof, wherein R$_1$ is phenyl or methylphenyl substituted with —O—(C$_1$-C$_6$)alkyl-C(O)—N(H)(C$_1$-C$_6$)alkyl-N(H)(C$_1$-C$_6$)alkyl.

In another embodiment, the compound is according to Formula I, or a pharmaceutically acceptable salt thereof, wherein R$_1$ is phenyl or methylphenyl substituted with —O—(C$_1$-C$_6$)alkyl-C(O)—N(H)(C$_1$-C$_6$)alkyl-N[(C$_1$-C$_6$)alkyl]$_2$. In a more specific example of this embodiment, R$_1$ is —O—(C$_1$-C$_6$)alkyl-C(O)—N(H)(C$_1$-C$_6$)alkyl-N(CH$_2$CH$_3$)$_2$.

In another embodiment, the compound is according to Formula I, or a pharmaceutically acceptable salt thereof, wherein R$_1$ is phenyl or methylphenyl substituted with —O—(C$_1$-C$_6$)alkyl-C(O)—N(H)(C$_1$-C$_6$)alkyl-phenoxy.

In another embodiment, the compound is according to Formula I, or a pharmaceutically acceptable salt thereof, wherein R$_1$ is phenyl or methylphenyl substituted with —O—(C$_1$-C$_6$)alkyl-C(O)—N(H)(C$_1$-C$_6$)alkyl-(4-10 membered)heterocycloalkyl or —O—(C$_1$-C$_6$)alkyl-C(O)—N[(C$_1$-C$_6$)alkyl]-C$_1$-C$_6$)alkyl-(4-10 membered) heterocycloalkyl, wherein the -(4-10 membered)heterocycloalkyl portion of the —O—(C$_1$-C$_6$)alkyl-C(O)—N(H)(C$_1$-C$_6$)alkyl-(4-10 membered)heterocycloalkyl or —O—(C$_1$-C$_6$)alkyl-C(O)—N[(C$_1$-C$_6$)alkyl]-(C$_1$-C$_6$)alkyl-(4-10 membered)heterocycloalkyl group in this embodiment is optionally substituted with 1, 2 or 3 groups independently selected from oxo, —(C$_1$-C$_6$)alkyl-phenyl, —O—(C$_1$-C$_6$)alkyl and —(C$_1$-C$_6$)alkyl. Non-limiting examples of the -(4-10 membered)heterocycloalkyl portion of the —O—(C$_1$-C$_6$)alkyl-C(O)—N(H)(C$_1$-C$_6$)alkyl-(4-10 membered)heterocycloalkyl or —O—(C$_1$-C$_6$)alkyl-C(O)—N[(C$_1$-C$_6$)alkyl]-(C$_1$-C$_6$)alkyl-(4-10 membered)heterocycloalkyl group in this embodiment include morpholinyl, piperazinyl, tetrahydrofuranyl and pyrrolidinyl.

In another embodiment, the compound is according to Formula I, or a pharmaceutically acceptable salt thereof, wherein R$_1$ is phenyl or methylphenyl substituted with —O—(C$_1$-C$_6$)alkyl-C(O)—N(H)(C$_1$-C$_6$)alkyl-(5-10 membered)heteroaryl or —O—(C$_1$-C$_6$)alkyl-C(O)—N[(C$_1$-C$_6$)alkyl]-(C$_1$-C$_6$)alkyl-(5-10 membered)heteroaryl, wherein the -(5-10 membered)heteroaryl portion of the —O—(C$_1$-C$_6$)alkyl-C(O)—N(H)(C$_1$-C$_6$)alkyl-(5-10 membered)heteroaryl or —O—(C$_1$-C$_6$)alkyl-C(O)—N[(C$_1$-C$_6$)alkyl]-(C$_1$-C$_6$)alkyl-(5-10 membered)heteroaryl group is optionally substituted with 1, 2 or 3 groups independently selected from —(C$_1$-C$_6$)alkyl-phenyl, —O—(C$_1$-C$_6$)alkyl and —(C$_1$-C$_6$)alkyl. Non-limiting examples of the -(5-10 membered)heteroaryl portion of the —O—(C$_1$-C$_6$)alkyl-C(O)—N(H)(C$_1$-C$_6$)alkyl-(5-10 membered)heteroaryl and —O—(C$_1$-C$_6$)alkyl-C(O)—N[(C$_1$-C$_6$)alkyl]-(C$_1$-C$_6$)alkyl-(5-10 membered)heteroaryl group in this embodiment include furanyl, pyrimidinyl, and thienyl.

In another embodiment, the compound is according to Formula I, or a pharmaceutically acceptable salt thereof, wherein R$_1$ is phenyl or methylphenyl substituted with —C(O)—N(H)(C$_1$-C$_6$)alkyl-(C$_6$-C$_{10}$)aryl or —C(O)—N[(C$_1$-C$_6$)alkyl]-(C$_1$-C$_6$)alkyl-(C$_6$-C$_{10}$)aryl wherein the —(C$_6$-C$_{10}$)aryl portion of the —C(O)—N(H)(C$_1$-C$_6$)alkyl-(C$_6$-C$_{10}$)aryl or —C(O)—N[(C$_1$-C$_6$)alkyl]-(C$_1$-C$_6$)alkyl-(C$_6$-C$_{10}$)aryl group in this embodiment is optionally substituted with 1, 2 or 3 groups independently selected from halo, —(C$_1$-C$_6$)alkyl and —O—(C$_1$-C$_6$)alkyl. In a more specific embodiment, the —(C$_6$-C$_{10}$)aryl portion of the —C(O)—N(H)(C$_1$-C$_6$)alkyl-(C$_6$-C$_{10}$)aryl or —C(O)—N[(C$_1$-C$_{10}$)alkyl]-(C$_1$-C$_6$)alkyl-(C$_6$-C$_{10}$)aryl group in this embodiment is substituted with —O—(C$_1$-C$_6$)alkyl. A non-limiting example of the —(C$_6$-C$_{10}$)aryl portion of this embodiment includes phenyl.

In another embodiment, the compound is according to Formula I, or a pharmaceutically acceptable salt thereof, wherein R$_1$ is phenyl or methylphenyl substituted with —C(O)—N(H)(C$_1$-C$_6$)alkyl-(5-10 membered)heteroaryl or —C(O)—N[(C$_1$-C$_6$)alkyl]-(C$_1$-C$_6$)alkyl-(5-10 membered)heteroaryl, wherein the -(5-10 membered) heteroaryl portion of the —C(O)—N(H)(C$_1$-C$_6$)alkyl-(5-10 membered)heteroaryl or —C(O)—N[(C$_1$-C$_6$)alkyl]-(C$_1$-C$_6$)alkyl-(5-10 membered)heteroaryl group in this embodiment is optionally substituted with 1, 2 or 3 groups independently selected from halo, —(C$_1$-C$_6$)alkyl, and —O—(C$_1$-C$_6$)alkyl. In another embodiment, the -(5-10 membered)heteroaryl portion of the —C(O)—N(H)(C$_1$-C$_6$)alkyl-(5-10 membered)heteroaryl or —C(O)—N[(C$_1$-C$_6$)alkyl]-(C$_1$-C$_6$)alkyl-(5-10 membered) heteroaryl group in this embodiment is substituted with —O—(C$_1$-C$_6$)alkyl. Non-limiting examples of the -(5-10 membered)heteroaryl portion of the —C(O)—N(H)(C$_1$-C$_6$)alkyl-(5-10 membered)heteroaryl or —C(O)—N[(C$_1$-C$_6$)alkyl]-(C$_1$-C$_6$)alkyl-(5-10 membered)heteroaryl group in this embodiment include thienyl, pyrimidinyl, and furanyl.

In another embodiment, the compound is according to Formula I, or a pharmaceutically acceptable salt thereof, wherein R$_1$ is phenyl or methylphenyl substituted with —C(O)—N(H)(C$_1$-C$_6$)alkyl-(4-10 membered)heterocycloalkyl, wherein the -(4-10 membered)heterocycloalkyl portion of the —C(O)—N(H)(C$_1$-C$_6$)alkyl-(4-10 membered) heterocycloalkyl group in this embodiment is optionally substituted with 1, 2 or 3-(C$_1$-C$_6$)alkyl groups. A non-limiting example of the -(4-10 membered)heterocycloalkyl portion of the —C(O)—N(H)(C$_1$-C$_6$)alkyl-(4-10 membered)heterocycloalkyl group is tetrahydrofuran.

In another embodiment, the compound is according to Formula I, or a pharmaceutically acceptable salt thereof, wherein $R_1$ is phenyl or methylphenyl substituted with —O—$(C_1-C_6)$alkyl-C(O)—N(H)$(C_1-C_6)$alkyl-$(C_3-C_{10})$cycloalkyl. Non-limiting examples of the —$(C_3-C_{10})$cycloalkyl portion of the —O—$(C_1-C_6)$alkyl-C(O)—N(H)$(C_1-C_6)$alkyl-$(C_3-C_{10})$cycloalkyl group in this embodiment include cyclopropyl, cyclobutyl, cyclopentyl and cyclohexyl.

In another embodiment, the compound is according to Formula I, or a pharmaceutically acceptable salt thereof, wherein $R_1$ is phenyl or methylphenyl substituted with —O—$(C_1-C_6)$alkyl-C(O)—N[$(C_1-C_6)$alkyl]-$(C_1-C_6)$alkyl-$(C_3-C_{10})$cycloalkyl. Non-limiting examples of the —$(C_3-C_{10})$cycloalkyl portion of the —O—$(C_1-C_6)$alkyl-C(O)—N[$(C_1-C_6)$alkyl]-$(C_1-C_6)$alkyl-$(C_3-C_{10})$cycloalkyl group in this embodiment include cyclopropyl, cyclobutyl, cyclopentyl and cyclohexyl.

In another embodiment, the compound is according to Formula I, or a pharmaceutically acceptable salt thereof, wherein $R_1$ is phenyl or methylphenyl substituted with —O—$(C_1-C_6)$alkyl-C(O)—N[$(C_1-C_6)$alkyl]-$(C_3-C_{10})$cycloalkyl. Non-limiting examples of the —$(C_3-C_{10})$cycloalkyl portion of the —O—$(C_1-C_6)$alkyl-C(O)—N[$(C_1-C_6)$alkyl]-$(C_3-C_{10})$cycloalkyl group in this embodiment include cyclopropyl, cyclobutyl, cyclopentyl and cyclohexyl.

In another embodiment, the compound is according to Formula I, or a pharmaceutically acceptable salt thereof, wherein $R_1$ is phenyl or methylphenyl substituted with —O—$(C_1-C_6)$alkyl-C(O)OH.

In another embodiment, the compound is according to Formula I, or a pharmaceutically acceptable salt thereof, wherein $R_1$ is phenyl or methylphenyl substituted with —C(O)—N(H)$(C_1-C_6)$alkyl-O—$(C_6-C_{10})$aryl.

In another embodiment, the compound is according to Formula I, or a pharmaceutically acceptable salt thereof, wherein $R_1$ is phenyl or methylphenyl substituted with —N(H)$(C_1-C_6)$alkyl-(4-10 membered)heterocycloalkyl or —N[$(C_1-C_6)$alkyl]-$(C_1-C_6)$alkyl-(4-10 membered)heterocycloalkyl.

In another embodiment, the compound is according to Formula I, or a pharmaceutically acceptable salt thereof, wherein $R_1$ is phenyl or methylphenyl substituted with —O—$(C_1-C_6)$alkyl-C(O)—N(H)$(C_1-C_6)$alkyl-$NR_{13}R_{14}$, wherein $R_{13}$ and $R_{14}$ are each selected from H and —$(C_1-C_6)$alkyl.

In another embodiment, the compound is according to Formula I, or a pharmaceutically acceptable salt thereof, wherein $R_1$ is phenyl or methylphenyl substituted with —N(H)$(C_1-C_6)$alkyl-N(H)(4-10 membered)heterocycloalkyl optionally substituted with $(C_1-C_6)$alkyl.

In another embodiment, the compound is according to Formula I, or a pharmaceutically acceptable salt thereof, wherein $R_1$ is phenyl or methylphenyl substituted with —N(H)$(C_1-C_6)$alkyl-N(H)(5-10 membered)heteroaryl optionally substituted with —$(C_1-C_6)$alkyl.

In another embodiment, the compound is according to Formula I, or a pharmaceutically acceptable salt thereof, wherein $R_1$ is phenyl or methylphenyl substituted with —O—$(C_1-C_6)$alkyl-C(O)—N(H)(4-10 membered)heterocycloalkyl. Non-limiting examples of the -(4-10 membered)heterocycloalkyl group in this embodiment include, piperidinyl, piperazinyl, tetrahydrofuran, pyrrolidinyl and morpholinyl. More specific examples of the -(4-10 membered)heterocycloalkyl group in this embodiment include piperidinyl and piperazinyl.

In another embodiment, the compound is according to Formula I, or a pharmaceutically acceptable salt thereof, wherein $R_1$ is phenyl or methylphenyl substituted with —N(H)$(C_1-C_6)$alkyl-(5-10 membered)heteroaryl optionally substituted with alkyl. Non-limiting examples of the -(5-10 membered)heteroaryl group in this embodiment include imidazolyl, pyrazolyl, furanyl and thienyl. A specific example of the -(5-10 membered)heteroaryl group is imidazolyl.

In another embodiment, the compound is according to Formula I, or a pharmaceutically acceptable salt thereof, wherein $R_1$ is phenyl or methylphenyl substituted with —N(H)$(C_1-C_6)$alkyl-$NH_2$.

In another embodiment, the compound is according to Formula I, or a pharmaceutically acceptable salt thereof, wherein $R_1$ is phenyl or methylphenyl substituted with —N(H)$(C_1-C_6)$alkyl-(4-10 membered)heterocycloalkyl optionally substituted with —$(C_1-C_6)$alkyl.

In another embodiment, the compound is according to Formula I, or a pharmaceutically acceptable salt thereof, wherein $R_1$ is phenyl or methylphenyl substituted with —N(H)(4-10 membered)heterocycloalkyl optionally substituted with alkyl.

In another embodiment, the compound is according to Formula I, or a pharmaceutically acceptable salt thereof, wherein $R_1$ is phenyl or methylphenyl substituted with —O—$(C_1-C_6)$alkyl-(4-10 membered)heterocycloalkyl.

In all of the above embodiments, $R_1$ in the compound Formula I, or a pharmaceutically acceptable salt thereof, can be additionally substituted with —O—$(C_1-C_6)$alkyl, —$(C_1-C_6)$alkyl, halo, —$NH_2$ or —OH.

In all of the above embodiments, $R_1$ in the compound Formula II, or a pharmaceutically acceptable salt thereof, can be additionally substituted with —O—$(C_1-C_6)$alkyl, —$(C_1-C_6)$alkyl, halo, —$NH_2$ or —OH.

In any of the above embodiments of the compound of Formula I, or a pharmaceutically acceptable salt thereof, the methylphenyl group in $R_1$ can be ortho-methylphenyl which is represented as follows:

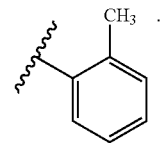

In other embodiments of the compound of Formula I, or a pharmaceutically acceptable salt thereof, and $R_1$ is phenyl or phenyl-$(C_1-C_6)$alkyl, wherein the phenyl is meta or para substituted by any of the $R_1$ substituents described in any of the above embodiments described hereinabove.

In other embodiments of the compound of Formula I, or a pharmaceutically acceptable salt thereof, and $R_1$ is phenyl or phenyl-$(C_1-C_6)$alkyl, wherein the phenyl is meta substituted by any of the $R_1$ substituents described in any of the embodiments described hereinabove.

In another embodiment of the compound of Formula I, or a pharmaceutically acceptable salt thereof, and $R_1$ is phenyl or phenyl-$(C_1-C_6)$alkyl, wherein the phenyl is para substituted by any of the $R_1$ substituents described in any of the embodiments hereinabove.

In another embodiment of the compound of Formula I, or a pharmaceutically acceptable salt thereof, and $R_1$ is phenyl or methylphenyl, wherein the phenyl is meta or para substituted by any of the $R_1$ substituents described in any of the embodiments hereinabove.

In another embodiment of the compound of Formula I, or a pharmaceutically acceptable salt thereof, and $R_1$ is phenyl or methylphenyl, wherein the phenyl is meta substituted by any of the $R_1$ substituents described in any of the embodiments hereinabove.

In another embodiment of the compound of Formula I, or a pharmaceutically acceptable salt thereof, and $R_1$ is phenyl or methylphenyl, wherein the phenyl is para substituted by any of the $R_1$ substituents described in any of the embodiments hereinabove.

In another embodiment of the compound of Formula I, and $R_2$ is phenyl substituted with methyl and —OH.

In another embodiment of the compound of Formula I, or a pharmaceutically acceptable salt thereof, and $R_2$ is

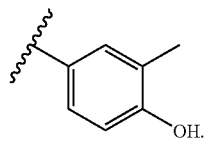

In another embodiment of Formula I, or a pharmaceutically acceptable salt thereof, $R^3$ is —$(C_3-C_6)$cycloalkyl or -(4-6 membered)heterocycloalkyl.

In another embodiment of Formula I, or a pharmaceutically acceptable salt thereof, $R^3$ is —$(C_3-C_6)$cycloalkyl.

In another embodiment of Formula I, or a pharmaceutically acceptable salt thereof, $R^3$ is -(4-6 membered)heterocycloalkyl.

In another embodiment of Formula I, or a pharmaceutically acceptable salt thereof, $R^4$ is -(4-6 membered)heterocycloalkyl, -(5-9 membered)heteroaryl, or —$(C_3-C_6)$cycloalkyl.

In another embodiment of Formula I, or a pharmaceutically acceptable salt thereof, $R^4$ is -(4-6 membered)heterocycloalkyl.

In another embodiment of Formula I, or a pharmaceutically acceptable salt thereof, $R^4$ is -(5-6 membered)heteroaryl.

In another embodiment of Formula I, or a pharmaceutically acceptable salt thereof, $R^4$ is —$(C_3-C_6)$cycloalkyl.

In another embodiment of Formula I, $R^5$ is H or $NH_2$.

In another embodiment of Formula I, or a pharmaceutically acceptable salt thereof, $R^5$ is H.

In another embodiment of Formula I, or a pharmaceutically acceptable salt thereof, $R^5$ is $NH_2$.

In another embodiment of Formula I, or a pharmaceutically acceptable salt thereof, $R^6$ is -(4-6 membered)heterocycloalkyl optionally substituted with oxo, -(5-6 membered)heteroaryl, —$(C_3-C_6)$cycloalkyl, —$N[(C_1-C_4)alkyl]_2$ or phenyl.

In another embodiment of Formula I, or a pharmaceutically acceptable salt thereof, $R^6$ is -(4-6 membered)heterocycloalkyl optionally substituted with oxo.

In another embodiment of Formula I, or a pharmaceutically acceptable salt thereof, $R^6$ is -(5-6 membered)heteroaryl.

In another embodiment of Formula I, or a pharmaceutically acceptable salt thereof, $R^6$ is —$(C_3-C_6)$cycloalkyl.

In another embodiment of Formula I, or a pharmaceutically acceptable salt thereof, $R^6$ is —$N[(C_1-C_4)alkyl]_2$.

In another embodiment of Formula I, or a pharmaceutically acceptable salt thereof, $R^6$ is phenyl.

In another embodiment of Formula I, or a pharmaceutically acceptable salt thereof, $R^7$ is -(4-6 membered)heterocycloalkyl optionally substituted with oxo, -(5-6 membered) heteroaryl or —$(C_3-C_6)$cycloalkyl.

In another embodiment of Formula I, or a pharmaceutically acceptable salt thereof, $R^7$ is -(4-6 membered)heterocycloalkyl optionally substituted with oxo.

In another embodiment of Formula I, or a pharmaceutically acceptable salt thereof, $R^7$ is -(5-6 membered)heteroaryl.

In another embodiment of Formula I, or a pharmaceutically acceptable salt thereof, $R^7$ is —$(C_3-C_6)$cycloalkyl.

In another embodiment of Formula I, or a pharmaceutically acceptable salt thereof, $R^8$ is —$(C_1-C_4)$alkyl-N(H)(4-6 membered)heterocycloalkyl, —$(C_1-C_4)$alkyl-(4-6 membered)heterocycloalkyl, —$(C_1-C_4)$alkyl-$NH_2$, —$(C_1-C_4)$alkyl-(5-6 membered)heteroaryl, or -(4-6 membered)heterocycloalkyl.

In another embodiment of Formula I, or a pharmaceutically acceptable salt thereof, $R^8$ is —$(C_1-C_4)$alkyl-N(H)(4-6 membered)heterocycloalkyl.

In another embodiment of Formula I, or a pharmaceutically acceptable salt thereof, $R^8$ is —$(C_1-C_4)$alkyl-(4-6 membered)heterocycloalkyl.

In another embodiment of Formula I, or a pharmaceutically acceptable salt thereof, $R^8$ is —$(C_1-C_4)$alkyl-$NH_2$.

In another embodiment of Formula I, or a pharmaceutically acceptable salt thereof, $R^8$ is —$(C_1-C_4)$alkyl-(5-6 membered)heteroaryl.

In another embodiment of Formula I, or a pharmaceutically acceptable salt thereof, $R^8$ is -(4-6 membered)heterocycloalkyl.

In another embodiment of Formula I, or a pharmaceutically acceptable salt thereof, $R^9$ is methyl.

In another embodiment of Formula I, or a pharmaceutically acceptable salt thereof, $R^{10}$ is —$(C_1-C_4)$alkyl-C(O)—$R^3$, —$(C_1-C_4)$alkyl-C(O)—N(H)$R^4$, —$(C_1-C_6)$alkyl-C(O)—N(H)$(C_1-C_6)$alkyl-$R^5$, —$(C_1-C_4)$alkyl-C(O)—N(H)$(C_1-C_4)$alkyl-N$[(C_1-C_6)$alkyl$]_2$—$(C_1-C_4)$alkyl-C(O)N(H)$(C_1-C_4)$alkyl-$R^7$, —$(C_1-C_6)$alkyl-C(O)N(H)$(C_1-C_4)$alkyl-aryl substituted at the aryl group with 1 or 2 groups independently selected from halo and —O—$(C_1-C_6)$alkyl, —$(C_1-C_6)$alkyl-(4-10 membered)heterocycloalkyl, —$(C_1-C_6)$alkyl-C(O)—N(H)$(C_1-C_6)$alkyl-$(C_1-C_6)$alkoxy, —$(C_1-C_6)$alkyl-C(O)—N(H)$(C_1-C_6)$alkyl-CN, or —$(C_1-C_6)$alkyl-C(O)—N$[(C_1-C_6)$alkyl$]_2$, wherein $R^3$, $R^4$, $R^5$ and $R^7$ are as defined in any of the above embodiments.

In another embodiment of Formula I, or a pharmaceutically acceptable salt thereof, $R^{10}$ is —$(C_1-C_4)$alkyl-C(O)—$R^3$ wherein $R^3$ is as defined in any of the above embodiments.

In another embodiment of Formula I, or a pharmaceutically acceptable salt thereof, $R^{10}$ is —$(C_1-C_4)$alkyl-C(O)—N(H)$R^4$ wherein $R^4$ is as defined in any of the above embodiments.

In another embodiment of Formula I, or a pharmaceutically acceptable salt thereof, $R^{10}$ is —$(C_1-C_4)$alkyl-C(O)—N(H)$(C_1-C_4)$alkyl-$R^5$, wherein $R^5$ is as defined in any of the above embodiments.

In another embodiment of Formula I, or a pharmaceutically acceptable salt thereof, $R^{10}$ is —$(C_1-C_4)$alkyl-C(O)—N(H)$(C_1-C_4)$alkyl-N(H)$[(C_1-C_4)$alkyl$]_2$.

In another embodiment of Formula I, or a pharmaceutically acceptable salt thereof, $R^{10}$ is $(C_1-C_4)$alkyl-C(O)N(H)$(C_1-C_4)$alkyl-$R^7$, wherein $R^7$ is as defined in any of the above embodiments.

In another embodiment of Formula I, or a pharmaceutically acceptable salt thereof, $R^{10}$—$(C_1-C_6)$alkyl-C(O)N(H)$(C_1-C_4)$alkyl-aryl substituted at the aryl group with 1 or 2 groups independently selected from halo and —O—$(C_1-C_3)$alkyl.

In another embodiment of Formula I, or a pharmaceutically acceptable salt thereof, $R^{10}$ is —$(C_1-C_6)$alkyl-(4-6 membered)heterocycloalkyl.

In another embodiment of Formula I, or a pharmaceutically acceptable salt thereof, $R^{10}$ is $(C_1-C_4)$alkyl-C(O)—N(H)$(C_1-C_6)$alkyl-$(C_{1-6})$alkoxy.

In another embodiment of Formula I, or a pharmaceutically acceptable salt thereof, $R^{10}$ is —$(C_1-C_4)$alkyl-C(O)—N(H)$(C_1-C_4)$alkyl-CN.

In another embodiment of Formula I, or a pharmaceutically acceptable salt thereof, $R^{10}$ is —$(C_1$-$C_4)$alkyl-C(O)—N[$(C_1$-$C_4)$alkyl]$_2$.

Each of said -(4-10 membered)heterocycloalkyl, -(5-10 membered)heteroaryl, —$(C_3$-$C_{10})$cycloalkyl, and —$(C_6$-$C_{10})$aryl for any one of the above embodiments of $R^1$, $R^3$, $R^4$, $R^6$ or $R^7$ can be unsubstituted or independently substituted at any ring position with 1, 2 or 3 substituents independently selected from —$(C_1$-$C_4)$alkyl, —NH$_2$, -(4-6 membered)heterocycloalkyl optionally substituted with —$(C_1$-$C_3)$alkyl, —N[$(C_1$-$C_4)$alkyl]$_2$, —$(C_1$-$C_6)$alkyl-NH$_2$, —$(C_1$-$C_4)$alkyl-$(C_1$-$C_4)$alkoxy, —N(H)C(O)—$(C_1$-$C_4)$alkyl, phenyl optionally substituted with —$(C_1$-$C_3)$alkoxy, halo, —C(O)—$(C_1$-$C_4)$alkyl, —C(O)-(5-6 membered)heteroaryl, —$(C_1$-$C_3)$alkyl-OH, —OH, —C(O)O—$(C_1$-$C_4)$alkyl, —C(O)-(4-6 membered)heterocycloalkyl, —$(C_1$-$C_3)$alkyl-phenyl, —$(C_1$-$C_3)$alkoxy, and -(5-6 membered)heteroaryl, and the substitutents for each of the -(4-6 membered)heterocycloalkyl, -(5-6 membered)heteroaryl, —$(C_3$-$C_6)$cycloalkyl, and phenyl can be the same or different for any one of $R^1$, $R^3$, $R^4$, $R^6$ or $R^7$.

In another embodiment of Formula I, or a pharmaceutically acceptable salt thereof, is phenyl substituted with 1 or 2 substituents independently selected from halo, —OH, —$(C_1$-$C_4)$alkyl, and —O—$(C_1$-$C_4)$alkyl.

In another embodiment of Formula I, or a pharmaceutically acceptable salt thereof, $R_{12}$ is phenyl substituted with 1 or 2 substituents independently selected from halo, —$(C_1$-$C_4)$alkyl, —O—$(C_1$-$C_4)$alkyl, —NH$_2$, and —N(H)$(C_1$-$C_4)$alkyl-(4-6 membered)heterocycloalkyl.

In another embodiment of Formula I, or a pharmaceutically acceptable salt thereof, each of E1, E2, E3, E4, E5, E6, E7, E8, E9, E10, E11, E12 and E13 are H.

All compounds of Formula I disclosed above include any of the disclosed alternative aspects or embodiments for each of $R_1$, $R_2$, $R_3$, $R_4$, $R_5$, $R_6$, $R_7$, $R_8$, $R_9$, $R_{10}$, $R_{11}$, $R_{12}$, X, Y, E1, E2, E3, E4, E5, E6, E7, E8, E9, E10, E11, E12 and E13 in combination with any other of the disclosed alternative aspects or embodiments of $R_1$, $R_2$, $R_3$, $R_4$, $R_5$, $R_6$, $R_7$, $R_8$, $R_9$, $R_{10}$, $R_{11}$, $R_{12}$, X, Y, E1, E2, E3, E4, E5, E6, E7, E8, E9, E10, E11, E12 and E13 as well as any pharmaceutically acceptable salt and stereoisomer of any such combination.

In another embodiment of the compound of Formula I, or a pharmaceutically acceptable salt thereof, $R_1$ is phenyl substituted with —C(O)-(4-10 membered)heterocycloalkyl optionally substituted at any ring position of the —C(O)-(4-10 membered)heterocycloalkyl with 1, 2 or 3 groups independently selected from —$(C_1$-$C_3)$alkyl, —$(C_6$-$C_{10})$aryl-O—$(C_1$-$C_3)$alkyl, —O—$(C_1$-$C_6)$alkyl, -(5-10 membered)heteroaryl, —C(O)-(5-10 membered)heteroaryl, -(4-10 membered)heterocycloalkyl, —C(O)-(4-10 membered)heterocycloalkyl, —OH, —C(O)O—$(C_1$-$C_3)$alkyl, —N(H)C(O)—$(C_1$-$C_3)$alkyl, —C(O)—$(C_1$-$C_3)$alkyl, —$(C_1$-$C_3)$alkyl-$(C_6$-$C_{10})$aryl optionally substituted with 1, 2 or 3 halo, —$(C_1$-$C_6)$alkyl-O—$(C_1$-$C_6)$alkyl, —$(C_1$-$C_6)$alkyl-OH, —NH$_2$, and —$(C_1$-$C_6)$alkyl-NH$_2$;
$R_2$ is

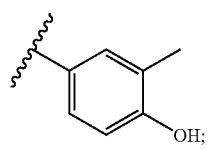

and
X is O.

In another embodiment of the compound of Formula I, or a pharmaceutically acceptable salt thereof, $R_1$ is phenyl substituted with —C(O)—N(H)$(C_1$-$C_6)$alkyl, —C(O)—N[$(C_1$-$C_6)$alkyl]$_2$ or —C(O)—N(H)$(C_1$-$C_6)$alkyl-N[$(C_1$-$C_6)$alkyl]$_2$;
$R_2$ is

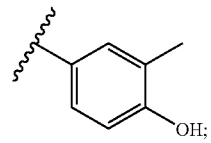

and
X is O.

In another embodiment of the compound of Formula I, or a pharmaceutically acceptable salt thereof, $R_1$ is phenyl substituted with —C(O)-piperizinyl-phenyl, wherein the phenyl group is optionally substituted with methoxy or ethoxy;
$R_2$ is

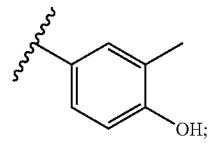

and
X is O.

In another embodiment of the compound of Formula I, or a pharmaceutically acceptable salt thereof, $R_1$ is phenyl substituted with —C(O)N(H)$(C_1$-$C_6)$alkyl-$(C_3$-$C_6)$cycloalkyl;
$R_2$ is

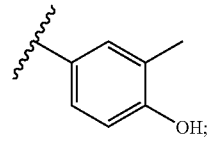

and
X is O.

In another embodiment of the compound of Formula I, or a pharmaceutically acceptable salt thereof, $R_1$ is phenyl substituted with —C(O)-(4-10 membered heterocycloalkyl)-C(O)—(O)—$(C_1$-$C_6)$alkyl;
$R_2$ is

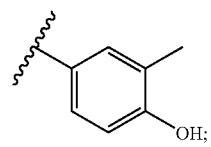

and
X is O.

In another embodiment of the compound of Formula I, or a pharmaceutically acceptable salt thereof, $R_1$ is phenyl substituted with —(O)-alkyl-C(O)-(4-10 membered)heterocycloalkyl optionally substituted at any ring position of the —(O)-alkyl-C(O)-(4-10 membered)heterocycloalkyl group with 1, 2 or 3 groups independently selected from —N(H)C(O)—(C$_1$-C$_6$)alkyl, —N[(C$_1$-C$_6$)alkyl]-C(O)—(C$_1$-C$_6$)alkyl, —C(O)-(5-10 membered)heteroaryl, —(C$_1$-C$_6$)alkyl-(C$_6$-C$_{10}$)aryl, —(C$_1$-C$_6$)alkyl-O—(C$_1$-C$_6$)alkyl, —C(O)—(C$_1$-C$_6$)alkyl, —OH, -(4-10 membered)heterocycloalkyl, —(C$_1$-C$_6$)alkyl-OH, -(5-10 membered)heteroaryl, —C(O)—O—(C$_1$-C$_6$)alkyl, —C(O)-(4-10 membered) heterocycloalkyl, —(C$_6$-C$_{10}$)aryl optionally substituted with —O—(C$_1$-C$_6$)alkyl and —(C$_1$-C$_6$)alkyl;
R$_2$ is

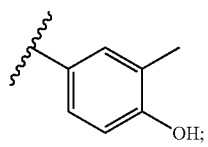

and
X is O.

In another embodiment of the compound of Formula I, or a pharmaceutically acceptable salt thereof, R$_1$ is phenyl substituted with —C(O)—N(H)(4-10 membered)heterocycloalkyl or —C(O)—N[(C$_1$-C$_6$)alkyl]-(4-10 membered) heterocycloalkyl, wherein the (4-10 membered)heterocycloalkyl portion is optionally substituted with 1 or 2 groups independently selected from —(C$_1$-C$_6$)alkyl and oxo;
R$_2$ is

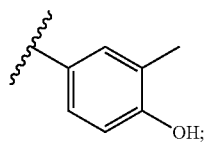

and
X is O.

In another embodiment of the compound of Formula I, or a pharmaceutically acceptable salt thereof, R$_1$ is phenyl substituted with —C(O)—N(H)(C$_3$-C$_7$)cycloalkyl, wherein the —(C$_3$-C$_7$)cycloalkyl portion of the —C(O)—N(H)(C$_3$-C$_7$)cycloalkyl group in this embodiment is optionally substituted with —(C$_1$-C$_6$)alkyl;
R$_2$ is

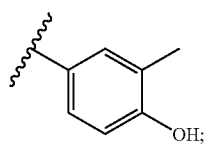

and
X is O.

In another embodiment of the compound of Formula I, or a pharmaceutically acceptable salt thereof, R$_1$ is phenyl substituted with —O—(C$_1$-C$_6$)alkyl-C(O)—N(H)(C$_1$-C$_{10}$)alkyl-(C$_6$-C$_{10}$)aryl or —O—(C$_1$-C$_6$)alkyl-C(O)—N[(C$_1$-C$_6$)alkyl]-(C$_1$-C$_6$)alkyl-(C$_6$-C$_{10}$)aryl, wherein the (C$_6$-C$_{10}$)aryl portion of the —O—(C$_1$-C$_6$)alkyl-C(O)—N(H)(C$_1$-C$_6$)alkyl-(C$_6$-C$_{10}$)aryl or —O—(C$_1$-C$_6$)alkyl-C(O)—N[(C$_1$-C$_6$)alkyl]-(C$_1$-C$_6$)alkyl-(C$_6$-C$_{10}$)aryl group in this embodiment is optionally substituted with 1, 2 or 3 groups independently selected from halo and —O—(C$_1$-C$_6$)alkyl;
R$_2$ is

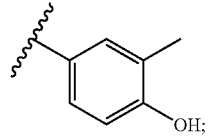

and
X is O.

In another embodiment of the compound of Formula I, or a pharmaceutically acceptable salt thereof, R$_1$ is phenyl substituted with —O—(C$_1$-C$_6$)alkyl-C(O)—N(H)(C$_1$-C$_6$)alkyl;
R$_2$ is

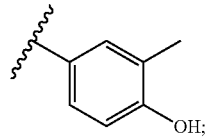

and
X is O.

In another embodiment of the compound of Formula I, or a pharmaceutically acceptable salt thereof, R$_1$ is phenyl substituted with —O—(C$_1$-C$_6$)alkyl-C(O)—N(H)(C$_1$-C$_6$)alkyl-CN;
R$_2$ is

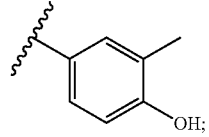

and
X is O.

In another embodiment of the compound of Formula I, or a pharmaceutically acceptable salt thereof, R$_1$ is phenyl substituted with —O—(C$_1$-C$_6$)alkyl-C(O)—N(H)(C$_1$-C$_6$)alkyl-O—(C$_1$-C$_6$)alkyl;
R$_2$ is

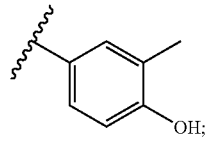

and
X is O.

In another embodiment of the compound of Formula I, or a pharmaceutically acceptable salt thereof, R$_1$ is phenyl substituted with —O—(C$_1$-C$_6$)alkyl-C(O)—N(H)(C$_1$-C$_6$)alkyl-(4-10 membered)heterocycloalkyl or —O—(C$_1$-C$_6$)alkyl-C(O)—N[(C$_1$-C$_6$)alkyl]-(C$_1$-C$_6$)alkyl-(4-10 membered) heterocycloalkyl, wherein the -(4-10 membered) heterocycloalkyl portion of the —O—(C$_1$-C$_6$)alkyl-C(O)—

N(H)(C$_1$-C$_6$)alkyl -(4-10 membered)heterocycloalkyl or —O—(C$_1$-C$_6$)alkyl-C(O)—N[(C$_1$-C$_6$)alkyl]-(C$_1$-C$_6$)alkyl-(4-10 membered)heterocycloalkyl group in this embodiment is optionally substituted with 1, 2 or 3 groups independently selected from oxo, —(C$_1$-C$_6$)alkyl-phenyl, —O—(C$_1$-C$_6$)alkyl and —(C$_1$-C$_6$)alkyl;
R$_2$ is

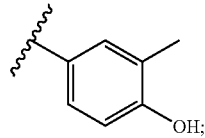

and
X is O.

In another embodiment of the compound of Formula I, or a pharmaceutically acceptable salt thereof, R$_1$ is phenyl substituted with —O—(C$_1$-C$_6$)alkyl-C(O)—N(H)(C$_1$-C$_6$)alkyl-(5-10 membered)heteroaryl or —O—(C$_1$-C$_6$)alkyl-C(O)—N[(C$_1$-C$_6$)alkyl]-(C$_1$-C$_6$)alkyl-(5-10 membered)heteroaryl, wherein the -(5-10 membered) heteroaryl portion of the —O—(C$_1$-C$_6$)alkyl-C(O)—N(H)(C$_1$-C$_6$)alkyl-(5-10 membered)heteroaryl or —O—(C$_1$-C$_6$)alkyl-C(O)—N[(C$_1$-C$_6$)alkyl]-(C$_1$-C$_6$)alkyl-(5-10 membered)heteroaryl group is optionally substituted with 1, 2 or 3 groups independently selected from —(C$_1$-C$_6$)alkyl-phenyl, —O—(C$_1$-C$_6$)alkyl and —(C$_1$-C$_6$)alkyl;
R$_2$ is

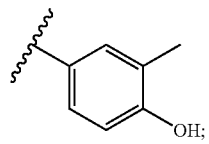

and
X is O.

In another embodiment of the compound of Formula I, or a pharmaceutically acceptable salt thereof, R$_1$ is phenyl substituted with —C(O)—N(H)(C$_1$-C$_6$)alkyl-(C$_6$-C$_{10}$)aryl or —C(O)—N[(C$_1$-C$_6$)alkyl]-(C$_1$-C$_6$)alkyl-(C$_6$-C$_{10}$)aryl, wherein the —(C$_6$-C$_{10}$)aryl portion of the —C(O)—N(H)(C$_1$-C$_6$)alkyl-(C$_6$-C$_{10}$)aryl or —C(O)—N[(C$_1$-C$_6$)alkyl]-(C$_1$-C$_6$)alkyl-(C$_6$-C$_{10}$)aryl group in this embodiment is optionally substituted with 1, 2 or 3 groups independently selected from halo, —(C$_1$-C$_6$)alkyl and —O—(C$_1$-C$_6$)alkyl;
R$_2$ is

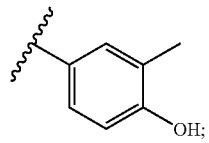

and
X is O.

In another embodiment of the compound of Formula I, or a pharmaceutically acceptable salt thereof, R$_1$ is phenyl substituted with —C(O)—N(H)(C$_1$-C$_6$)alkyl-(5-10 membered)heteroaryl or —C(O)—N[(C$_1$-C$_6$)alkyl]-(C$_1$-C$_6$)alkyl-(5-10 membered)heteroaryl, wherein the -(5-10 membered)heteroaryl portion of the —C(O)—N(H)(C$_1$-C$_6$)alkyl-(5-10 membered)heteroaryl or —C(O)—N[(C$_1$-C$_6$)alkyl]-(C$_1$-C$_6$)alkyl-(5-10 membered)heteroaryl group in this embodiment is optionally substituted with 1, 2 or 3 groups independently selected from halo, —(C$_1$-C$_6$)alkyl, and —O—(C$_1$-C$_6$)alkyl;
R$_2$ is

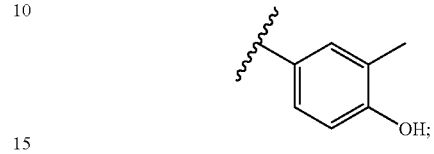

and
X is O.

In another embodiment of the compound of Formula I, or a pharmaceutically acceptable salt thereof, R$_1$ is phenyl substituted with —C(O)—N(H)(C$_1$-C$_6$)alkyl-(4-10 membered)heterocycloalkyl, wherein the -(4-10 membered) heterocycloalkyl portion of the —C(O)—N(H)(C$_1$-C$_6$)alkyl-(4-10 membered)heterocycloalkyl group in this embodiment is optionally substituted with 1, 2 or 3-(C$_1$-C$_6$)alkyl groups;
R$_2$ is

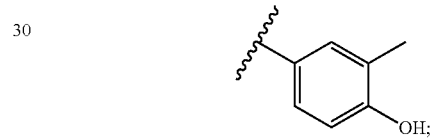

and
X is O.

In another embodiment of the compound of Formula I, or a pharmaceutically acceptable salt thereof, R$_1$ is phenyl substituted with —O—(C$_1$-C$_6$)alkyl-C(O)—N(H)(C$_1$-C$_6$)alkyl-(C$_3$-C$_{10}$)cycloalkyl;
R$_2$ is

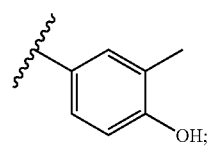

and
X is O.

In another embodiment of the compound of Formula I, or a pharmaceutically acceptable salt thereof, R$_1$ is phenyl substituted with —O—(C$_1$-C$_6$)alkyl-C(O)—N[(C$_1$-C$_6$)alkyl]-(C$_1$-C$_6$)alkyl-(C$_3$-C$_{10}$)cycloalkyl;
R$_2$ is

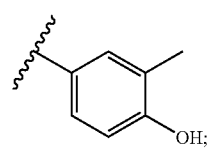

and
X is O.

In another embodiment of the compound of Formula I, or a pharmaceutically acceptable salt thereof, $R_1$ is phenyl substituted with —O—$(C_1-C_6)$alkyl-C(O)—N[$(C_1-C_6)$alkyl]-$(C_1-C_6)$alkyl-$(C_3-C_{10})$cycloalkyl;
$R_2$ is

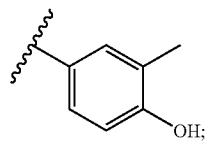

and
X is O.

In another embodiment of the compound of Formula I, or a pharmaceutically acceptable salt thereof, $R_1$ is phenyl substituted with —O—$(C_1-C_6)$alkyl-C(O)—N[$(C_1-C_6)$alkyl]-$(C_3-C_{10})$cycloalkyl;
$R_2$ is

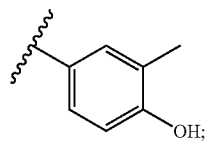

and
X is O.

In another embodiment of the compound of Formula I, or a pharmaceutically acceptable salt thereof, $R_1$ is phenyl substituted with —O—$(C_1-C_6)$alkyl-C(O)OH;
$R_2$ is

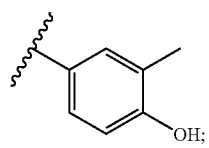

and
X is O.

In another embodiment of the compound of Formula I, or a pharmaceutically acceptable salt thereof, $R_1$ is phenyl substituted with —C(O)—N(H)$(C_1-C_6)$alkyl-O—$(C_6-C_{10})$aryl;
$R_2$ is

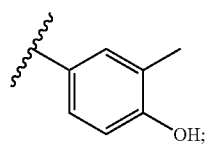

and
X is O.

In another embodiment of the compound of Formula I, or a pharmaceutically acceptable salt thereof, $R_1$ is phenyl substituted with —N(H)$(C_1-C_6)$alkyl-(4-10 membered)heterocycloalkyl or —N[$(C_1-C_6)$alkyl]-$(C_1-C_6)$alkyl-(4-10 membered)heterocycloalkyl;
$R_2$ is

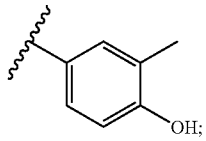

and
X is O.

In another embodiment of the compound of Formula I, or a pharmaceutically acceptable salt thereof, $R_1$ is phenyl or methylphenyl substituted with —O—$(C_1-C_6)$alkyl-C(O)—N(H)$(C_1-C_6)$alkyl-$NR_{13}R_{14}$, wherein $R_{13}$ and $R_{14}$ are each selected from H and —$(C_1-C_6)$alkyl;
$R_2$ is

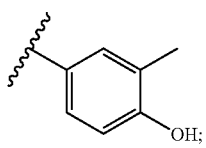

and
X is O.

In another embodiment of the compound of Formula I, or a pharmaceutically acceptable salt thereof, $R_1$ is phenyl or methylphenyl substituted with —N(H)$(C_1-C_6)$alkyl-N(H)(4-10 membered)heterocycloalkyl optionally substituted with $(C_1-C_6)$alkyl;
$R_2$ is

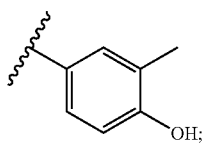

and
X is O.

In another embodiment of the compound of Formula I, or a pharmaceutically acceptable salt thereof, $R_1$ is phenyl or methylphenyl substituted with —N(H)$(C_1-C_6)$alkyl-N(H)(5-10 membered)heteroaryl optionally substituted with —$(C_1-C_6)$alkyl;
$R_2$ is

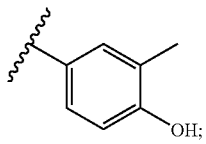

and
X is O.

In another embodiment of the compound of Formula I, or a pharmaceutically acceptable salt thereof, $R_1$ is phenyl or methylphenyl substituted with —O—$(C_1-C_6)$alkyl-C(O)—N(H)(4-10 membered)heterocycloalkyl;

$R_2$ is

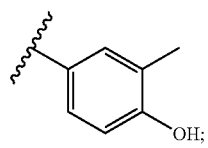

and
X is O.

In another embodiment of the compound of Formula I, or a pharmaceutically acceptable salt thereof, $R_1$ is phenyl or methylphenyl substituted with —N(H)($C_1$-$C_6$)alkyl-(5-10 membered)heteroaryl optionally substituted with alkyl;
$R_2$ is

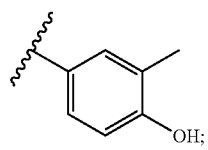

and
X is O.

In another embodiment of the compound of Formula I, or a pharmaceutically acceptable salt thereof, $R_1$ is phenyl or methylphenyl substituted with —N(H)($C_1$-$C_6$)alkyl-$NH_2$;
$R_2$ is

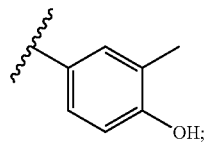

and
X is O.

In another embodiment of the compound of Formula I, or a pharmaceutically acceptable salt thereof, $R_1$ is phenyl or methylphenyl substituted with —N(H)($C_1$-$C_6$)alkyl-(4-10 membered)heterocycloalkyl optionally substituted with —($C_1$-$C_6$)alkyl;
$R_2$ is

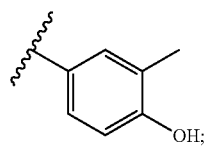

and
X is O.

In another embodiment of the compound of Formula I, or a pharmaceutically acceptable salt thereof, $R_1$ is phenyl or methylphenyl substituted with —N(H)(4-10 membered)heterocycloalkyl optionally substituted with alkyl;

$R_2$ is

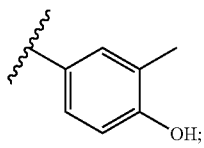

and
X is O.

In another embodiment of the compound of Formula I, or a pharmaceutically acceptable salt thereof, $R_1$ is phenyl or methylphenyl substituted with —O—($C_1$-$C_6$)alkyl-(4-10 membered)heterocycloalkyl;
$R_2$ is

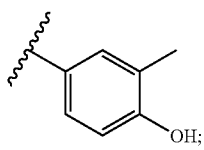

and
X is O.

In another embodiment of the compound of Formula I, or a pharmaceutically acceptable salt thereof, $R_1$ is phenyl or methylphenyl substituted with —O—($C_1$-$C_6$)alkyl-C(O)—N(H)($C_1$-$C_6$)alkyl-$NH_2$;
$R_2$ is

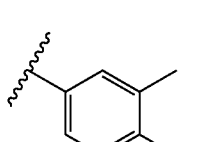

and
X is O.

In another embodiment, the compound is according to Formula I;
$R_1$ is phenyl or methylphenyl substituted with —O—($C_1$-$C_6$)alkyl-C(O)—N(H)($C_1$-$C_6$)alkyl-N(H)($C_1$-$C_6$)alkyl;
$R_2$ is

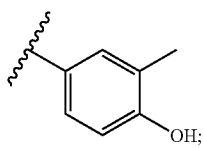

and
X is O.

In another embodiment, the compound is according to Formula I; $R_1$ is phenyl or methylphenyl substituted with —O—($C_1$-$C_6$)alkyl-C(O)—N(H)($C_1$-$C_6$)alkyl-N[($C_1$-$C_6$)alkyl]$_2$.

$R_2$ is

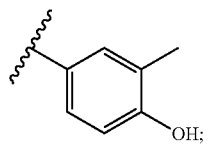

and

X is O.

Another aspect of the invention relates to a pharmaceutical composition comprising a compound according to Formula I or Formula II, or a pharmaceutically acceptable salt thereof, and a pharmaceutically acceptable carrier, excipient, or diluent.

Another aspect of the invention relates to a method of inhibiting PIM in a cell, comprising contacting a cell in which inhibition of PIM is desired with a compound according to Formula I or Formula II, or a pharmaceutically acceptable salt thereof.

Another aspect of the invention relates to a method of inhibiting PIM in a cell, comprising contacting a cell in which inhibition of PIM is desired with a pharmaceutical composition comprising a compound according to Formula I or Formula II, or a pharmaceutically acceptable salt thereof, and a pharmaceutically acceptable carrier, excipient, or diluent.

Another aspect of the invention relates to a method of treating a disease or condition that involves PIM comprising administering to a patient, in need of the treatment, a compound according to Formula I or Formula II, or a pharmaceutically acceptable salt thereof. Non-limiting examples of the disease or condition that can be treated include cancer such as ovarian cancer, cervical cancer, breast cancer, colorectal cancer, or glioblastomas.

Another aspect of the invention relates to a method of treating a disease or condition that involves PIM comprising administering to a patient, in need of the treatment, a pharmaceutical composition comprising a compound according to Formula I or Formula II, or a pharmaceutically acceptable salt thereof, and a pharmaceutically acceptable carrier, excipient, or diluent. Non-limiting examples of the disease or condition that can be treated include cancer such as ovarian cancer, cervical cancer, breast cancer, colorectal cancer, or glioblastomas.

Another aspect of the invention relates to a method of treating a disease or condition that involves PIM comprising administering to a patient, in need of the treatment, a compound according to Formula I or Formula II, or a pharmaceutically acceptable salt thereof in combination with radiation treatment and/or one or more therapeutic agents selected from Camptothecin, Topotecan, 9-Nitrocamptothecin, 9-Aminocamptothecin, Karenitecin, Irinotecan, Etoposide, Etoposide Phosphate, Teniposide, Amsacrine, Razoxane, Dexrazoxane, Mechlorethamine, Cyclophosphamide, Ifosfamide, Chlorambucil, Melphalan, Thiotepa, Trenimon, Triethylenemelamine, Rapamycin, Dianhydrogalactitol, Dibromodulcitol, Busulfan, dimethylsulfate, Chloroethylnitrosourea, BCNU, CCNU, Methyl-CCNU, Streptozotocin, Chlorozotocin, Prednimustine, Estramustine, Procarbazine, Dacarbazine, Hexamethylmelamine, Pentamethylmelamine, Temozolomide, Cisplatin, Carboplatin, Oxaliplatin, Bleomycin, Dactinomycin, Mithramycin, Mitomycin C, Daunorubicin, Doxorubicin, Epirubicin, Idarubicin, Methotrexate, Edatrexate, Trimethoprim, Nolatrexed, Raltitrexed, Hydroxyurea, 5-fluorouracil, Ftorafur, Capecitabine, Furtulon, Eniluracil, ara-C, 5-azacytidine, Gemcitabine, Mercaptopurine, Thioguanine, Pentostatin, antisense DNA, antisense RNA, an antisense DNA/RNA hybrid, a ribozyme, ultraviolet radiation, Vincristine, Vinblastine, Paclitaxel, Docetaxel, L-Asparaginase, a kinase inhibitor, Imatinib, Mitotane, Aminoglutethimide, Diethylstilbestrol, Ethinyl estradiol, Tamoxifen, Anastrozole, Testosterone propionate, Fluoxymesterone, Flutamide, Leuprolide, Prednisone, Hydroxyprogesterone caproate, Medroxyprogesterone acetate, Megestrol acetate, Interferon-alfa, and Interleukin. In a more specific embodiment, the combination is with Rapamycin.

In another embodiment, the compound of Formula I or II, or pharmaceutically acceptable salt thereof, is selected from one of the compounds from Tables 1 or 2 below. The compounds in Tables 1 and 2 are merely illustrative, and do not limit the scope of the invention in any way.

TABLE 1

| STRUCTURE | NAME |
|---|---|
| 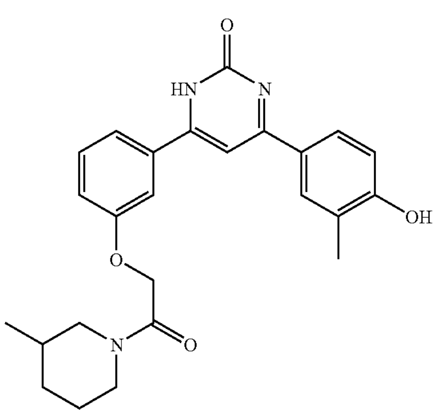 | 4-(4-hydroxy-3-methylphenyl)-6-(3-{[2-(3-methylpiperidin-1-yl)-2-oxoethyl]oxy}phenyl)pyrimidin-2(1H)-one |

TABLE 1-continued

| STRUCTURE | NAME |
|---|---|
| 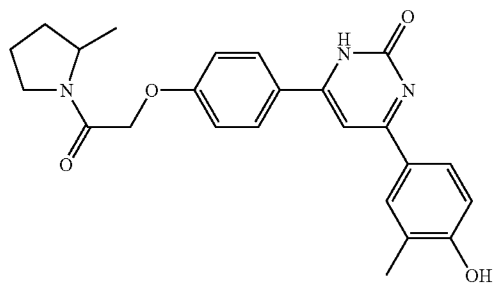 | 4-(4-hydroxy-3-methylphenyl)-6-(4-{[2-(2-methylpyrrolidin-1-yl)-2-oxoethyl]oxy}phenyl)pyrimidin-2(1H)-one |
| 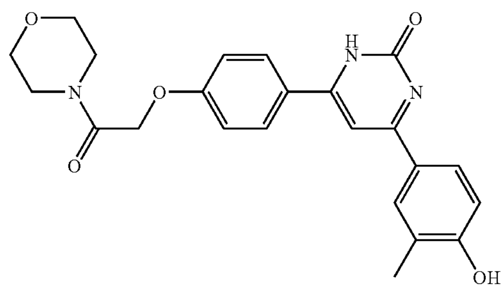 | 4-(4-hydroxy-3-methylphenyl)-6-{4-[(2-morpholin-4-yl-2-oxoethyl)oxy]phenyl}pyrimidin-2(1H)-one |
| 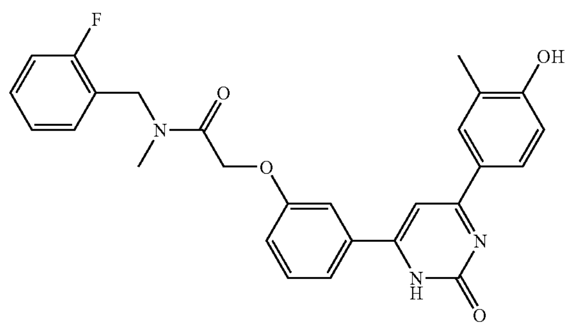 | N-[(2-fluorophenyl)methyl]-2-({3-[6-(4-hydroxy-3-methylphenyl)-2-oxo-2,3-dihydropyrimidin-4-yl]phenyl}oxy)-N-methylacetamide |
| 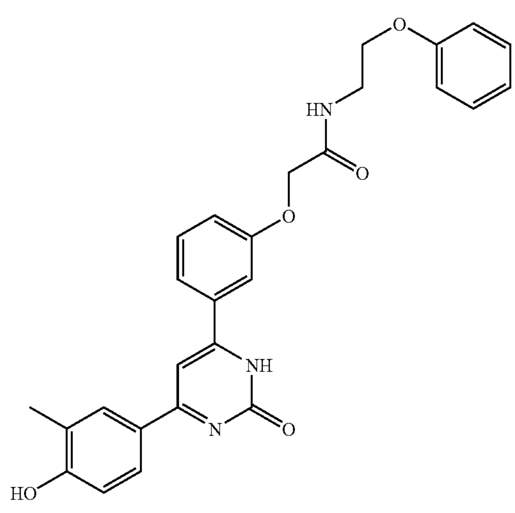 | 2-({3-[6-(4-hydroxy-3-methylphenyl)-2-oxo-2,3-dihydropyrimidin-4-yl]phenyl}oxy)-N-[2-(phenyloxy)ethyl]acetamide |

TABLE 1-continued

| STRUCTURE | NAME |
|---|---|
| 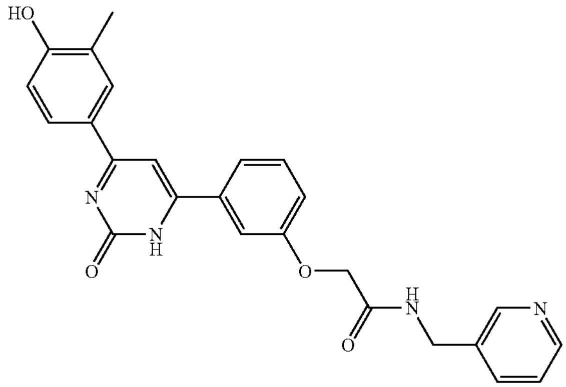 | 2-({3-[6-(4-hydroxy-3-methylphenyl)-2-oxo-2,3-dihydropyrimidin-4-yl]phenyl}oxy)-N-(pyridin-3-ylmethyl)acetamide |
| 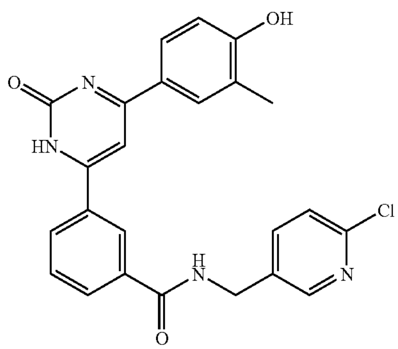 | N-[(6-chloropyridin-3-yl)methyl]-3-[6-(4-hydroxy-3-methylphenyl)-2-oxo-2,3-dihydropyrimidin-4-yl]benzamide |
| 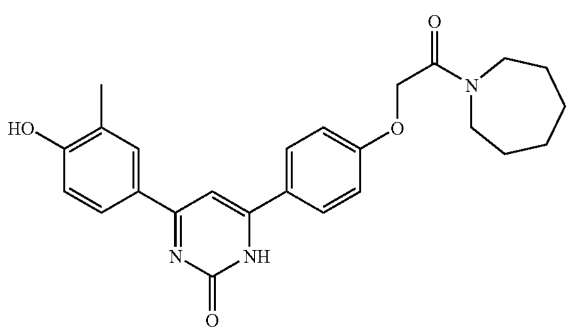 | 6-{4-[(2-azepan-1-yl-2-oxoethyl)oxy]phenyl}-4-(4-hydroxy-3-methylphenyl)pyrimidin-2(1H)-one |
| 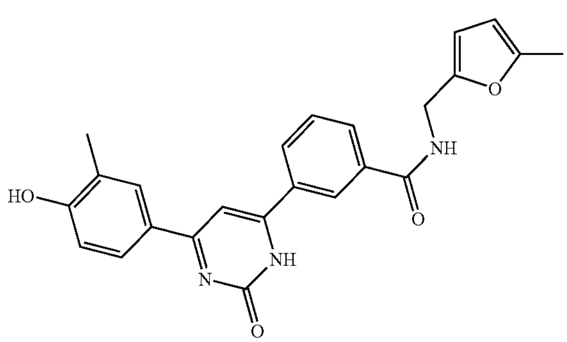 | 3-[6-(4-hydroxy-3-methylphenyl)-2-oxo-2,3-dihydropyrimidin-4-yl]-N-[(5-methylfuran-2-yl)methyl]benzamide |

TABLE 1-continued

| STRUCTURE | NAME |
|---|---|
| 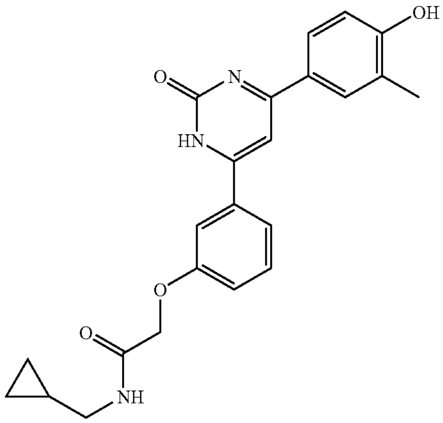 | N-(cyclopropylmethyl)-2-({3-[6-(4-hydroxy-3-methylphenyl)-2-oxo-2,3-dihydropyrimidin-4-yl]phenyl}oxy)acetamide |
| 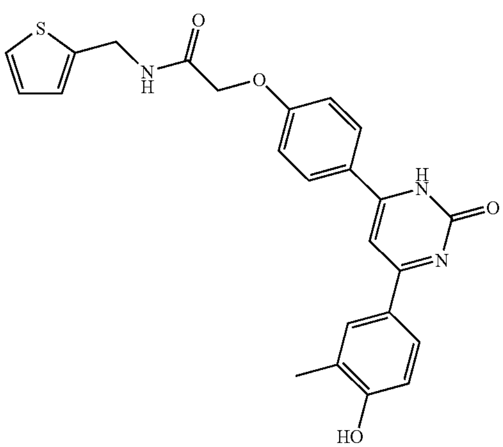 | 2-({4-[6-(4-hydroxy-3-methylphenyl)-2-oxo-2,3-dihydropyrimidin-4-yl]phenyl}oxy)-N-(2-thienylmethyl)acetamide |
| 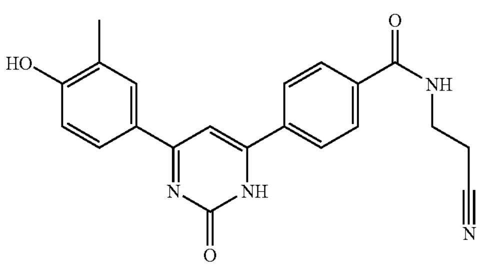 | N-(2-cyanoethyl)-4-[6-(4-hydroxy-3-methylphenyl)-2-oxo-2,3-dihydropyrimidin-4-yl]benzamide |
| 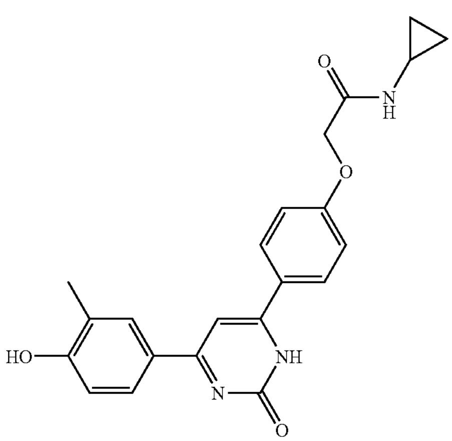 | N-cyclopropyl-2-({4-[6-(4-hydroxy-3-methylphenyl)-2-oxo-2,3-dihydropyrimidin-4-yl]phenyl}oxy)acetamide |

TABLE 1-continued

| STRUCTURE | NAME |
|---|---|
| 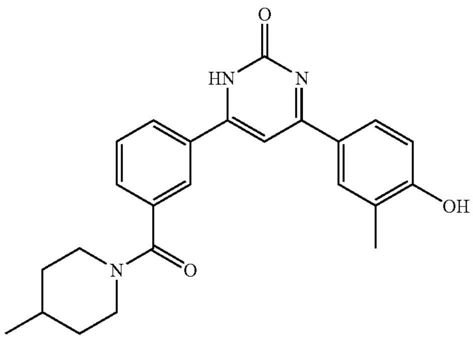 | 4-(4-hydroxy-3-methylphenyl)-6-{3-[(4-methylpiperidin-1-yl)carbonyl]phenyl}pyrimidin-2(1H)-one |
| 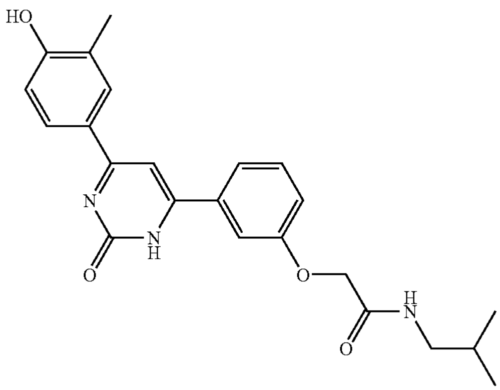 | 2-({3-[6-(4-hydroxy-3-methylphenyl)-2-oxo-2,3-dihydropyrimidin-4-yl]phenyl}oxy)-N-(2-methylpropyl)acetamide |
| 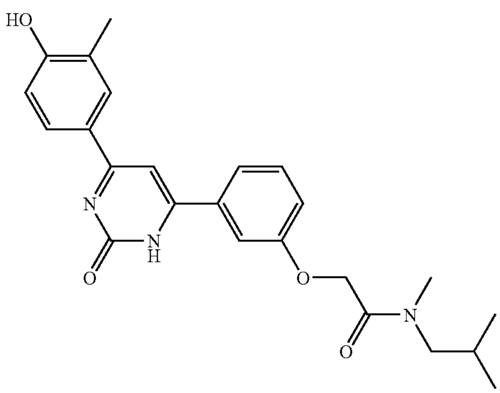 | 2-({3-[6-(4-hydroxy-3-methylphenyl)-2-oxo-2,3-dihydropyrimidin-4-yl]phenyl}oxy)-N-methyl-N-(2-methylpropyl)acetamide |
| 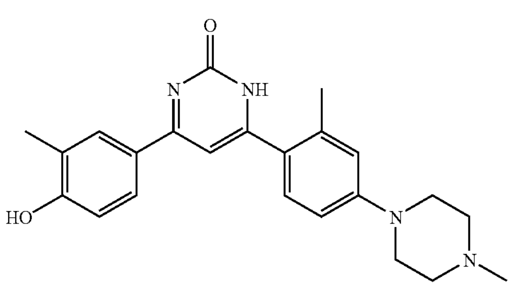 | 4-(4-hydroxy-3-methylphenyl)-6-[2-methyl-4-(4-methylpiperazin-1-yl)phenyl]pyrimidin-2(1H)-one |

TABLE 1-continued

| STRUCTURE | NAME |
| --- | --- |
| 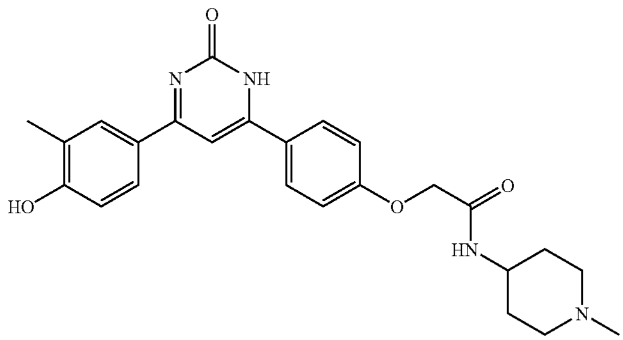 | 2-({4-[6-(4-hydroxy-3-methylphenyl)-2-oxo-2,3-dihydropyrimidin-4-yl]phenyl}oxy)-N-(1-methylpiperidin-4-yl)acetamide |
| 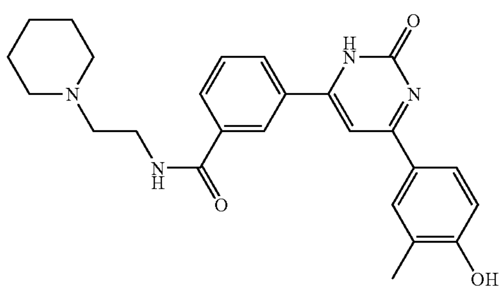 | 3-[6-(4-hydroxy-3-methylphenyl)-2-oxo-2,3-dihydropyrimidin-4-yl]-N-(2-piperidin-1-ylethyl)benzamide |
| 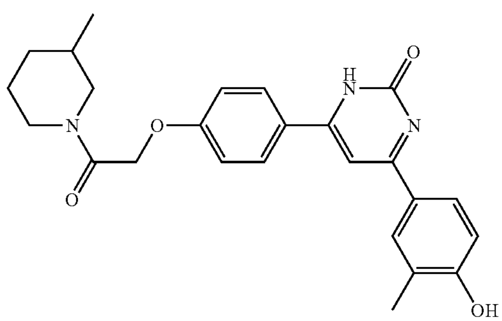 | 4-(4-hydroxy-3-methylphenyl)-6-(4-{[2-(3-methylpiperidin-1-yl)-2-oxoethyl]oxy}phenyl)pyrimidin-2(1H)-one |
| 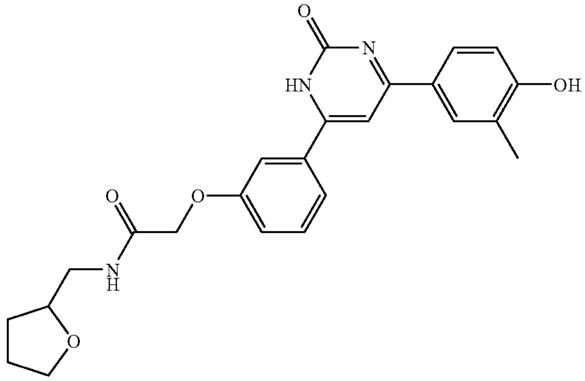 | 2-({3-[6-(4-hydroxy-3-methylphenyl)-2-oxo-2,3-dihydropyrimidin-4-yl]phenyl}oxy)-N-(tetrahydrofuran-2-ylmethyl)acetamide |

TABLE 1-continued

| STRUCTURE | NAME |
|---|---|
| 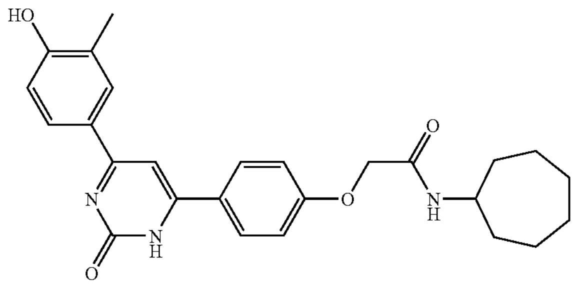 | N-cycloheptyl-2-({4-[6-(4-hydroxy-3-methylphenyl)-2-oxo-2,3-dihydropyrimidin-4-yl]phenyl}oxy)acetamide |
| 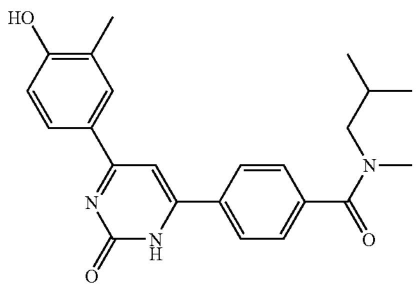 | 4-[6-(4-hydroxy-3-methylphenyl)-2-oxo-2,3-dihydropyrimidin-4-yl]-N-methyl-N-(2-methylpropyl)benzamide |
| 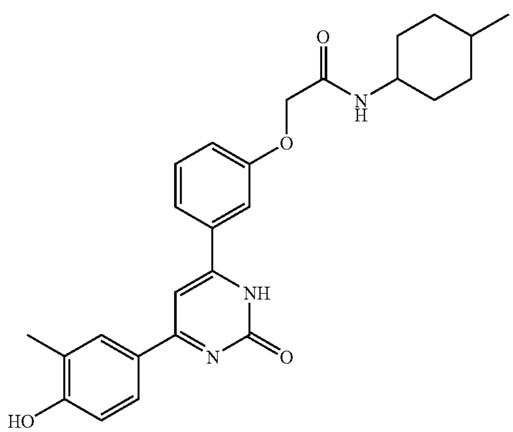 | 2-({3-[6-(4-hydroxy-3-methylphenyl)-2-oxo-2,3-dihydropyrimidin-4-yl]phenyl}oxy)-N-(4-methylcyclohexyl)acetamide |
| 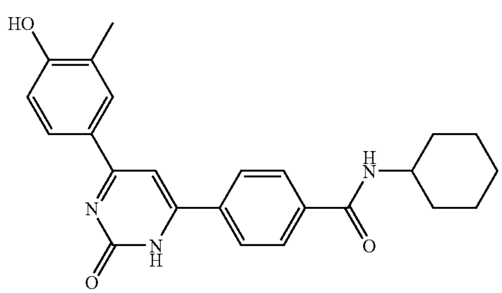 | N-cyclohexyl-4-[6-(4-hydroxy-3-methylphenyl)-2-oxo-2,3-dihydropyrimidin-4-yl]benzamide |

TABLE 1-continued

| STRUCTURE | NAME |
|---|---|
| 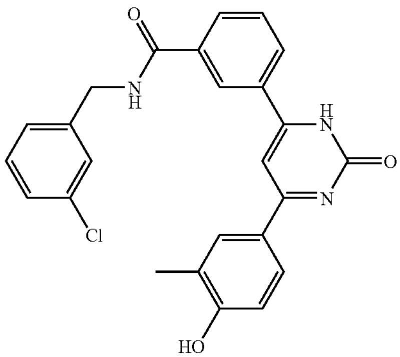 | N-[(3-chlorophenyl)methyl]-3-[6-(4-hydroxy-3-methylphenyl)-2-oxo-2,3-dihydropyrimidin-4-yl]benzamide |
| 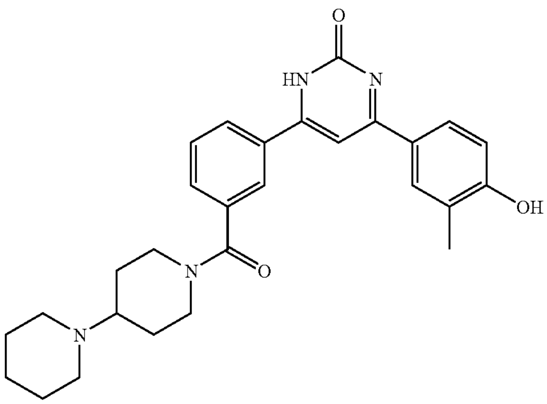 | 6-[3-(1,4'-bipiperidin-1'-ylcarbonyl)phenyl]-4-(4-hydroxy-3-methylphenyl)pyrimidin-2(1H)-one |
| 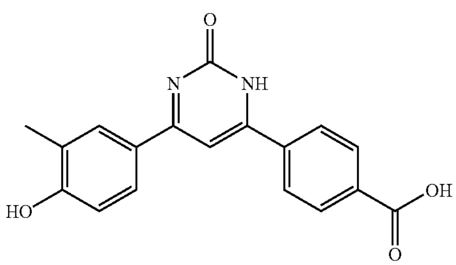 | 4-[6-(4-hydroxy-3-methylphenyl)-2-oxo-2,3-dihydropyrimidin-4-yl]benzoic acid |
| 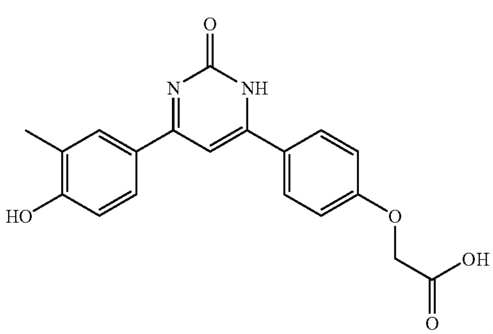 | ({4-[6-(4-hydroxy-3-methylphenyl)-2-oxo-2,3-dihydropyrimidin-4-yl]phenyl}oxy)acetic acid |

TABLE 1-continued

| STRUCTURE | NAME |
|---|---|
| 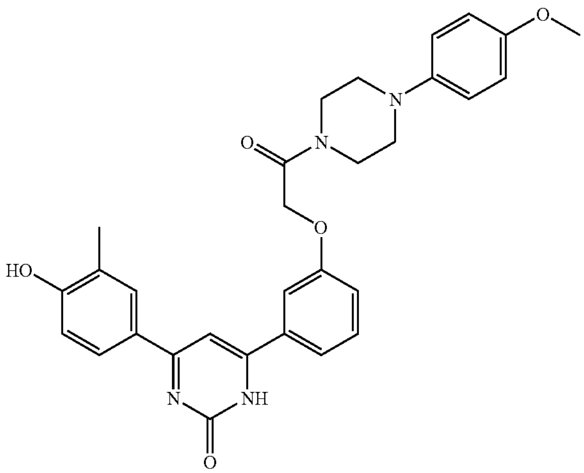 | 4-(4-hydroxy-3-methylphenyl)-6-{3-[(2-{4-[4-(methyloxy)phenyl]piperazin-1-yl}-2-oxoethyl)oxy]phenyl}pyrimidin-2(1H)-one |
| 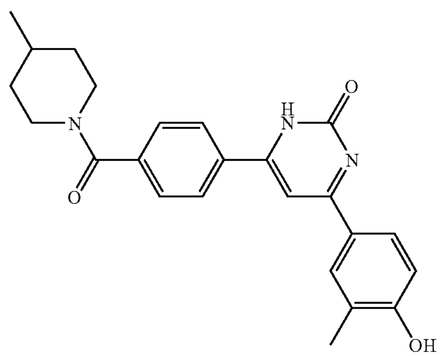 | 4-(4-hydroxy-3-methylphenyl)-6-{4-[(4-methylpiperidin-1-yl)carbonyl]phenyl}pyrimidin-2(1H)-one |
| 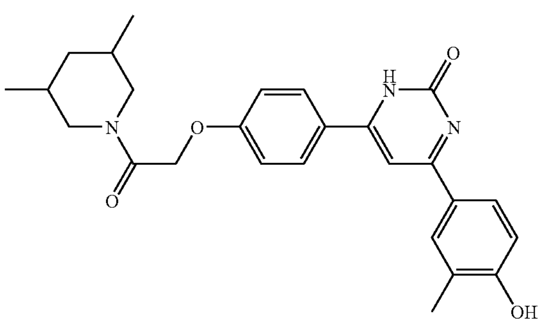 | 6-(4-{[2-(3,5-dimethylpiperidin-1-yl)-2-oxoethyl]oxy}phenyl)-4-(4-hydroxy-3-methylphenyl)pyrimidin-2(1H)-one |
| 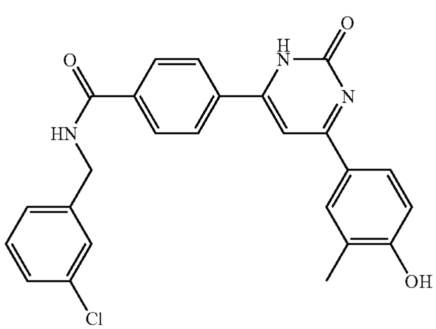 | N-[(3-chlorophenyl)methyl]-4-[6-(4-hydroxy-3-methylphenyl)-2-oxo-2,3-dihydropyrimidin-4-yl]benzamide |

TABLE 1-continued

| STRUCTURE | NAME |
|---|---|
| 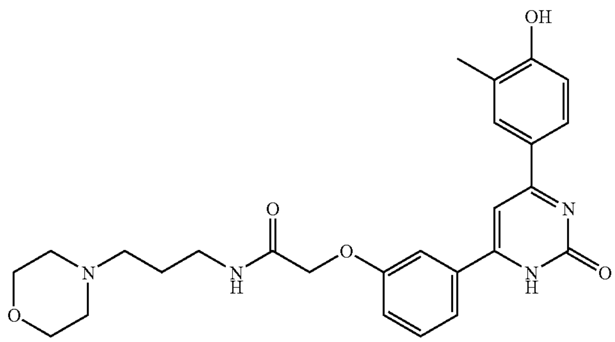 | 2-({3-[6-(4-hydroxy-3-methylphenyl)-2-oxo-2,3-dihydropyrimidin-4-yl]phenyl}oxy)-N-(3-morpholin-4-ylpropyl)acetamide |
| 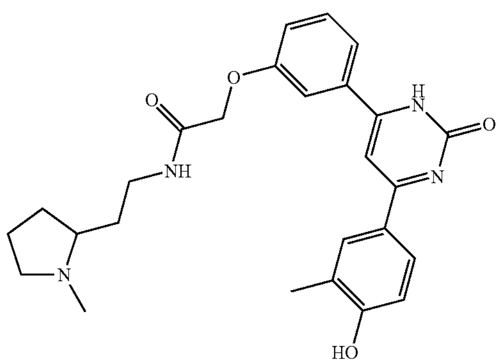 | 2-({3-[6-(4-hydroxy-3-methylphenyl)-2-oxo-2,3-dihydropyrimidin-4-yl]phenyl}oxy)-N-[2-(1-methylpyrrolidin-2-yl)ethyl]acetamide |
| 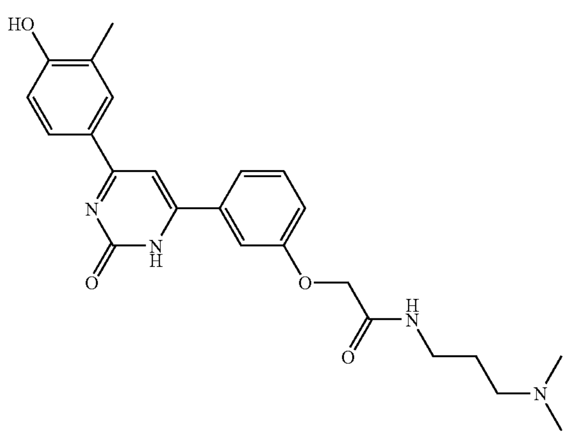 | N-[3-(dimethylamino)propyl]-2-({3-[6-(4-hydroxy-3-methylphenyl)-2-oxo-2,3-dihydropyrimidin-4-yl]phenyl}oxy)acetamide |
| 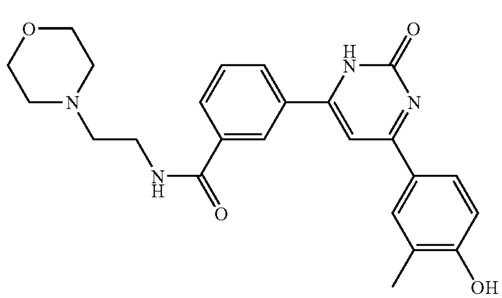 | 3-[6-(4-hydroxy-3-methylphenyl)-2-oxo-2,3-dihydropyrimidin-4-yl]-N-(2-morpholin-4-ylethyl)benzamide |

TABLE 1-continued

| STRUCTURE | NAME |
|---|---|
| 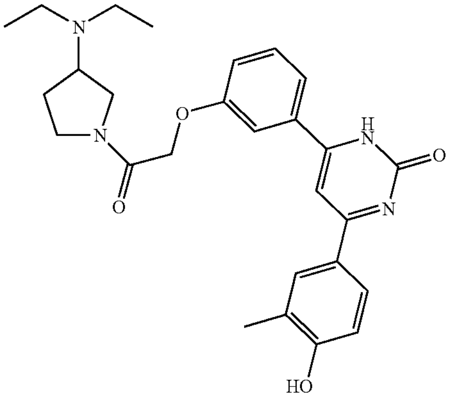 | 6-[3-({2-[3-(diethylamino)pyrrolidin-1-yl]-2-oxoethyl}oxy)phenyl]-4-(4-hydroxy-3-methylphenyl)pyrimidin-2(1H)-one |
| 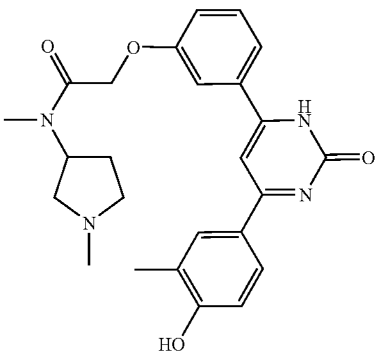 | 2-({3-[6-(4-hydroxy-3-methylphenyl)-2-oxo-2,3-dihydropyrimidin-4-yl]phenyl}oxy)-N-methyl-N-(1-methylpyrrolidin-3-yl)acetamide |
| 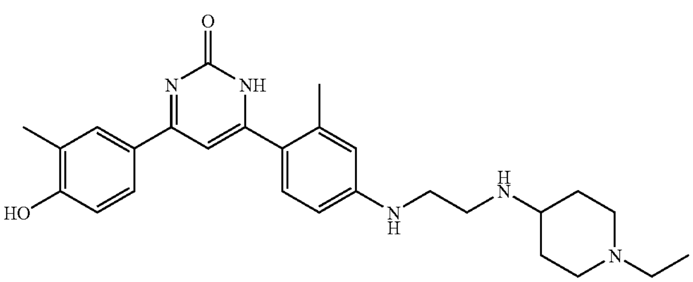 | 6-[4-({2-[(1-ethylpiperidin-4-yl)amino]ethyl}amino)-2-methylphenyl]-4-(4-hydroxy-3-methylphenyl)pyrimidin-2(1H)-one |
| 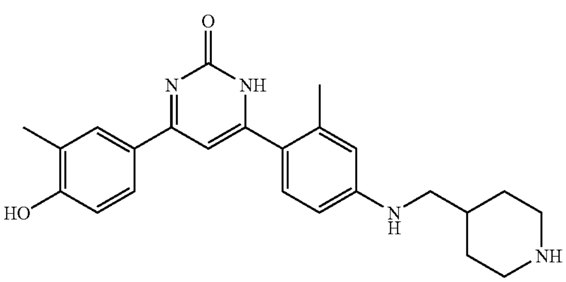 | 4-(4-hydroxy-3-methylphenyl)-6-{2-methyl-4-[(piperidin-4-ylmethyl)amino]phenyl}pyrimidin-2(1H)-one |
| 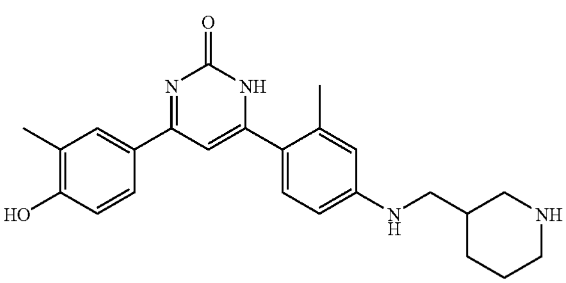 | 4-(4-hydroxy-3-methylphenyl)-6-{2-methyl-4-[(piperidin-3-ylmethyl)amino]phenyl}pyrimidin-2(1H)-one |

TABLE 1-continued

| STRUCTURE | NAME |
|---|---|
| 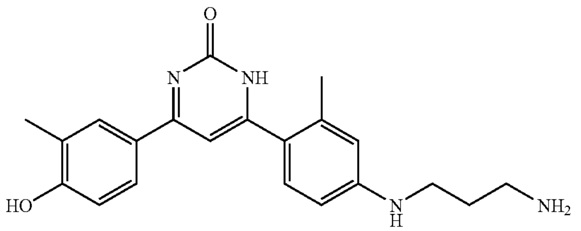 | 6-{4-[(3-aminopropyl)amino]-2-methylphenyl}-4-(4-hydroxy-3-methylphenyl)pyrimidin-2(1H)-one |
| 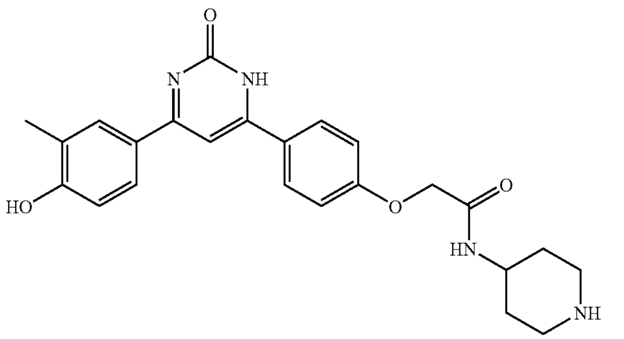 | 2-({4-[6-(4-hydroxy-3-methylphenyl)-2-oxo-2,3-dihydropyrimidin-4-yl]phenyl}oxy)-N-piperidin-4-ylacetamide |
| 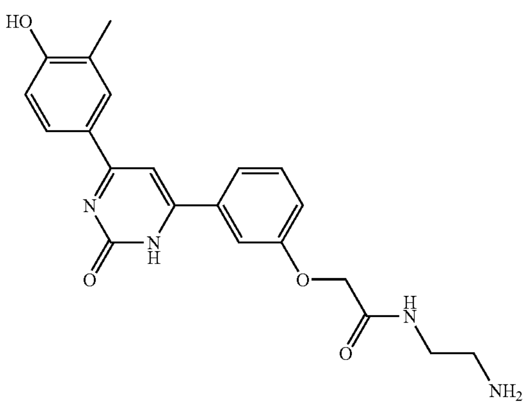 | N-(2-aminoethyl)-2-({3-[6-(4-hydroxy-3-methylphenyl)-2-oxo-2,3-dihydropyrimidin-4-yl]phenyl}oxy)acetamide |
| 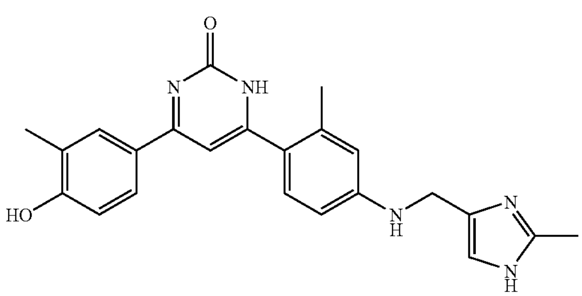 | 4-(4-hydroxy-3-methylphenyl)-6-(2-methyl-4-{[(2-methyl-1H-imidazol-4-yl)methyl]amino}phenyl)pyrimidin-2(1H)-one |
| 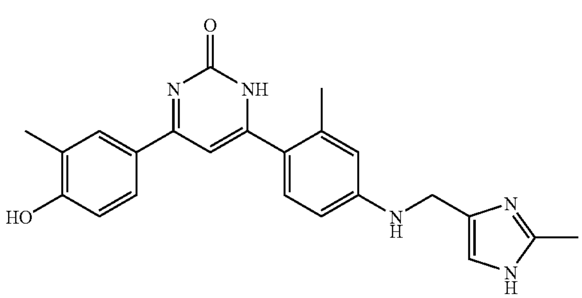 | N-(3-aminopropyl)-2-({3-[6-(4-hydroxy-3-methylphenyl)-2-oxo-2,3-dihydropyrimidin-4-yl]phenyl}oxy)acetamide |

TABLE 1-continued

| STRUCTURE | NAME |
|---|---|
| 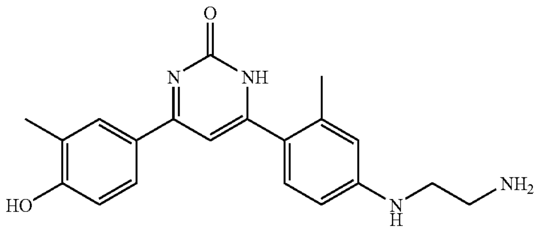 | 6-{4-[(2-aminoethyl)amino]-2-methylphenyl}-4-(4-hydroxy-3-methylphenyl)pyrimidin-2(1H)-one |
| 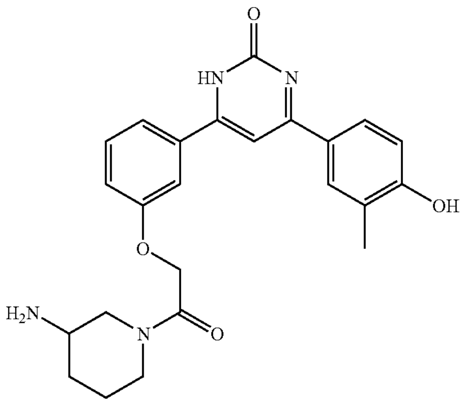 | 6-(3-{[2-(3-aminopiperidin-1-yl)-2-oxoethyl]oxy}phenyl)-4-(4-hydroxy-3-methylphenyl)pyrimidin-2(1H)-one |
| 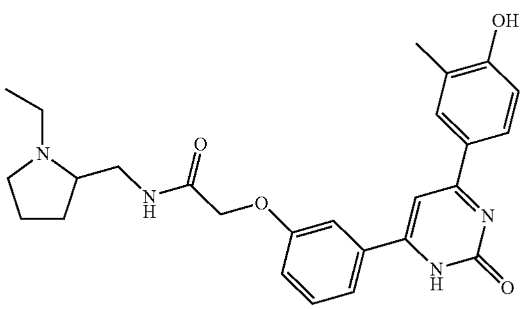 | N-[(1-ethylpyrrolidin-2-yl)methyl]-2-({3-[6-(4-hydroxy-3-methylphenyl)-2-oxo-2,3-dihydropyrimidin-4-yl]phenyl}oxy)acetamide |
| 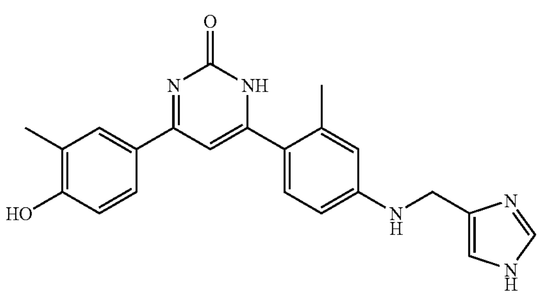 | 4-(4-hydroxy-3-methylphenyl)-6-{4-[(1H-imidazol-4-ylmethyl)amino]-2-methylphenyl}pyrimidin-2(1H)-one |
| 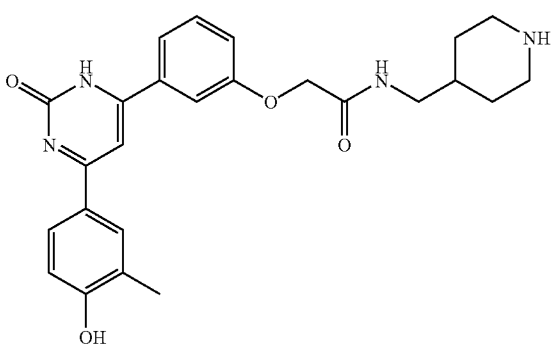 | 2-({3-[6-(4-hydroxy-3-methylphenyl)-2-oxo-2,3-dihydropyrimidin-4-yl]phenyl}oxy)-N-(piperidin-4-ylmethyl)acetamide |

TABLE 1-continued

| STRUCTURE | NAME |
|---|---|
| 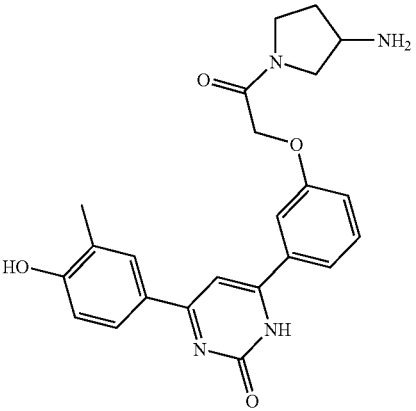 | 6-(3-{[2-(3-aminopyrrolidin-1-yl)-2-oxoethyl]oxy}phenyl)-4-(4-hydroxy-3-methylphenyl)pyrimidin-2(1H)-one |
| 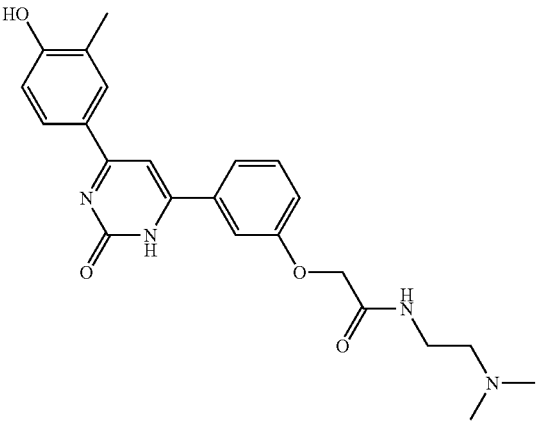 | N-[2-(dimethylamino)ethyl]-2-({3-[6-(4-hydroxy-3-methylphenyl)-2-oxo-2,3-dihydropyrimidin-4-yl]phenyl}oxy)acetamide |
| 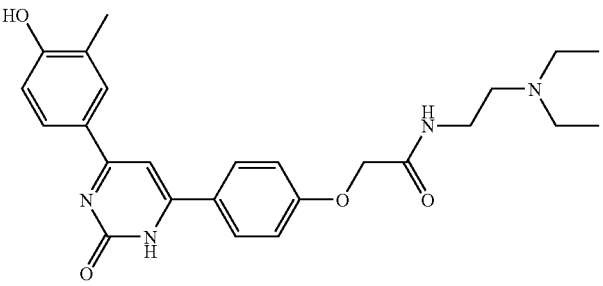 | N-[2-(diethylamino)ethyl]-2-({4-[6-(4-hydroxy-3-methylphenyl)-2-oxo-2,3-dihydropyrimidin-4-yl]phenyl}oxy)acetamide |
| 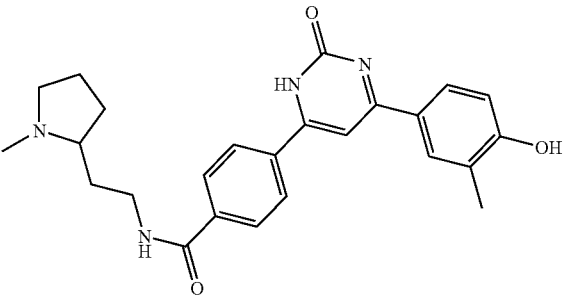 | 4-[6-(4-hydroxy-3-methylphenyl)-2-oxo-2,3-dihydropyrimidin-4-yl]-N-[2-(1-methylpyrrolidin-2-yl)ethyl]benzamide |

TABLE 1-continued

| STRUCTURE | NAME |
| --- | --- |
| 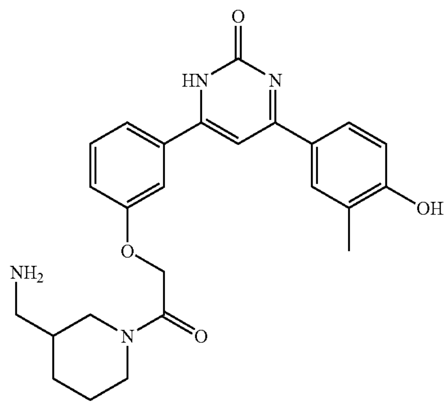 | 6-(3-{[3-(aminoethyl)piperidin-1-yl]carbonyl}phenyl)-4-(4-hydroxy-3-methylphenyl)pyrimidin-2(1H)-one |
| 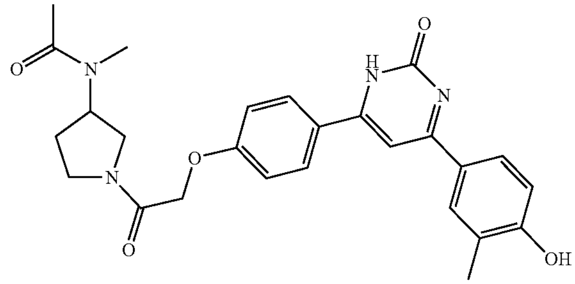 | N-{1-[({4-[6-(4-hydroxy-3-methylphenyl)-2-oxo-2,3-dihydropyrimidin-4-yl]phenyl}oxy)acetyl]pyrrolidin-3-yl}-N-methylacetamide |
| 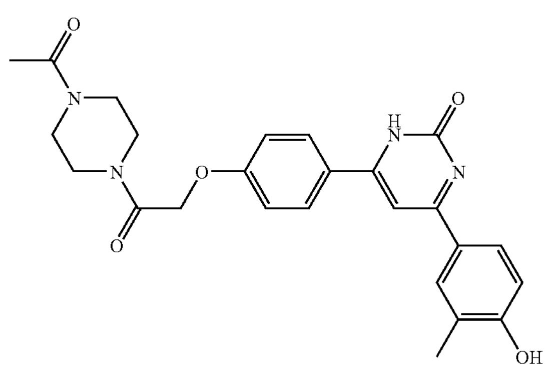 | 6-(4-{[2-(4-acetylpiperazin-1-yl)-2-oxoethyl]oxy}phenyl)-4-(4-hydroxy-3-methylphenyl)pyrimidin-2(1H)-one |
| 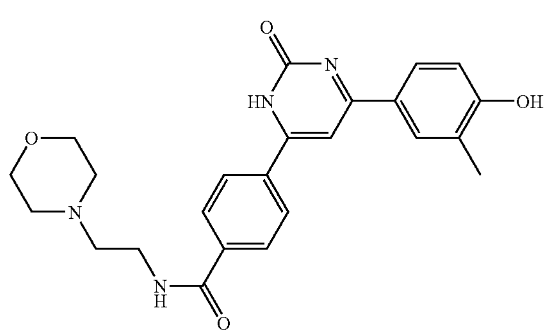 | 4-[6-(4-hydroxy-3-methylphenyl)-2-oxo-2,3-dihydropyrimidin-4-yl]-N-(2-morpholin-4-ylethyl)benzamide |

TABLE 1-continued

| STRUCTURE | NAME |
|---|---|
| | 4-(4-hydroxy-3-methylphenyl)-6-{4-[(2-{4-[4-(methyloxy)phenyl]piperazin-1-yl}-2-oxoethyl)oxy]phenyl}pyrimidin-2(1H)-one |
| 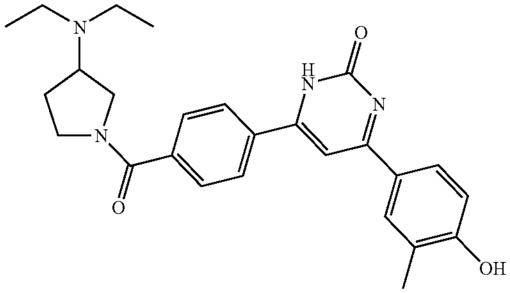 | 6-(4-{[3-(diethylamino)pyrrolidin-1-yl]carbonyl}phenyl)-4-(4-hydroxy-3-methylphenyl)pyrimidin-2(1H)-one |
| 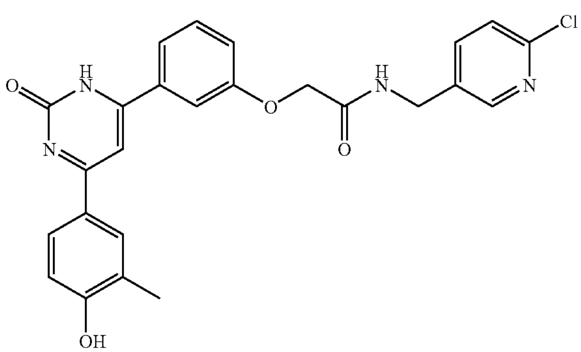 | N-[(6-chloropyridin-3-yl)methyl]-2-({3-[6-(4-hydroxy-3-methylphenyl)-2-oxo-2,3-dihydropyrimidin-4-yl]phenyl}oxy)acetamide |
| 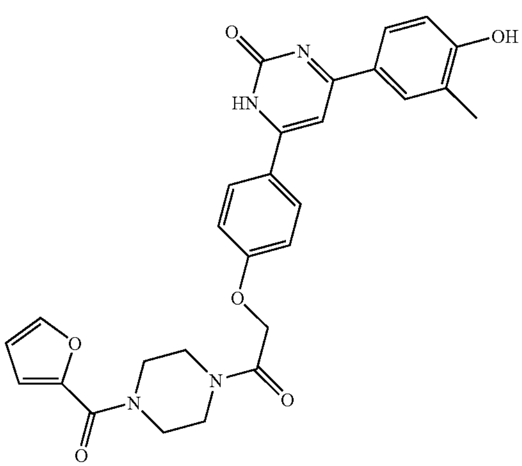 | 6-[4-({2-[4-(furan-2-ylcarbonyl)piperazin-1-yl]-2-oxoethyl}oxy)phenyl]-4-(4-hydroxy-3-methylphenyl)pyrimidin-2(1H)-one |

TABLE 1-continued

| STRUCTURE | NAME |
|---|---|
| 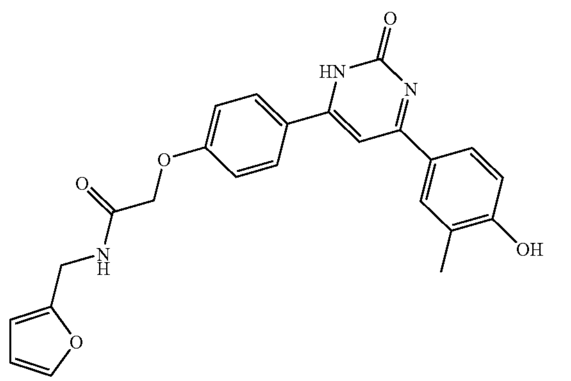 | N-(furan-2-ylmethyl)-2-({4-[6-(4-hydroxy-3-methylphenyl)-2-oxo-2,3-dihydropyrimidin-4-yl]phenyl}oxy)acetamide |
| 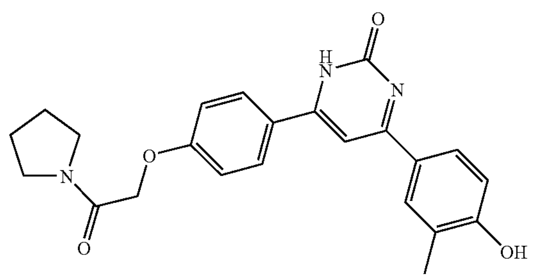 | 4-(4-hydroxy-3-methylphenyl)-6-{4-[(2-oxo-2-pyrrolidin-1-ylethyl)oxy]phenyl}pyrimidin-2(1H)-one |
| 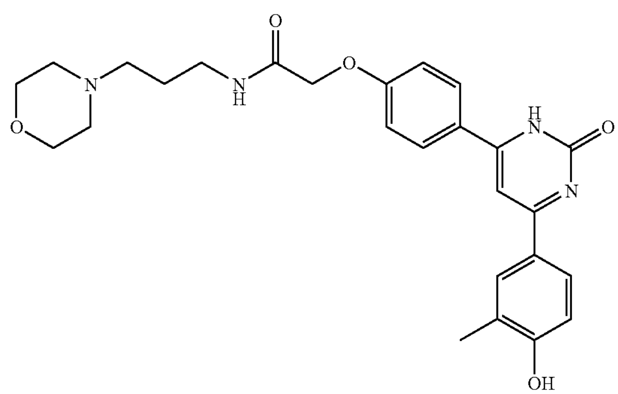 | 2-({4-[6-(4-hydroxy-3-methylphenyl)-2-oxo-2,3-dihydropyrimidin-4-yl]phenyl}oxy)-N-(3-morpholin-4-ylpropyl)acetamide |
| 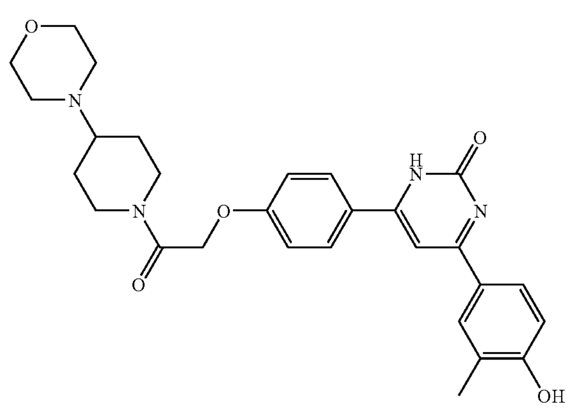 | 4-(4-hydroxy-3-methylphenyl)-6-(4-{[2-(4-morpholin-4-ylpiperidin-1-yl)-2-oxoethyl]oxy}phenyl)pyrimidin-2(1H)-one |

TABLE 1-continued

| STRUCTURE | NAME |
|---|---|
| 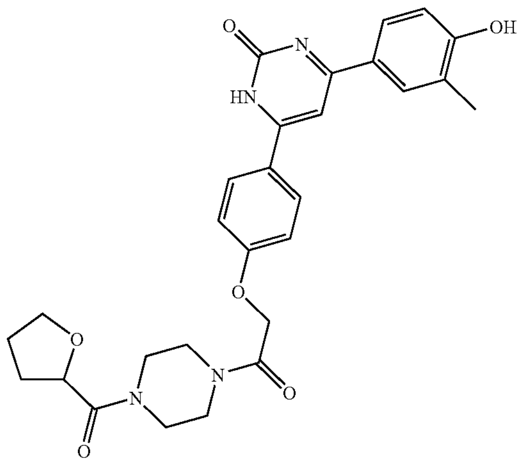 | 4-(4-hydroxy-3-methylphenyl)-6-[4-({2-oxo-2-[4-(tetrahydrofuran-2-ylcarbonyl)piperazin-1-yl]ethyl}oxy)phenyl]pyrimidin-2(1H)-one |
| 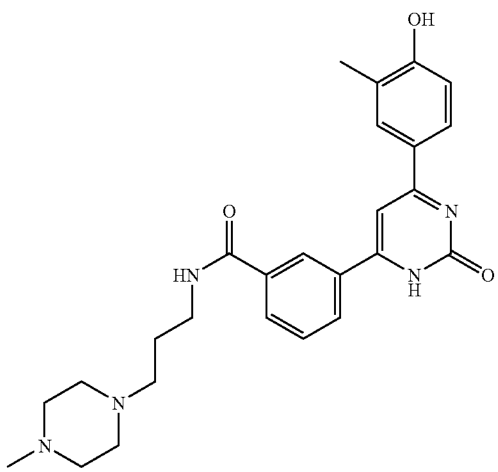 | 3-[6-(4-hydroxy-3-methylphenyl)-2-oxo-2,3-dihydropyrimidin-4-yl]-N-[3-(4-methylpiperazin-1-yl)propyl]benzamide |
| 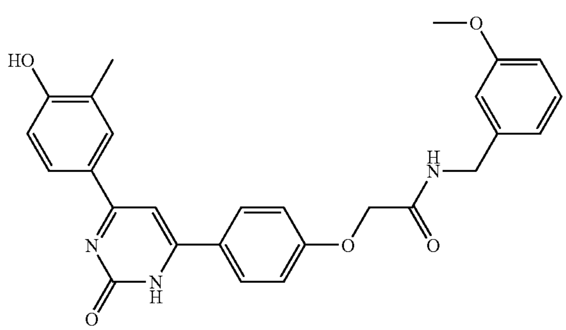 | 2-({4-[6-(4-hydroxy-3-methylphenyl)-2-oxo-2,3-dihydropyrimidin-4-yl]phenyl}oxy)-N-{[3-(methyloxy)phenyl]methyl}acetamide |
| 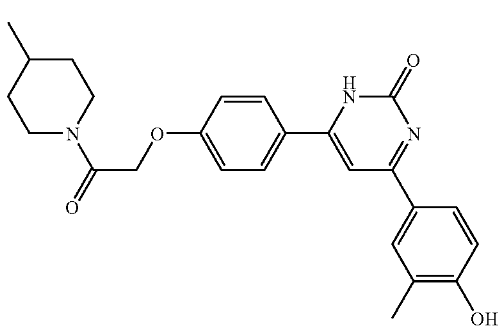 | 4-(4-hydroxy-3-methylphenyl)-6-(4-{[2-(4-methylpiperidin-1-yl)-2-oxoethyl]oxy}phenyl)pyrimidin-2(1H)-one |

TABLE 1-continued

| STRUCTURE | NAME |
|---|---|
| 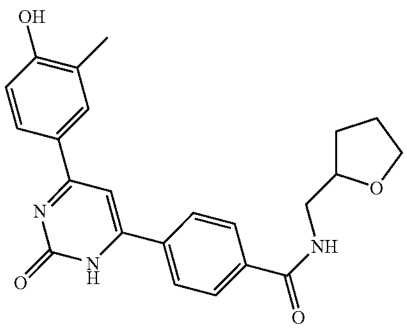 | 4-[6-(4-hydroxy-3-methylphenyl)-2-oxo-2,3-dihydropyrimidin-4-yl]-N-(tetrahydrofuran-2-ylmethyl)benzamide |
| 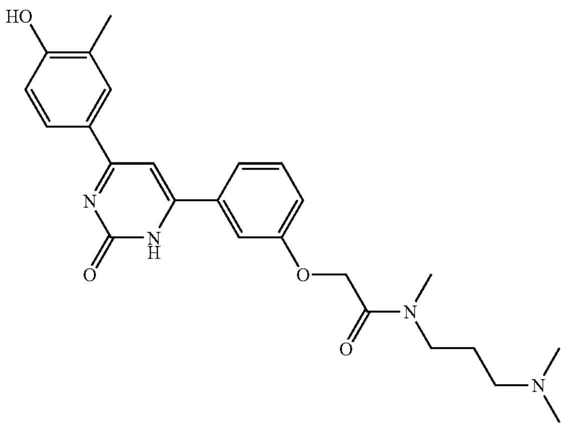 | N-[3-(dimethylamino)propyl]-2-({3-[6-(4-hydroxy-3-methylphenyl)-2-oxo-2,3-dihydropyrimidin-4-yl]phenyl}oxy)-N-methylacetamide |
| 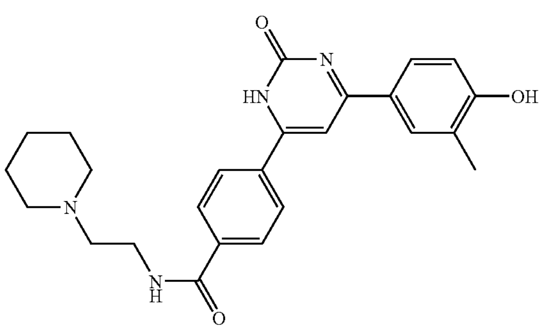 | 4-[6-(4-hydroxy-3-methylphenyl)-2-oxo-2,3-dihydropyrimidin-4-yl]-N-(2-piperidin-1-ylethyl)benzamide |
| 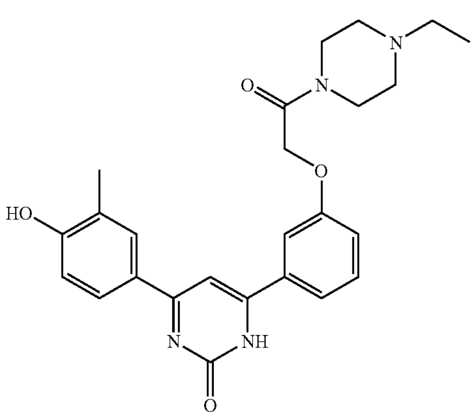 | 6-(3-{[2-(4-ethylpiperazin-1-yl)-2-oxoethyl]oxy}phenyl)-4-(4-hydroxy-3-methylphenyl)pyrimidin-2(1H)-one |

TABLE 1-continued

| STRUCTURE | NAME |
|---|---|
| 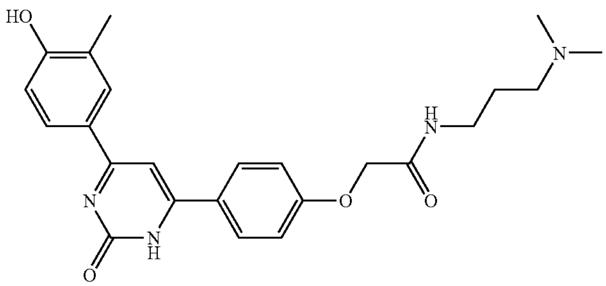 | N-[3-(dimethylamino)propyl]-2-({4-[6-(4-hydroxy-3-methylphenyl)-2-oxo-2,3-dihydropyrimidin-4-yl]phenyl}oxy)acetamide |
| 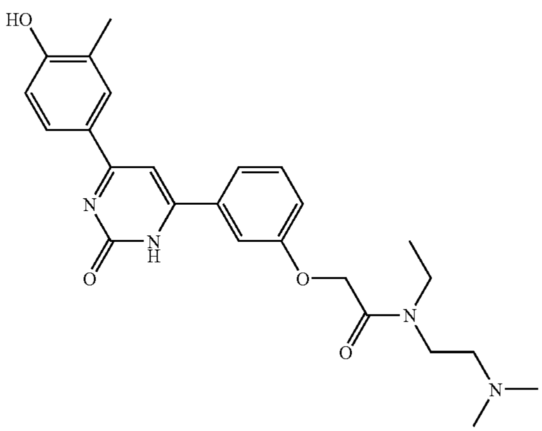 | N-[2-(dimethylamino)ethyl]-N-ethyl-2-({3-[6-(4-hydroxy-3-methylphenyl)-2-oxo-2,3-dihydropyrimidin-4-yl]phenyl}oxy)acetamide |
| 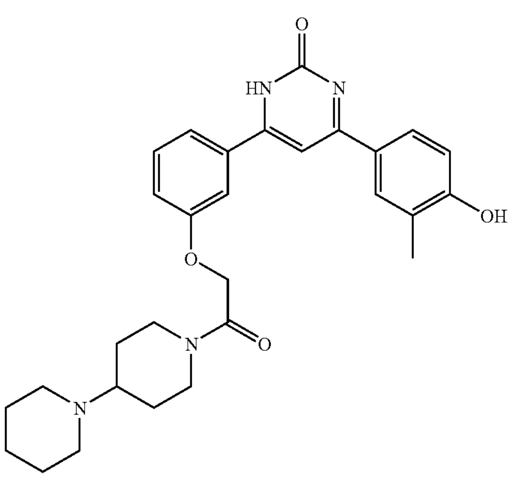 | 6-(3-{[2-(1,4'-bipiperidin-1'-yl)-2-oxoethyl]oxy}phenyl)-4-(4-hydroxy-3-methylphenyl)pyrimidin-2(1H)-one |
| 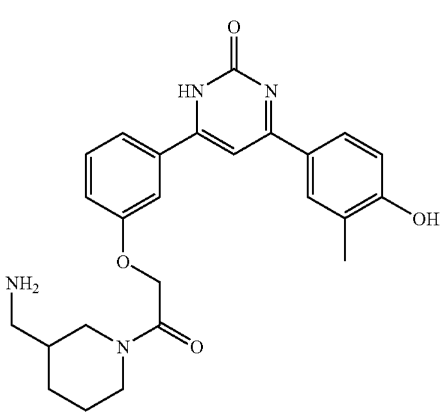 | 6-[3-({2-[3-(aminomethyl)piperidin-1-yl]-2-oxoethyl}oxy)phenyl]-4-(4-hydroxy-3-methylphenyl)pyrimidin-2(1H)-one |

TABLE 1-continued

| STRUCTURE | NAME |
|---|---|
| 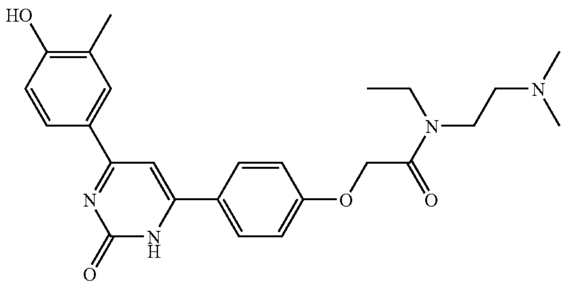 | N-[2-(dimethylamino)ethyl]-N-ethyl-2-({4-[6-(4-hydroxy-3-methylphenyl)-2-oxo-2,3-dihydropyrimidin-4-yl]phenyl}oxy)acetamide |
| 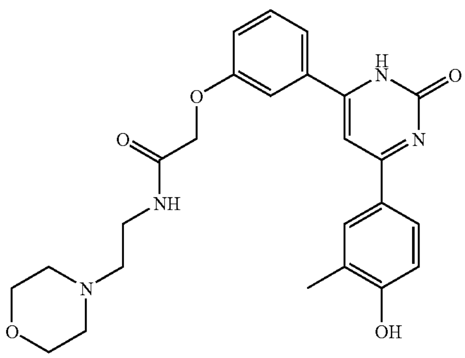 | 2-({3-[6-(4-hydroxy-3-methylphenyl)-2-oxo-2,3-dihydropyrimidin-4-yl]phenyl}oxy)-N-(2-morpholin-4-ylethyl)acetamide |
| 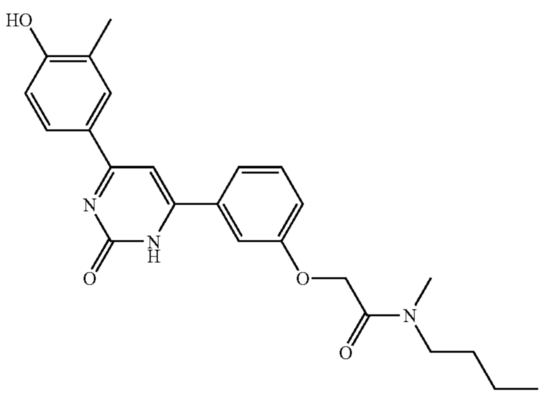 | N-butyl-2-({3-[6-(4-hydroxy-3-methylphenyl)-2-oxo-2,3-dihydropyrimidin-4-yl]phenyl}oxy)-N-methylacetamide |
| 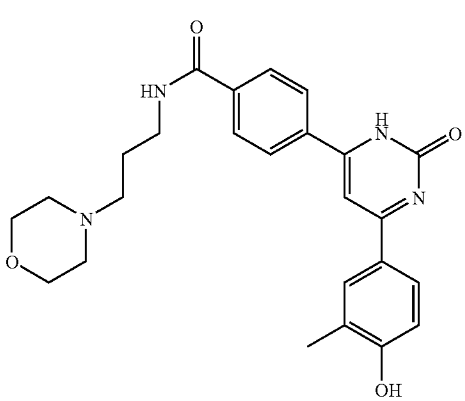 | 4-[6-(4-hydroxy-3-methylphenyl)-2-oxo-2,3-dihydropyrimidin-4-yl]-N-(3-morpholin-4-ylpropyl)benzamide |

TABLE 1-continued
| STRUCTURE | NAME |
|---|---|
| 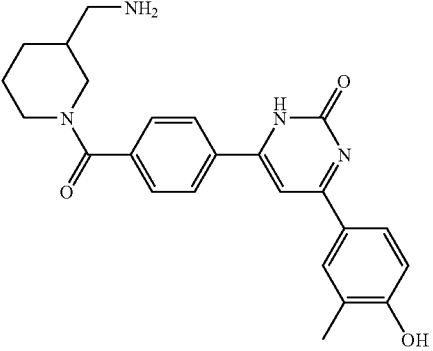 | 6-(4-{[3-(aminomethyl)piperidin-1-yl]carbonyl}phenyl)-4-(4-hydroxy-3-methylphenyl)pyrimidin-2(1H)-one |
| 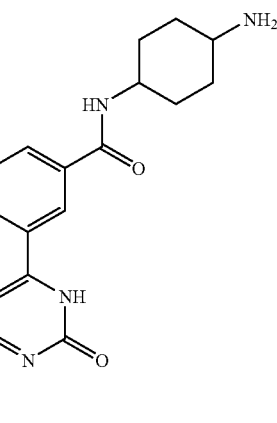 | N-(4-aminocyclohexyl)-3-[6-(4-hydroxy-3-methylphenyl)-2-oxo-2,3-dihydropyrimidin-4-yl]benzamide |
| 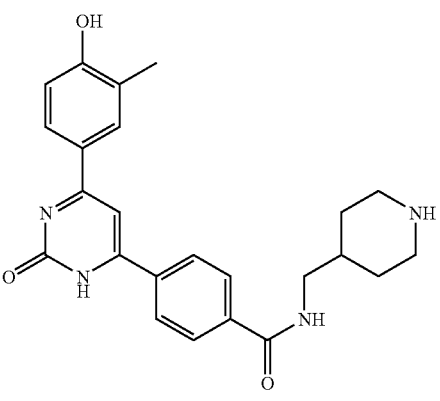 | 4-[6-(4-hydroxy-3-methylphenyl)-2-oxo-2,3-dihydropyrimidin-4-yl]-N-(piperidin-4-ylmethyl)benzamide |
| 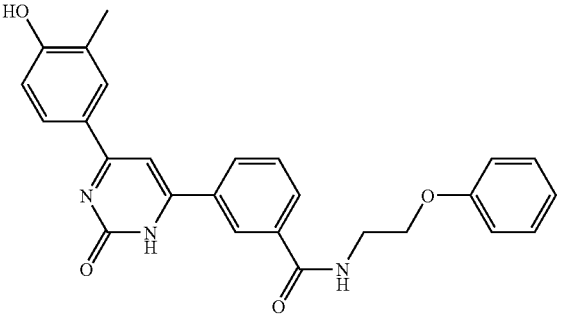 | 3-[6-(4-hydroxy-3-methylphenyl)-2-oxo-2,3-dihydropyrimidin-4-yl]-N-[2-(phenyloxy)ethyl]benzamide |

TABLE 1-continued

| STRUCTURE | NAME |
|---|---|
| 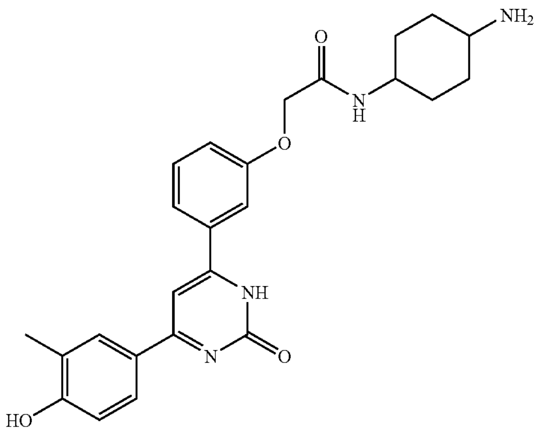 | N-(4-aminocyclohexyl)-2-({3-[6-(4-hydroxy-3-methylphenyl)-2-oxo-2,3-dihydropyrimidin-4-yl]phenyl}oxy)acetamide |
| 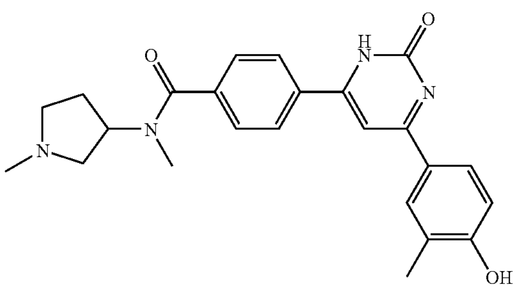 | 4-[6-(4-hydroxy-3-methylphenyl)-2-oxo-2,3-dihydropyrimidin-4-yl]-N-methyl-N-(1-methylpyrrolidin-3-yl)benzamide |
| 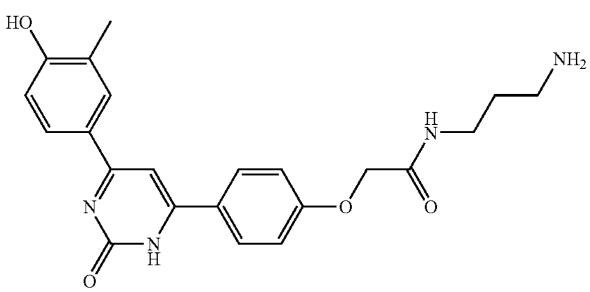 | N-(3-aminopropyl)-2-({4-[6-(4-hydroxy-3-methylphenyl)-2-oxo-2,3-dihydropyrimidin-4-yl]phenyl}oxy)acetamide |
| 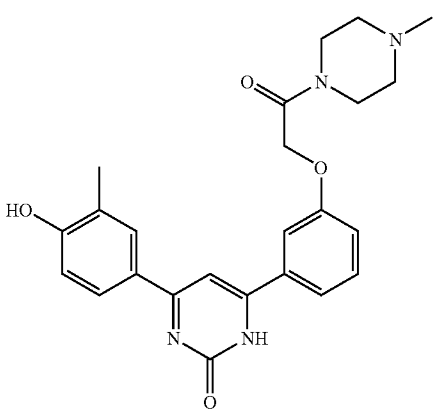 | 4-(4-hydroxy-3-methylphenyl)-6-(3-{[2-(4-methylpiperazin-1-yl)-2-oxoethyl]oxy}phenyl)pyrimidin-2(1H)-one |

TABLE 1-continued

| STRUCTURE | NAME |
| --- | --- |
| 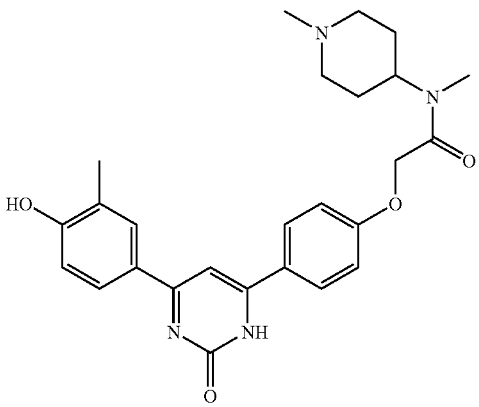 | 2-({4-[6-(4-hydroxy-3-methylphenyl)-2-oxo-2,3-dihydropyrimidin-4-yl]phenyl}oxy)-N-methyl-N-(1-methylpiperidin-4-yl)acetamide |
| 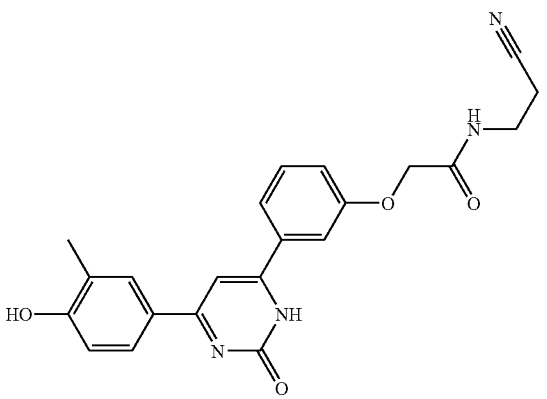 | N-(2-cyanoethyl)-2-({3-[6-(4-hydroxy-3-methylphenyl)-2-oxo-2,3-dihydropyrimidin-4-yl]phenyl}oxy)acetamide |
| 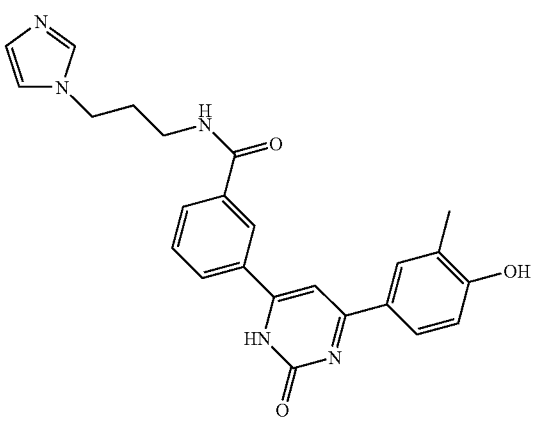 | 3-[6-(4-hydroxy-3-methylphenyl)-2-oxo-2,3-dihydropyrimidin-4-yl]-N-[3-(1H-imidazol-1-yl)propyl]benzamide |
| 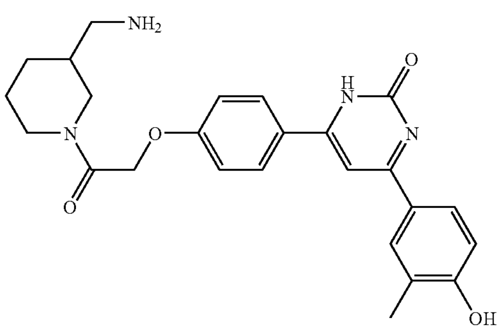 | 6-[4-({2-[3-(aminomethyl)piperidin-1-yl]-2-oxoethyl}oxy)phenyl]-4-(4-hydroxy-3-methylphenyl)pyrimidin-2(1H)-one |

TABLE 1-continued

| STRUCTURE | NAME |
|---|---|
| 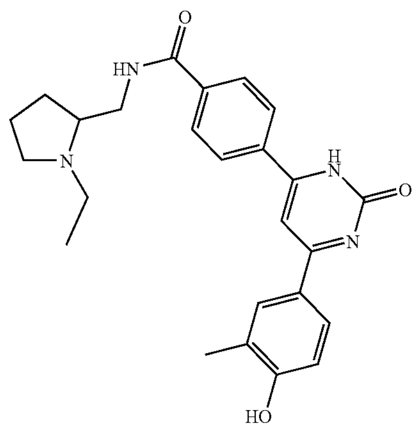 | N-[(1-ethylpyrrolidin-2-yl)methyl]-4-[6-(4-hydroxy-3-methylphenyl)-2-oxo-2,3-dihydropyrimidin-4-yl]benzamide |
| 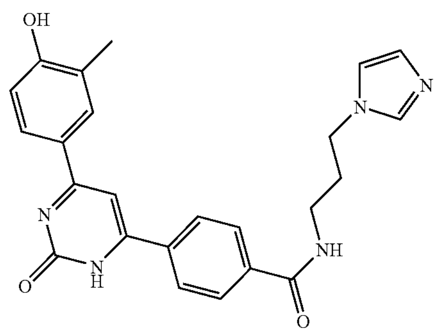 | 4-[6-(4-hydroxy-3-methylphenyl)-2-oxo-2,3-dihydropyrimidin-4-yl]-N-[3-(1H-imidazol-1-yl)propyl]benzamide |
| 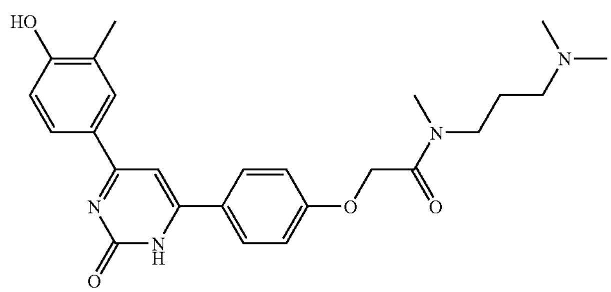 | N-[3-(dimethylamino)propyl]-2-({4-[6-(4-hydroxy-3-methylphenyl)-2-oxo-2,3-dihydropyrimidin-4-yl]phenyl}oxy)-N-methylacetamide |
| 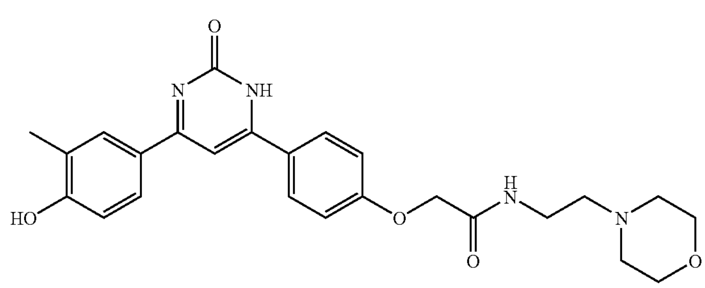 | 2-({4-[6-(4-hydroxy-3-methylphenyl)-2-oxo-2,3-dihydropyrimidin-4-yl]phenyl}oxy)-N-(2-morpholin-4-ylethyl)acetamide |

TABLE 1-continued

| STRUCTURE | NAME |
|---|---|
| 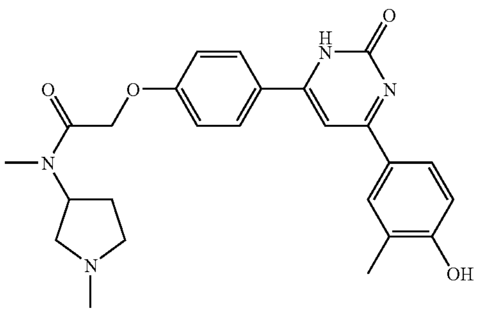 | 2-({4-[6-(4-hydroxy-3-methylphenyl)-2-oxo-2,3-dihydropyrimidin-4-yl]phenyl}oxy)-N-methyl-N-(1-methylpyrrolidin-3-yl)acetamide |
| 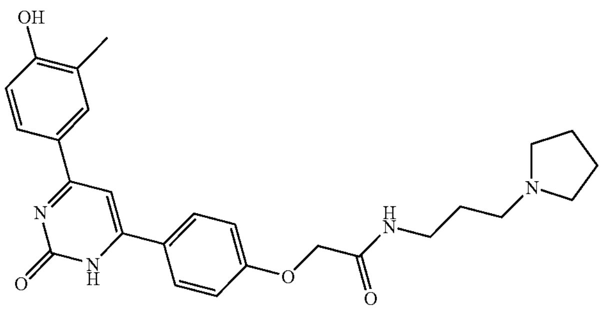 | 2-({4-[6-(4-hydroxy-3-methylphenyl)-2-oxo-2,3-dihydropyrimidin-4-yl]phenyl}oxy)-N-(3-pyrrolidin-1-ylpropyl)acetamide |
| 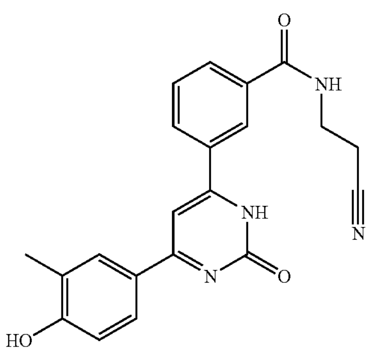 | N-(2-cyanoethyl)-3-[6-(4-hydroxy-3-methylphenyl)-2-oxo-2,3-dihydropyrimidin-4-yl]benzamide |
| 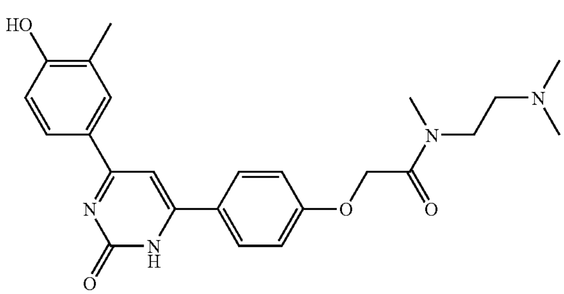 | N-[2-(dimethylamino)ethyl]-2-({4-[6-(4-hydroxy-3-methylphenyl)-2-oxo-2,3-dihydropyrimidin-4-yl]phenyl}oxy)-N-methylacetamide |
| 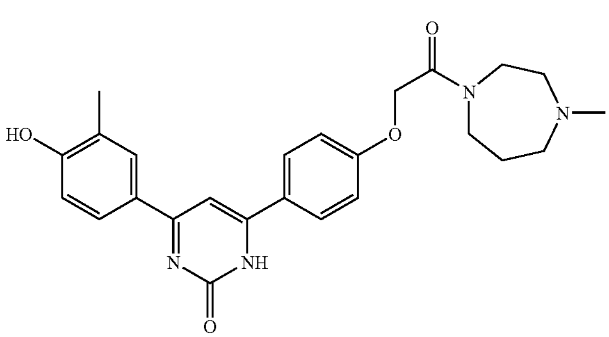 | 4-(4-hydroxy-3-methylphenyl)-6-(4-{[2-(4-methyl-1,4-diazepan-1-yl)-2-oxoethyl]oxy}phenyl)pyrimidin-2(1H)-one |

TABLE 1-continued

| STRUCTURE | NAME |
|---|---|
| 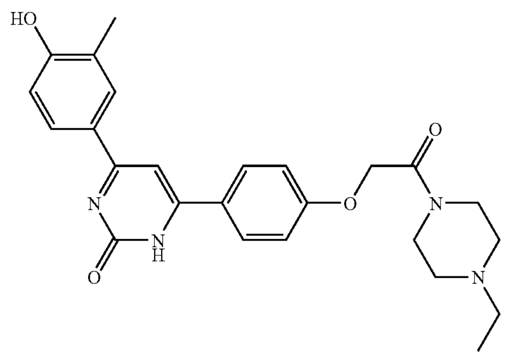 | 6-(4-{[2-(4-ethylpiperazin-1-yl)-2-oxoethyl]oxy}phenyl)-4-(4-hydroxy-3-methylphenyl)pyrimidin-2(1H)-one |
| 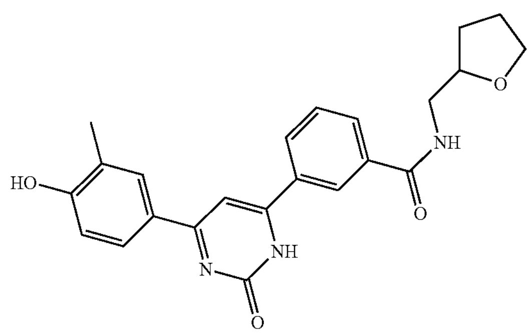 | 3-[6-(4-hydroxy-3-methylphenyl)-2-oxo-2,3-dihydropyrimidin-4-yl]-N-(tetrahydrofuran-2-ylmethyl)benzamide |
| 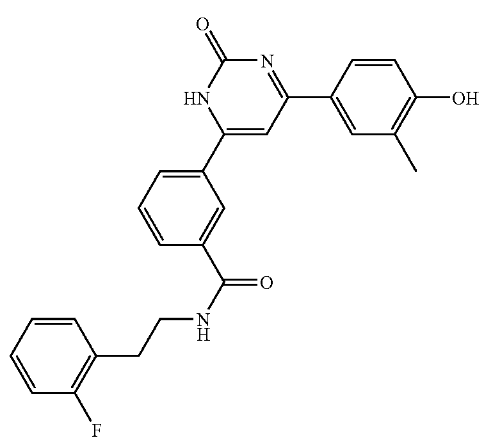 | N-[2-(2-fluorophenyl)ethyl]-3-[6-(4-hydroxy-3-methylphenyl)-2-oxo-2,3-dihydropyrimidin-4-yl]benzamide |
| 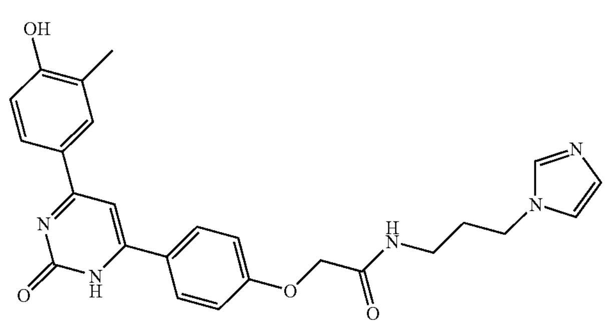 | 2-({4-[6-(4-hydroxy-3-methylphenyl)-2-oxo-2,3-dihydropyrimidin-4-yl]phenyl}oxy)-N-[3-(1H-imidazol-1-yl)propyl]acetamide |

TABLE 1-continued

| STRUCTURE | NAME |
|---|---|
| 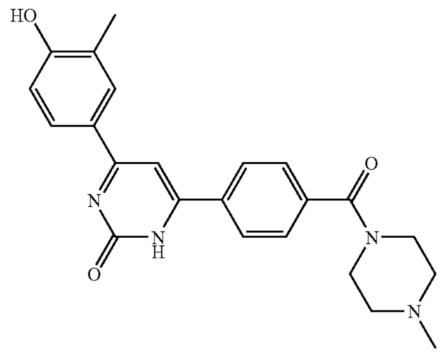 | 4-(4-hydroxy-3-methylphenyl)-6-{4-[(4-methylpiperazin-1-yl)carbonyl]phenyl}pyrimidin-2(1H)-one |
| 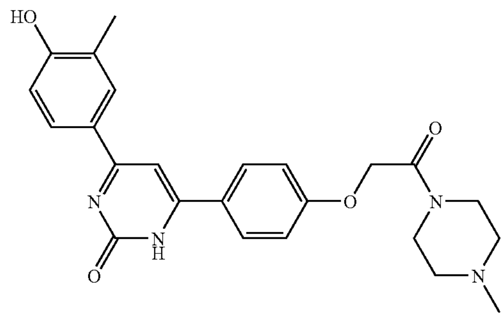 | 4-(4-hydroxy-3-methylphenyl)-6-(4-{[2-(4-methylpiperazin-1-yl)-2-oxoethyl]oxy}phenyl)pyrimidin-2(1H)-one |
| 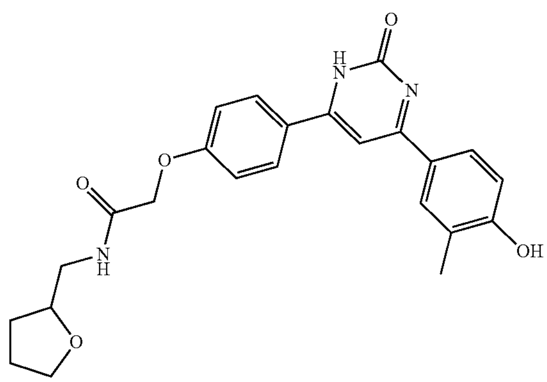 | 2-({4-[6-(4-hydroxy-3-methylphenyl)-2-oxo-2,3-dihydropyrimidin-4-yl]phenyl}oxy)-N-(tetrahydrofuran-2-ylmethyl)acetamide |
| 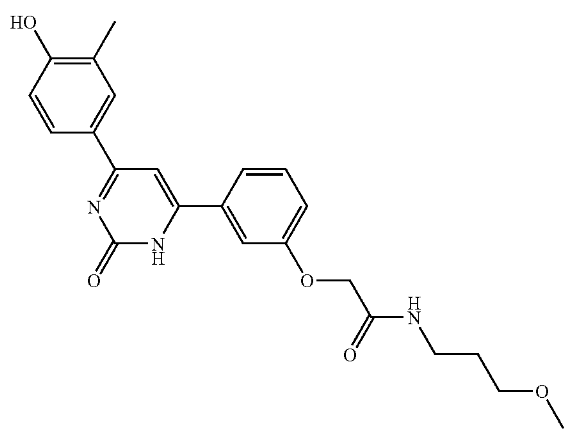 | 2-({3-[6-(4-hydroxy-3-methylphenyl)-2-oxo-2,3-dihydropyrimidin-4-yl]phenyl}oxy)-N-[3-(methyloxy)propyl]acetamide |

| STRUCTURE | NAME |
|---|---|
| 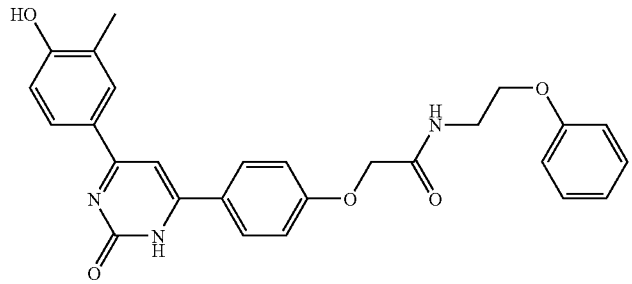 | 2-({4-[6-(4-hydroxy-3-methylphenyl)-2-oxo-2,3-dihydropyrimidin-4-yl]phenyl}oxy)-N-[2-(phenyloxy)ethyl]acetamide |
| 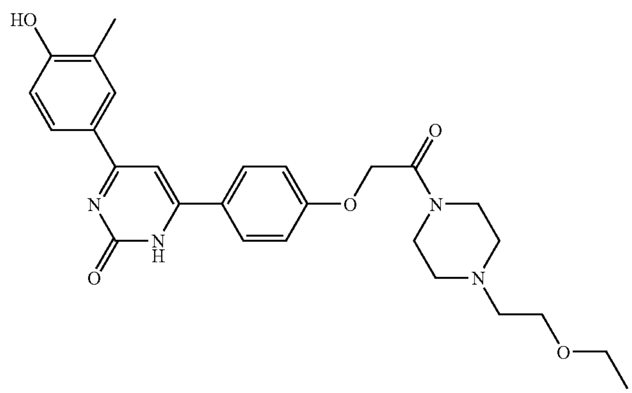 | 6-{4-[(2-{4-[2-(ethyloxy)ethyl]piperazin-1-yl}-2-oxoethyl)oxy]phenyl}-4-(4-hydroxy-3-methylphenyl)pyrimidin-2(1H)-one |
| 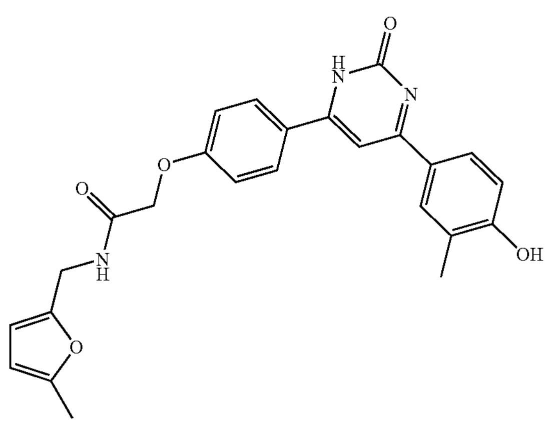 | 2-({4-[6-(4-hydroxy-3-methylphenyl)-2-oxo-2,3-dihydropyrimidin-4-yl]phenyl}oxy)-N-[(5-methylfuran-2-yl)methyl]acetamide |
| 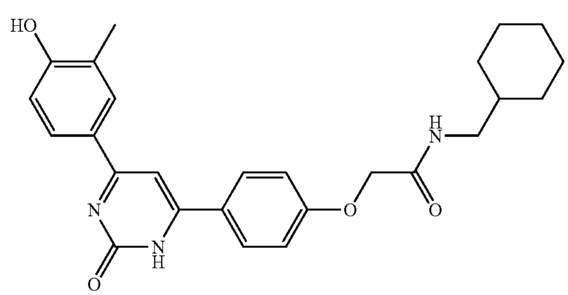 | N-(cyclohexylmethyl)-2-({4-[6-(4-hydroxy-3-methylphenyl)-2-oxo-2,3-dihydropyrimidin-4-yl]phenyl}oxy)acetamide |

TABLE 1-continued

| STRUCTURE | NAME |
| --- | --- |
| 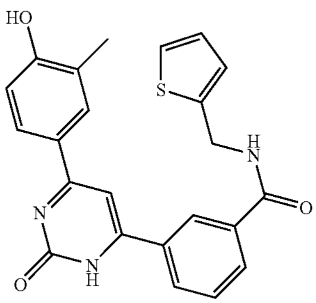 | 3-[6-(4-hydroxy-3-methylphenyl)-2-oxo-2,3-dihydropyrimidin-4-yl]-N-(2-thienylmethyl)benzamide |
| 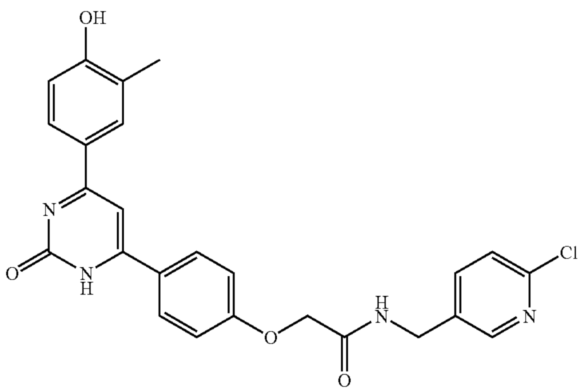 | N-[(6-chloropyridin-3-yl)methyl]-2-({4-[6-(4-hydroxy-3-methylphenyl)-2-oxo-2,3-dihydropyrimidin-4-yl]phenyl}oxy)acetamide |
| 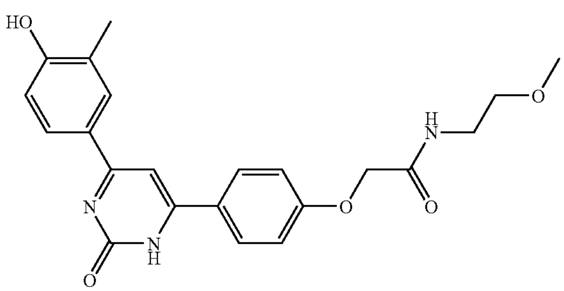 | 2-({4-[6-(4-hydroxy-3-methylphenyl)-2-oxo-2,3-dihydropyrimidin-4-yl]phenyl}oxy)-N-[2-(methyloxy)ethyl]acetamide |
| 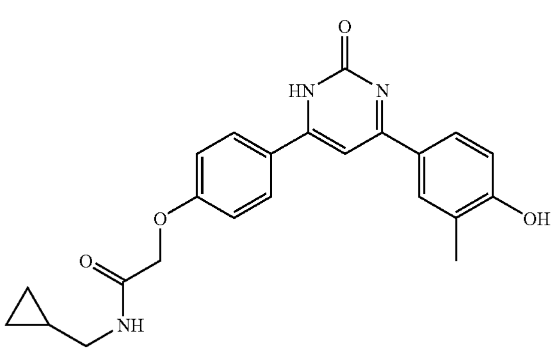 | N-(cyclopropylmethyl)-2-({4-[6-(4-hydroxy-3-methylphenyl)-2-oxo-2,3-dihydropyrimidin-4-yl]phenyl}oxy)acetamide |

TABLE 1-continued

| STRUCTURE | NAME |
|---|---|
| 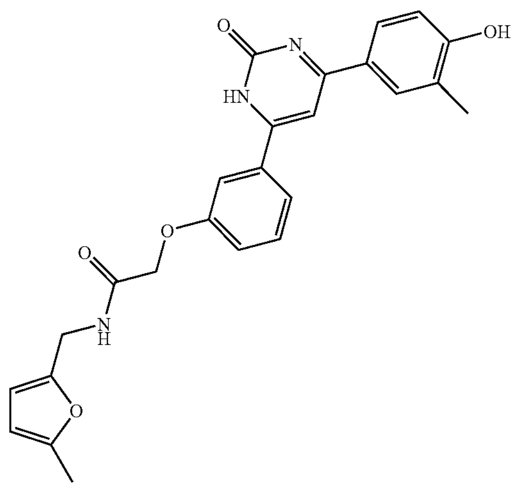 | 2-({3-[6-(4-hydroxy-3-methylphenyl)-2-oxo-2,3-dihydropyrimidin-4-yl]phenyl}oxy)-N-[(5-methylfuran-2-yl)methyl]acetamide |
| 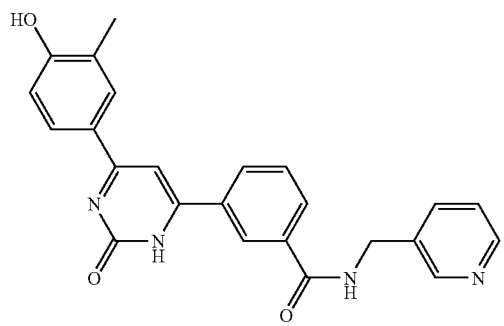 | 3-[6-(4-hydroxy-3-methylphenyl)-2-oxo-2,3-dihydropyrimidin-4-yl]-N-(pyridin-3-ylmethyl)benzamide |
| 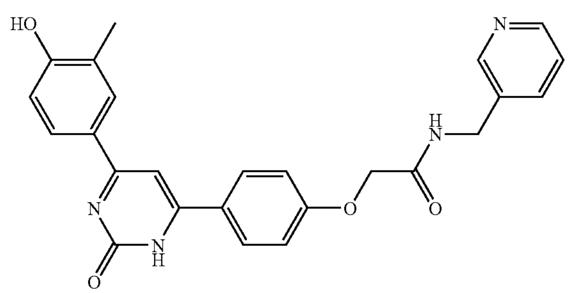 | 2-({4-[6-(4-hydroxy-3-methylphenyl)-2-oxo-2,3-dihydropyrimidin-4-yl]phenyl}oxy)-N-(pyridin-3-ylmethyl)acetamide |
| 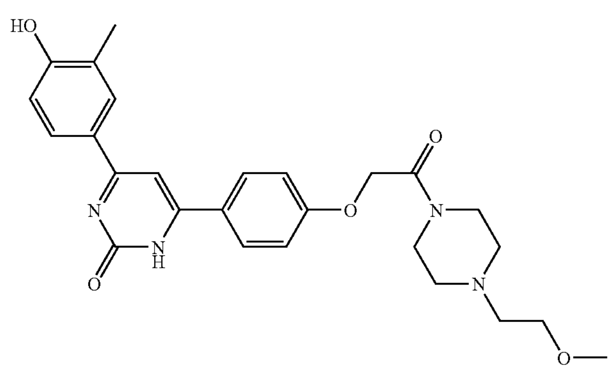 | 4-(4-hydroxy-3-methylphenyl)-6-{4-[(2-{4-[2-(methyloxy)ethyl]piperazin-1-yl}-2-oxoethyl)oxy]phenyl}pyrimidin-2(1H)-one |

TABLE 1-continued

| STRUCTURE | NAME |
|---|---|
| 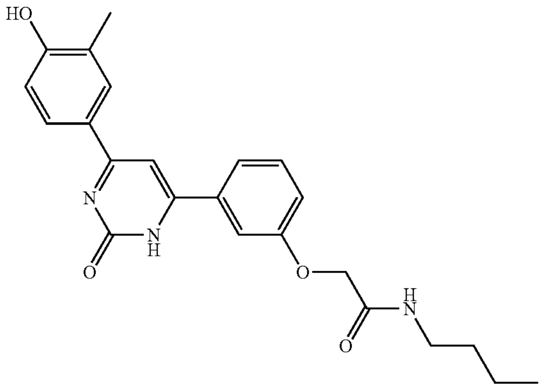 | N-butyl-2-({3-[6-(4-hydroxy-3-methylphenyl)-2-oxo-2,3-dihydropyrimidin-4-yl]phenyl}oxy)acetamide |
| 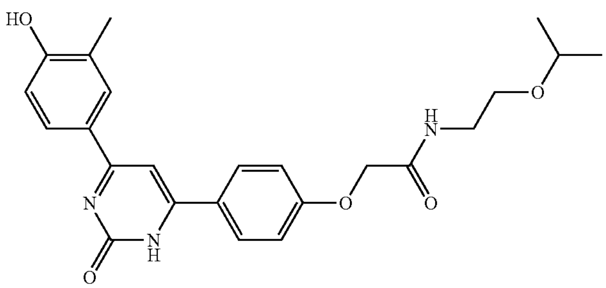 | 2-({4-[6-(4-hydroxy-3-methylphenyl)-2-oxo-2,3-dihydropyrimidin-4-yl]phenyl}oxy)-N-{2-[(1-methylethyl)oxy]ethyl}acetamide |
| 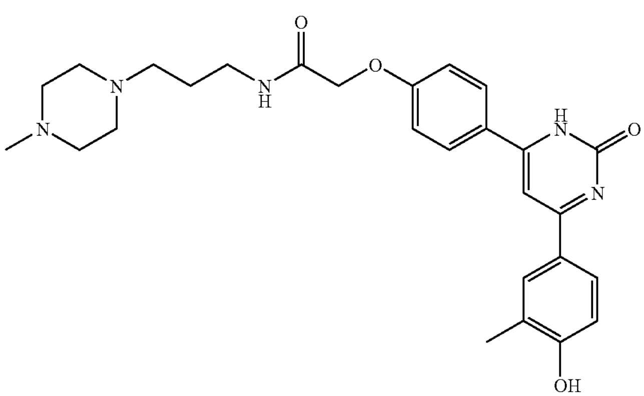 | 2-({4-[6-(4-hydroxy-3-methylphenyl)-2-oxo-2,3-dihydropyrimidin-4-yl]phenyl}oxy)-N-[3-(4-methylpiperazin-1-yl)propyl]acetamide |
| 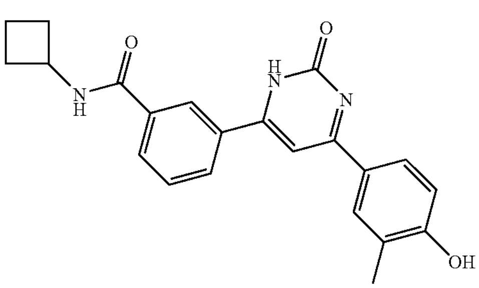 | N-cyclobutyl-3-[6-(4-hydroxy-3-methylphenyl)-2-oxo-2,3-dihydropyrimidin-4-yl]benzamide |

TABLE 1-continued

| STRUCTURE | NAME |
| --- | --- |
| 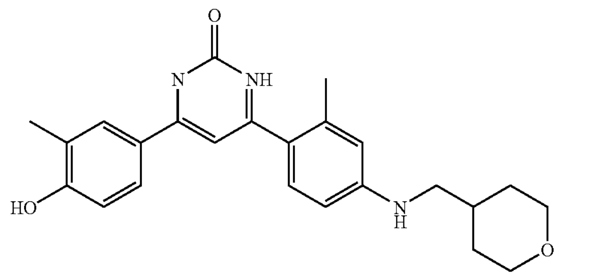 | 4-(4-hydroxy-3-methylphenyl)-6-{2-methyl-4-[(tetrahydro-2H-pyran-4-ylmethyl)amino]phenyl}pyrimidin-2(1H)-one |
| 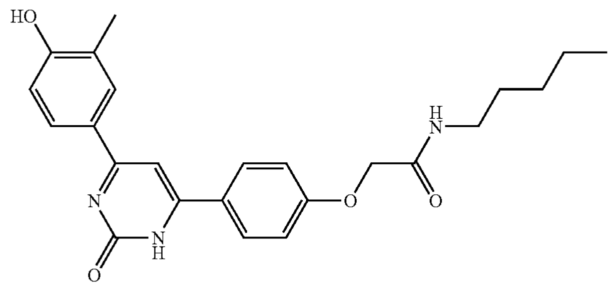 | 2-({4-[6-(4-hydroxy-3-methylphenyl)-2-oxo-2,3-dihydropyrimidin-4-yl]phenyl}oxy)-N-pentylacetamide |
| 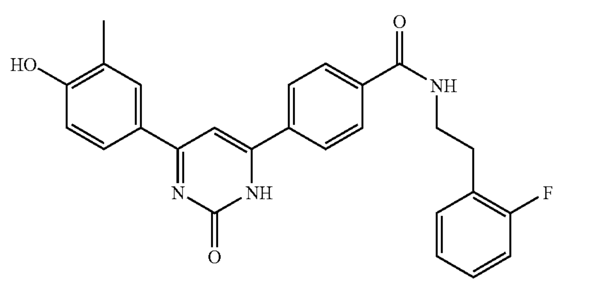 | N-[2-(2-fluorophenyl)ethyl]-4-[6-(4-hydroxy-3-methylphenyl)-2-oxo-2,3-dihydropyrimidin-4-yl]benzamide |
| 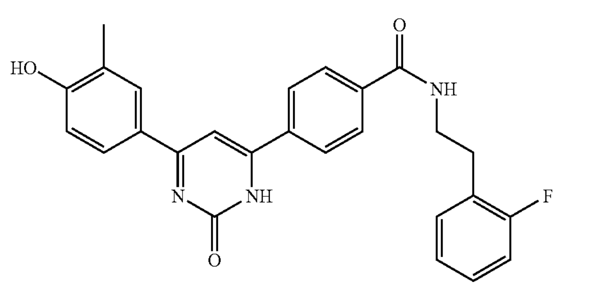 | N-cyclohexyl-3-[6-(4-hydroxy-3-methylphenyl)-2-oxo-2,3-dihydropyrimidin-4-yl]benzamide |
| 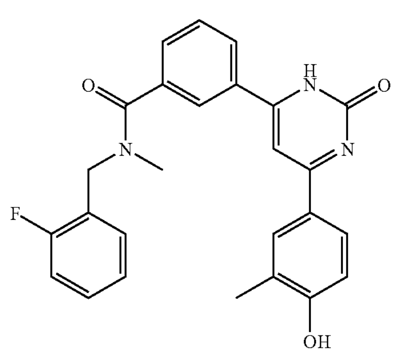 | N-[(2-fluorophenyl)methyl]-3-[6-(4-hydroxy-3-methylphenyl)-2-oxo-2,3-dihydropyrimidin-4-yl]-N-methylbenzamide |

TABLE 1-continued

| STRUCTURE | NAME |
|---|---|
| 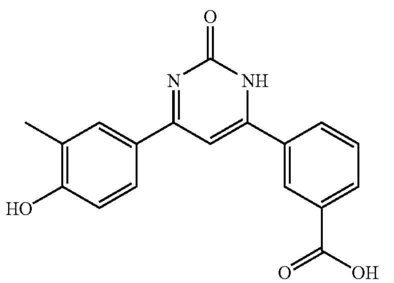 | 3-[6-(4-hydroxy-3-methylphenyl)-2-oxo-2,3-dihydropyrimidin-4-yl]benzoic acid |
| 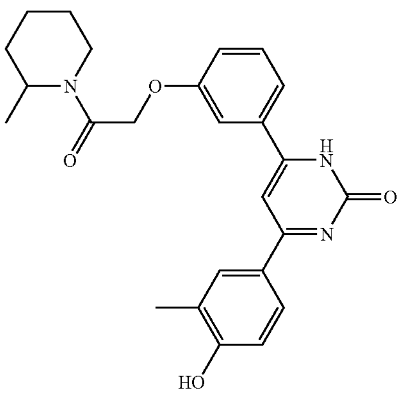 | 4-(4-hydroxy-3-methylphenyl)-6-(3-{[2-(2-methylpiperidin-1-yl)-2-oxoethyl]oxy}phenyl)pyrimidin-2(1H)-one |
| 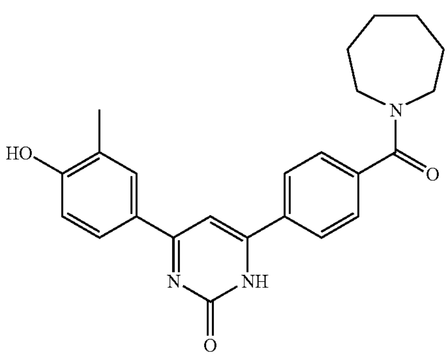 | 6-[4-(azepan-1-ylcarbonyl)phenyl]-4-(4-hydroxy-3-methylphenyl)pyrimidin-2(1H)-one |
| 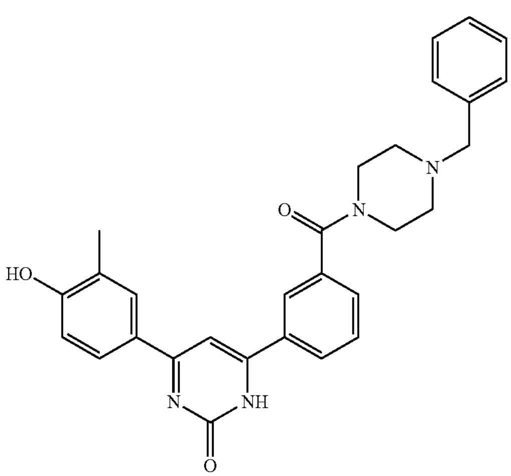 | 4-(4-hydroxy-3-methylphenyl)-6-(3-{[4-(phenylmethyl)piperazin-1-yl]carbonyl}phenyl)pyrimidin-2(1H)-one |

TABLE 1-continued

| STRUCTURE | NAME |
|---|---|
| 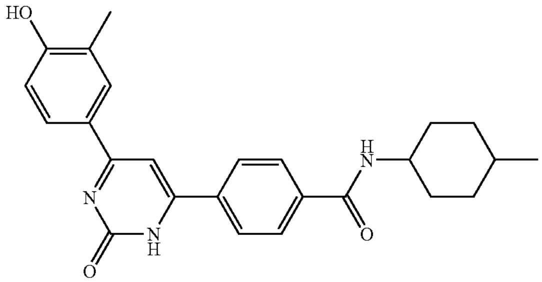 | 4-[6-(4-hydroxy-3-methylphenyl)-2-oxo-2,3-dihydropyrimidin-4-yl]-N-(4-methylcyclohexyl)benzamide |
| 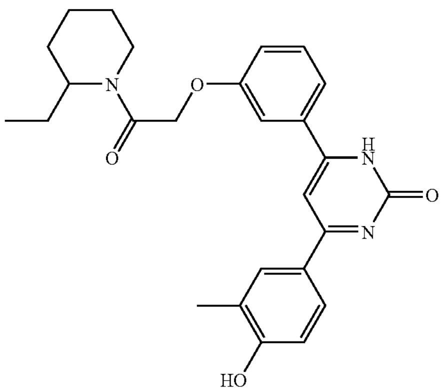 | 6-(3-{[2-(2-ethylpiperidin-1-yl)-2-oxoethyl]oxy}phenyl)-4-(4-hydroxy-3-methylphenyl)pyrimidin-2(1H)-one |
| 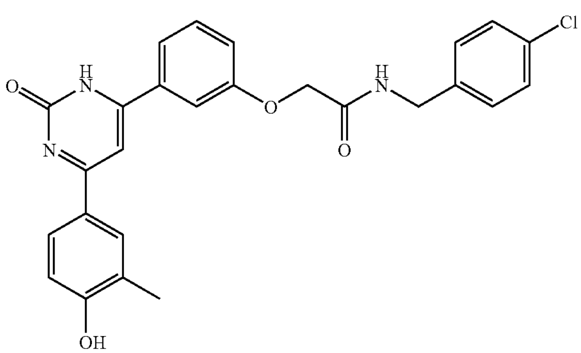 | N-[(4-chlorophenyl)methyl]-2-({3-[6-(4-hydroxy-3-methylphenyl)-2-oxo-2,3-dihydropyrimidin-4-yl]phenyl}oxy)acetamide |
| 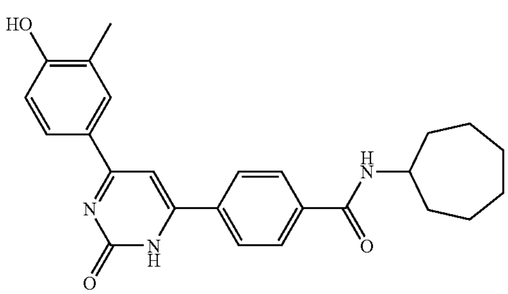 | N-cycloheptyl-4-[6-(4-hydroxy-3-methylphenyl)-2-oxo-2,3-dihydropyrimidin-4-yl]benzamide |

TABLE 1-continued

| STRUCTURE | NAME |
|---|---|
| 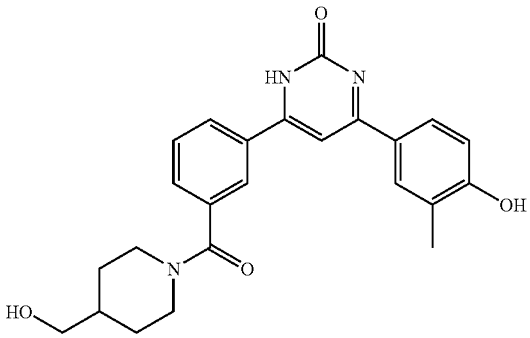 | 4-(4-hydroxy-3-methylphenyl)-6-(3-{[4-(hydroxymethyl)piperidin-1-yl]carbonyl}phenyl)pyrimidin-2(1H)-one |
| 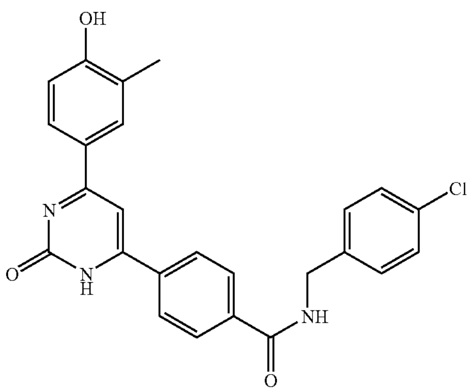 | N-[(4-chlorophenyl)methyl]-4-[6-(4-hydroxy-3-methyl)phenyl)-2-oxo-2,3-dihydropyrimidin-4-yl]benzamide |
| 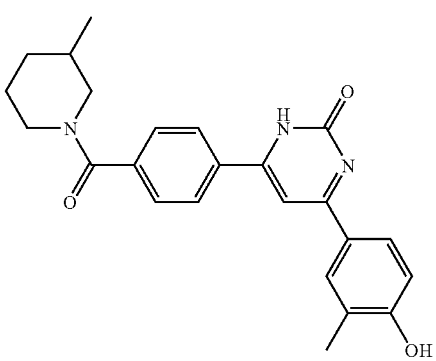 | 4-(4-hydroxy-3-methylphenyl)-6-{4-[(3-methylpiperidin-1-yl)carbonyl]phenyl}pyrimidin-2(1H)-one |
| 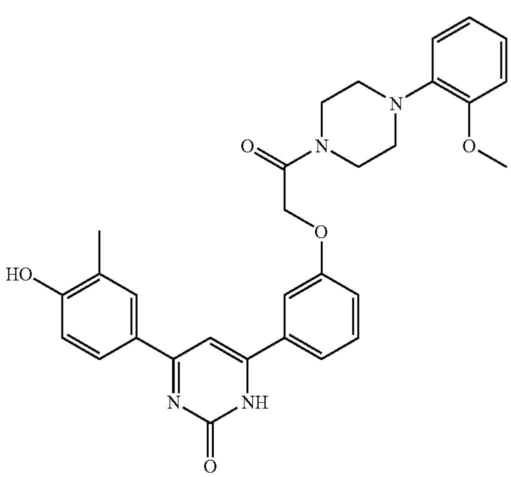 | 4-(4-hydroxy-3-methylphenyl)-6-{3-[(2-{4-[2-(methyloxy)phenyl]piperazin-1-yl}-2-oxoethyl)oxy]phenyl}pyrimidin-2(1H)-one |

TABLE 1-continued

| STRUCTURE | NAME |
|---|---|
| 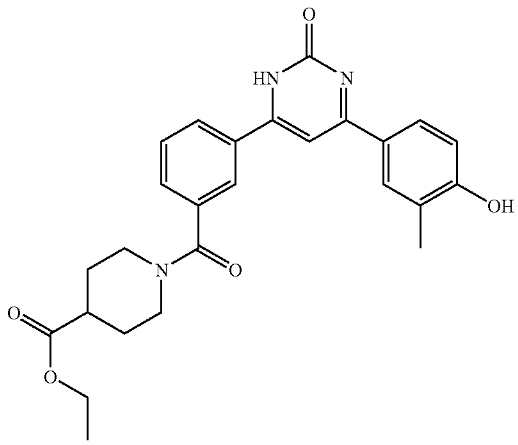 | ethyl 1-({3-[6-(4-hydroxy-3-methylphenyl)-2-oxo-2,3-dihydropyrimidin-4-yl]phenyl}carbonyl)piperidine-4-carboxylate |
| 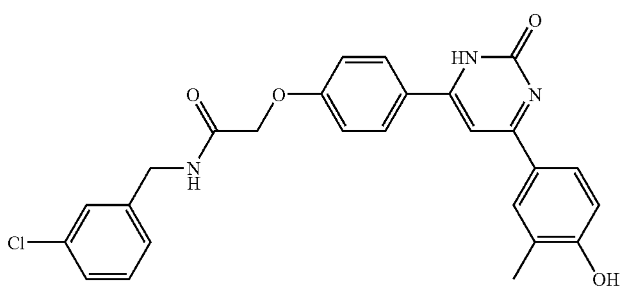 | N-[(3-chlorophenyl)methyl]-2-({4-[6-(4-hydroxy-3-methylphenyl)-2-oxo-2,3-dihydropyrimidin-4-yl]phenyl}oxy)acetamide |
| 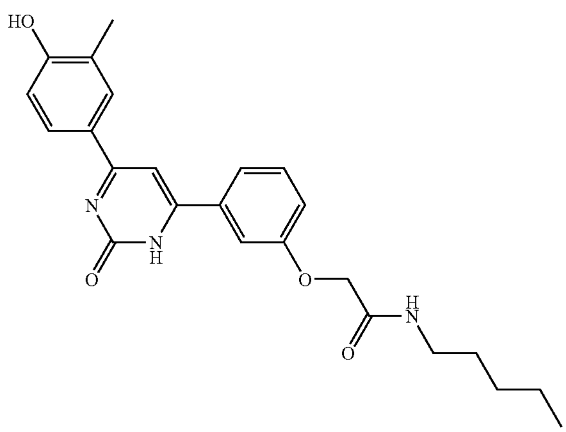 | 2-({3-[6-(4-hydroxy-3-methylphenyl)-2-oxo-2,3-dihydropyrimidin-4-yl]phenyl}oxy)-N-pentylacetamide |
| 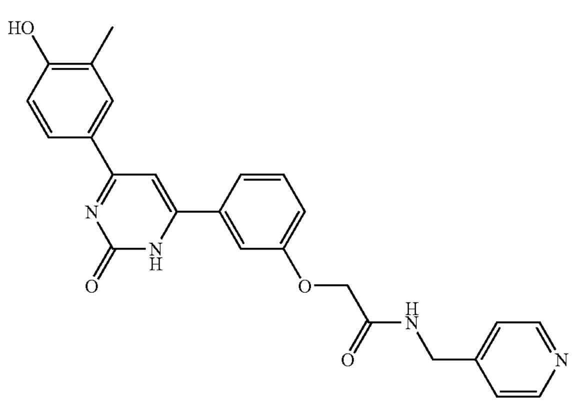 | 2-({3-[6-(4-hydroxy-3-methylphenyl)-2-oxo-2,3-dihydropyrimidin-4-yl]phenyl}oxy)-N-(pyridin-4-ylmethyl)acetamide |

TABLE 1-continued

| STRUCTURE | NAME |
|---|---|
| 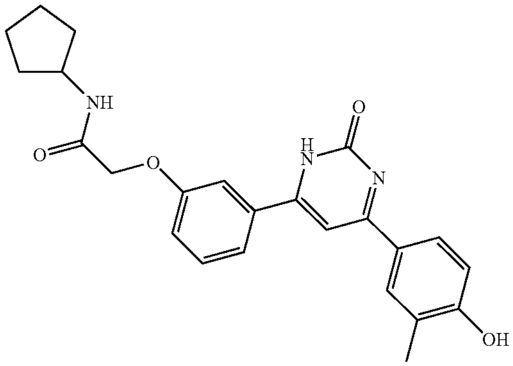 | N-cyclopentyl-2-({3-[6-(4-hydroxy-3-methylphenyl)-2-oxo-2,3-dihydropyrimidin-4-yl]phenyl}oxy)acetamide |
| 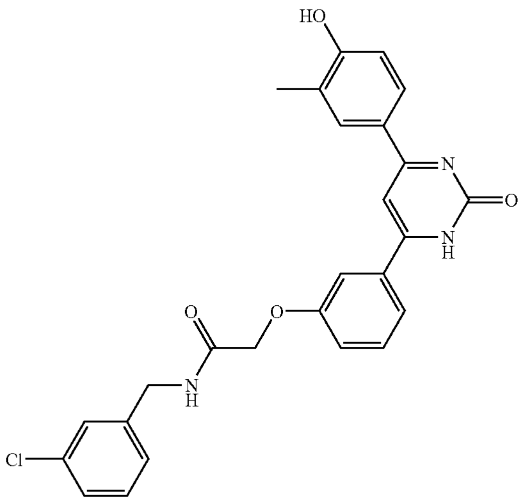 | N-[(3-chlorophenyl)methyl]-2-({3-[6-(4-hydroxy-3-methylphenyl)-2-oxo-2,3-dihydropyrimidin-4-yl]phenyl}oxy)acetamide |
| 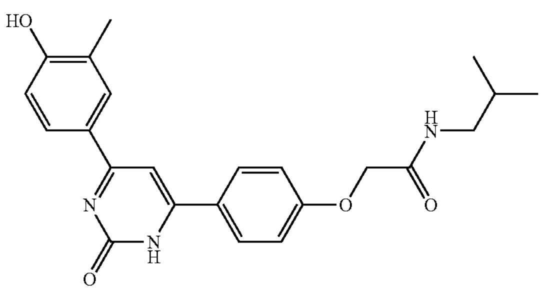 | 2-({4-[6-(4-hydroxy-3-methylphenyl)-2-oxo-2,3-dihydropyrimidin-4-yl]phenyl}oxy)-N-(2-methylpropyl)acetamide |
| 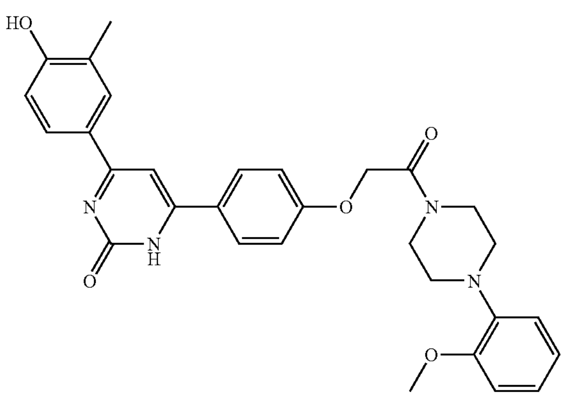 | 4-(4-hydroxy-3-methylphenyl)-6-{4-[(2-{4-[2-(methyloxy)phenyl]piperazin-1-yl}-2-oxoethyl)oxy]phenyl}pyrimidin-2(1H)-one |

TABLE 1-continued

| STRUCTURE | NAME |
|---|---|
| 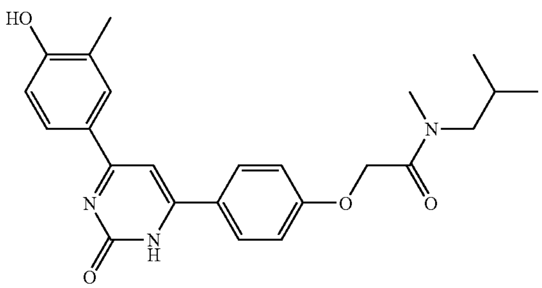 | 2-({4-[6-(4-hydroxy-3-methylphenyl)-2-oxo-2,3-dihydropyrimidin-4-yl]phenyl}oxy)-N-methyl-N-(2-methylpropyl)acetamide |
| 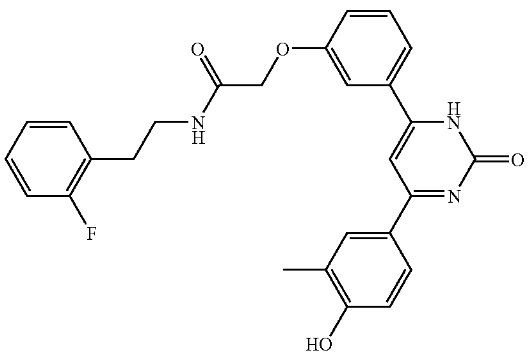 | N-[2-(2-fluorophenyl)ethyl]-2-({3-[6-(4-hydroxy-3-methylphenyl)-2-oxo-2,3-dihydropyrimidin-4-yl]phenyl}oxy)acetamide |
| 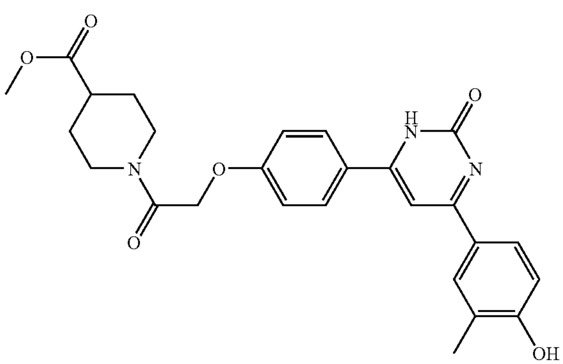 | methyl 1-[({4-[6-(4-hydroxy-3-methylphenyl)-2-oxo-2,3-dihydropyrimidin-4-yl]phenyl}oxy)acetyl]piperidine-4-carboxylate |
| 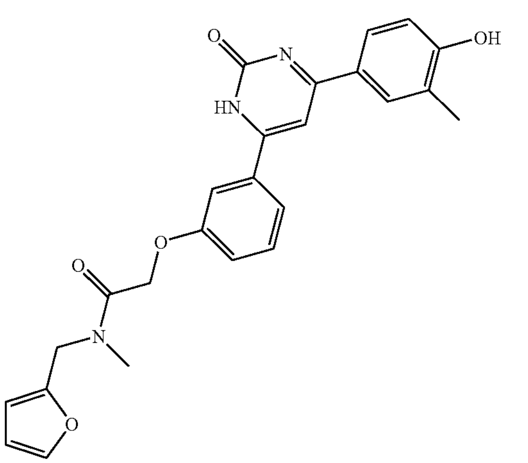 | N-(furan-2-ylmethyl)-2-({3-[6-(4-hydroxy-3-methylphenyl)-2-oxo-2,3-dihydropyrimidin-4-yl]phenyl}oxy)-N-methylacetamide |

TABLE 1-continued

| STRUCTURE | NAME |
|---|---|
| 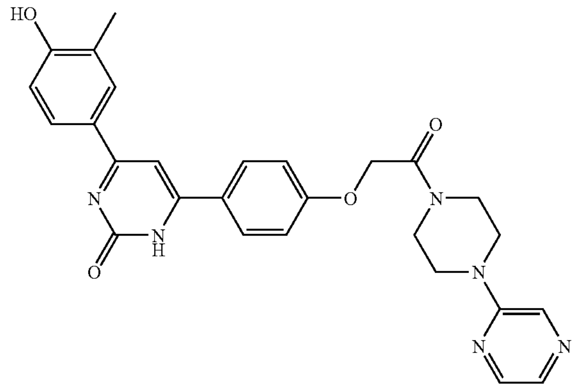 | 4-(4-hydroxy-3-methylphenyl)-6-(4-{[2-oxo-2-(4-pyrazin-2-ylpiperazin-1-yl)ethyl]oxy}phenyl)pyrimidin-2(1H)-one |
| 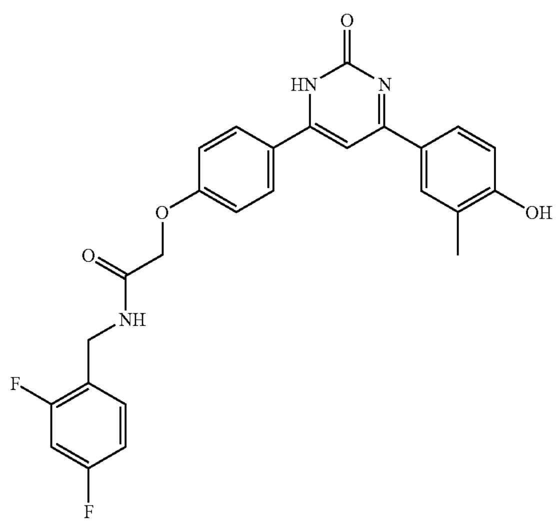 | N-[(2,4-difluorophenyl)methyl]-2-({4-[6-(4-hydroxy-3-methylphenyl)-2-oxo-2,3-dihydropyrimidin-4-yl]phenyl}oxy)acetamide |
| 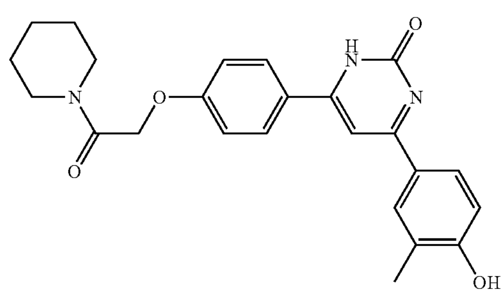 | 4-(4-hydroxy-3-methylphenyl)-6-{4-[(2-oxo-2-piperidin-1-ylethyl)oxy]phenyl}pyrimidin-2(1H)-one |
| 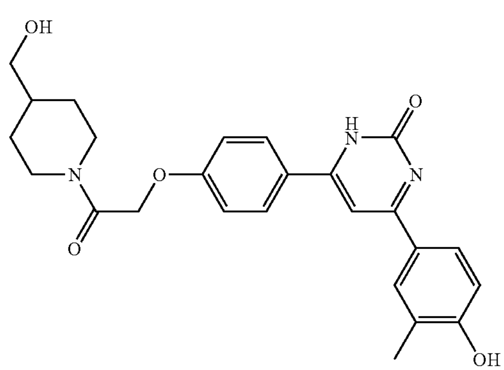 | 4-(4-hydroxy-3-methylphenyl)-6-[4-({2-[4-(hydroxymethyl)piperidin-1-yl]-2-oxoethyl}oxy)phenyl]pyrimidin-2(1H)-one |

TABLE 1-continued

| STRUCTURE | NAME |
|---|---|
| 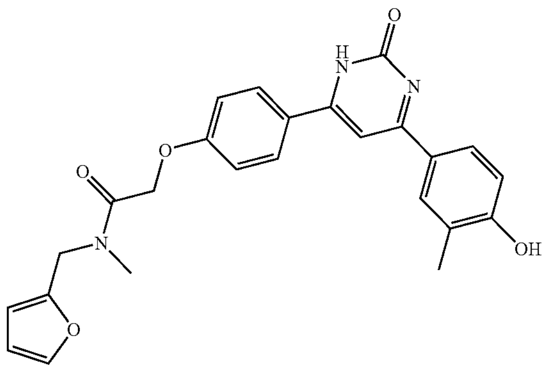 | N-(furan-2-ylmethyl)-2-({4-[6-(4-hydroxy-3-methylphenyl)-2-oxo-2,3-dihydropyrimidin-4-yl]phenyl}oxy)-N-methylacetamide |
| 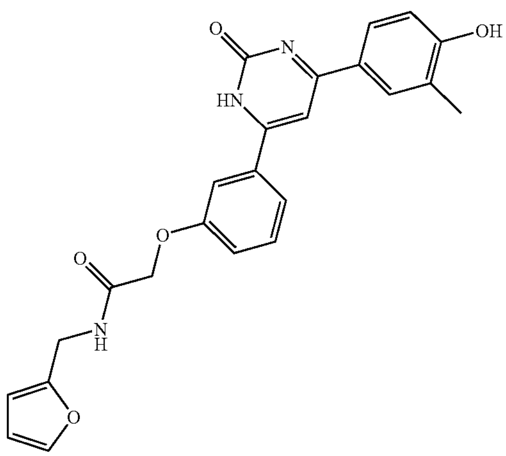 | N-(furan-2-ylmethyl)-2-({3-[6-(4-hydroxy-3-methylphenyl)-2-oxo-2,3-dihydropyrimidin-4-yl]phenyl}oxy)acetamide |
| 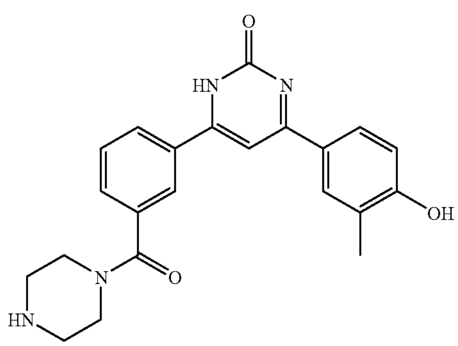 | 4-(4-hydroxy-3-methylphenyl)-6-[3-(piperazin-1-ylcarbonyl)phenyl]pyrimidin-2(1H)-one |
| 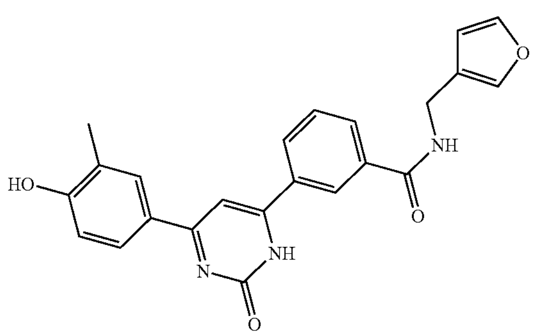 | N-(furan-2-ylmethyl)-3-[6-(4-hydroxy-3-methylphenyl)-2-oxo-2,3-dihydropyrimidin-4-yl]benzamide |

TABLE 1-continued

| STRUCTURE | NAME |
|---|---|
| 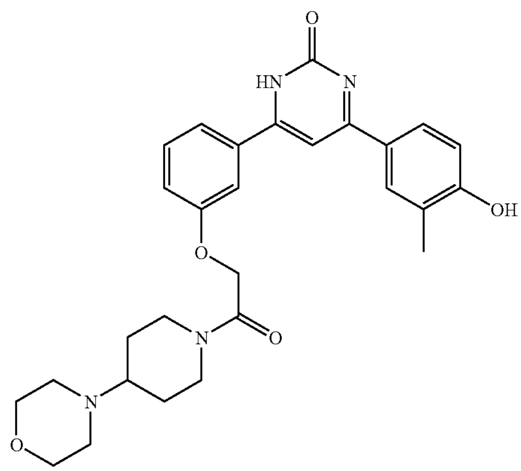 | 4-(4-hydroxy-3-methylphenyl)-6-(3-{[2-(4-morpholin-4-ylpiperidin-1-yl)-2-oxoethyl]oxy}phenyl)pyrimidin-2(1H)-one |
| 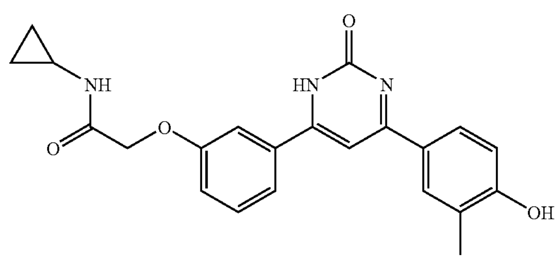 | N-cyclopropyl-2-({3-[6-(4-hydroxy-3-methylphenyl)-2-oxo-2,3-dihydropyrimidin-4-yl]phenyl}oxy)acetamide |
| 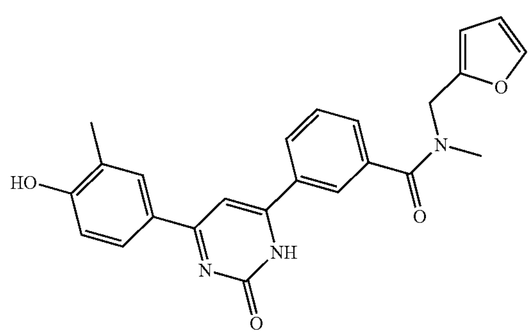 | N-(furan-2-ylmethyl)-3-[6-(4-hydroxy-3-methylphenyl)-2-oxo-2,3-dihydropyrimidin-4-yl]-N-methylbenzamide |
| 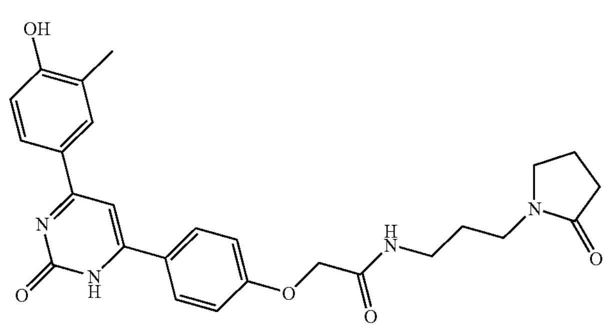 | 2-({4-[6-(4-hydroxy-3-methylphenyl)-2-oxo-2,3-dihydropyrimidin-4-yl]phenyl}oxy)-N-[3-(2-oxopyrrolidin-1-yl)propyl]acetamide |

TABLE 1-continued

| STRUCTURE | NAME |
|---|---|
| 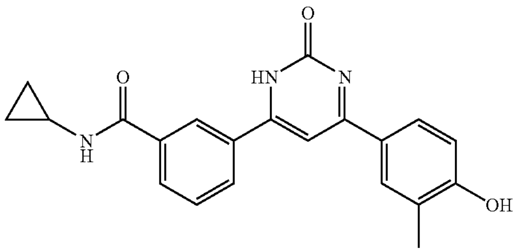 | N-cyclopropyl-3-[6-(4-hydroxy-3-methylphenyl)-2-oxo-2,3-dihydropyrimidin-4-yl]benzamide |
| 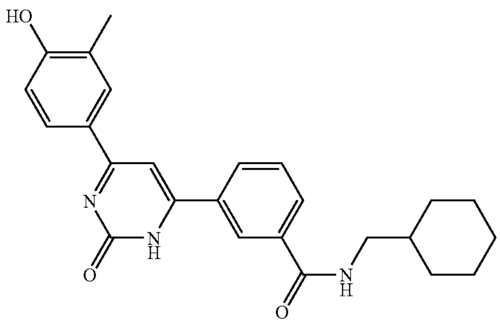 | N-(cyclohexylmethyl)-3-[6-(4-hydroxy-3-methylphenyl)-2-oxo-2,3-dihydropyrimidin-4-yl]benzamide |
| 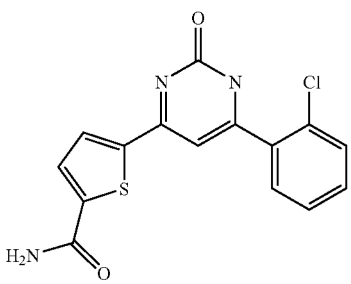 | 5-[6-(2-Chlorophenyl)-2-oxo-1,2-dihydropyrimidin-4-yl]thiophene-2-carboxamide |
| 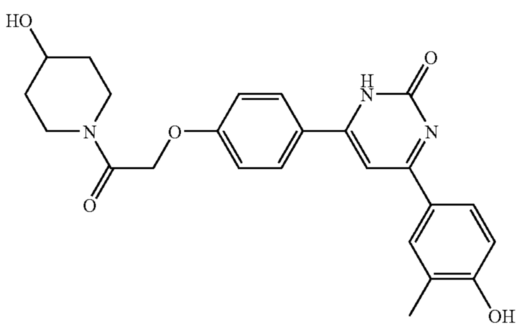 | 4-(4-hydroxy-3-methylphenyl)-6-(4-{[2-(4-hydroxypiperidin-1-yl)-2-oxoethyl]oxy}phenyl)pyrimidin-2(1H)-one |
| 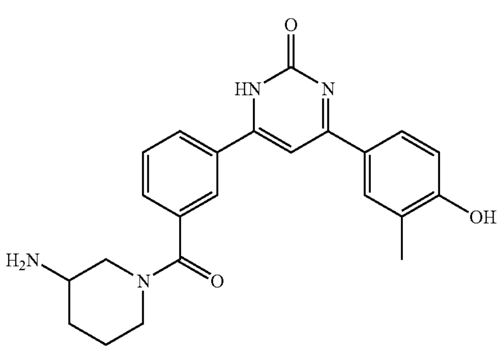 | 6-{3-[(3-aminopiperidin-1-yl)carbonyl]phenyl}-4-(4-hydroxy-3-methylphenyl)pyrimidin-2(1H)-one |

| STRUCTURE | NAME |
|---|---|
| 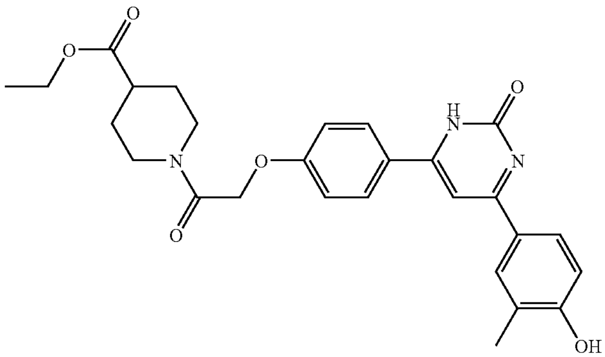 | ethyl 1-[({4-[6-(4-hydroxy-3-methylphenyl)-2-oxo-2,3-dihydropyrimidin-4-yl]phenyl}oxy)acetyl]piperidine-4-carboxylate |
| 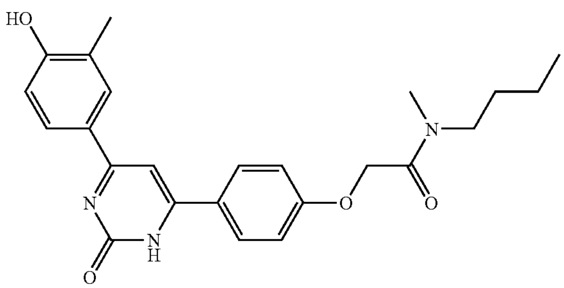 | N-butyl-2-({4-[6-(4-hydroxy-3-methylphenyl)-2-oxo-2,3-dihydropyrimidin-4-yl]phenyl}oxy)-N-methylacetamide |
| 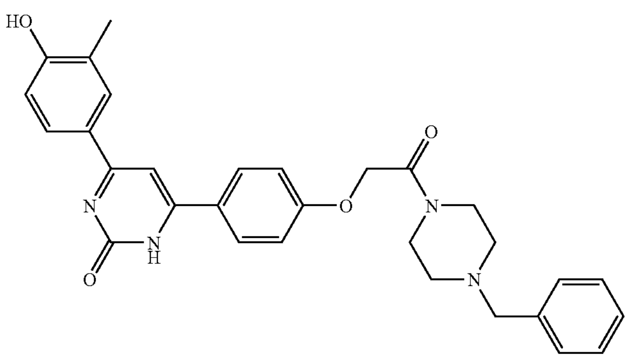 | 4-(4-hydroxy-3-methylphenyl)-6-[4-({2-oxo-2-[4-(phenylmethyl)piperazin-1-yl]ethyl}oxy)phenyl]pyrimidin-2(1H)-one |
| 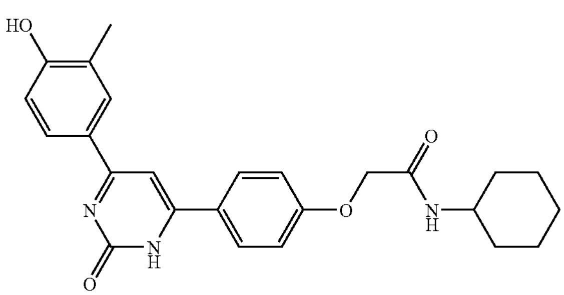 | N-cyclohexyl-2-({4-[6-(4-hydroxy-3-methylphenyl)-2-oxo-2,3-dihydropyrimidin-4-yl]phenyl}oxy)acetamide |

TABLE 1-continued

| STRUCTURE | NAME |
|---|---|
| 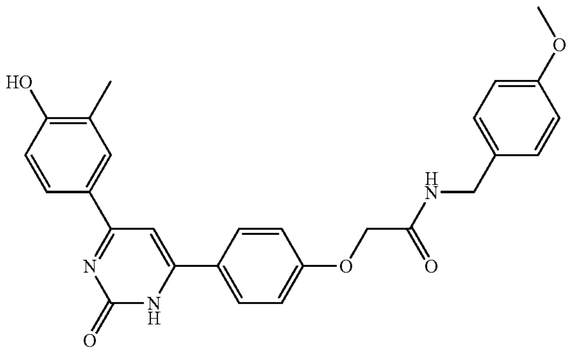 | 2-({4-[6-(4-hydroxy-3-methylphenyl)-2-oxo-2,3-dihydropyrimidin-4-yl]phenyl}oxy)-N-{[4-(methyloxy)phenyl]methyl}acetamide |
| 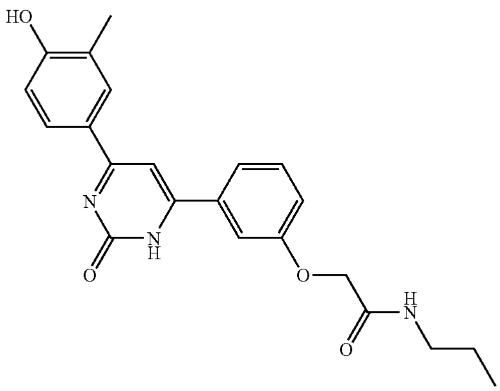 | 2-({3-[6-(4-hydroxy-3-methylphenyl)-2-oxo-2,3-dihydropyrimidin-4-yl]phenyl}oxy)-N-propylacetamide |
| 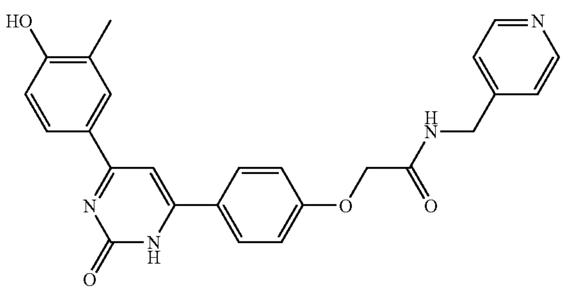 | 2-({4-[6-(4-hydroxy-3-methylphenyl)-2-oxo-2,3-dihydropyrimidin-4-yl]phenyl}oxy)-N-(pyridin-4-ylmethyl)acetamide |
| 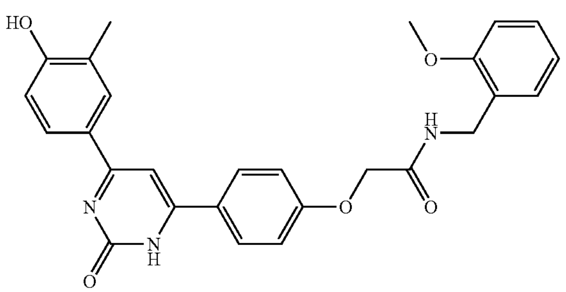 | 2-({4-[6-(4-hydroxy-3-methylphenyl)-2-oxo-2,3-dihydropyrimidin-4-yl]phenyl}oxy)-N-{[2-(methyloxy)phenyl]methyl}acetamide |
| 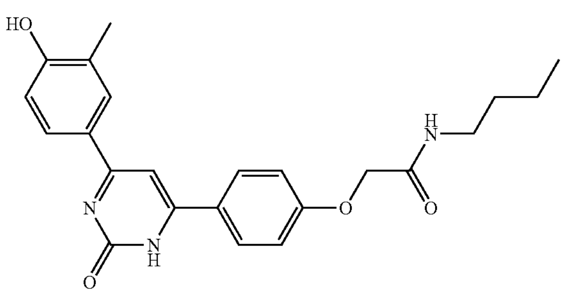 | N-butyl-2-({4-[6-(4-hydroxy-3-methylphenyl)-2-oxo-2,3-dihydropyrimidin-4-yl]phenyl}oxy)acetamide |

TABLE 1-continued
| STRUCTURE | NAME |
|---|---|
| 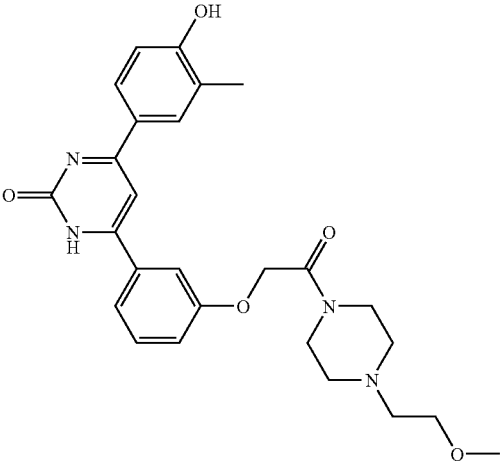 | 4-(4-hydroxy-3-methylphenyl)-6-{3-[(2-{4-[2-(methyloxy)ethyl]piperazin-1-yl}-2-oxoethyl)oxy]phenyl}pyrimidin-2(1H)-one |
| 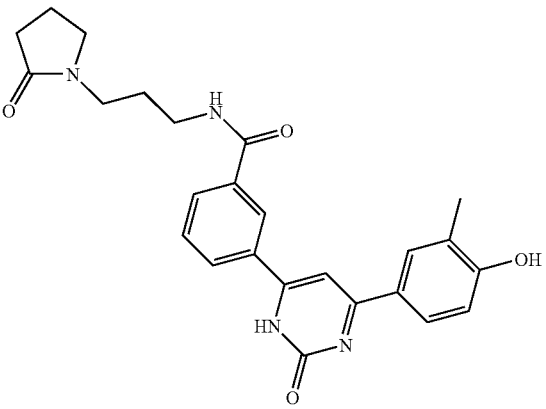 | 3-[6-(4-hydroxy-3-methylphenyl)-2-oxo-2,3-dihydropyrimidin-4-yl]-N-[3-(2-oxopyrrolidin-1-yl)propyl]benzamide |
| 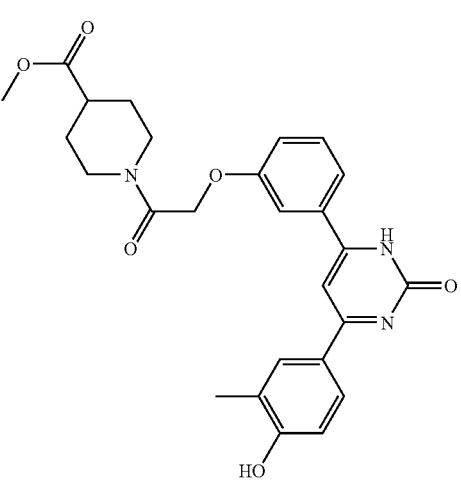 | methyl 1-[({3-[6-(4-hydroxy-3-methylphenyl)-2-oxo-2,3-dihydropyrimidin-4-yl]phenyl}oxy)acetyl]piperidine-4-carboxylate |

TABLE 1-continued

| STRUCTURE | NAME |
|---|---|
| 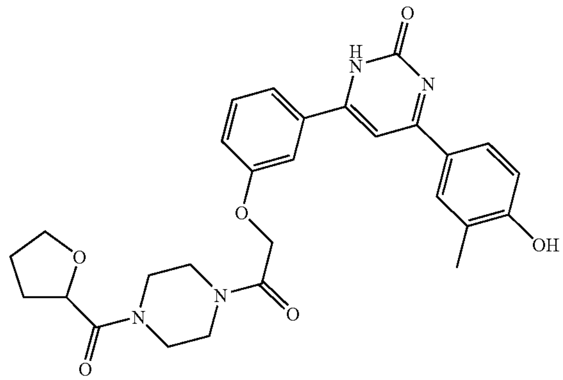 | 4-(4-hydroxy-3-methylphenyl)-6-[3-({2-oxo-2-[4-(tetrahydrofuran-2-ylcarbonyl)piperazin-1-yl]ethyl}oxy)phenyl]pyrimidin-2(1H)-one |
| 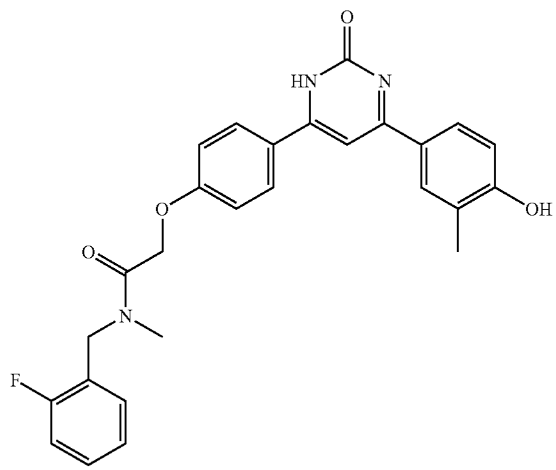 | N-[(2-fluorophenyl)methyl]-2-({4-[6-(4-hydroxy-3-methylphenyl)-2-oxo-2,3-dihydropyrimidin-4-yl]phenyl}oxy)-N-methylacetamide |
| 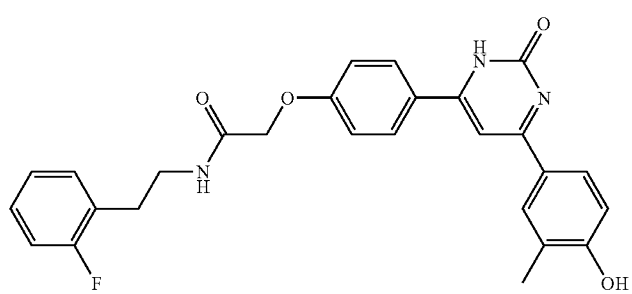 | N-[2-(2-fluorophenyl)ethyl]-2-({4-[6-(4-hydroxy-3-methylphenyl)-2-oxo-2,3-dihydropyrimidin-4-yl]phenyl}oxy)acetamide |
| 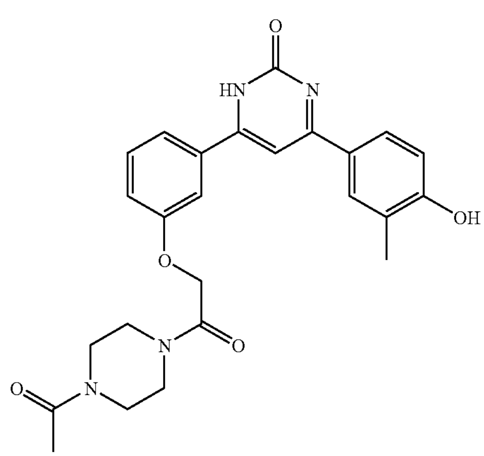 | 6-(3-{[2-(4-acetylpiperazin-1-yl)-2-oxoethyl]oxy}phenyl)-4-(4-hydroxy-3-methylphenyl)pyrimidin-2(1H)-one |

TABLE 1-continued
| STRUCTURE | NAME |
|---|---|
| 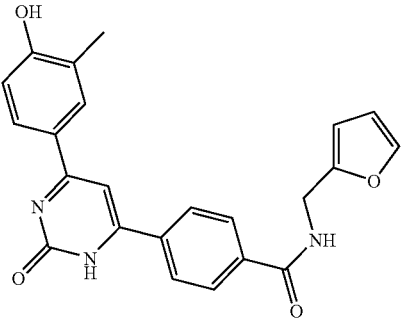 | N-(furan-2-ylmethyl)-4-[6-(4-hydroxy-3-methylphenyl)-2-oxo-2,3-dihydropyrimidin-4-yl]benzamide |
| 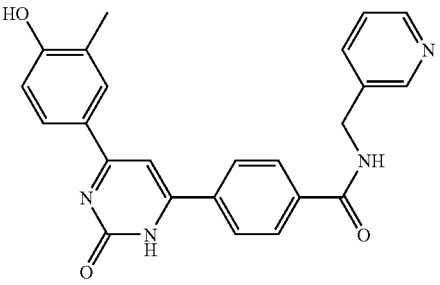 | 4-[6-(4-hydroxy-3-methylphenyl)-2-oxo-2,3-dihydropyrimidin-4-yl]-N-(pyridin-3-ylmethyl)benzamide |
| 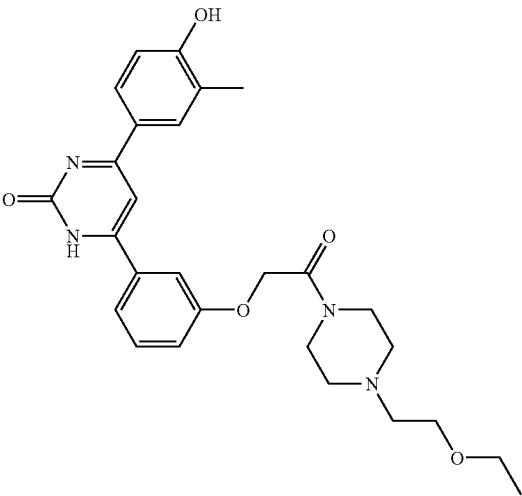 | 6-{3-[(2-{4-[2-(ethyloxy)ethyl]piperazin-1-yl}-2-oxoethyl)oxy]phenyl}-4-(4-hydroxy-3-methylphenyl)pyrimidin-2(1H)-one |
| 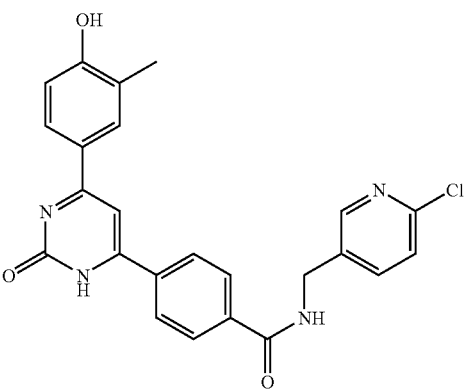 | N-[(6-chloropyridin-3-yl)methyl]-4-[6-(4-hydroxy-3-methylphenyl)-2-oxo-2,3-dihydropyrimidin-4-yl]benzamide |

TABLE 1-continued

| STRUCTURE | NAME |
|---|---|
| 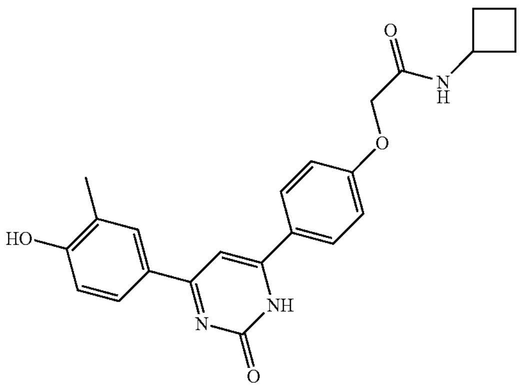 | N-cyclobutyl-2-({4-[6-(4-hydroxy-3-methylphenyl)-2-oxo-2,3-dihydropyrimidin-4-yl]phenyl}oxy)acetamide |
| 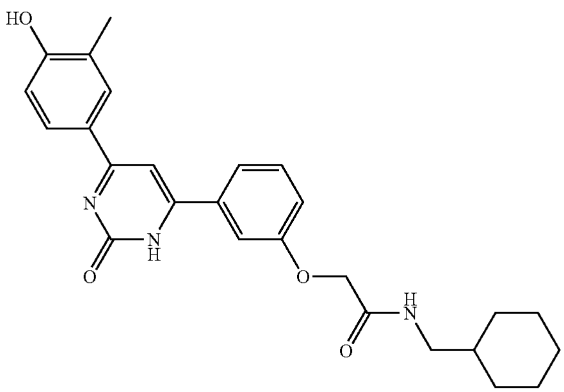 | N-(cyclohexylmethyl)-2-({3-[6-(4-hydroxy-3-methylphenyl)-2-oxo-2,3-dihydropyrimidin-4-yl]phenyl}oxy)acetamide |
| 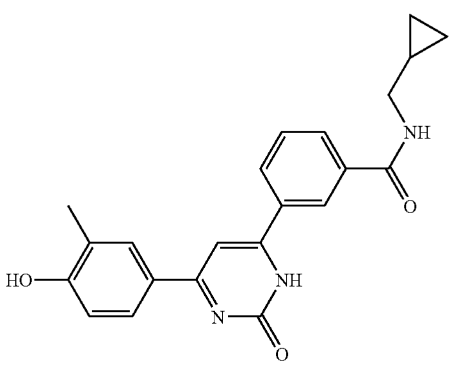 | N-(cyclopropylmethyl)-3-[6-(4-hydroxy-3-methylphenyl)-2-oxo-2,3-dihydropyrimidin-4-yl]benzamide |
| 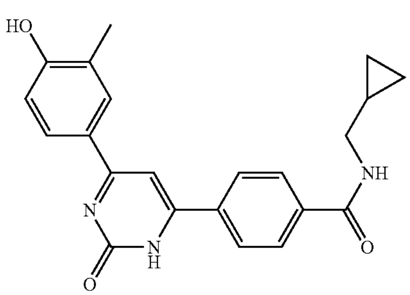 | N-(cyclopropylmethyl)-4-[6-(4-hydroxy-3-methylphenyl)-2-oxo-2,3-dihydropyrimidin-4-yl]benzamide |

TABLE 1-continued

| STRUCTURE | NAME |
|---|---|
| 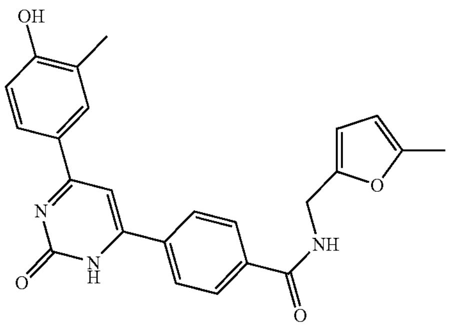 | 4-[6-(4-hydroxy-3-methylphenyl)-2-oxo-2,3-dihydropyrimidin-4-yl]-N-[(5-methylfuran-2-yl)methyl]benzamide |
| 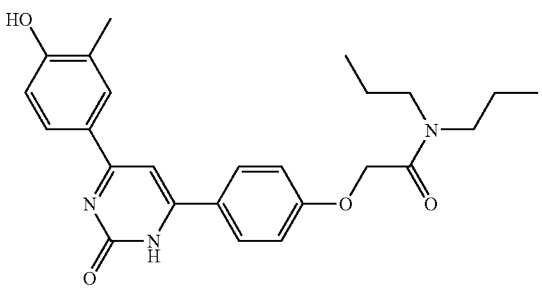 | 2-({4-[6-(4-hydroxy-3-methylphenyl)-2-oxo-2,3-dihydropyrimidin-4-yl]phenyl}oxy)-N,N-dipropylacetamide |
| 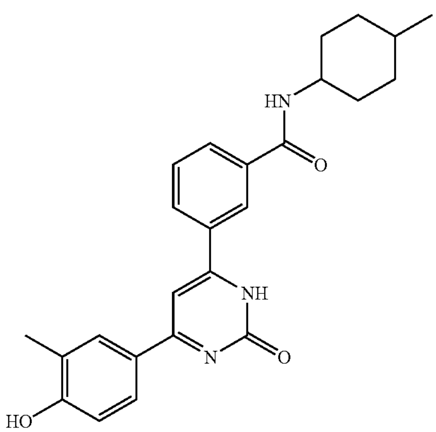 | 3-[6-(4-hydroxy-3-methylphenyl)-2-oxo-2,3-dihydropyrimidin-4-yl]-N-(4-methylcyclohexyl)benzamide |
| 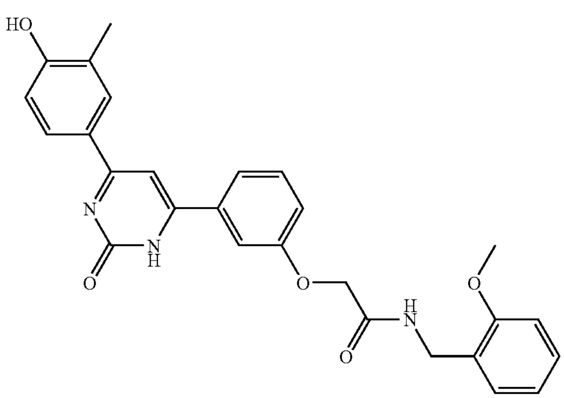 | 2-({3-[6-(4-hydroxy-3-methylphenyl)-2-oxo-2,3-dihydropyrimidin-4-yl]phenyl}oxy)-N-{[2-(methyloxy)phenyl]methyl}acetamide |

TABLE 1-continued

| STRUCTURE | NAME |
|---|---|
| 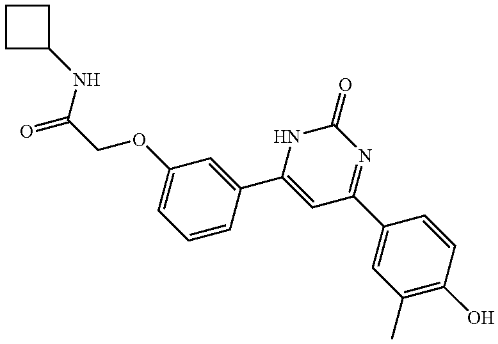 | N-cyclobutyl-2-({3-[6-(4-hydroxy-3-methylphenyl)-2-oxo-2,3-dihydropyrimidin-4-yl]phenyl}oxy)acetamide |
| 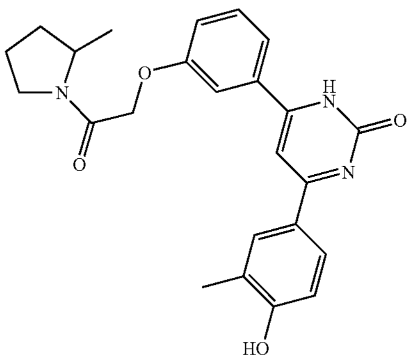 | 4-(4-hydroxy-3-methylphenyl)-6-(3-{[2-(2-methylpyrrolidin-1-yl)-2-oxoethyl]oxy}phenyl)pyrimidin-2(1H)-one |
| 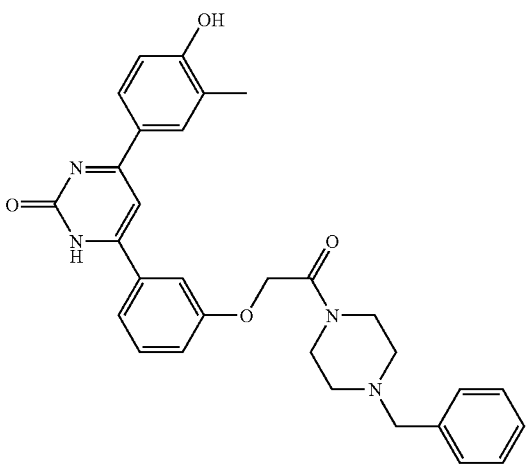 | 4-(4-hydroxy-3-methylphenyl)-6-[3-({2-oxo-2-[4-(phenylmethyl)piperazin-1-yl]ethyl}oxy)phenyl]pyrimidin-2(1H)-one |
| 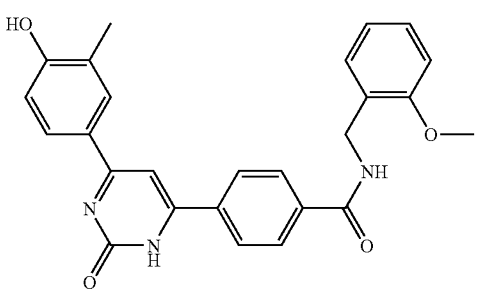 | 4-[6-(4-hydroxy-3-methylphenyl)-2-oxo-2,3-dihydropyrimidin-4-yl]-N-{[2-(methyloxy)phenyl]methyl}benzamide |

TABLE 1-continued

| STRUCTURE | NAME |
|---|---|
| 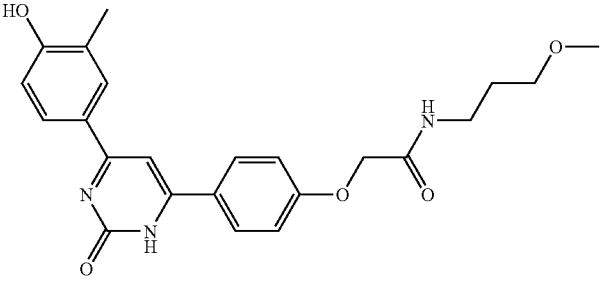 | 2-({4-[6-(4-hydroxy-3-methylphenyl)-2-oxo-2,3-dihydropyrimidin-4-yl]phenyl}oxy)-N-[3-(methyloxy)propyl]acetamide |
| 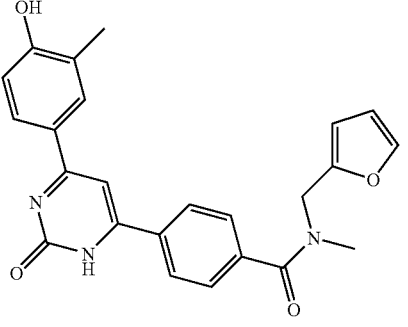 | N-(furan-2-ylmethyl)-4-[6-(4-hydroxy-3-methylphenyl)-2-oxo-2,3-dihydropyrimidin-4-yl]-N-methylbenzamide |
| 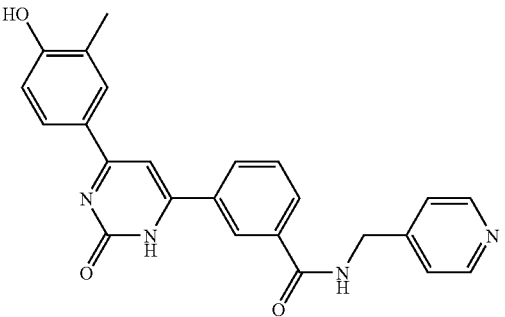 | 3-[6-(4-hydroxy-3-methylphenyl)-2-oxo-2,3-dihydropyrimidin-4-yl]-N-(pyridin-4-ylmethyl)benzamide |
| 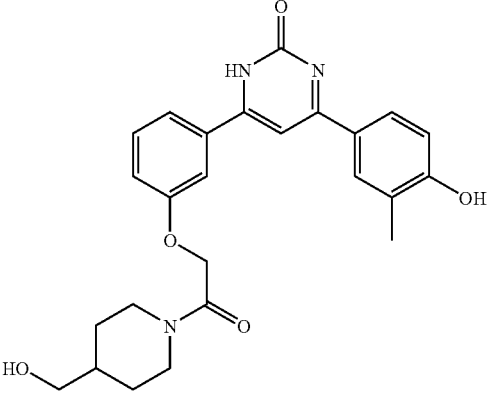 | 4-(4-hydroxy-3-methylphenyl)-6-[3-({2-[4-(hydroxymethyl)piperidin-1-yl]-2-oxoethyl}oxy)phenyl]pyrimidin-2(1H)-one |

TABLE 1-continued

| STRUCTURE | NAME |
|---|---|
| 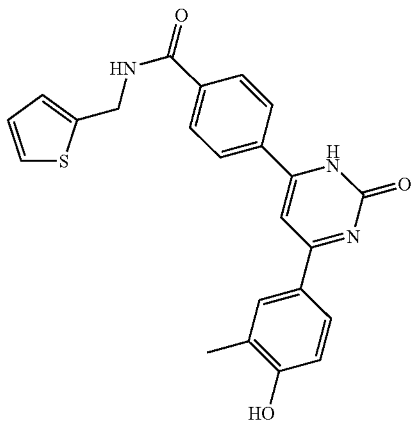 | 4-[6-(4-hydroxy-3-methylphenyl)-2-oxo-2,3-dihydropyrimidin-4-yl]-N-(2-thienylmethyl)benzamide |
| 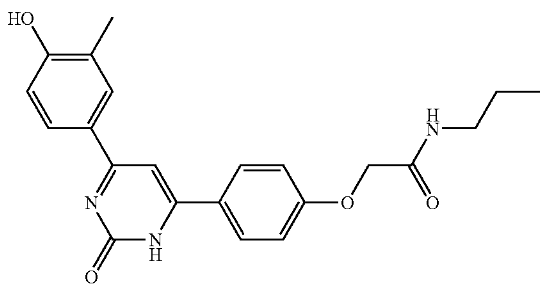 | 2-({4-[6-(4-hydroxy-3-methylphenyl)-2-oxo-2,3-dihydropyrimidin-4-yl]phenyl}oxy)-N-propylacetamide |
| 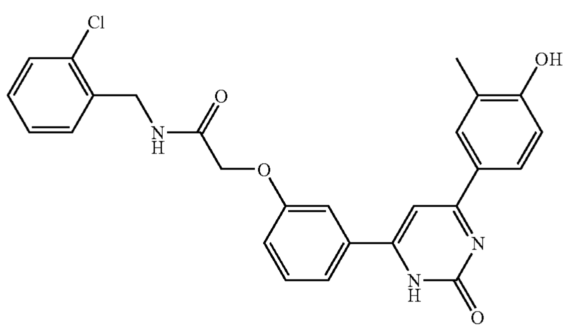 | N-[(2-chlorophenyl)methyl]-2-({3-[6-(4-hydroxy-3-methylphenyl)-2-oxo-2,3-dihydropyrimidin-4-yl]phenyl}oxy)acetamide |
| 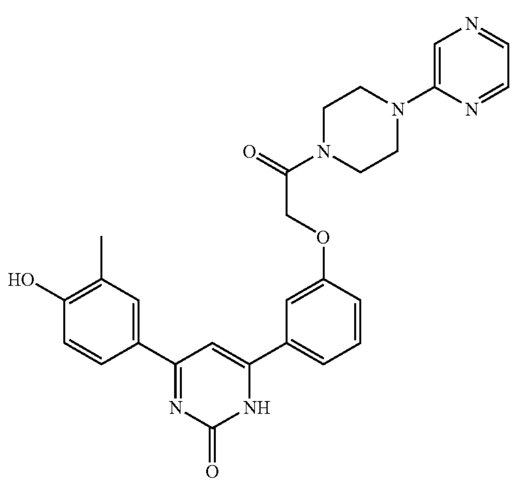 | 4-(4-hydroxy-3-methylphenyl)-6-(3-{[2-oxo-2-(4-pyrazin-2-ylpiperazin-1-yl)ethyl]oxy}phenyl)pyrimidin-2(1H)-one |

TABLE 1-continued

| STRUCTURE | NAME |
|---|---|
| 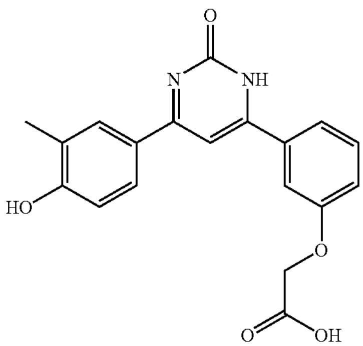 | ({3-[6-(4-hydroxy-3-methylphenyl)-2-oxo-2,3-dihydropyrimidin-4-yl]phenyl}oxy)acetic acid |
| 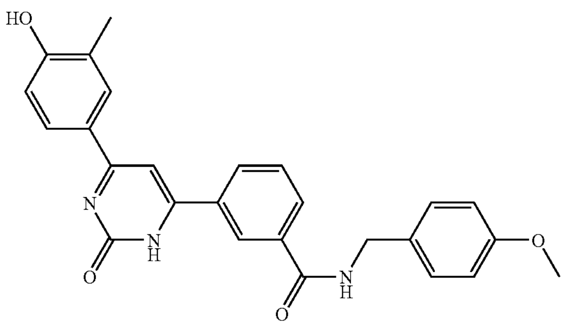 | 3-[6-(4-hydroxy-3-methylphenyl)-2-oxo-2,3-dihydropyrimidin-4-yl]-N-{[4-(methyloxy)phenyl]methyl}benzamide |
| 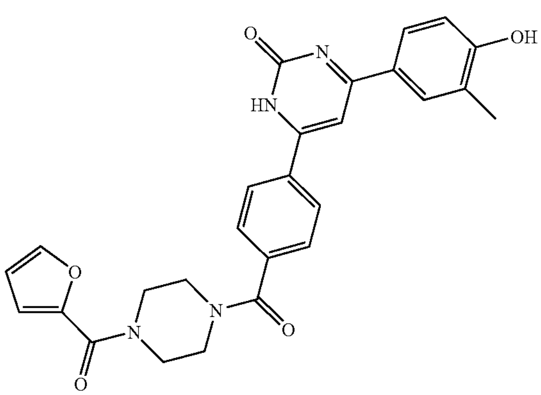 | 6-(4-{[4-furan-2-ylcarbonyl)piperazin-1-yl]carbonyl}phenyl)-4-(4-hydroxy-3-methylphenyl)pyrimidin-2(1H)-one |
| 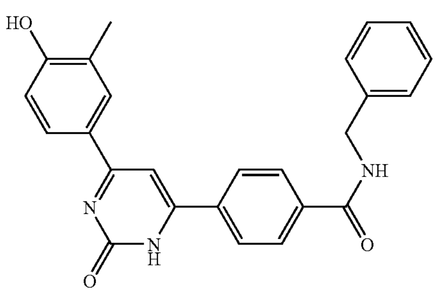 | 4-[6-(4-hydroxy-3-methylphenyl)-2-oxo-2,3-dihydropyrimidin-4-yl]-N-(phenylmethyl)benzamide |

TABLE 1-continued

| STRUCTURE | NAME |
|---|---|
| 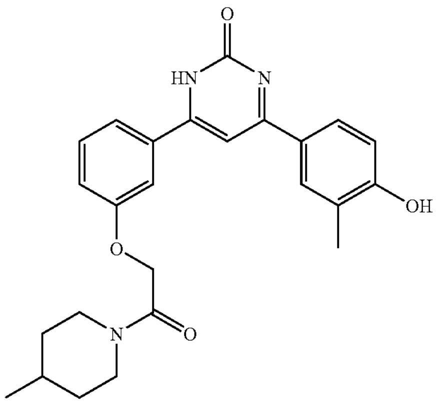 | 4-(4-hydroxy-3-methylphenyl)-6-(3-{[2-(4-methylpiperidin-1-yl)-2-oxoethyl]oxy}phenyl)pyrimidin-2(1H)-one |
| 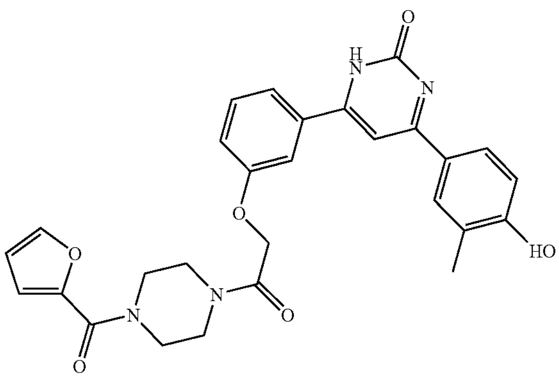 | 6-[3-({2-[4-(furan-2-ylcarbonyl)piperiazin-1-yl]-2-oxoethyl}oxy)phenyl]-4-(4-hydroxy-3-methylphenyl)pyrimidin-2(1H)-one |
| 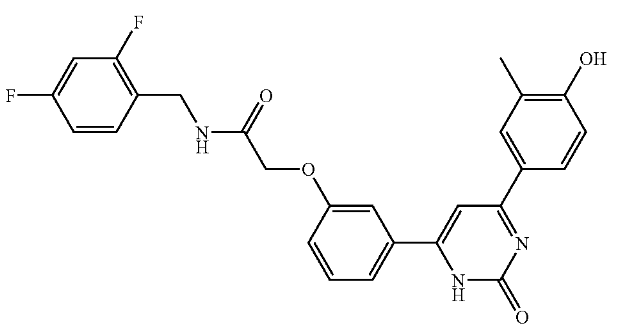 | N-[(2,4-difluorophenyl)methyl]-2-({3-[6-(4-hydroxy-3-methylphenyl)-2-oxo-2,3-dihydropyrimidin-4-yl]phenyl}oxy)acetamide |
| 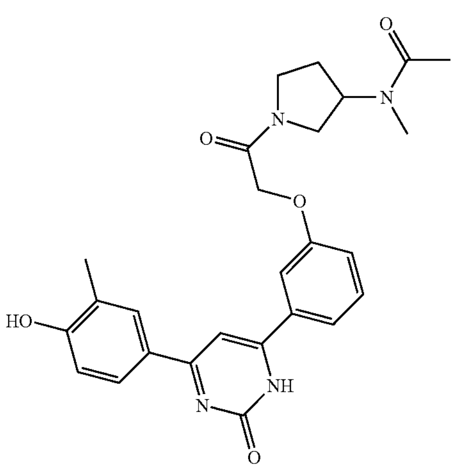 | N-{1-[({3-[6-(4-hydroxy-3-methylphenyl)-2-oxo-2,3-dihydropyrimidin-4-yl]phenyl}oxy)acetyl]pyrrolidin-3-yl}-N-methylacetamide |

TABLE 1-continued

| STRUCTURE | NAME |
|---|---|
| 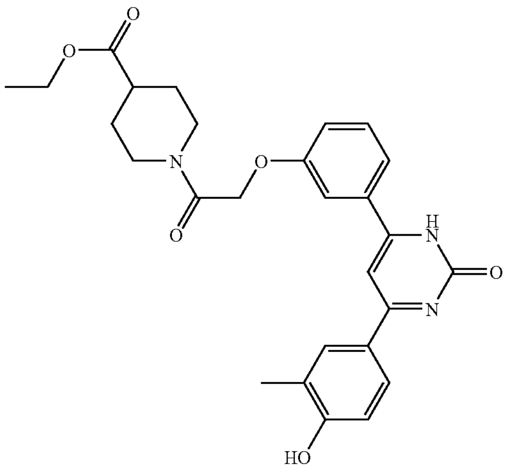 | ethyl 1-[({3-[6-(4-hydroxy-3-methylphenyl)-2-oxo-2,3-dihydropyrimidin-4-yl]phenyl}oxy)acetyl]piperidine-4-carboxylate |
| 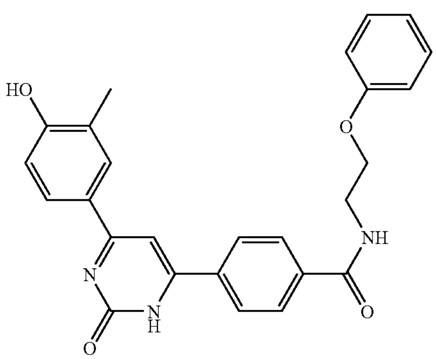 | 4-[6-(4-hydroxy-3-methylphenyl)-2-oxo-2,3-dihydropyrimidin-4-yl]-N-[2-(phenyloxy)ethyl]benzamide |
| 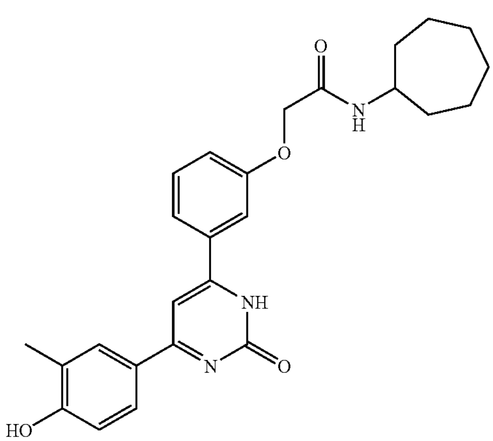 | N-cycloheptyl-2-({3-[6-(4-hydroxy-3-methylphenyl)-2-oxo-2,3-dihydropyrimidin-4-yl]phenyl}oxy)acetamide |

TABLE 1-continued

| STRUCTURE | NAME |
|---|---|
| 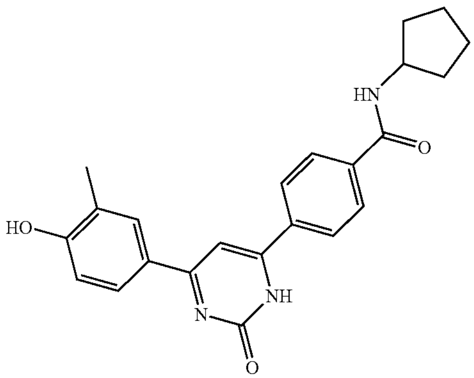 | N-cyclopentyl-4-[6-(4-hydroxy-3-methylphenyl)-2-oxo-2,3-dihydropyrimidin-4-yl]benzamide |
| 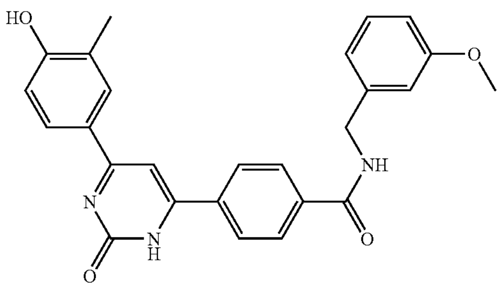 | 4-[6-(4-hydroxy-3-methylphenyl)-2-oxo-2,3-dihydropyrimidin-4-yl]-N-{[3-(methyloxy)phenyl]methyl}benzamide |
| 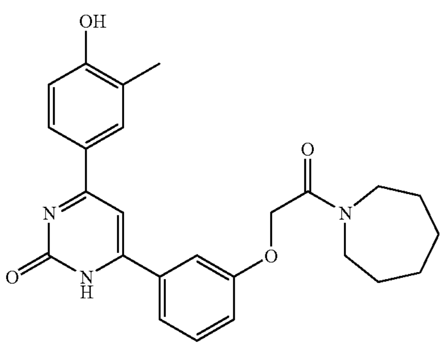 | 6-{3-[(2-azepan-1-yl-2-oxoethyl)oxy]phenyl}-4-(4-hydroxy-3-methylphenyl)pyrimidin-2(1H)-one |
| 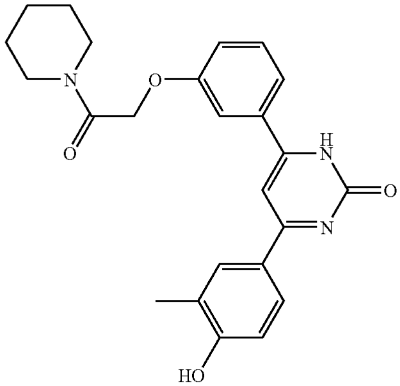 | 4-(4-hydroxy-3-methylphenyl)-6-{3-[(2-oxo-2-piperidin-1-ylethyl)oxy]phenyl}pyrimidin-2(1H)-one |

| STRUCTURE | NAME |
|---|---|
| 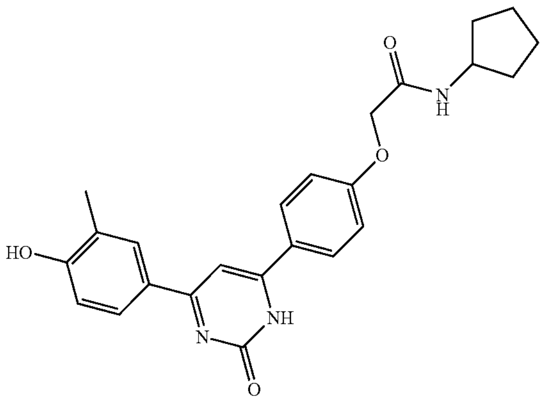 | N-cyclopentyl-2-({4-[6-(4-hydroxy-3-methylphenyl)-2-oxo-2,3-dihydropyrimidin-4-yl]phenyl}oxy)acetamide |
| 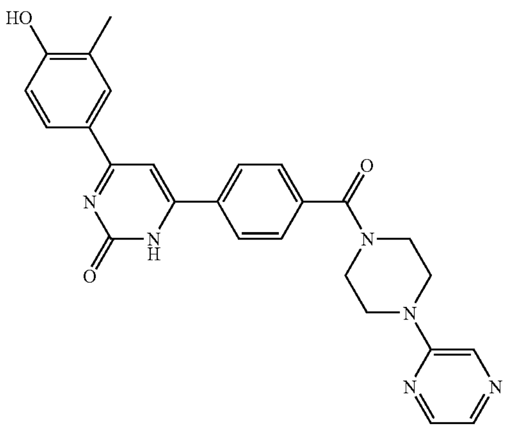 | 4-(4-hydroxy-2-methylphenyl)-6-{4-[(4-pyrazin-2-ylpiperazin-1-yl)carbonyl]phenyl}pyrimidin-2(1H)-one |
| 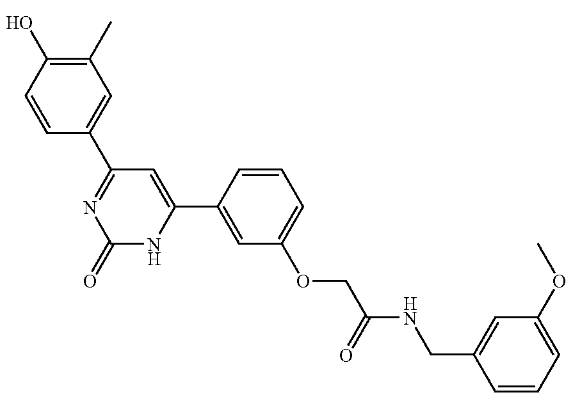 | 2-({3-[6-(4-hydroxy-3-methylphenyl)-2-oxo-2,3-dihydropyrimidin-4-yl]phenyl}oxy)-N-{[3-(methyloxy)phenyl]methyl}acetamide |
| 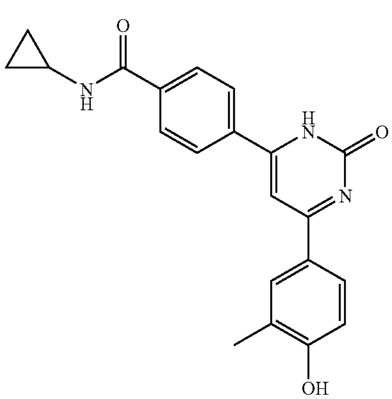 | N-cyclopropyl-4-[6-(4-hydroxy-3-methylphenyl)-2-oxo-2,3-dihydropyrimidin-4-yl]benzamide |

TABLE 1-continued

| STRUCTURE | NAME |
| --- | --- |
| 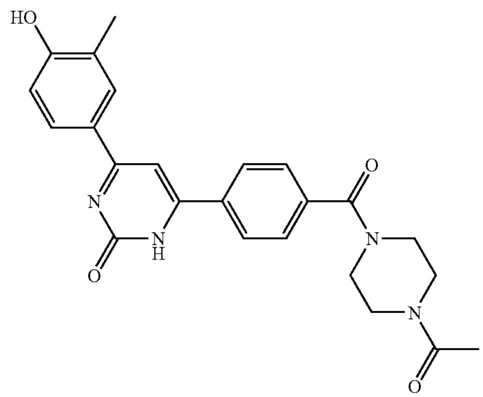 | 6-{4-[(4-acetylpiperazin-1-yl)carbonyl]phenyl}-4-(4-hydroxy-3-methylphenyl)pyrimidin-2(1H)-one |
| 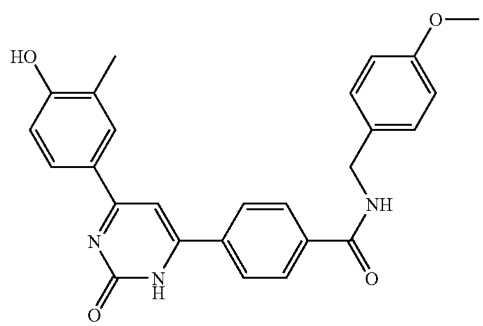 | 4-[6-(4-hydroxy-3-methylphenyl)-2-oxo-2,3-dihydropyrimidin-4-yl]-N-{[4-(methyloxy)phenyl]methyl}benzamide |
| 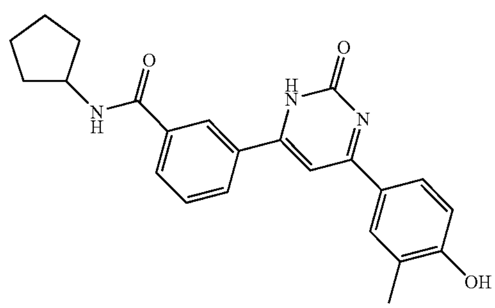 | N-cyclopentyl-3-[6-(4-hydroxy-3-methylphenyl)-2-oxo-2,3-dihydropyrimidin-4-yl]benzamide |
| 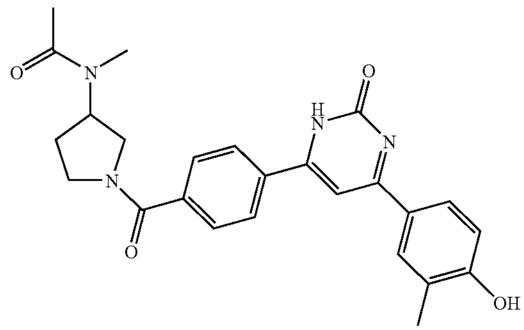 | N-[1-({4-[6-(4-hydroxy-3-methylphenyl)-2-oxo-2,3-dihydropyrimidin-4-yl]phenyl}carbonyl)pyrrolidin-3-yl]-N-methylacetamide |

TABLE 1-continued

| STRUCTURE | NAME |
|---|---|
| 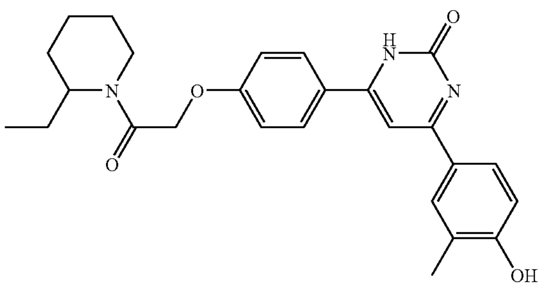 | 6-(4-{[2-(2-ethylpiperidin-1-yl)-2-oxoethyl]oxy}phenyl)-4-(4-hydroxy-3-methylphenyl)pyrimidin-2(1H)-one |
| 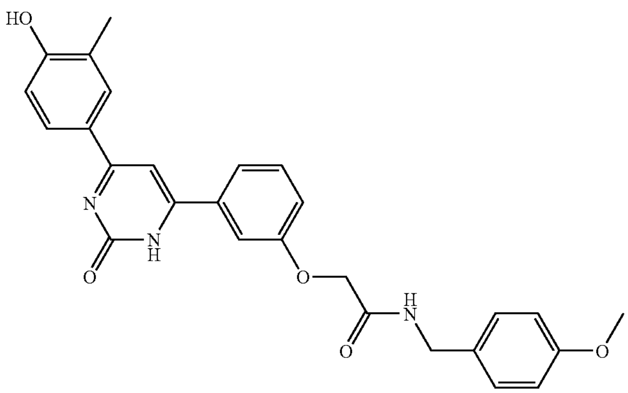 | 2-({3-[6-(4-hydroxy-3-methylphenyl)-2-oxo-2,3-dihydropyrimidin-4-yl]phenyl}oxy)-N-{[4-(methyloxy)phenyl]methyl}acetamide |
| 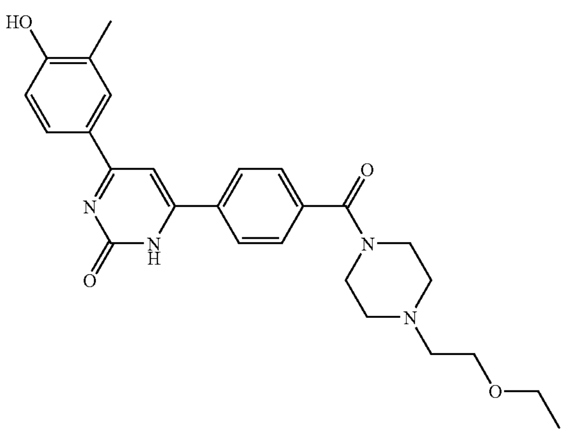 | 6-[4-({4-[2-(ethyloxy)ethyl]piperazin-1-yl}carbonyl)phenyl]-4-(4-hydroxy-3-methylphenyl)pyrimidin-2(1H)-one |
| 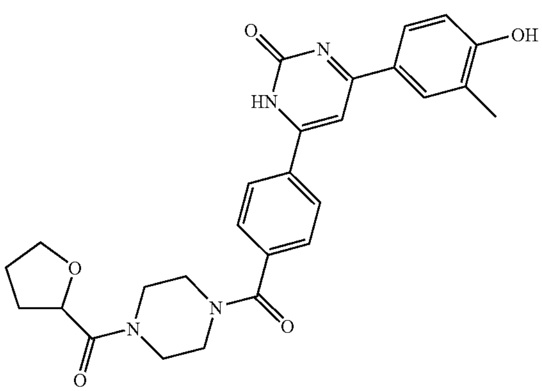 | 4-(4-hydroxy-3-methylphenyl)-6-(4-{[4-(tetrahydrofuran-2-ylcarbonyl)piperazin-1-yl]carbonyl}phenyl)pyrimidin-2(1H)-one |

TABLE 1-continued

| STRUCTURE | NAME |
|---|---|
| 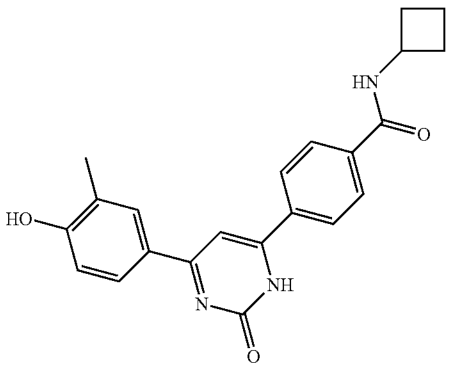 | N-cyclobutyl-4-[6-(4-hydroxy-3-methylphenyl)-2-oxo-2,3-dihydropyrimidin-4-yl]benzamide |
| 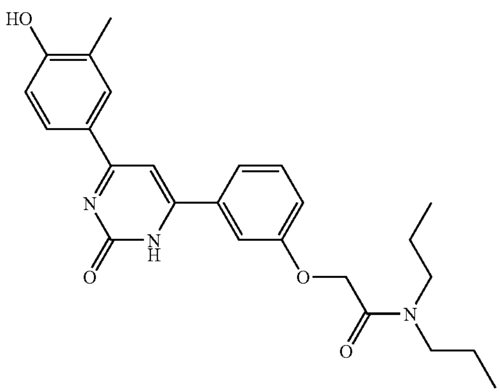 | 2-({3-[6-(4-hydroxy-3-methylphenyl)-2-oxo-2,3-dihydropyrimidin-4-yl]phenyl}oxy)-N,N-dipropylacetamide |
| 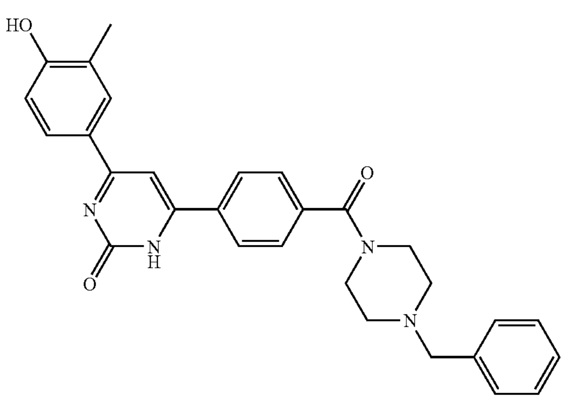 | 4-(4-hydroxy-3-methylphenyl)-6-(4-{[4-(phenylmethyl)piperazin-1-yl]carbonyl}phenyl)pyrimidin-2(1H)-one |

TABLE 1-continued
| STRUCTURE | NAME |
|---|---|
| 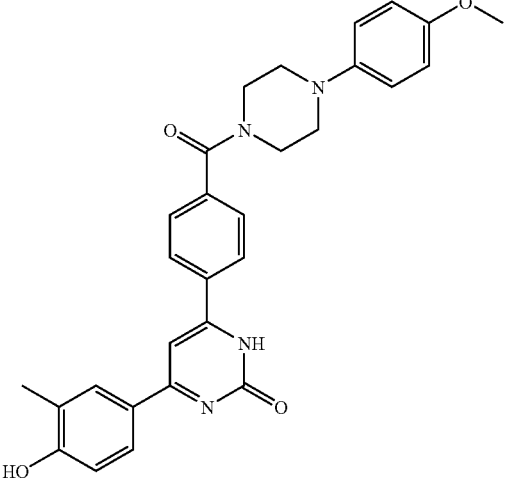 | 4-(4-hydroxy-3-methylphenyl)-6-[4-({4-[4-(methyloxy)phenyl]piperazin-1-yl}carbonyl)phenyl]pyrimidin-2(1H)-one |
| 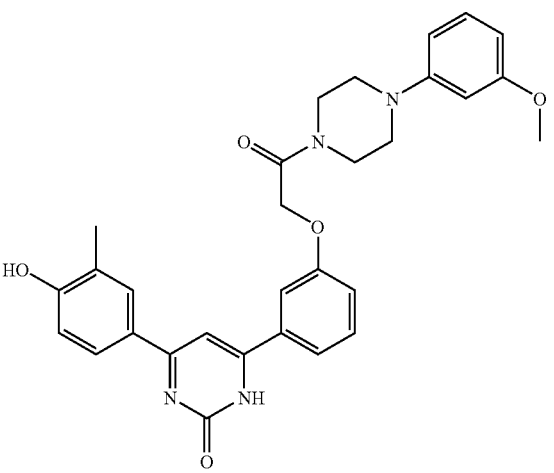 | 4-(4-hydroxy-3-methylphenyl)-6-{3-[(2-{4-[3-(methyloxy)phenyl]piperazin-1-yl}-2-oxoethyl)oxy]phenyl}pyrimidin-2(1H)-one |
| 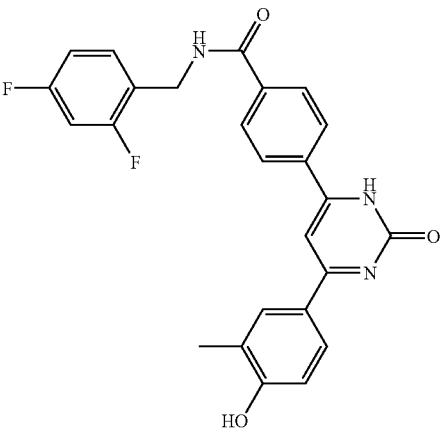 | N-[(2,4-difluorophenyl)methyl]-4-[6-(4-hydroxy-3-methylphenyl)-2-oxo-2,3-dihydropyrimidin-4-yl]benzamide |

TABLE 1-continued

| STRUCTURE | NAME |
| --- | --- |
| 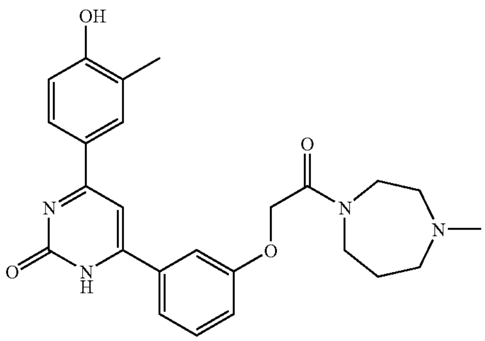 | 4-(4-hydroxy-3-methylphenyl)-6-(3-{[2-(4-methyl-1,4-diazepan-1-yl)-2-oxoethyl]oxy}phenyl)pyrimidin-2(1H)-one |
| 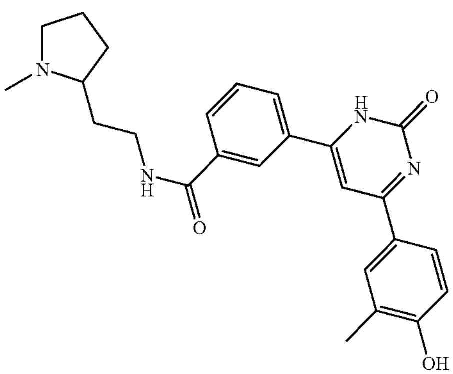 | 3-[6-(4-hydroxy-3-methylphenyl)-2-oxo-2,3-dihydropyrimidin-4-yl]-N-[2-(1-methylpyrrolidin-2-yl)ethyl]benzamide |
| 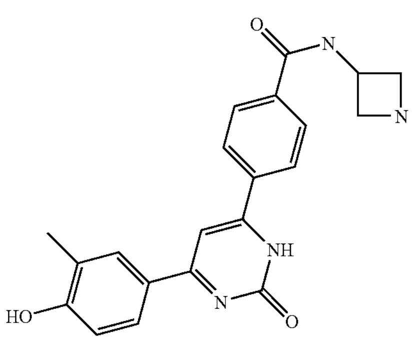 | N-azetidin-3-yl-4-[6-(4-hydroxy-3-methylphenyl)-2-oxo-2,3-dihydropyrimidin-4-yl]benzamide |
| 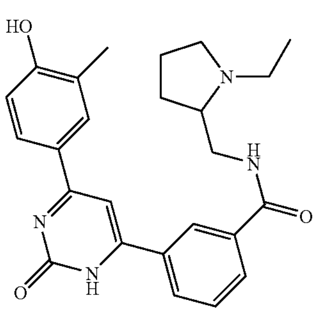 | N-[(1-ethylpyrrolidin-2-yl)methyl]-3-[6-(4-hydroxy-3-methylphenyl)-2-oxo-2,3-dihydropyrimidin-4-yl]benzamide |

TABLE 1-continued

| STRUCTURE | NAME |
|---|---|
| 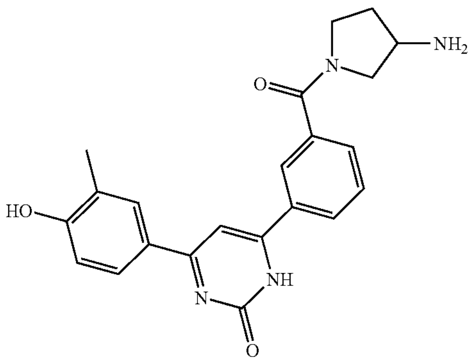 | 6-{3-[(3-aminopyrrolidin-1-yl)carbonyl]phenyl}-4-(4-hydroxy-3-methylphenyl)pyrimidin-2(1H)-one |
| 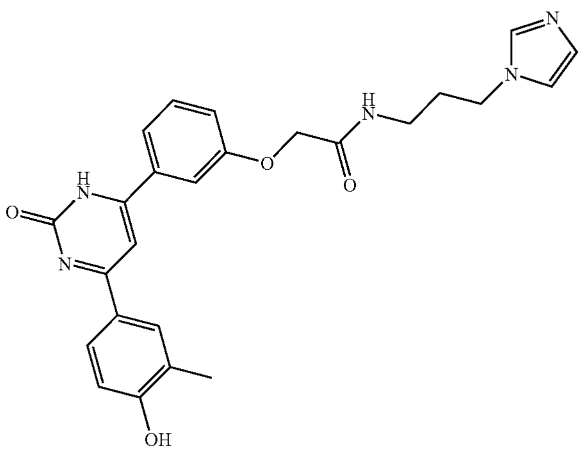 | 2-({3-[6-(4-hydroxy-3-methylphenyl)-2-oxo-2,3-dihydropyrimidin-4-yl]phenyl}oxy)-N-[3-(1H-imidazol-1-yl)propyl]acetamide |
| 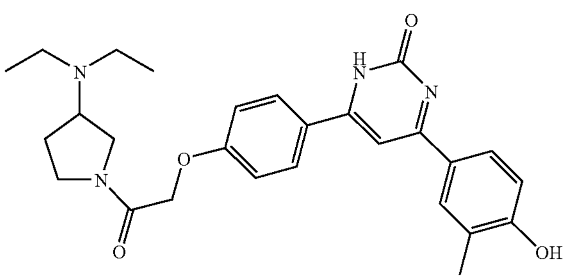 | 6-[4-({2-[3-(diethylamino)pyrrolidin-1-yl]-2-oxoethyl}oxy)phenyl]-4-(4-hydroxy-3-methylphenyl)pyrimidin-2(1H)-one |
| 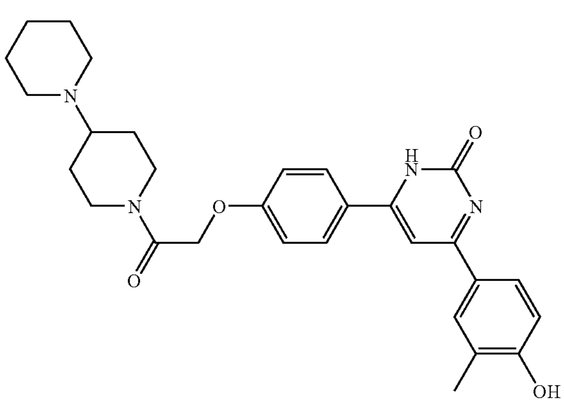 | 6-(4-{[2-(1,4'-bipiperidin-1'-yl)-2-oxoethyl]oxy}phenyl)-4-(4-hydroxy-3-methylphenyl)pyrimidin-2(1H)-one |

TABLE 1-continued

| STRUCTURE | NAME |
|---|---|
| 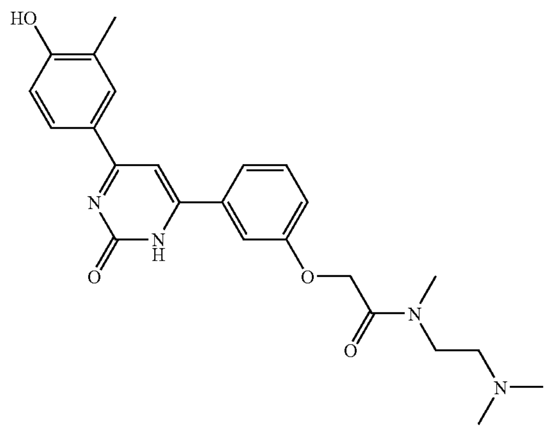 | N-[2-(dimethylamino)ethyl]-2-({3-[6-(4-hydroxy-3-methylphenyl)-2-oxo-2,3-dihydropyrimidin-4-yl]phenyl}oxy)-N-methylacetamide |
| 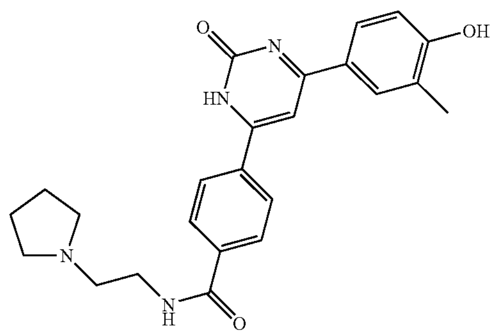 | 4-[6-(4-hydroxy-3-methylphenyl)-2-oxo-2,3-dihydropyrimidin-4-yl]-N-(2-pyrrolidin-1-ylethyl)benzamide |
| 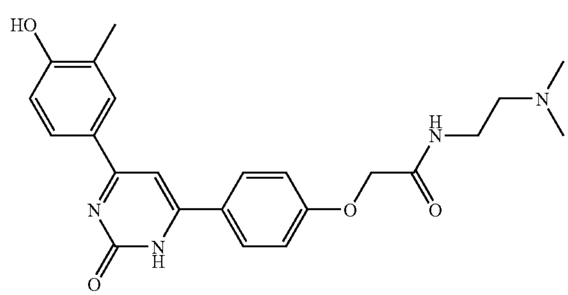 | N-[2-(dimethylamino)ethyl]-2-({4-[6-(4-hydroxy-3-methylphenyl)-2-oxo-2,3-dihydropyrimidin-4-yl]phenyl}oxy)acetamide |
| 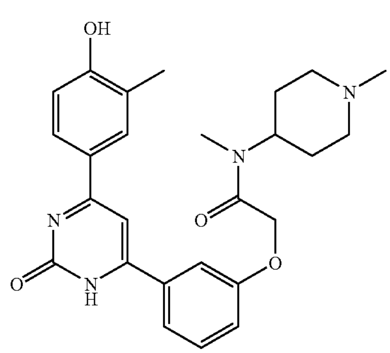 | 2-({3-[6-(4-hydroxy-3-methylphenyl)-2-oxo-2,3-dihydropyrimidin-4-yl]phenyl}oxy)-N-methyl-N-(1-methylpiperidin-4-yl)acetamide |

TABLE 1-continued

| STRUCTURE | NAME |
|---|---|
| 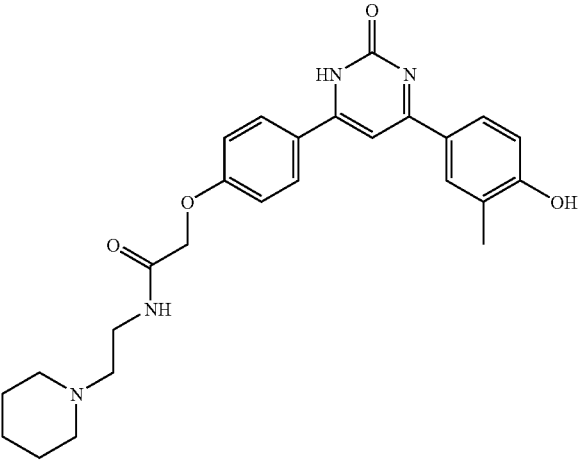 | 2-({4-[6-(4-hydroxy-3-methylphenyl)-2-oxo-2,3-dihydropyrimidin-4-yl]phenyl}oxy)-N-(2-piperidin-1-ylethyl)acetamide |
| 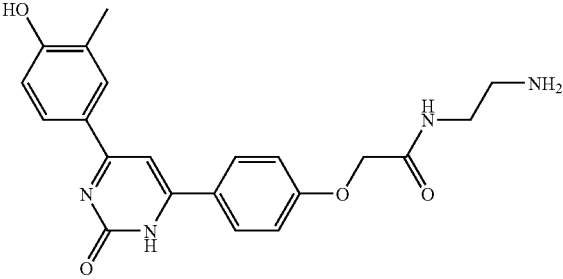 | N-(2-aminoethyl)-2-({4-[6-(4-hydroxy-3-methylphenyl)-2-oxo-2,3-dihydropyrimidin-4-yl]phenyl}oxy)acetamide |
| 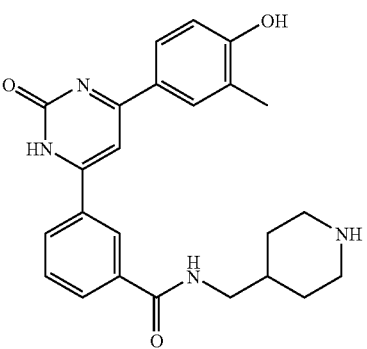 | 3-[6-(4-hydroxy-3-methylphenyl)-2-oxo-2,3-dihydropyrimidin-4-yl]-N-(piperidin-4-ylmethyl)benzamide |
| 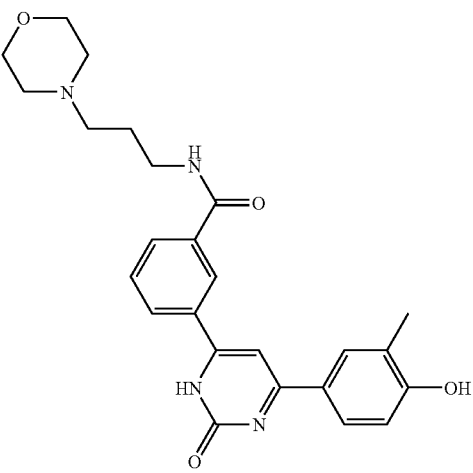 | 3-[6-(4-hydroxy-3-methylphenyl)-2-oxo-2,3-dihydropyrimidin-4-yl]-N-(3-morpholin-4-ylpropyl)benzamide |

TABLE 1-continued

| STRUCTURE | NAME |
|---|---|
| 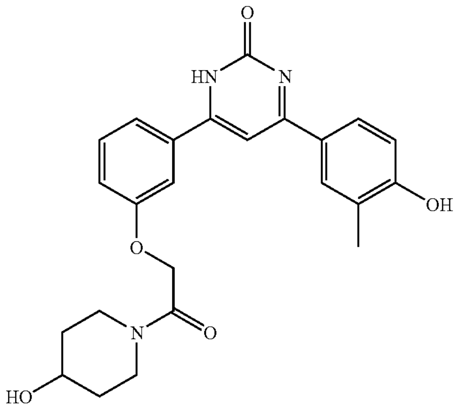 | 4-(4-hydroxy-3-methylphenyl)-6-(3-{[2-(4-hydroxypiperidin-1-yl)-2-oxoethyl]oxy}phenyl)pyrimidin-2(1H)-one |
| 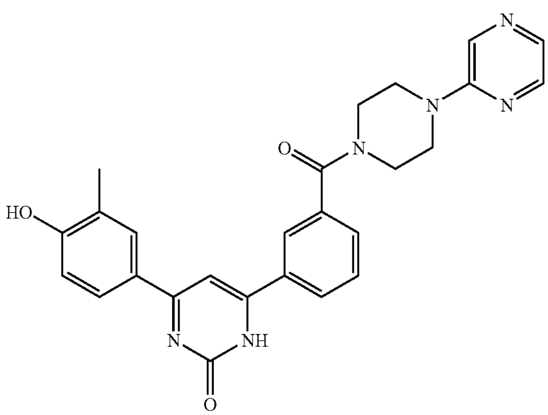 | 4-(4-hydroxy-3-methylphenyl)-6-{3-[(4-pyrazin-2-ylpiperazin-1-yl)carbonyl]phenyl}pyrimidin-2(1H)-one |
| 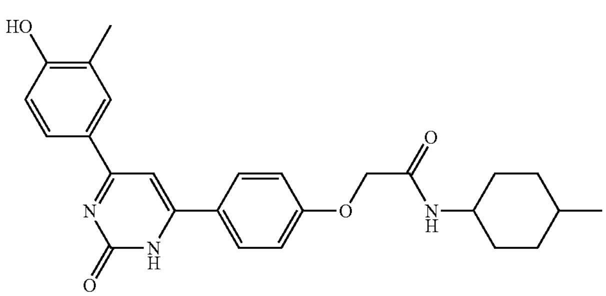 | 2-({4-[6-(4-hydroxy-3-methylphenyl)-2-oxo-2,3-dihydropyrimidin-4-yl]phenyl}oxy)-N-(4-methylcyclohexyl)acetamide |
| 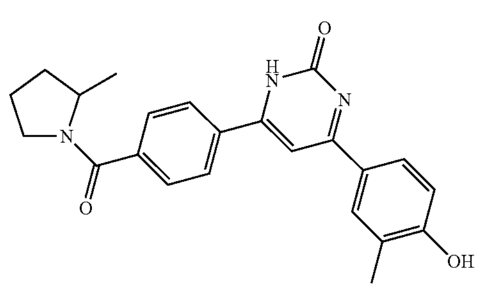 | 4-(4-hydroxy-3-methylphenyl)-6-{4-[(2-methylpyrrolidin-1-yl)carbonyl]phenyl}pyrimidin-2(1H)-one |

TABLE 1-continued

| STRUCTURE | NAME |
|---|---|
| 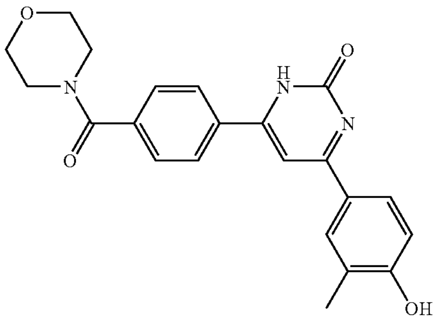 | 4-(4-hydroxy-3-methylphenyl)-6-[4-(morpholin-4-ylcarbonyl)phenyl]pyrimidin-2(1H)-one |
| 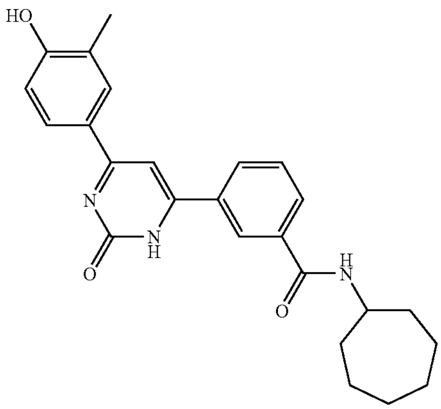 | N-cycloheptyl-3-[6-(4-hydroxy-3-methylphenyl)-2-oxo-2,3-dihydropyrimidin-4-yl]benzamide |
| 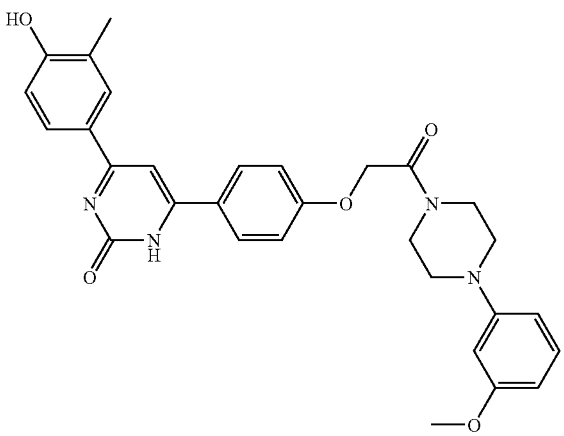 | 4-(4-hydroxy-3-methylphenyl)-6-{4-[(2-{4-[3-(methyloxy)phenyl]piperazin-1-yl}-2-oxoethyl)oxy]phenyl}pyrimidin-2(1H)-one |
| 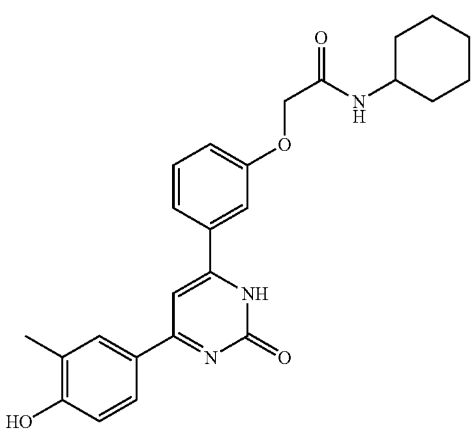 | N-cyclohexyl-2-({3-[6-(4-hydroxy-3-methylphenyl)-2-oxo-2,3-dihydropyrimidin-4-yl]phenyl}oxy)acetamide |

TABLE 1-continued

| STRUCTURE | NAME |
|---|---|
| 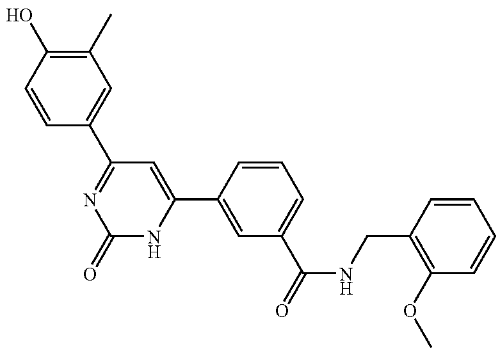 | 3-[6-(4-hydroxy-3-methylphenyl)-2-oxo-2,3-dihydropyrimidin-4-yl]-N-{[2-(methyloxy)phenyl]methyl}benzamide |
| 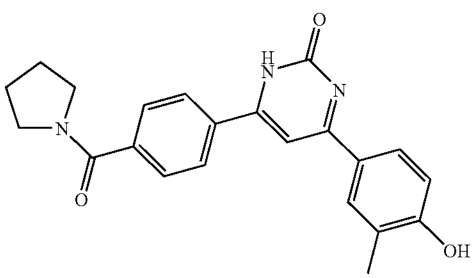 | 4-(4-hydroxy-3-methylphenyl)-6-[4-(pyrrolidin-1-ylcarbonyl)phenyl]pyrimidin-2(1H)-one |
| 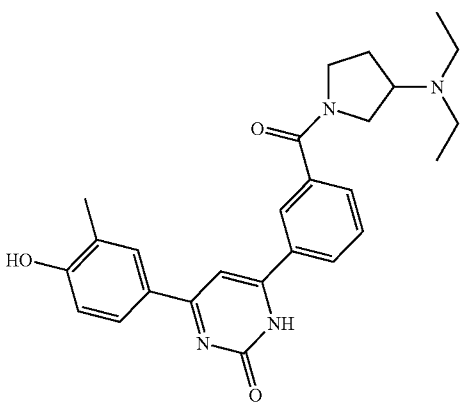 | 6-(3-{[3-(diethylamino)pyrrolidin-1-yl]carbonyl}phenyl)-4-(4-hydroxy-3-methylphenyl)pyrimidin-2(1H)-one |
| 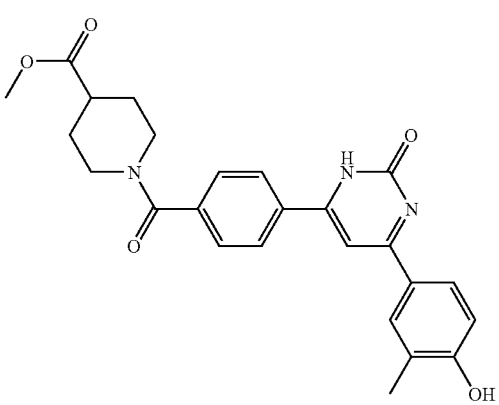 | methyl 1-({4-[6-(4-hydroxy-3-methylphenyl)-2-oxo-2,3-dihydropyrimidin-4-yl]phenyl}carbonyl)piperidine-4-carboxylate |

| STRUCTURE | NAME |
|---|---|
| 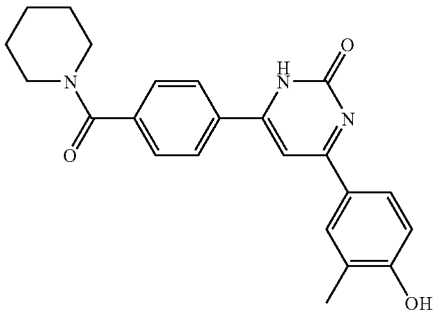 | 4-(4-hydroxy-3-methylphenyl)-6-[4-(piperidin-1-ylcarbonyl)phenyl]pyrimidin-2(1H)-one |
| 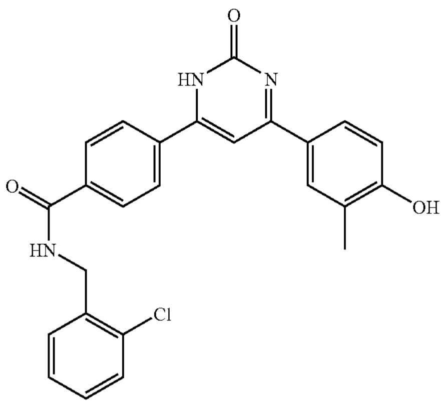 | N-[(2-chlorophenyl)methyl]-4-[6-(4-hydroxy-3-methylphenyl)-2-oxo-2,3-dihydropyrimidin-4-yl]benzamide |
| 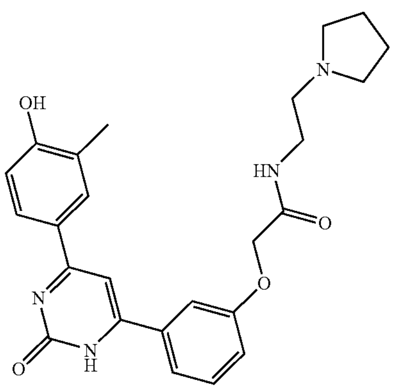 | 2-({3-[6-(4-hydroxy-3-methylphenyl)-2-oxo-2,3-dihydropyrimidin-4-yl]phenyl}oxy)-N-(2-pyrrolidin-1-ylethyl)acetamide |
| 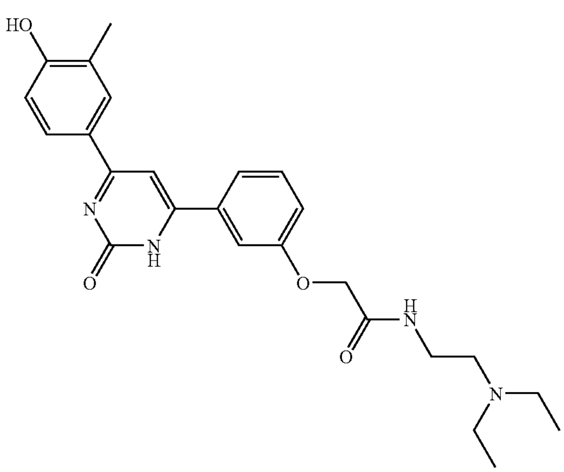 | N-[2-(diethylamino)ethyl]-2-({3-[6-(4-hydroxy-3-methylphenyl)-2-oxo-2,3-dihydropyrimidin-4-yl]phenyl}oxy)acetamide |

TABLE 1-continued

| STRUCTURE | NAME |
|---|---|
| 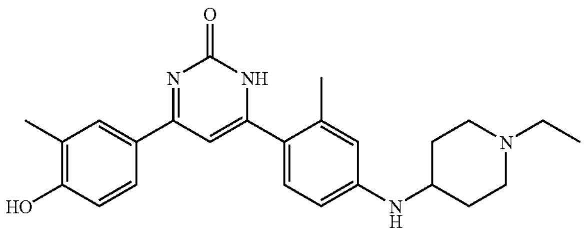 | 6-{4-[(1-ethylpiperidin-4-yl)amino]-2-methylphenyl}-4-(4-hydroxy-3-methylphenyl)pyrimidin-2(1H)-one |
| 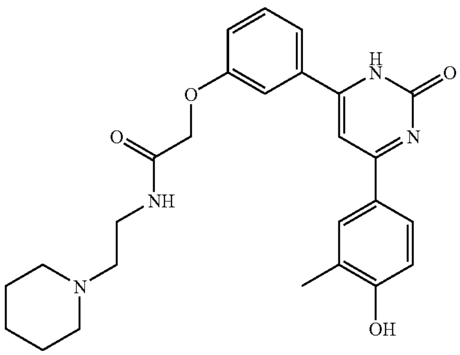 | 2-({3-[6-(4-hydroxy-3-methylphenyl)-2-oxo-2,3-dihydrpyrimidin-4-yl]phenyl}oxy)-N-(2-piperidin-1-ylethyl)acetamide |
| 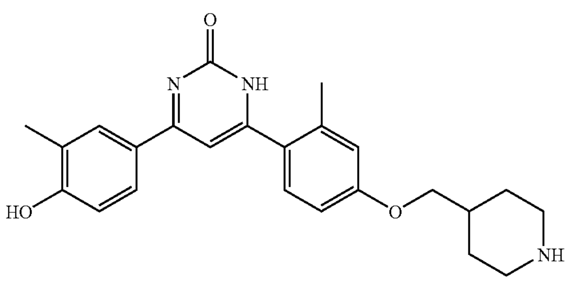 | 4-(4-hydroxy-3-methylphenyl)-6-{2-methyl-4-[(piperidin-4-ylmethyl)oxy]phenyl}pyrimidin-2(1H)-one |
| 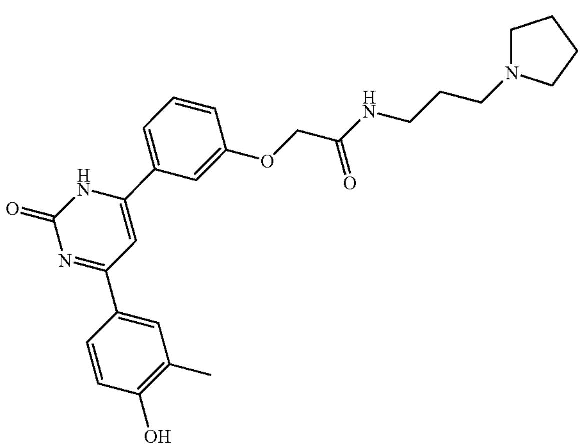 | 2-({3-[6-(4-hydroxy-3-methylphenyl)-2-oxo-2,3-dihydropyrimidin-4-yl]phenyl}oxy)-N-(3-pyrrolidin-1-ylpropyl)acetamide |

TABLE 1-continued

| STRUCTURE | NAME |
| --- | --- |
| 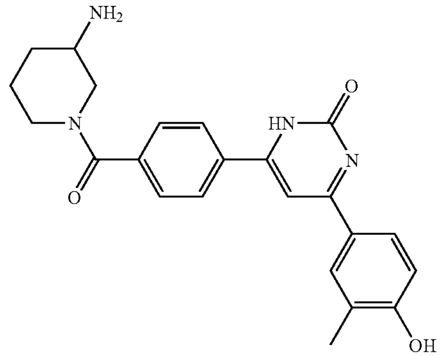 | 6-{4-[(3-aminopiperidin-1-yl)carbonyl]phenyl}-4-(4-hydroxy-3-methylphenyl)pyrimidin-2(1H)-one |
| 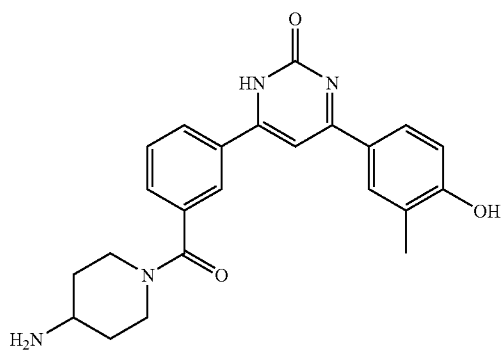 | 6-{3-[(4-aminopiperidin-1-yl)carbonyl]phenyl}-4-(4-hydroxy-3-methylphenyl)pyrimidin-2(1H)-one |
| 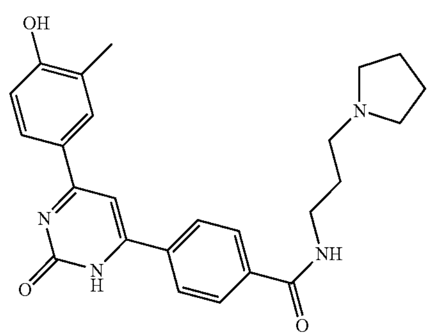 | 4-[6-(4-hydroxy-3-methylphenyl)-2-oxo-2,3-dihydropyrimidin-4-yl]-N-(3-pyrrolidin-1-ylpropyl)benzamide |
| 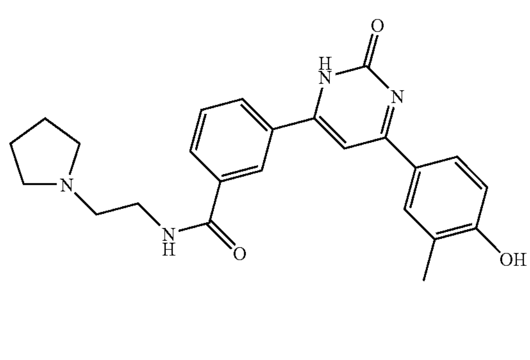 | 3-[6-(4-hydroxy-3-methylphenyl)-2-oxo-2,3-dihydropyrimidin-4-yl]-N-(2-pyrrolidin-1-ylethyl)benzamide |

TABLE 1-continued

| STRUCTURE | NAME |
|---|---|
| 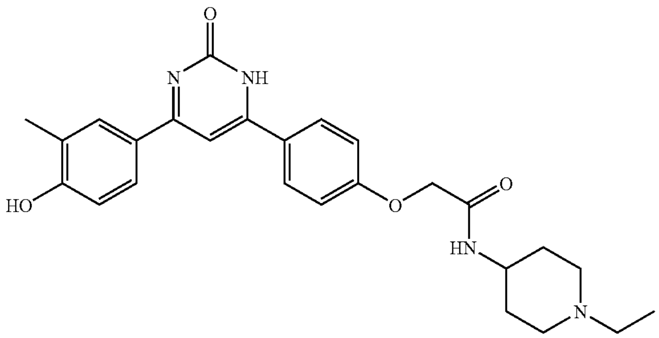 | N-(1-ethylpiperidin-4-yl)-2-({4-[6-(4-hydroxy-3-methylphenyl)-2-oxo-2,3-dihydropyrimidin-4-yl]phenyl}oxy)acetamide |
| 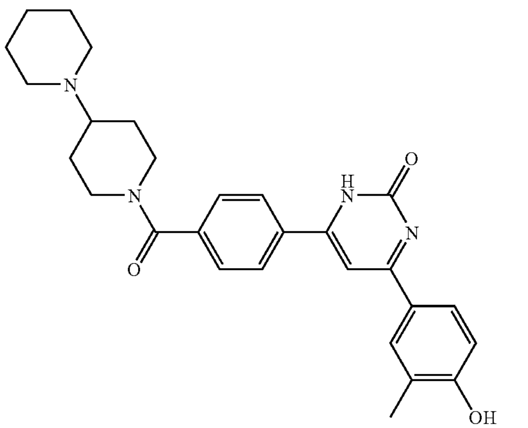 | 6-[4-(1,4'-bipiperidin-1'-ylcarbonyl)phenyl]-4-(4-hydroxy-3-methylphenyl)pyrimidin-2(1H)-one |
| 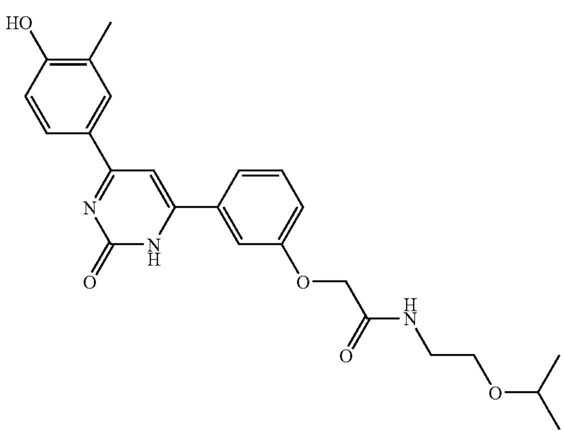 | 2-({3-[6-(4-hydroxy-3-methylphenyl)-2-oxo-2,3-dihydropyrimidin-4-yl]phenyl}oxy)-N-{2-[(1-methylethyl)oxy]ethyl}acetamide |
| 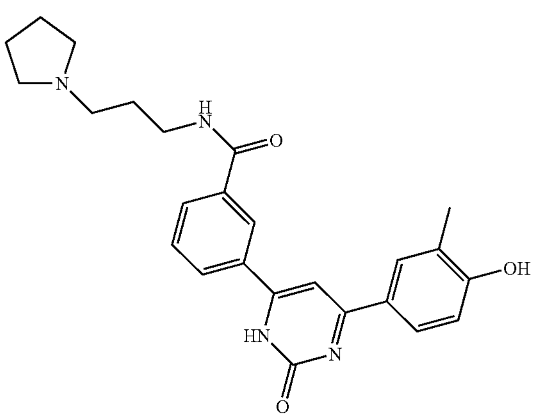 | 3-[6-(4-hydroxy-3-methylphenyl)-2-oxo-2,3-dihydropyrimidin-4-yl]-N-(3-pyrrolidin-1-ylpropyl)benzamide |

TABLE 1-continued

| STRUCTURE | NAME |
|---|---|
| 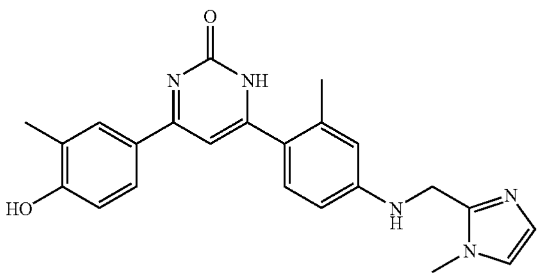 | 4-(4-hydroxy-3-methylphenyl)-6-(2-methyl-4-{[(1-methyl-1H-imidazolo-2-yl)methyl]amino}phenyl)pyrimidin-2(1H)-one |
| 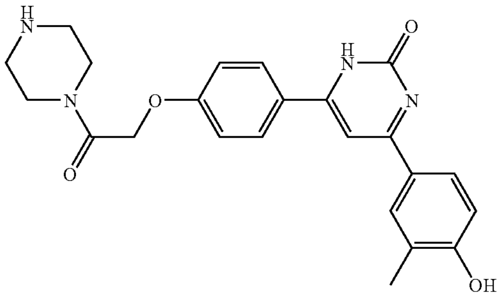 | 4-(4-hydroxy-3-methylphenyl)-6-{4-[(2-oxo-2-piperazin-1-ylethyl)oxy]phenyl}pyrimidin-2(1H)-one |
| 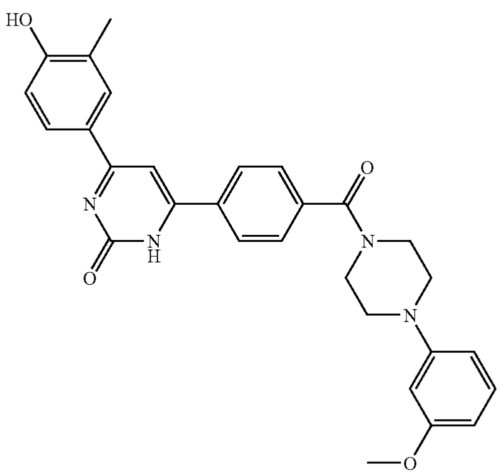 | 4-(4-hydroxy-3-methylphenyl)-6-[4-({4-[3-(methyloxy)phenyl]piperazin-1-yl}carbonyl)phenyl]pyrimidin-2(1H)-one |
| 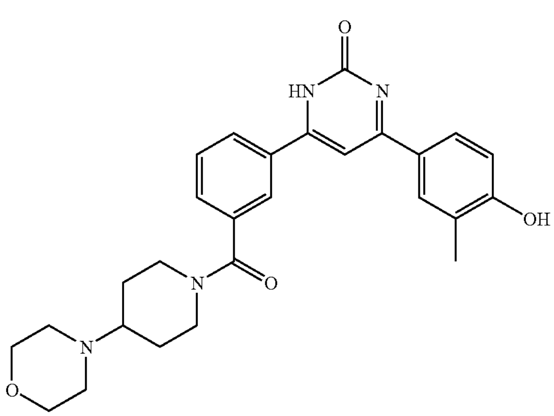 | 4-(4-hydroxy-3-methylphenyl)-6-{3-[(4-morpholin-4-ylpiperidin-1-yl)carbonyl]phenyl}pyrimidin-2(1H)-one |

TABLE 1-continued

| STRUCTURE | NAME |
|---|---|
| 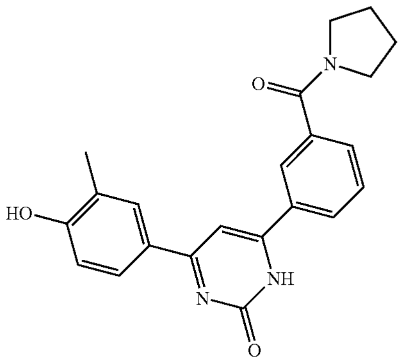 | 4-(4-hydroxy-3-methylphenyl)-6-[3-(pyrrolidin-1-ylcarbonyl)phenyl]pyrimidin-2(1H)-one |
| 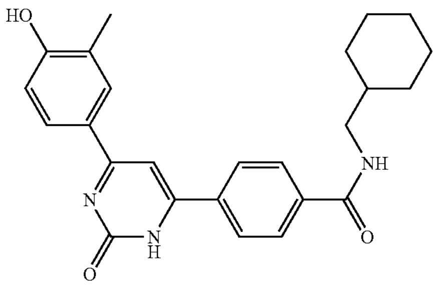 | N-(cyclohexylmethyl)-4-[6-(4-hydroxy-3-methylphenyl)-2-oxo-2,3-dihydropyrimidin-4-yl]benzamide |
| 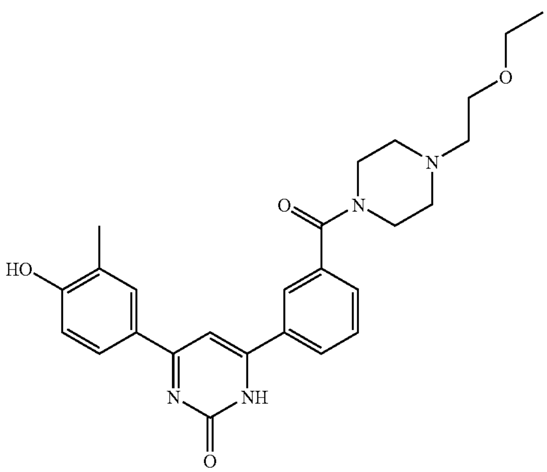 | 6-[3-({4-[2-(ethyloxy)ethyl]piperazin-1-yl}carbonyl)phenyl]-4-(4-hydroxy-3-methylphenyl)pyrimidin-2(1H)-one |
| 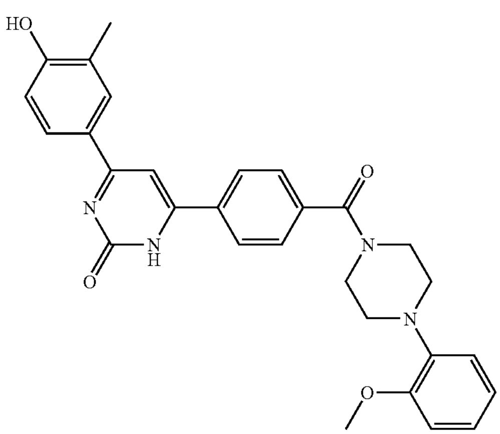 | 4-(4-hydroxy-3-methylphenyl)-6-[4-({4-[2-(methyloxy)phenyl]piperazin-1-yl}carbonyl)phenyl]pyrimidin-2(1H)-one |

TABLE 1-continued

| STRUCTURE | NAME |
|---|---|
| 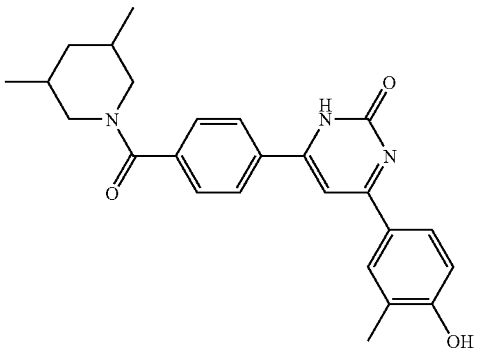 | 6-{4-[(3,5-dimethylpiperidin-1-yl)carbonyl]phenyl}-4-(4-hydroxy-3-methylphenyl)pyrimidin-2(1H)-one |
| 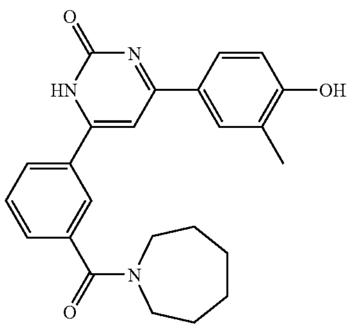 | 6-[3-(azepan-1-ylcarbonyl)phenyl]-4-(4-hydroxy-3-methylphenyl)pyrimidin-2(1H)-one |
| 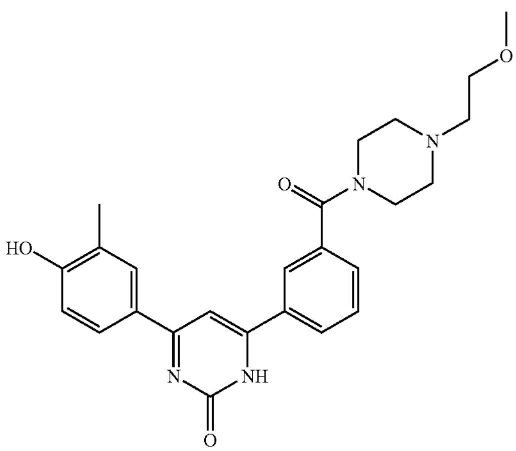 | 4-(4-hydroxy-3-methylphenyl)-6-[3-({4-[2-(methyloxy)ethyl]piperazin-1-yl}carbonyl)phenyl]pyrimidin-2(1H)-one |
| 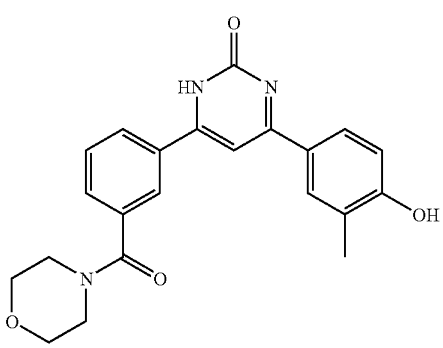 | 4-(4-hydroxy-3-methylphenyl)-6-[3-(morpholin-4-ylcarbonyl)phenyl]pyrimidin-2(1H)-one |

TABLE 1-continued

| STRUCTURE | NAME |
|---|---|
| 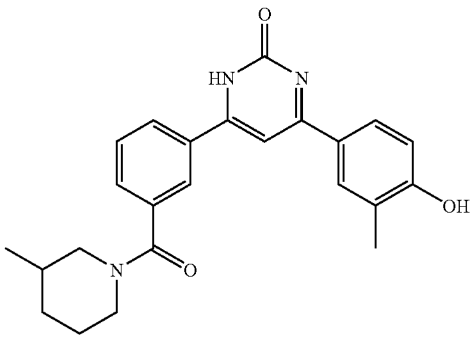 | 4-(4-hydroxy-3-methylphenyl)-6-{3-[(3-methylpiperidin-1-yl)carbonyl]phenyl}pyrimidin-2(1H)-one |
| 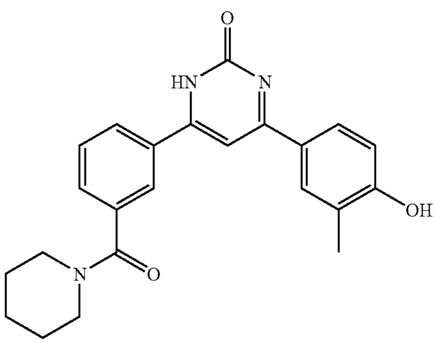 | 4-(4-hydroxy-3-methylphenyl)-6-[3-(piperidin-1-ylcarbonyl)phenyl]pyrimidin-2(1H)-one |
| 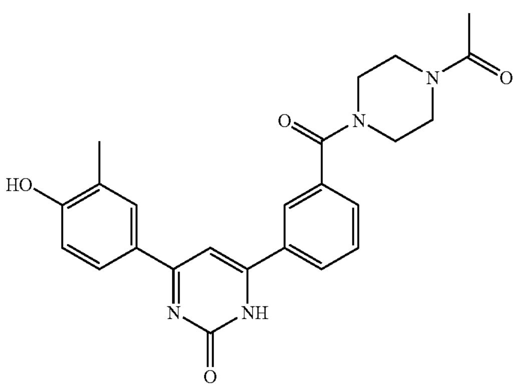 | 6-{3-[(4-acetylpiperazin-1-yl)carbonyl]phenyl}-4-(4-hydroxy-3-methylphenyl)pyrimidin-2(1H)-one |
| 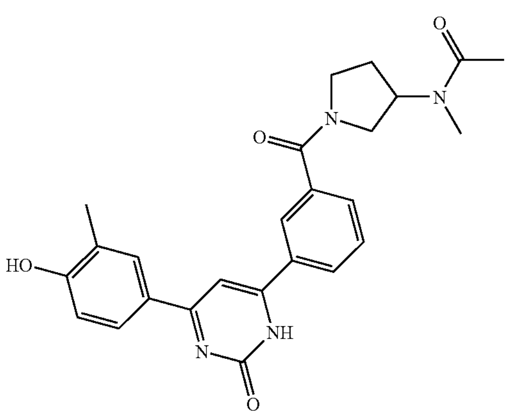 | N-[1-({3-[6-(4-hydroxy-3-methylphenyl)-2-oxo-2,3-dihydropyrimidin-4-yl]phenyl}carbonyl)pyrrolidin-3-yl]-N-methylacetamide |

TABLE 1-continued

| STRUCTURE | NAME |
|---|---|
| 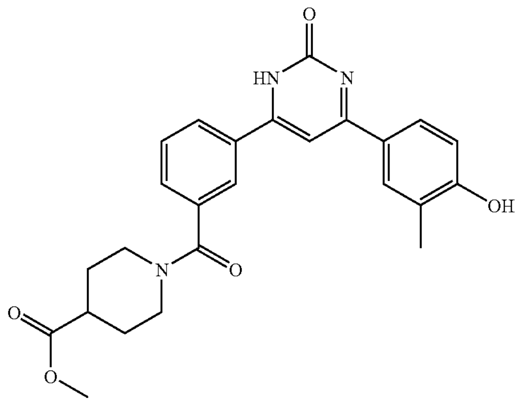 | methyl 1-({3-[6-(4-hydroxy-3-methylphenyl)-2-oxo-2,3-dihydropyrimidin-4-yl]phenyl}carbonyl)piperidine-4-carboxylate |
| 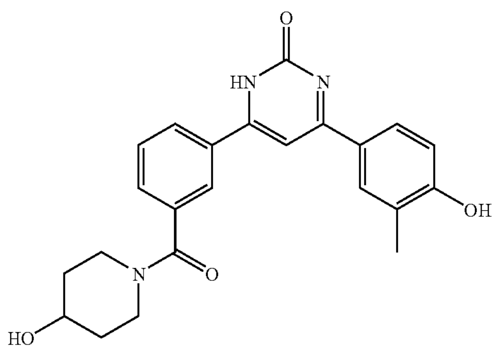 | 4-(4-hydroxy-3-methylphenyl)-6-{3-[(4-hydroxypiperidin-1-yl)carbonyl]phenyl}pyrimidin-2(1H)-one |
| 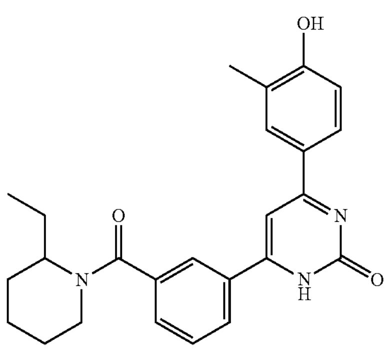 | 6-{3-[(1-ethylpiperidin-1-yl)carbonyl]phenyl}-4-(4-hydroxy-3-methylphenyl)pyrimidin-2(1H)-one |
| 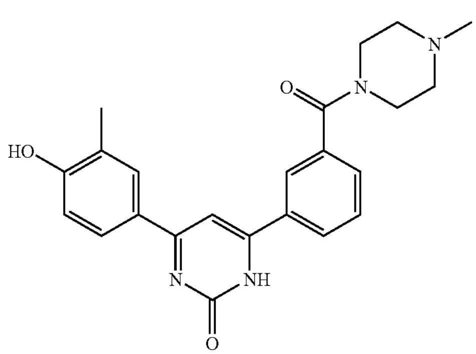 | 4-(4-hydroxy-3-methylphenyl)-6-{3-[(4-methylpiperazin-1-yl)carbonyl]phenyl}pyrimidin-2(1H)-one |

TABLE 1-continued

| STRUCTURE | NAME |
|---|---|
| 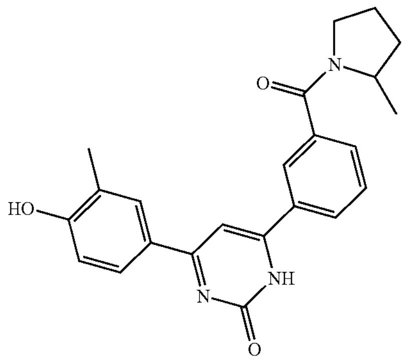 | 4-(4-hydroxy-3-methylphenyl)-6-{3-[(2-methylpyrrolidin-1-yl)carbonyl]phenyl}pyrimidin-2(1H)-one |
| 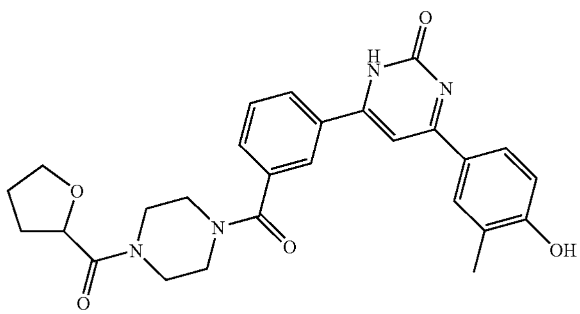 | 4-(4-hydroxy-3-methylphenyl)-6-(3-{[4-(tetrahydrofuran-2-ylcarbonyl)piperazin-1-yl]carbonyl}phenyl)pyrimidin-2(1H)-one |
| 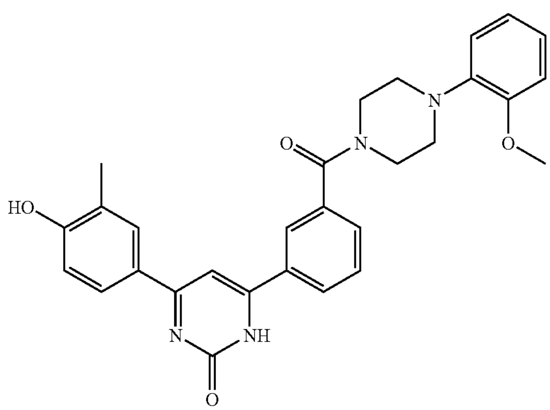 | 4-(4-hydroxy-3-methylphenyl)-6-[3-({4-[2-(methyloxy)phenyl]piperazin-1-yl}carbonyl)phenyl]pyrimidin-2(1H)-one |
| 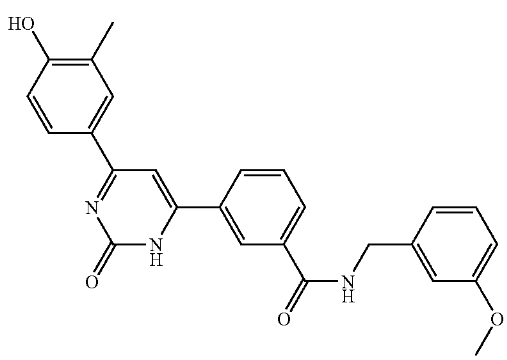 | 3-[6-(4-hydroxy-3-methylphenyl)-2-oxo-2,3-dihydropyrimidin-4-yl]-N-{[3-(methyloxy)phenyl]methyl}benzamide |

TABLE 1-continued

| STRUCTURE | NAME |
|---|---|
| 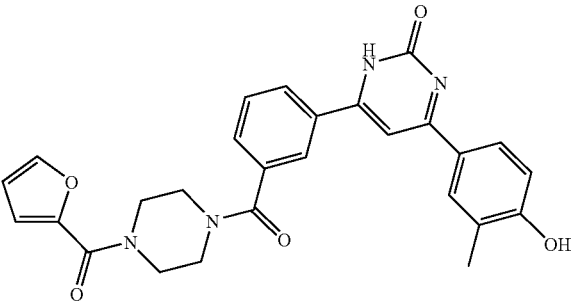 | 6-(3-{[4-(furan-2-ylcarbonyl)piperazin-1-yl]carbonyl}phenyl)-4-(4-hydroxy-3-methylphenyl)pyrimidin-2(1H)-one |
| 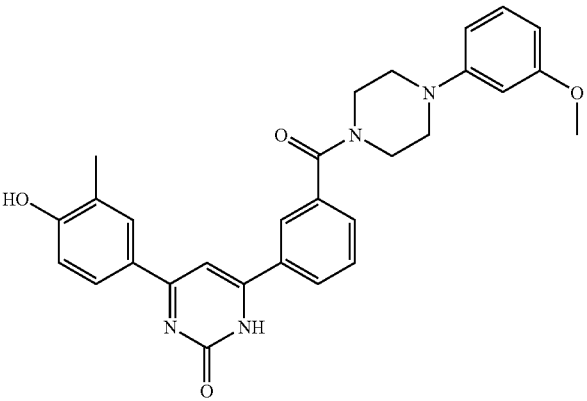 | 4-(4-hydroxy-3-methylphenyl)-6-[3-({4-[3-(methyloxy)phenyl]piperazin-1-yl}carbonyl)phenyl]pyrimidin-2(1H)-one |
| 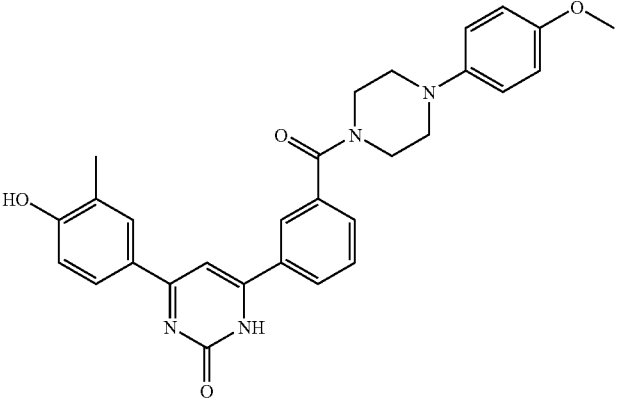 | 4-(4-hydroxy-3-methylphenyl)-6-[3-({4-[4-(methyloxy)phenyl]piperazin-1-yl}carbonyl)phenyl]pyrimidin-2(1H)-one |
| 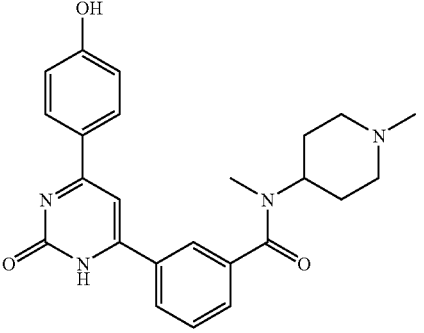 | 3-[6-(4-hydroxy-3-methylphenyl)-2-oxo-2,3-dihydropyrimidin-4-yl]-N-methyl-N-(1-methylpiperidin-4-yl)benzamide |

TABLE 1-continued

| STRUCTURE | NAME |
|---|---|
| 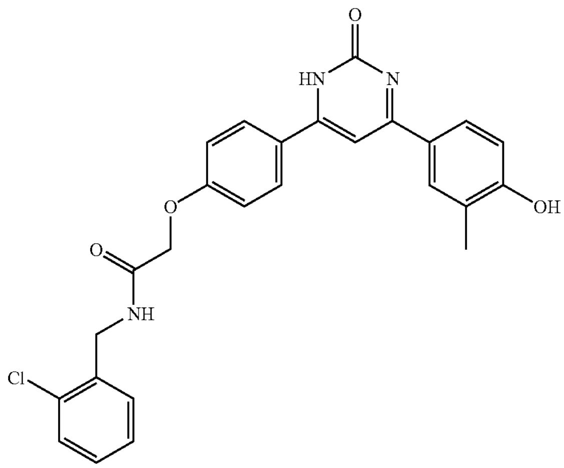 | N-[(2-chlorophenyl)methyl]-2-({4-[6-(4-hydroxy-3-methylphenyl)-2-oxo-2,3-dihydropyrimidin-4-yl]phenyl}oxy)acetamide |
| 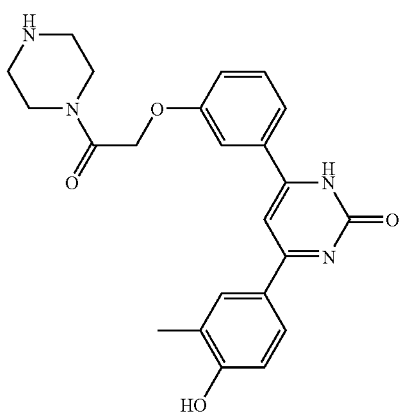 | 4-(4-hydroxy-3-methylphenyl)-6-{3-[(2-oxo-2-piperazin-1-ylethyl)phenyl}pyrimidin-2(1H)-one |
| 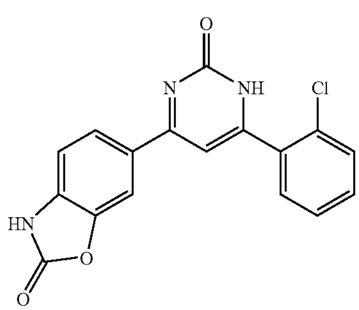 | 6-[6-(2-chlorophenyl)-2-oxo-1,2-dihydropyrimidin-4-yl]-1,3-benzoxazol-2(3H)-one |
| 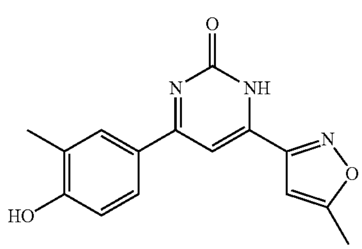 | 4-(4-hydroxy-3-methylphenyl)-6-(5-methylisoxazol-3-yl)pyrimidin-2(1H)-one |

TABLE 1-continued

| STRUCTURE | NAME |
|---|---|
| 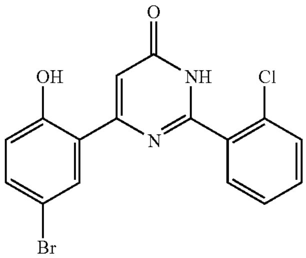 | 6-(5-Bromo-2-hydroxyphenyl)-2-(2-chlorophenyl)pyrimidin-4(3H)-one |
| 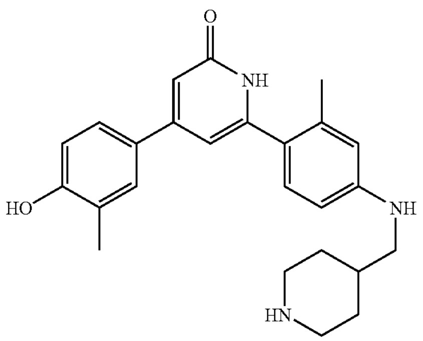 | 4-(4-hydroxy-3-methylphenyl)-6-{2-methyl-4-[(piperidin-4-ylmethyl)amino-]phenyl}pyridin-2(1H)-one |
| 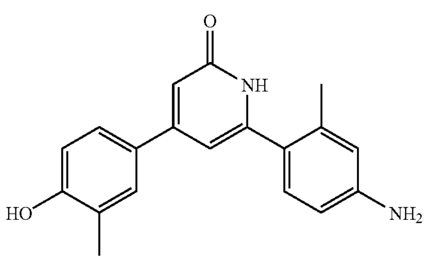 | 6-(2-chlorophenyl)-4-(4-hydroxy-3-methylphenyl)pyridin-2(1H)-one |
| 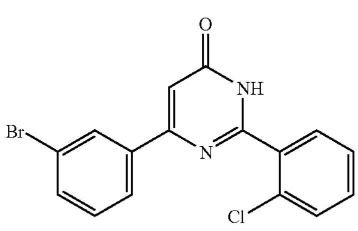 | 6-(3-bromophenyl)-2-(2-chlorophenyl)pyrimidin-4(3H)-one |
| 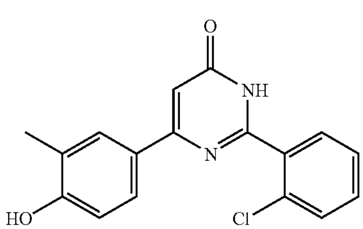 | 2-(2-chlorophenyl)-6-(4-hydroxy-3-methylphenyl)pyrimidin-4(3H)-one |

TABLE II
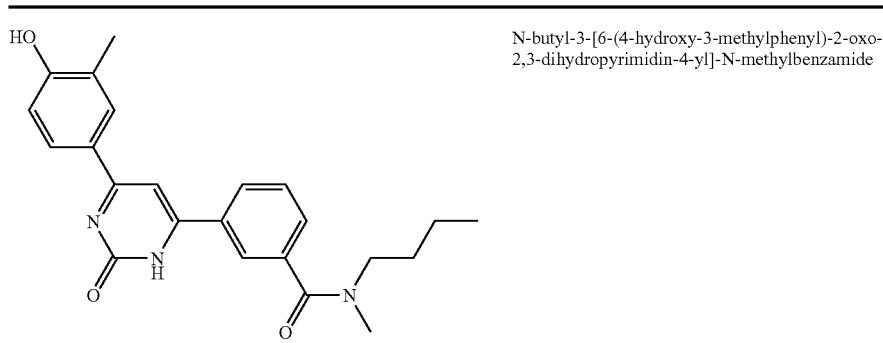
N-butyl-3-[6-(4-hydroxy-3-methylphenyl)-2-oxo-2,3-dihydropyrimidin-4-yl]-N-methylbenzamide
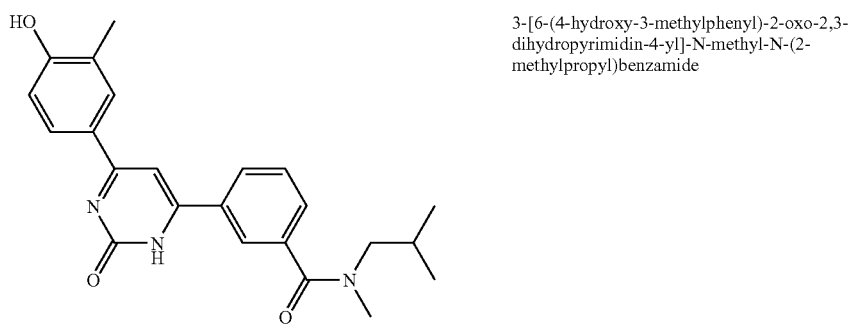
3-[6-(4-hydroxy-3-methylphenyl)-2-oxo-2,3-dihydropyrimidin-4-yl]-N-methyl-N-(2-methylpropyl)benzamide
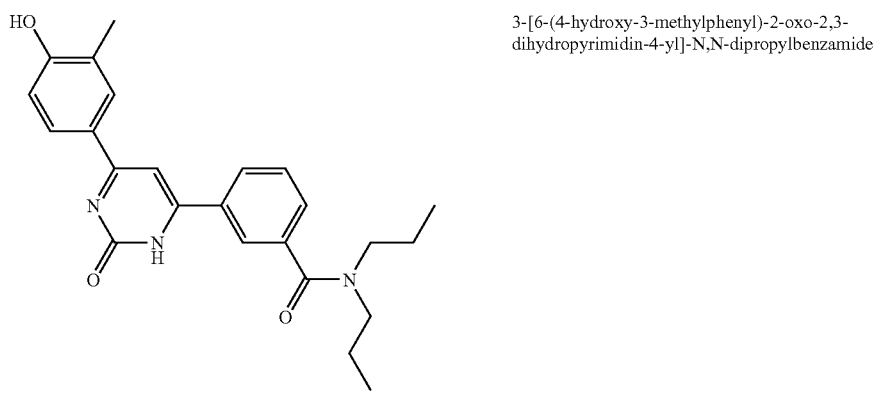
3-[6-(4-hydroxy-3-methylphenyl)-2-oxo-2,3-dihydropyrimidin-4-yl]-N,N-dipropylbenzamide
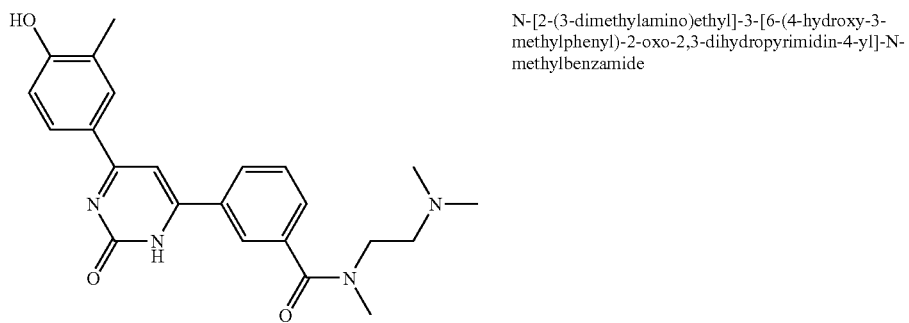
N-[2-(3-dimethylamino)ethyl]-3-[6-(4-hydroxy-3-methylphenyl)-2-oxo-2,3-dihydropyrimidin-4-yl]-N-methylbenzamide TABLE II-continued

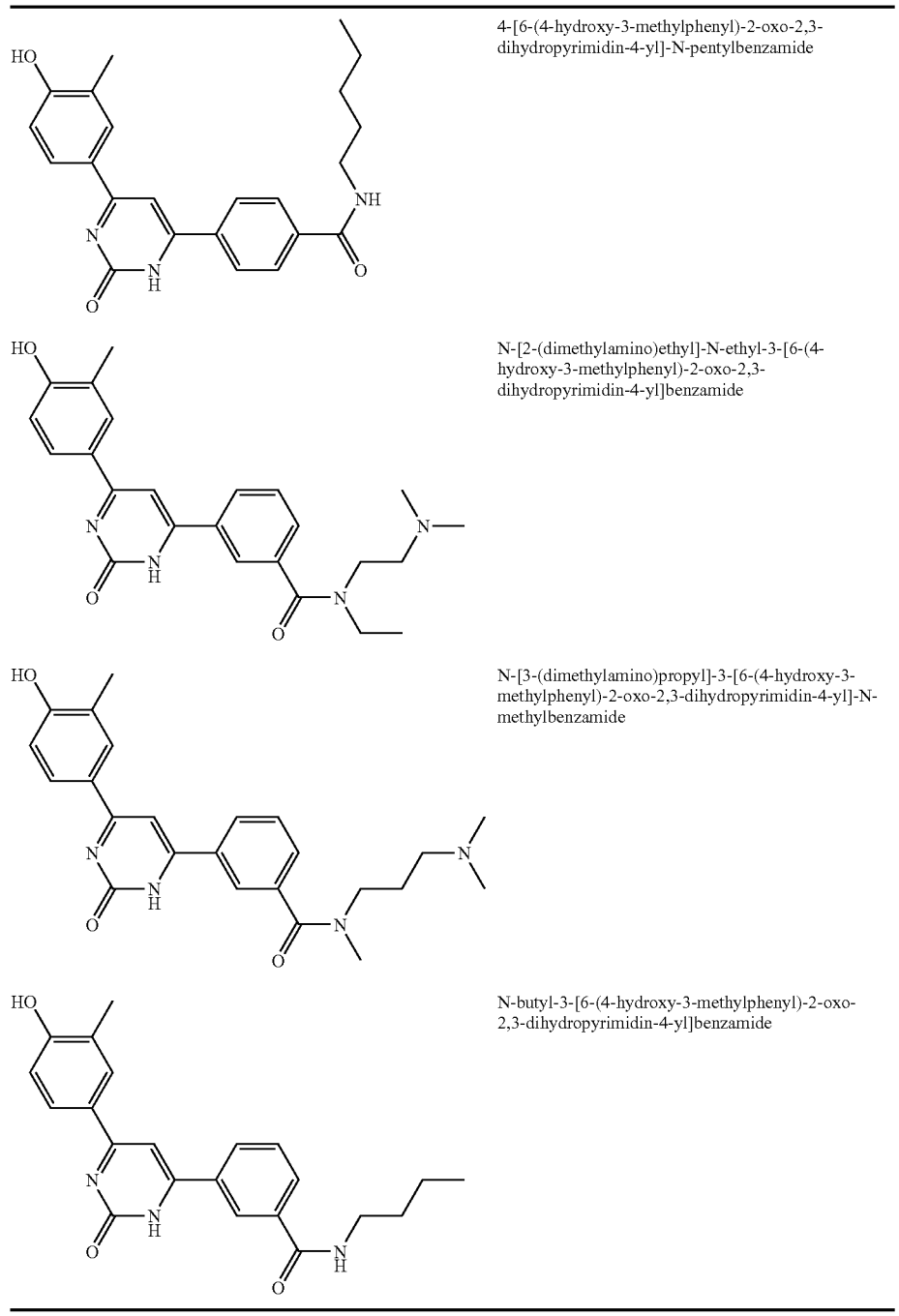

| Structure | Name |
|---|---|
| 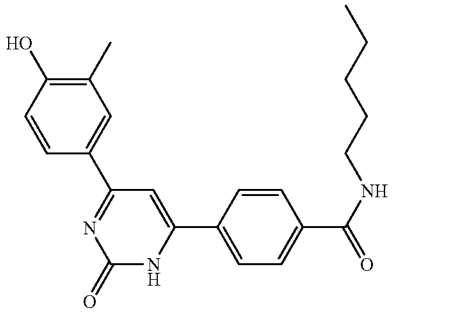 | 4-[6-(4-hydroxy-3-methylphenyl)-2-oxo-2,3-dihydropyrimidin-4-yl]-N-pentylbenzamide |
| 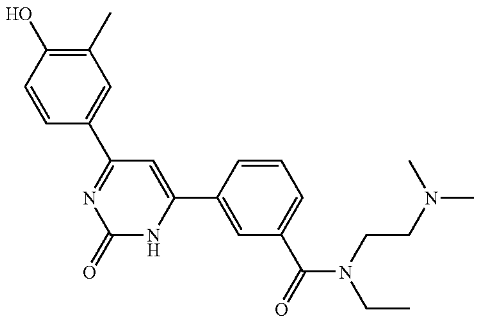 | N-[2-(dimethylamino)ethyl]-N-ethyl-3-[6-(4-hydroxy-3-methylphenyl)-2-oxo-2,3-dihydropyrimidin-4-yl]benzamide |
| 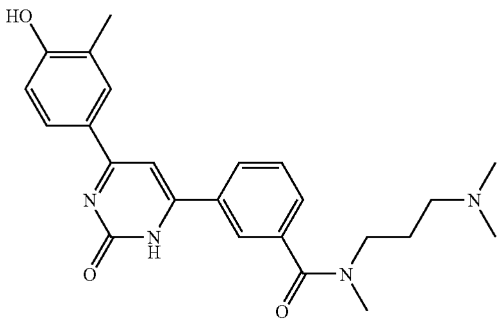 | N-[3-(dimethylamino)propyl]-3-[6-(4-hydroxy-3-methylphenyl)-2-oxo-2,3-dihydropyrimidin-4-yl]-N-methylbenzamide |
| 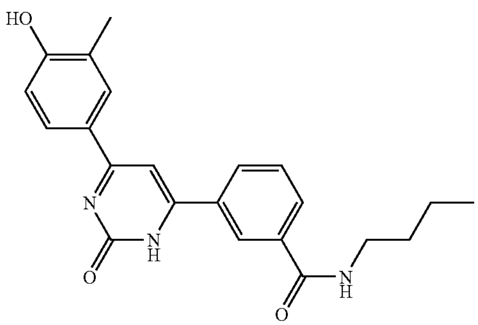 | N-butyl-3-[6-(4-hydroxy-3-methylphenyl)-2-oxo-2,3-dihydropyrimidin-4-yl]benzamide |

The compounds in the tables above can be prepared using methods known to the skilled artisan, and by making any appropriate substitutions in reactants, reagents, or reaction conditions, if necessary, that one skilled in the art would recognize how to do.

In another embodiment, the compound of Formula I or II is selected from a compound in Table 1.

In another embodiment, the compound of Formula I or II is selected from a compound in Table 2.

ABBREVIATIONS AND DEFINITIONS

The following abbreviations and terms have the indicated meanings throughout:

| Abbreviation | Meaning |
|---|---|
| Ac | Acetyl |
| ° C. | degrees Celsius |
| CBZ | CarboBenZoxy = benzyloxycarbonyl |
| D | Doublet |
| DIPEA | N,N-diisopropylethylamine |
| DMF | N,N-dimethylformamide |
| DMSO | dimethyl sulfoxide |
| EI | Electron Impact ionization |
| Et | Ethyl |
| G | gram(s) |

| Abbreviation | Meaning |
|---|---|
| GC | gas chromatography |
| h or hr | hour(s) |
| HOAc | acetic acid |
| HOBt | Hydroxybenzotriazole |
| HPLC | high pressure liquid chromatography |
| l or L | liter(s) |
| M | molar or molarity |
| M | Multiplet |
| Me | Methyl |
| Mesyl | Methanesulfonyl |
| Mg or mg | milligram(s) |
| MHz | megahertz (frequency) |
| Min | minute(s) |
| mL | milliliter(s) |
| mM | Millimolar |
| Mmol | millimole(s) |
| Mol or mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | Nanomolar |
| NMO | N-methylmorpholine oxide |
| NMR | nuclear magnetic resonance spectroscopy |
| Ph | Phenyl |
| PhOH | Phenol |
| PPTS | Pyridinium p-toluenesulfonate |
| Q | Quartet |
| RT or rt | Room temperature |
| Sat'd | Saturated |
| S | Singlet |
| t | Triplet |
| TFA | trifluoroacetic acid |
| THF | Tetrahydrofuran |
| TMOF | trimethyl orthoformate |
| TMS | Trimethylsilyl |
| Tosyl | p-toluenesulfonyl |
| uL | microliter(s) |
| uM | Micromole(s) or micromolar |
| LS/MSD | A type of Liquid Chromatography Mass Spectrometer |
| PPh$_3$ | Triphenylphosphine |

Definitions

As used in the present specification, the following words and phrases are generally intended to have the meanings as set forth below, except to the extent that the context in which they are used indicates otherwise or they are expressly defined to mean something different.

The symbol "—" means a single bond and/or the point of attachment of a particular group to the parent moeity, "=" means a double bond, "≡" means a triple bond, "---" means a single or double bond. When a group is depicted removed from its parent formula, the "⌇" symbol will be used at the end of the bond which was theoretically cleaved in order to separate the group from its parent structural formula. Thus, the point of attachment of a —(C$_1$-C$_6$)alkyl-(C$_6$-C$_{10}$)aryl group to the parent moiety is at the —(C$_1$-C$_6$)alkyl moiety of this group.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

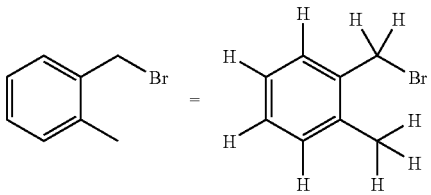

If a group "R" is depicted as "floating" on a ring system, as for example in the formula:

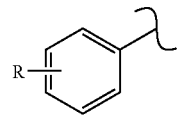

then, unless otherwise defined, a substituent "R" can reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

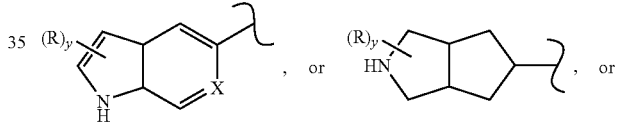

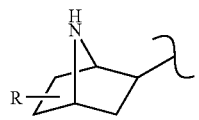

then, unless otherwise defined, a substituent "R" can reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group can reside on either the 5-membered or the 6-membered ring of the fused ring system. In the formula depicted above, when y is 2 for example, then the two "R's" can reside on any two atoms of the ring system, again assuming each replaces a depicted, implied, or expressly defined hydrogen on the ring.

When a group "R" is depicted as existing on a ring system containing saturated carbons, as for example in the formula:

where, in this example, "y" can be more than one, assuming each replaces a currently depicted, implied, or expressly defined hydrogen on the ring; then, unless otherwise defined, where the resulting structure is stable, two "R's" can reside on the same carbon. A simple example is when R is a methyl group; there can exist a geminal dimethyl on a carbon of the depicted ring (an "annular" carbon). In another example, two R's on the same carbon, including that carbon, can form a ring, thus creating a spirocyclic ring (a "spirocyclyl" group) structure with the depicted ring as for example in the formula:

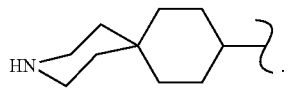

"($C_1$-$C_6$)alkyl" is intended to mean $C_1$-$C_6$ linear or branched structures and combinations thereof, inclusively. For example, "$C_6$ alkyl" can refer to an n-hexyl, iso-hexyl, and the like. ($C_1$-$C_6$)alkyl is intended to include, without limitation, ($C_1$-$C_4$)alkyl and ($C_1$-$C_3$)alkyl. Examples of ($C_1$-$C_6$)alkyl groups include methyl, ethyl, propyl, isopropyl, butyl, s-butyl, t-butyl, isobutyl, pentyl, hexyl and the like. In this application, alkyl refers to alkanyl, alkenyl, and alkynyl residues (and combinations thereof); it is intended to include vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl.

"($C_3$-$C_{10}$)cycloalkyl" means a non-aromatic mono- or multicyclic ring system comprising about 3 to 10 carbon atoms. ($C_3$-$C_{10}$)cycloalkyl is intended to include, without limitation, ($C_5$-$C_6$)cycloalkyl. Non-limiting examples of monocyclic cycloalkyls include cyclopropyl, cyclopentyl, cyclohexyl, cycloheptyl and the like. Non-limiting examples of multicyclic cycloalkyls include 1-decalin, norbornyl, adamantyl and the like. Cycloalkyls can be fused or bridge ring systems or spirocyclic systems.

"Alkylene" is a subset of alkyl and refers to straight or branched chain divalent group consisting solely of carbon and hydrogen atoms, containing no unsaturation and having from one to six carbon atoms, for example, methylene, ethylene, propylene, n-butylene and the like. Alkylene refers to the same residues as alkyl, but having two points of attachment and, specifically, fully saturated. Examples of alkylene include ethylene (—$CH_2CH_2$—), propylene (—$CH_2CH_2CH_2$—), and dimethylpropylene (—$CH_2C(CH_3)_2CH_2$—).

"alkylene," when optionally substituted, can contain alkyl substitution which itself contains unsaturation "($C_1$-$C_6$)alkoxy" refers to the group O—($C_1$-$C_6$)alkyl, wherein the term "($C_1$-$C_6$)alkyl" is as defined hereinabove. "($C_1$-$C_6$)alkoxy" is intended to include, without limitation, ($C_1$-$C_4$)alkoxy and ($C_1$-$C_3$)alkoxy. Examples include methoxy, ethoxy, propoxy, isopropoxy, and the like.

"($C_6$-$C_{10}$)aryl" means a monovalent six- to ten-membered mono- or multicyclic ring, wherein the monocyclic ring is aromatic and at least one of the rings in the multicyclic ring is aromatic. "($C_6$-$C_{10}$)aryl" is intended to include "($C_6$)aryl. Representative non-limiting examples of aryl include phenyl, naphthyl, and indanyl, and the like.

"—($C_1$-$C_6$)alkyl-($C_6$-$C_{10}$)aryl," is intended to mean a ($C_6$-$C_{10}$)aryl moiety attached to a parent structure via ($C_1$-$C_6$) alkylene group. Examples include benzyl, phenethyl, and the like.

In some examples, as appreciated by one of ordinary skill in the art, two adjacent groups on an aromatic system can be fused together to form a ring structure. The fused ring structure can contain heteroatoms and can be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems includes non-aromatic and aromatic systems. Typically, but not necessarily, fused-polycyclics share a vicinal set of atoms, for example naphthalene or 1,2,3,4-tetrahydro-naphthalene. A Spiro ring system is not a fused-polycyclic by this definition, but fused polycyclic ring systems of the invention can themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl groups that are substituted with one or more halogens, respectively. Non-limiting examples of "haloalkyl" include —$CH_2F$, —$CHCl_2$ or —$CF_3$.

"Heteroatom" refers to O, S, N, or P.

"(4-10 membered)heterocycloalkyl" refers to a stable four- to ten-membered ring substituent that consists of carbon atoms and from one to five heteroatoms selected from the nitrogen, phosphorus, oxygen and sulfur. For purposes of this invention, the heterocycloalkyl substituent can be a monocyclic or a multicyclic ring system, which can include fused or bridged ring systems as well as spirocyclic systems. "(4-10 membered)heterocycloalkyl" is intended to include without limitation, (4-6 membered)heterocycloalkyl.

"(5-10 membered)heteroaryl" refers to a stable five- to ten-membered ring substituent that consists of carbon atoms and from one to five heteroatoms selected from the nitrogen, phosphorus, oxygen and sulfur. For purposes of this invention, the heteroaryl substituent can be a monocyclic or a multicyclic ring system, which can include fused or bridged ring systems as well as spirocyclic systems. "(5-10 membered)heteroaryl" is intended to include without limitation, (5-6 membered)heteroaryl.

In the above heteroaryl and heterocycloalkyl substituents, the nitrogen, phosphorus, carbon or sulfur atoms can be optionally oxidized to various oxidation states. In a specific example, the group —$S(O)_{0-2}$—, refers to —S-(sulfide), —S(O)— (sulfoxide), and —$SO_2$— (sulfone) respectively. For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms can be optionally quaternized; and the ring substituent can be partially or fully saturated or aromatic.

Non-limiting examples of (4-10 membered)heterocycloalkyl and (5-10 membered)heteroaryl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, tetrahydrofuranyl, tetrahydroisoquinolinyl, and tetrahydroquinolinyl.

Other examples of "(5-10 membered)heteroaryl" include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzdioxolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Fused, bridged, and Spiro moieties are also included within the scope of this definition.

When a group is referred to as "—$(C_1-C_6)$alkyl-(4-10 membered)heterocycloalkyl" the heterocycloalkyl is attached to a parent structure via one of an alkylene, alkylidene, or alkylidyne group. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl and the corresponding alkylene, alkylidene, or alkylidyne portion of a heterocyclylalkyl group can be optionally substituted.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" means "substituted or unsubstituted" and refers to all subsequent modifiers in a term unless otherwise specified. So, for example, in the term "optionally substituted aryalkyl," both the "alkyl" portion and the "aryl" portion of the molecule may or may not be substituted. A list of exemplary optional substitutions is presented below in the definition of "substituted."

"Saturated bridged ring system" refers to a bicyclic or polycyclic ring system that is not aromatic. Such a system can contain isolated or conjugated unsaturation, but not aromatic or heteroaromatic rings in its core structure (but can have aromatic substitution thereon). For example, hexahydro-furo[3,2-b]furan, 2,3,3a,4,7,7a-hexahydro-1H-indene, 7-azabicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

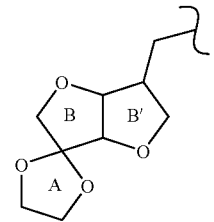

Some of the compounds of the invention can have imino, amino, oxo or hydroxy substituents off aromatic heterocyclyl systems. For purposes of this disclosure, it is understood that such imino, amino, oxo or hydroxy substituents can exist in their corresponding tautomeric form, i.e., amino, imino, hydroxy or oxo, respectively.

The compounds of the invention, or their pharmaceutically acceptable salts, can have asymmetric carbon atoms, oxidized sulfur atoms or quaternized nitrogen atoms in their structure.

The compounds of the invention and their pharmaceutically acceptable salts can exist as single stereoisomers, racemates, and as mixtures of enantiomers and diastereomers. The compounds can also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that theoretically some constructs which would not normally be considered as stable compounds (that is, sterically practical and/or synthetically feasible, supra).

When a particular group with its bonding structure is denoted as being bonded to two partners; that is, a divalent group, for example, —$OCH_2$—, then it is understood that either of the two partners can be bound to the particular group at one end, and the other partner is necessarily bound to the other end of the particular group, unless stated explicitly otherwise. Stated another way, divalent groups are not to be construed as limited to the depicted orientation, for example "—$OCH_2$—" is meant to mean not only "—$OCH_2$—" as drawn, but also "—$CH_2O$—."

In addition to the various embodiments recited hereinabove, also encompassed by this invention are combinations of the embodiments described herein.

Methods for the preparation and/or separation and isolation of single stereoisomers from racemic mixtures or non-racemic mixtures of stereoisomers are well known in the art. For example, optically active (R)- and (S)-isomers can be prepared using chiral synthons or chiral reagents, or resolved using conventional techniques. Enantiomers (R- and S-isomers) can be resolved by methods known to one of ordinary skill in the art, for example by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step can be required to liberate the desired enantiomeric form. Alternatively, specific enantiomer can be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer can be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, can also modulate, either directly or indirectly, phosphatase activity. This additional modulation, if present, can be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to, benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt can be the biologically active form of the compound in the body. In one example, a prodrug can be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention. All compounds of this invention described in all aspects and embodiments herein are intended to include both solvated and unsolvated forms thereof.

It is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition can be necessary, and will be ascertainable with routine experimentation by one of ordinary skill in the art.

One of ordinary skill in the art would understand that certain crystallized, protein-ligand complexes, in particular PIM-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods can be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods can further entail: performing rational drug design with the model of the three-dimensional structure, and selecting a potential candidate agent in conjunction with computer modeling.

Additionally, one skilled in the art would appreciate that such methods can further entail: employing a candidate agent, so-determined to fit spatially into the ligand binding domain, in a biological activity assay for kinase modulation, and determining whether said candidate agent modulates kinase activity in the assay. Such methods can also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method can be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

In another aspect, the invention provides pharmaceutical compositions comprising an inhibitor of PIM according to the invention and a pharmaceutically acceptable carrier, excipient, or diluent. In other embodiments, administration can preferably be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions can include a conventional pharmaceutical carrier or excipient and a compound of the invention as the/an active agent, and, in addition, can include other medicinal agents, pharmaceutical agents, carriers, adjuvants, etc. Compositions of the invention can be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It can also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention can also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid dosage forms as described above can be prepared with coatings and shells, such as enteric coatings and others well known in the art. They can contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, can contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with, for example, suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as can be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example PIM, the protein is bound to a support, and a compound of the invention is added to the assay. Alternatively, the compound of the invention is bound to the support and the protein is added. Classes of candidate agents among which novel binding agents can be sought include specific antibodies, non-natural binding agents identified in screens of chemical libraries, peptide analogs, etc. Of particular interest are screening assays for candidate agents that have a low toxicity for human cells. A wide variety of assays can be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, PIM can be done in a number of ways. In one example, the candidate agent (the compound of the invention) is labeled, for example, with a fluorescent or radioactive moiety and binding determined directly. For example, this can be done by attaching all or a portion of the PIM protein to a solid support, adding a labeled agent (for example a compound of the invention in which at least one atom has been replaced by a detectable isotope), washing off excess reagent, and determining whether the amount of the label is that present on the solid support. Various blocking and washing steps can be utilized as is known in the art.

The term "labeled" as used herein is meant to include both direct and indirect labeling with a compound that provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, PIM protein can be labeled at tyrosine positions using $^{125}$I, or with fluorophores. Alternatively, more than one component can be labeled with different labels; using $^{125}$I for the proteins, for example, and a fluorophor for the candidate agents.

The compounds of the invention can also be used as competitors to screen for additional drug candidates. The terms "candidate bioactive agent" or "drug candidate" or grammatical equivalents as used herein describe any molecule, e.g., protein, oligopeptide, small organic molecule, polysaccharide, polynucleotide, etc., to be tested for bioactivity. They can be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to PIM.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to IGF1R, such as an antibody, peptide, binding partner, ligand, etc. Under certain circumstances, there can be competitive binding as between the candidate agent and the binding moiety, with the binding moiety displacing the candidate agent.

In some embodiments, the candidate agent is labeled. Either the candidate agent, or the competitor, or both, is added first to PIM protein for a time sufficient to allow binding, if present. Incubations can be performed at any temperature that facilitates optimal activity, typically between 4° C. and 40° C. Incubation periods are selected for optimum activity, but can also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to PIM and thus is capable of binding to, and potentially modulating, the activity of the PIM. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor can indicate the candidate agent is bound to PIM with a higher affinity. Thus, if the candidate agent is labeled, the presence of the label on the support, coupled with a lack of competitor binding, can indicate the candidate agent is capable of binding to PIM.

It can be of value to identify the binding site of PIM. This can be done in a variety of ways. In one embodiment, once PIM is identified as binding to the candidate agent, the PIM is fragmented or modified and the assays repeated to identify the necessary components for binding.

Modulation is tested by screening for candidate agents capable of modulating the activity of PIM comprising the steps of combining a candidate agent with PIM, as above, and determining an alteration in the biological activity of the PIM. Thus, in this embodiment, the candidate agent should both bind to (although this can not be necessary), and alter its biological or biochemical activity as defined herein. The methods include both in vitro screening methods and in vivo screening of cells for alterations in cell viability, morphology, and the like.

Alternatively, differential screening can be used to identify drug candidates that bind to native PIM, but cannot bind to modified PIM.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which can be used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components can be added in any order that provides for the requisite binding.

One of ordinary skill in the art would understand that certain crystallized, protein-ligand complexes, in particular PIM-ligand complexes, and their corresponding x-ray structure coordinates can be used to reveal new structural information useful for understanding the biological activity of PIM kinases as described herein. As well, the key structural features of the aforementioned proteins, particularly, the shape of the ligand binding site, are useful in methods for designing or identifying selective modulators of PIM kinases and in solving the structures of other proteins with similar features. Ligands of such complexes can include compounds of the invention as described herein.

As well, one of ordinary skill in the art would appreciate that such suitable x-ray quality crystals can be used as part of a method of identifying a candidate agent capable of binding to and modulating the activity of PIM kinases. Such methods can be characterized by the following aspects: a) introducing into a suitable computer program, information defining a ligand binding domain of a PIM kinase in a conformation (e.g. as defined by x-ray structure coordinates obtained from suitable x-ray quality crystals as described above) the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods can further entail: performing rational drug design with the model of the three-dimensional structure, and selecting a potential candidate agent in conjunction with computer modeling.

Additionally, one skilled in the art would appreciate that such methods can further entail: employing a candidate agent, so-determined to fit spatially into the ligand binding domain, in a biological activity assay for PIM kinase modulation, and determining whether said candidate agent modulates PIM kinase activity in the assay. Such methods can also include administering the candidate agent, determined to modulate PIM kinase activity, to a mammal suffering from a condition treatable by PIM kinase modulation, such as those described above.

Also, one skilled in the art would appreciate that compounds of the invention can be used in a method of evaluating the ability of a test agent to associate with a molecule or molecular complex comprising a ligand binding domain of a PIM kinase. Such a method can be characterized by the following aspects: a) creating a computer model of a PIM kinase binding pocket using structure coordinates obtained from suitable x-ray quality crystals of the PIM kinase, b) employing computational algorithms to perform a fitting operation between the test agent and the computer model of the binding pocket, and c) analyzing the results of the fitting operation to quantify the association between the test agent and the computer model of the binding pocket.

Synthetic Procedures

Generally, the compounds listed below were identified by LC-MS, and/or isolated, and characterized by $^1$H-NMR (most typically 400 MHz). Liquid chromatography-mass spectral (LC-MS) analyses were performed using at least one of: a Hewlett-Packard Series 1100 MSD, an Agilent 1100 Series LC/MSD (available from Agilent Technologies Deutschland GmbH of Waldbronn Germany), or a Waters 8-Channel MUX System (available from Waters Corporation of Milford, Mass.). Compounds were identified according to either their observed mass [M+1] or [M+Na] ion (positive mode) or [M−1] ion (negative mode). $^1$H-NMR data for compounds was taken with a Varian AS400 Spectrometer (400 MHz, available from Varian GmbH, Darmstadt, Germany).

Compound Synthesis

Compounds of the invention that are of the 4,6-diarylpyrimidin-2(1H)-one class can be synthesized by the synthetic route outlined in Scheme 1. Commercially available 4-hydroxy-3-methyl-benzaldehyde (1) is condensed with appropriately substituted 4-acetamido-acetophenone by heating the mixture in the presence of a base, such as sodium hydroxide or potassium hydroxide, to give the enone (2) with concomitant deacylation of the aniline. Reaction with urea under acidic conditions with heating affords a pyrimidin-2(1H)-one (3), which can then be further derivatized through reductive alkylation with the appropriate aldehyde to afford compounds of the 4,6-diarylpyrimidin-2(1H)-one class (4) (i.e., HC(O)—R'→—R$_8$ via reductive alkylation).

Scheme 1

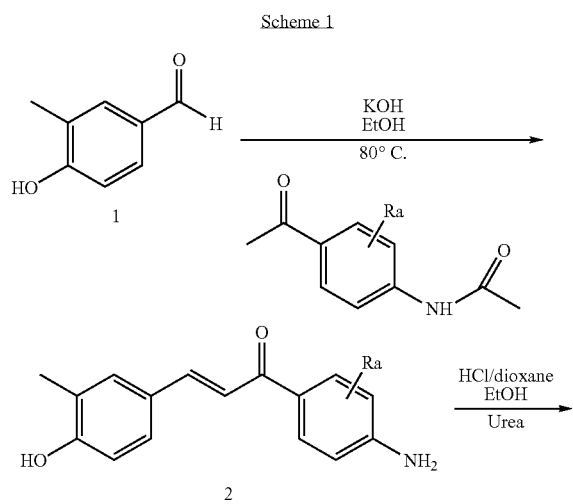

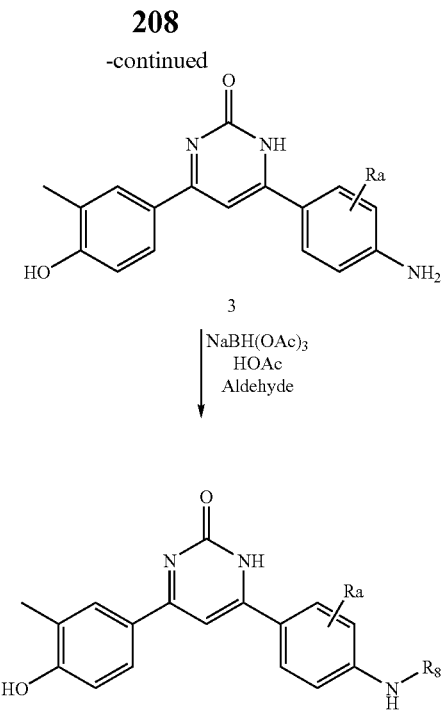

wherein Ra is H or ——(C$_1$-C$_6$)alkyl, and R$_8$ as defined in the specification.

Compounds of the invention that are of the 4,6-diarylpyrimidin-2(1H)-one class where the p-aniline (3) is di-alkylated can be synthesized through a Buchwald coupling as outlined in Scheme 2. Commercially available appropriately substituted 4-bromo-benzoic acid is esterified by heating in methanol under acidic conditions. The methyl ester (6) is then heated in the absence of oxygen with a palladium catalyst, ligand, base, and an appropriate amine N(H)R$^8$R$^9$, to give the di-substituted aniline (7). Condensation with a suitably functionalized acetophenone is typically carried out by heating the mixture in the presence of a base such as sodium hydride to give a diketone intermediate (8). Reaction with urea under acidic conditions with heating affords a pyrimidin-2(1H)-one (9).

Scheme 2

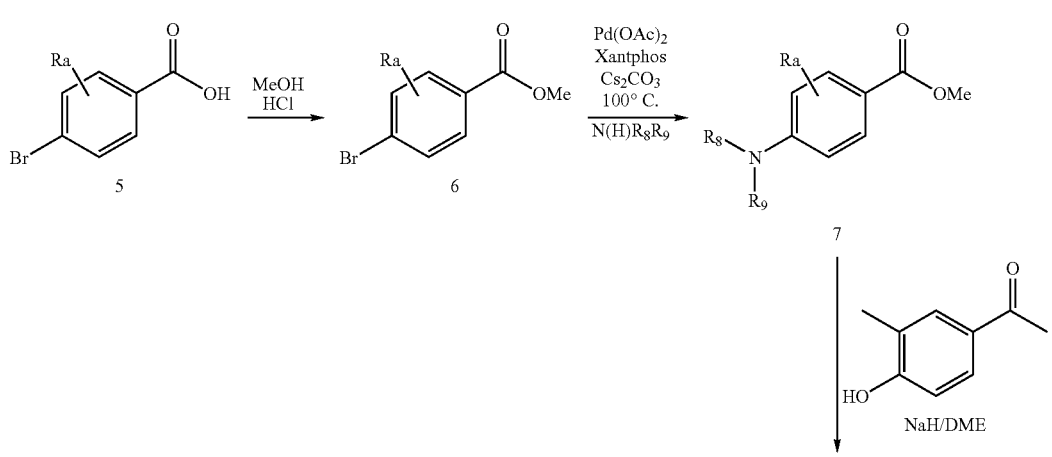

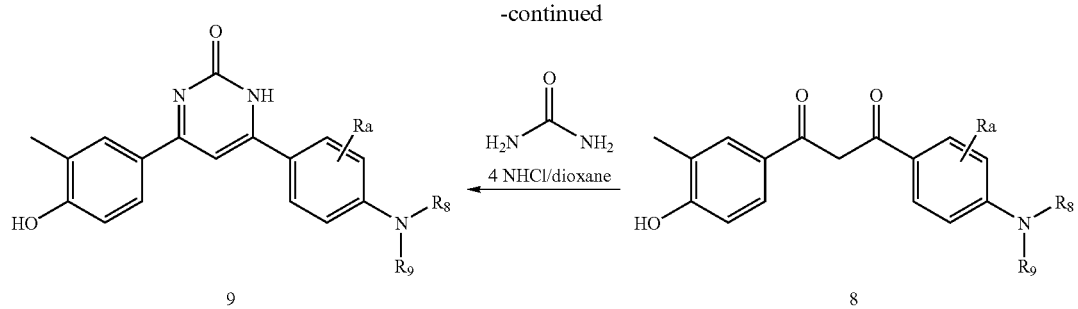

wherein Ra in is H or —(C$_1$-C$_6$)alkyl, and R$_8$ and R$_9$ are as defined in the specification.

Compounds of the invention that are of the 4,6-diarylpyrimidin-2(1H)-one class where the p-aniline (4) is an aryl ether can be synthesized through a phenol alkylation of an appropriately substituted alkyl or aryl bromide as outlined in Scheme 3. Commercially available appropriately substituted 4-hydroxy-acetophenone (10) is heated together with a suitable alkyl or aryl bromide (BrR$_{10}$), in the presence of DMF and a base such as K$_2$CO$_3$ to give the corresponding substituted ether (11). The ether can then be condensed with 4-acetamido-2-methyl acetophenone by heating the mixture in the presence of a base such as sodium hydroxide or potassium hydroxide to give enone (12). Reaction with urea under acidic conditions with heating affords a pyrimidin-2(1H)-one (13).

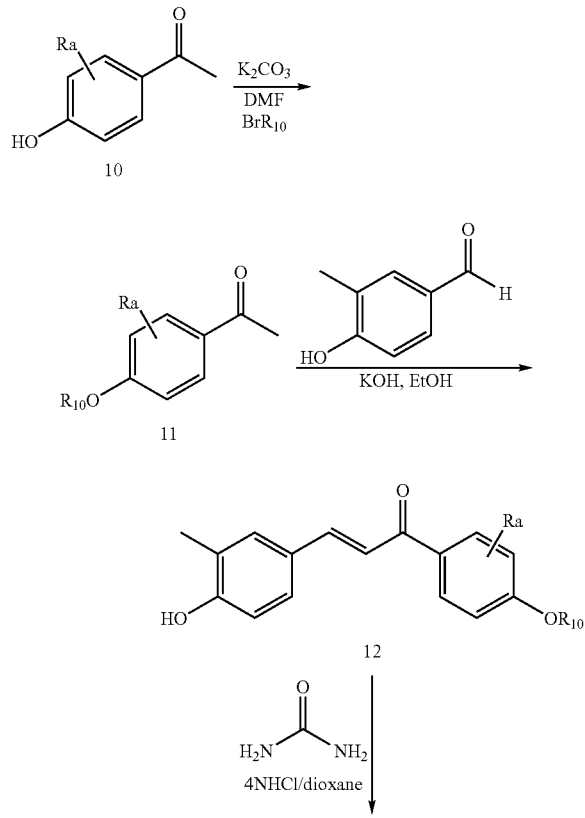

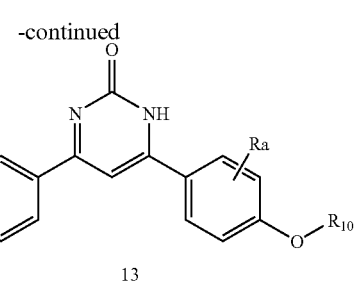

wherein Ra in is H or —(C$_1$-C$_6$)alkyl and R$_{10}$ is defined in the specification.

Example 1

4-(4-hydroxy-3-methylphenyl)-6-{2-methyl-4-[(piperidin-4-ylmethyl)amino]phenyl}-pyrimidin-2(1H)-one Step 1

(E)-1-(4-amino-2-methylphenyl)-3-(4-hydroxy-3-methylphenyl)prop-2-en-1-one (2)

To a round bottomed flask was added EtOH (30 mL) and potassium hydroxide (6.0 g, 109.5 mmol). The mixture was stirred until homogeneous before adding commercially available 4-hydroxy-3-methyl benzaldehyde (3.0 g, 21.9 mmol) and commercially available 4-acetamido-2-methyl acetophenone (4.2 g, 21.9 mmol). The reaction was heated to 80° C. overnight, cooled to rt, and concentrated via rotary evaporation. The solid was dissolved in H$_2$O and neutralized with 1N HCl until pH=7. The aqueous mixture was extracted 5× with EtOAc. The combined EtOAc layers were concentrated and column purified on silica gel (1:1 EtOAc:Hexanes) to afford (E)-1-(4-amino-2-methylphenyl)-3-(4-hydroxy-3-methylphenyl) prop-2-en-1-one (2) (3.1 g, 55% yield).
$^1$H NMR (400 MHz, d6-DMSO) δ 7.64 (dd, 2H), 7.37 (s, 2H), 6.81 (d, 1H), 6.42 (m, 2H), 5.87 (d, 2H), 2.38 (d, 4H), 2.15 (s, 2H); MS (EI) for C$_{17}$H$_{17}$NO$_2$: 268.2 (MH+).

Step 2

6-(4-amino-2-methylphenyl)-4-(4-hydroxy-3-methylphenyl)pyrimidin-2(1H)-one (3)

To a sealed pressure vessel was added (E)-1-(4-amino-2-methylphenyl)-3-(4-hydroxy-3-methylphenyl)prop-2-en-1-one (2) (1.5 g, 5.6 mmol), EtOH (10 mL), 4N HCl in dioxanes (20 mL, 80 mmol), and urea (1.74 g, 29.1 mmol). The pressure vessel was sealed and heated to 110° C. overnight. Another 1 g of urea was added and heated for another 5 h. The reaction was then cooled to rt, concentrated via rotary evaporation and columned purified on silica gel (10:90 to 20:80 MeOH:EtOAc) to give 6-(4-amino-2-methylphenyl)-4-(4-hydroxy-3-methylphenyl)pyrimidin-2(1H)-one (3) (1.1 g, 64% yield).

$^1$H NMR (400 MHz, d6-DMSO) δ 11.21 (br s, 1H), 8.01 (d, 1H), 7.91 (dd, 1H), 7.49 (s, 2H), 7.41 (d, 1H), 7.36 (s, 2H), 7.23 (br s, 2H), 7.17 (s, 1H), 7.11 (d, 1H), 6.67 (br s, 2H), 2.42 (s, 3H), 2.19 (s, 3H); MS (EI) for $C_{18}H_{17}N_3O_2$: 308.2 (MH+).

Step 3

4-(4-hydroxy-3-methylphenyl)-6-{2-methyl-4-[(piperidin-4-ylmethyl)amino]phenyl}pyrimidin-2(1H)-one In a round bottom flask was added 6-(4-amino-2-methylphenyl)-4-(4-hydroxy-3-methylphenyl)pyrimidin-2(1H)-one (3) (30 mg, 0.10 mmol), 1,2 dichloroethane (2.0 mL), acetic acid (0.1 mL), and commercially available N-Boc-4-formyl piperidine (29 uL, 0.14 mmol). The reaction was stirred at room temperature for 15 minutes before adding sodium triacetoxy borohydride (30 mg, 0.14 mmol). Stirring was continued at room temperature overnight. The reaction was then quenched with saturated NaHCO$_3$, extracted with EtOAc, dried over Na$_2$SO$_4$ and concentrated to dryness. The resultant oil was then dissolved in 4N HCl/dioxane (1.0 mL) and allowed to sit at RT for 30 min. or until Boc deprotection was complete. The 4N HCl/dioxane was decanted, and the residual solid product was rinsed with EtOAc 4×. The resulting orange solid was then dissolved in MeOH and purified by preparatory HPLC (5-85% gradient of AmAc/ACN, 15 min.) to give the product 4-(4-hydroxy-3-methylphenyl)-6-{2-methyl-4-[(piperidin-4 ylmethyl)amino]phenyl}pyrimidin-2 (1H)-one as the acetate salt after lyopholyzation (24 mg, 59% yield).

$^1$H NMR (400 MHz, d6-DMSO) δ 7.91 (s, 1H), 7.82 (dd, 1H), 7.20 (d, 1H), 6.84 (d, 1H), 6.79 (s, 1H), 6.50 (m, 2H), 6.19 (br t, 1H), 2.99 (m, 4H), 2.48 (m, 2H), 2.33 (s, 3H), 2.20 (s, 3H), 1.82 (s, 3H), 1.73 (m, 4H), 1.10 (m, 1H); MS (EI) for $C_{24}H_{28}N_4O_2$: 405.4 (MH$^+$).

Example 2

4-(4-hydroxy-3-methylphenyl)-6-{2-methyl-4-[(piperidin-3 ylmethyl)amino]phenyl}pyrimidin-2(1H)-one 4-(4-hydroxy-3-methylphenyl)-6-{2-methyl-4-[(piperidin-3-ylmethyl)amino]phenyl}pyrimidin-2(1H)-one was synthesized in a manner similar to Example 1, wherein N-Boc-4-Formyl piperidine was substituted with N-Boc-3-Formyl piperidine, commercially available from ArchCorp. Purification by preparative HPLC resulted in 12 mg (30% Yield) of 4-(4-hydroxy-3-methylphenyl)-6-{2-methyl-4-[(piperidin-3-ylmethyl)amino]phenyl}pyrimidin-2(1H)-one as the acetate salt.

$^1$H NMR (400 MHz, d$_6$-DMSO) δ 7.91 (s, 1H), 7.82 (dd, 1H), 7.20 (d, 1H), 6.84 (d, 1H), 6.79 (s, 1H), 6.50 (m, 2H), 6.19 (br t, 1H), 2.90 (m, 4H), 2.48 (m, 1H), 2.33 (s, 3H), 2.24 (m, 1H), 2.20 (s, 3H), 1.89 (s, 1H), 1.83 (m, 1H), 1.75 (m, 1H), 1.59 (m, 1H), 1.23 (m, 1H), 1.13 (m, 1H); MS (EI) for $C_{24}H_{28}N_4O_2$: 405.2 (MH$^+$).

Example 3

6-{4-[(3-aminopropyl)amino]-2-methylphenyl}-4-(4-hydroxy-3-methylphenyl)pyrimidin-2(1H)-one 6-{4-[(3-aminopropyl)amino]-2-methylphenyl}-4-(4-hydroxy-3-methylphenyl)pyrimidin-2(1H)-one was synthesized in a manner similar to Example 1, wherein N-Boc-4-formyl piperidine was substituted with 3-(1,3-Dioxo-1,3-dihydroisoindol-2-yl)-propionaldehyde, commercially available from Oakwood. The pthalamide protected product was then deprotected with hydrazine monohydrate (excess). Purification by preparative HPLC resulted in 6.0 mg (16% Yield) of 6-{4-[(3-aminopropyl)amino]-2-methylphenyl}-4-(4-hydroxy-3-methylphenyl)pyrimidin-2(1H)-one as the acetate salt.

$^1$H NMR (400 MHz, d$_6$-DMSO) δ 7.91 (s, 1H), 7.82 (dd, 1H), 7.22 (d, 1H), 6.84 (d, 1H), 6.79 (s, 1H), 6.49 (m, 2H), 6.15 (br t, 1H), 3.18 (m, 2H), 2.72 (t, 2H), 2.38 (s, 3H), 2.20 (s, 3H), 1.89 (s, 3H), 1.68 (q, 2H); MS (EI) for $C_{21}H_{24}N_4O_2$: 365.4 (MH$^+$).

Example 4

4-(4-hydroxy-3-methylphenyl)-6-(2-methyl-4-{[(2-methyl-1H-imidazol-4-yl)methyl]amino}phenyl)pyrimidin-2(1H)-one 4-(4-hydroxy-3-methylphenyl)-6-(2-methyl-4-{[(2-methyl-1H-imidazol-4-yl)methyl]amino}phenyl)pyrimidin-2(1H)-one was synthesized in a manner similar to Example 1, wherein N-Boc-4-formyl piperidine was substituted with 4-formyl-2-methyl imidazole, commercially available from Maybridge. Purification by preparative HPLC resulted in 11.0 mg (27% Yield) of 4-(4-hydroxy-3-methylphenyl)-6-(2-methyl-4-{[(2-methyl-1H-imidazol-4-yl)methyl]amino}phenyl)pyrimidin-2(1H)-one as the acetate salt.

$^1$H NMR (400 MHz, d$_6$-DMSO) δ 7.91 (s, 1H), 7.82 (d, 1H), 7.21 (br d, 1H), 6.89 (d, 1H), 6.80 (m, 2H), 6.55 (m, 2H), 6.30 (br t, 1H), 4.10 (br s, 2H), 2.32 (s, 3H), 2.21 (s, 3H), 2.18 (s, 3H), 1.90 (s, 3H); MS (EI) for $C_{23}H_{23}N_5O_2$: 402.4 (MH$^+$).

Example 5

6-{4-[(2-aminoethyl)amino]-2-methylphenyl}-4-(4-hydroxy-3-methylphenyl)pyrimidin-2(1H)-one 6-{4-[(2-aminoethyl)amino]-2-methylphenyl}-4-(4-hydroxy-3-methylphenyl)pyrimidin-2(1H)-one was synthesized in a manner similar to Example 1, wherein N-Boc-4-formyl piperidine was substituted with N-Boc-2-aminoacetaldehyde, commercially available from Aldrich. Purification by preparative HPLC resulted in 5.0 mg (18% Yield) of 6-{4-[(2-aminoethyl)amino]-2-methylphenyl}-4-(4-hydroxy-3-methylphenyl)pyrimidin-2(1H)-one as the acetate salt.

$^1$H NMR (400 MHz, d$_6$-DMSO) δ 7.92 (s, 1H), 7.80 (d, 1H), 7.21 (d, 1H), 6.85 (d, 1H), 6.79 (s, 1H), 6.50 (m, 2H), 6.10 (br t, 1H), 3.15 (m, 2H), 2.73 (t, 2H), 2.31 (s, 3H), 2.20 (s, 3H), 1.81 (s, 3H); MS (EI) for $C_{20}H_{22}N_4O_2$: 351.2 (MH$^+$).

Example 6

4-(4-hydroxy-3-methylphenyl)-6-{4-[(1H-imidazol-4-ylmethyl)amino]-2-methylphenyl}pyrimidin-2(1H)-one '4-(4-hydroxy-3-methylphenyl)-6-{4-[(1H-imidazol-4-ylmethyl)amino]-2-methylphenyl}pyrimidin-2(1H)-one was synthesized in a manner similar to Example 1, wherein N-Boc-4-Formyl piperidine was substituted with 4(5)-imidazolecarboxaldehyde, commercially available from Aldrich. Purification by preparative HPLC resulted in 13.0 mg (33% Yield) of 4-(4-hydroxy-3-methylphenyl)-6-{4-[(1H-imidazol-4-ylmethyl)amino]-2-methylphenyl}pyrimidin-2(1H)-one as the acetate salt.

$^1$H NMR (400 MHz, d$_6$-DMSO) δ 7.92 (s, 1H), 7.80 (d, 1H), 7.60 (s, 1H), 7.21 (br s, 1H), 7.00 (br s, 1H), 6.89 (d, 1H), 6.79 (s, 1H), 6.58 (m, 2H), 6.37 (br t, 1H), 4.20 (br s, 2H), 2.38 (s, 3H), 2.20 (s, 3H), 1.81 (s, 2H); MS (EI) for C$_{22}$H$_{21}$N$_5$O$_2$: 388.2 (MH$^+$).

Example 7

6-{4-[(1-ethylpiperidin-4-yl)amino]-2-methylphenyl}-4-(4-hydroxy-3-methylphenyl)pyrimidin-2 (1H)-one 6-{4-[(1-ethylpiperidin-4-yl)amino]-2-methylphenyl}-4-(4-hydroxy-3-methylphenyl)pyrimidin-2(1H)-one was synthesized in a manner similar to Example 1, wherein N-Boc-4-formyl piperidine was substituted with 1-ethyl-4-piperidone, commercially available from Acros. Purification by preparative HPLC resulted in 11.0 mg (26% yield) of 6-{4-[(1-ethylpiperidin-4-yl)amino]-2-methylphenyl}-4-(4-hydroxy-3-methylphenyl)pyrimidin-2(1H)-one as the acetate salt.

$^1$H NMR (400 MHz, d$_6$-DMSO) δ 7.91 (s, 1H), 7.82 (dd, 1H), 7.20 (d, 1H), 6.84 (d, 1H), 6.79 (s, 1H), 6.50 (m, 2H), 5.98 (d, 1H), 3.35 (m, 1H), 2.82 (br d, 2H), 2.38 (m, 5H), 2.20 (s, 3H), 2.09 (t, 2H), 1.89 (m, 5H), 1.40 (q, 2H), 1.00 (t, 3H); MS (EI) for C$_{25}$H$_{30}$N$_4$O$_2$: 419.4 (MH$^+$).

Example 8

4-(4-hydroxy-3-methylphenyl)-6-(2-methyl-4-{[(1-methyl-1H-imidazol-2-yl)methyl]amino}phenyl) pyrimidin-2(1H)-one 4-(4-hydroxy-3-methylphenyl)-6-(2-methyl-4-[(1-methyl-1H-imidazol-2-yl)methyl]amino phenyl)pyrimidin-2 (1H)-one was synthesized in a manner similar to Example 1, wherein N-Boc-4-Formyl piperidine was substituted with 1-methyl-2-imidazole carboxaldehyde, commercially available from Aldrich. Purification by preparative HPLC resulted in 32.0 mg (79% Yield) of 4-(4-hydroxy-3-methylphenyl)-6-(2-methyl-4-{[(1-methyl-1H-imidazol-2-yl)methyl]amino}phenyl)pyrimidin-2(1H)-one as the acetate salt.

$^1$H NMR (400 MHz, d$_6$-DMSO) δ 7.91 (s, 1H), 7.82 (dd, 1H), 7.21 (br d, 1H), 7.10 (s, 1H), 6.84 (d, 1H), 6.79 (m, 2H), 6.50 (m, 2H), 6.59 (br t, 1H), 4.38 (d, 2H), 3.62 (s, 3H), 2.57 (s, 3H), 2.20 (s, 3H), 1.89 (m, 2H); MS (EI) for C$_{23}$H$_{23}$N$_5$O$_2$: 402.4 (MH$^+$).

Example 9

4-(4-hydroxy-3-methylphenyl)-6-{2-methyl-4-[(tetrahydro-2H-pyran-4-ylmethyl)amino] phenyl}pyrimidin-2(1H)-one 4-(4-hydroxy-3-methylphenyl)-6-{2-methyl-4-[(tetrahydro-2H-pyran-4-ylmethyl)amino]phenyl}pyrimidin-2(1H)-one was synthesized in a manner similar to Example 1, wherein N-Boc-4-formyl piperidine was substituted with tetrahydropyranyl-4-carboxaldehyde, commercially available from Apollo Chem. Purification by preparative HPLC resulted in 12.0 mg (18% yield) of 4-(4-hydroxy-3-methylphenyl)-6-{2-methyl-4-[(tetrahydro-2H-pyran-4-ylmethyl)amino]phenyl}pyrimidin-2(1H)-one as the acetate salt.

$^1$H NMR (400 MHz, d$_6$-DMSO) δ 7.91 (s, 1H), 7.82 (d, 1H), 7.23 (br d, 1H), 6.90 (d, 1H), 6.80 (s, 1H), 6.50 (m, 2H), 6.21 (br t, 1H), 3.91 (dd, 2H), 3.02 (1, 2H), 2.36 (s, 3H), 2.20 (s, 3H), 1.89 (s, 1H), 1.80 (m, 2H), 1.72 (d, 2H), 1.32 (q, 2H); MS (ET) for C$_{24}$H$_{27}$N$_3$O$_3$: 406.2 (MH$^+$).

Example 10

6-[4-({2-[(1-ethylpiperidin-4-yl)amino] ethyl}amino)-2-methylphenyl]-4-(4-hydroxy-3-methylphenyl)pyrimidin-2(1H)-one 6-[4-({2-[(1-ethylpiperidin-4-yl)amino]ethyl}amino)-2-methylphenyl]-4-(4-hydroxy-3-methylphenyl)pyrimidin-2 (1H)-one was synthesized in a manner similar to Example 1, wherein N-Boc-4-formyl piperidine was substituted with N-Boc-2-aminoacetaldehyde, commercially available from Aldrich. The resulting de-Boc'ed product (50 mg, 0.143 mmol) was then dissolved in 1,2 dichloroethane (2.0 mL), acetic acid (0.1 mL), 1-ethyl-4-piperidine (18 ul, 0.143 mmol), and NaBH(OAC)$_3$ (45 mg, 0.214 mmol). The reaction was stirred at rt overnight, concentrated, extracted with NaHCO$_3$ (sat.) and dissolved in methanol. Purification by preparative HPLC resulted in 24.0 mg (36% Yield) of 6-[4-({2-[(1-ethylpiperidin-4-yl)amino]ethyl}amino)-2-methylphenyl]-4-(4-hydroxy-3-methylphenyl)pyrimidin-2(1H)-one as the acetate salt.

$^1$H NMR (400 MHz, d$_6$-DMSO) δ 7.93 (s, 1H), 7.81 (d, 1H), 7.21 (br d, 1H), 6.88 (d, 1H), 6.80 (s, 1H), 6.51 (m, 2H), 6.05 (br t, 1H), 3.18 (m, 6H), 2.80 (m, 6H), 2.30 (m, 3H), 2.20 (s, 3H), 1.89 (s, 3H), 1.80 (m, 2H), 1.21 (q, 2H), 1.00 (t, 3H); MS (EI) for C$_{27}$H$_{35}$N$_5$O$_2$: 462.5 (MH$^+$).

Example 11

4-(4-hydroxy-3-methylphenyl)-6-[2-methyl-4-(4-methylpiperazin-1-yl)phenyl]pyrimidin-2(1H)-one Step 1

Methyl 4-bromo-2-methylbenzoate

To a round bottomed flask was added MeOH (25 mL) and commercially available 4-bromo-2-methyl benzoic acid (7.0 g, 32.8 mmol). Then 4N HCL/dioxanes (25 mL) was added to the insoluble mixture and stirred under reflux for 3 h. The reaction was concentrated. EtOAc and H$_2$O were added to the slurry and partitioned. The EtOAc layer was washed with NaHCO$_3$ (sat.) 3×, washed with brine and dried with Na$_2$SO$_4$ and concentrated to give methyl 4-bromo-2-methylbenzoate as a light brown oil (6.7 g, 89% yield).

$^1$H NMR (400 MHz, d6-DMSO) δ 7.64 (dd, 2H), 7.37 (s, 2H), 6.81 (d, 1H), 6.42 (m, 2H), 5.87 (d, 2H), 2.38 (d, 4H), 2.15 (s, 2H); MS (EI) for C$_{17}$H$_{17}$NO$_2$: 268.2 (MH$^+$).

Step 2

Methyl 2-methyl-4-(4-methylpiperazin-1-yl)benzoate

In a pressure vessel was added methyl 4-bromo-2-methylbenzoate (500 mg, 2.18 mmol), Dioxane (5.0 mL), Cs$_2$CO$_3$ (1.4 g, 4.36 mmol), and Xantphos (92.0 mg, 0.16 mmol). The mixture was stirred and nitrogen was bubbled into the reaction for 5 min before adding in Palladium(II) acetate (58 mg, 0.08 mmol), and commercially available N-methyl piperazine (0.26 mL, 2.62 mmol). The vessel was then sealed and heated to 100° C. overnight. The reaction was cooled and filtered through celite. The supernatant was then concentrated and column purified (5:95 EtOAc:Hexanes) to give methyl 2-methyl-4-(4-methylpiperazin-1-yl)benzoate (480 mg, 89% yield).

$^1$H NMR (400 MHz, d6-DMSO) δ 7.78 (d, 1H), 6.81 (m, 2H), 3.79 (s, 3H), 3.30 (t, 4H), 2.40 (t, 4H), 2.21 (s, 31-1); MS (EI) for $C_{23}H_{26}N_4O_2$: 249.2 (MH$^+$).

Step 3

1-(4-hydroxy-3-methylphenyl)-3-(2-methyl-4-(4-methylpiperazin-1-yl)phenyl)propane-1,3-dione In a pressure vessel was added NaH (175 mg, 4.4 mmol) and DME (5.0 mL). A mixture of 2-methyl-4-(4-methylpiperazin-1-yl)benzoate (420 mg, 1.69 mmol) and commercially available 4-hydroxy-3-methyl acetophenone (254 mg, 1.69 mmol) in 2 mL of DME was added dropwise to the NaH/DME solution. The reaction was sealed and heated to 115° C. for 3 days. The reaction was cooled, quenched with water and acidified with 4N HCl until a yellow precipitate formed (pH=9-10). The yellow precipitate was extracted into EtOAc, washed with brine, dried with Na$_2$SO$_4$ and concentrated to give 1-(4-hydroxy-3-methylphenyl)-3-(2-methyl-4-(4-methylpiperazin-1-yl)phenyl)propane-1,3-dione as a yellow solid (356 mg, 57% yield).

$^1$H NMR (400 MHz, d6-DMSO) δ 10.3 (br s, 1δH), 7.70 (m, 3H), 6.80 (m, 3H), 3.30 (m, 4H), 2.50 (m, 8H), 2.21 (m, 4H); MS (EI) for $C_{22}H_{26}N_2O_3$: 367.2 (MH$^+$).

Step 4

4-(4-hydroxy-3-methylphenyl)-6-(2-methyl-4-(4-methylpiperazin-1-yl)phenyl)pyrimidin-2(1H)-one To a sealed pressure vessel was added 1-(4-hydroxy-3-methylphenyl)-3-(2-methyl-4-(4-methylpiperazin-1-yl)phenyl)propane-1,3-dione (500 mg, 0.41 mmol), 4N HCl in dioxanes (2.0 mL), and urea (491 mg, 8.2 mmol). The pressure vessel was sealed and heated to 110° C. overnight. The reaction was then cooled to rt, decanted to remove dioxanes, and neutralized with NaHCO$_3$ until a precipitate formed (pH=7). The precipitate was collected and purified via preparatory HPLC (5-80% TFA) to give 4-(4-hydroxy-3-methylphenyl)-6-(2-methyl-4-(4-methylpiperazin-1-yl)phenyl)pyrimidin-2(1H)-one as the TFA salt. The TFA salt was converted to an HCl salt (38.0 mg, 7% yield).

$^1$H NMR (400 MHz, MeOD) δ 7.88 (br s, 1H), 7.81 (dd, 1H), 7.52 (d, 1H), 7.10 (s, 1H), 7.05 (m, 2H), 6.97 (d, 1H), 4.12 (br s, 2H), 3.61 (br s, 3H), 3.21 (m, 3H), 3.00 (s, 1H), 2.53 (s, 3H), 2.28 (s, 3H); MS (EI) for $C_{23}H_{26}N_4O_2$: 390.2 (MH$^+$).

Example 12

4-(4-hydroxy-3-methylphenyl)-6-(2-methyl-4-[(piperidin-4-ylmethyl)oxy]phenyl)pyrimidin-2(1H)-one Step 1 tert-butyl 4-((4-acetyl-3-methylphenoxy)methyl)piperidine-1-carboxylate

To a round bottomed flask was added commercially available 4-hydroxy-2-methyl acetophenone (500 mg, 3.3 mmol), DMF (5 mL), commercially available 4-bromomethyl-piperidine-1-carboxylic acid tert butyl ester (900 mg, 3.3 mmol) and K$_2$CO$_3$ (500 mg, 3.63 mmol). The reaction was heated to 70° C. for 9 h or until the reaction was completed. The precipitated was filtered off and the supernatant was concentrated and column purified on silica gel with 20:80 EtOAc:Hexanes to give tert-butyl 4-((4-acetyl-3-methylphenoxy)methyl)piperidine-1-carboxylate (636 mg, 55% yield).

$^1$H NMR (400 MHz, CDCl$_3$) δ 7.79 (d, 1H), 6.71 (s, 2H), 4.20 (br s, 2H), 3.82 (d, 2H), 2.77 (m, 2H), 2.59 (d, 6H), 1.95 (m, 1H), 1.82 (br d, 2H), 1.42 (s, 9H), 1.22 (m, 2H); MS (EI) for $C_{20}H_{29}NO_4$: 248.2 (MH$^+$–Boc).

Step 2

(E)-tert-butyl 4-((4-(3-(4-hydroxy-3-methylphenyl)acryloyl)-3-methylphenoxy)methyl)piperidine-1-carboxylate To a round bottomed flask was added EtOH (10 mL) and potassium hydroxide (507 mg, 9.05 mmol). The mixture was stirred until homogeneous before adding commercially available 4-hydroxy-3-methyl benzaldehyde (247 mg, 1.81 mmol) and tert-butyl 4-((4-acetyl-3-methylphenoxy)methyl)piperidine-1-carboxylate (630 mg, 1.81 mmol). The reaction was heated to 80° C. for 5 h, cooled to rt, and concentrated via rotary evaporation. The product was dry-loaded onto a silica gel column and purified through flash chromatography (1:1 EtOAc:Hexanes) to afford (E)-tert-butyl 4-((4-(3-(4-hydroxy-3-methylphenyl)acryloyl)-3-methylphenoxy)methyl)piperidine-1-carboxylate (400 mg, 47% yield).

$^1$H NMR (400 MHz, d6-DMSO) δ 7.82 (d, 1H), 6.82 (m, 2H), 3.98 (m, 1H), 3.90 (d, 1H), 2.70 (br s, 2H), 2.42 (s, 3H), 1.95 (m, 1H), 1.77 (br d, 2H), 1.40 (s, 9H); MS (EI) for $C_{28}H_{35}NO_5$: 464.3 (M–H).

Step 3

4-(4-hydroxy-3-methylphenyl)-6-(2-methyl-4-(piperidin-4-ylmethoxy)phenyl)pyrimidin-2(1H)-one To a sealed pressure vessel was added (E)-tert-butyl 4-((4-(3-(4-hydroxy-3-methylphenyl)acryloyl)-3-methylphenoxy)methyl)piperidine-1-carboxylate (100 mg, 0.215 mmol), 4N HCl in dioxanes (2.0 mL), and urea (64 mg, 1.07 mmol). The pressure vessel was sealed and heated to 110° C. overnight. The reaction was then cooled to rt, concentrated via rotary evaporation and purified via preparatory HPLC (5-85% AmAc) to give 4-(4-hydroxy-3-methylphenyl)-6-(2-methyl-4-(piperidin-4-ylmethoxy)phenyl)pyrimidin-2(1H)-one (6.0 mg, 7% yield).

$^1$H NMR (400 MHz, d6-DMSO) δ 7.96 (br s, 1H), 7.81 (d, 1H), 7.38 (dd, 1H), 6.91 (m, 4H), 3.85 (d, 2H), 2.98 (d, 4H), 2.35 (s, 3H), 2.19 (s, 3H), 1.88 (s, 3H), 1.75 (d, 4H), 1.20 (br q, 3H); MS (EI) for $C_{24}H_{27}N_3O_3$: 406.4 (MH$^+$).

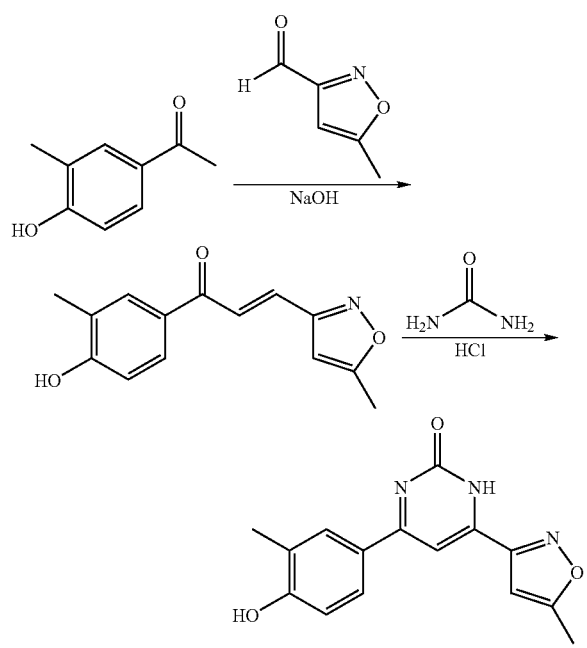

Example 13

4-(4-hydroxy-3-methylphenyl)-6-(5-methylisoxazol-3-yl)pyrimidin-2(1H)-one

Step 1

(E)-1-(4-hydroxy-3-methylphenyl)-3-(5-methylisoxazol-3-yl)prop-2-en-1-one

To a mixture of commercially available 4'-hydroxy-3'-methylacetophenone (700 mg, 4.66 mmol) and NaOH (365 mg, 9.1 mmol) in 10 mL of absolute EtOH was added commercially available 5-methylisoxazole-3-carbaldehyde (518 mg, 4.66 mmol). The reaction mixture was stirred at room temperature for 18 hr. 5 mL of water was added and the reaction mixture was acidified with concentrated HCl to pH 5-6. The precipitate was filtered, washed with water and dried to give (E)-1-(4-hydroxy-3-methylphenyl)-3-(5-methylisoxazol-3-yl)prop-2-en-1-one. MS (EI) for $C_{14}H_{13}NO_3$: 244 (MH+).

Step 2

4-(4-hydroxy-3-methylphenyl)-6-(5-methylisoxazol-3-yl)pyrimidin-2(1H)-one

A mixture of (E)-1-(4-hydroxy-3-methylphenyl)-3-(5-methylisoxazol-3-yl)prop-2-en-1-one (200 mg, 0.8 mmol) and urea (56 mg, 4.0 mmol) in 4M HCl/dioxane (5 mL) was heated to 120° C. in a sealed vessel overnight. After cooling, the crude reaction mixture was purified by reverse-phase HPLC to give 9 mg of product.

$^1$H-NMR (400 MHz, d6-DMSO): δ 7.89 (s, 1H), 7.79 (d, 1H), 7.38 (s, 1H), 6.92 (d, 1H), 6.82 (s, 1H), 2.20 (s, 3H), 1.88 (s, 3H). MS (EI) for $C_{15}H_{13}N_3O_3$: 284 (MH+).

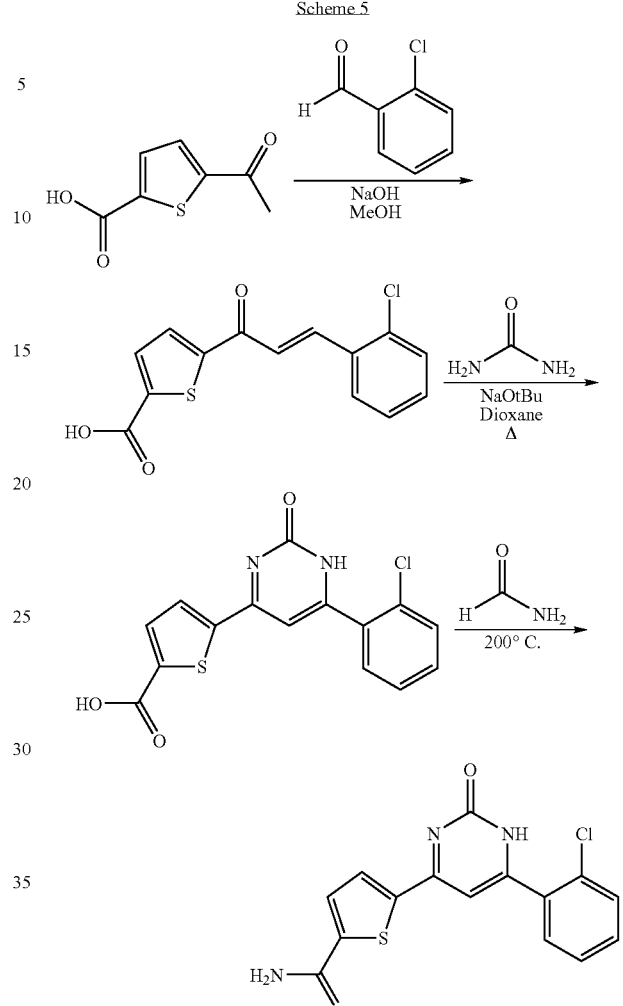

Example 14

5-[6-(2-Chlorophenyl)-2-oxo-1,2-dihydropyrimidin-4-yl]thiophene-2-carboxamide

Step 1

(E)-5-(3-(2-Chlorophenyl)acryloyl)thiophene-2-carboxylic acid

Commercially available 5-acetylthiophene-2-carboxylic acid (1.0 g, 5.9 mmol) and commercially available 2-chlorobenzaldehyde (670 uL, 5.9 mmol) were dissolved in 30 mL of methanol. The solution was cooled in an ice bath and solid sodium hydroxide (940 mg, 23.5 mmol) was added. The cold bath was removed and the reaction was stirred for 2 hours at room temperature. The reaction was then heated at 50° C. for another 2 hours. Concentrated HCl was added to lower the pH to 3. The reaction was filtered, washed with water and air dried to give 1.5 g of product. MS (EI) for $C_{14}H_9ClO_3S$: 292 (MH$^+$).

Step 2

5-[6-(2-Chlorophenyl)-2-oxo-1,2-dihydropyrimidin-4-yl]thiophene-2-carboxylic acid (E)-5-(3-(2-chlorophenyl)acryloyl)thiophene-2-carboxylic acid (1.0 g, 3.4 mmol), urea (1.0 g, 16.6 mmol), and sodium t-butoxide (1.6 g, 16.6 mmol) were suspended in 17 mL of 1,4-dioxane. The reaction mixture was stirred overnight at 80° C. After cooling, the suspension was neutralized by the addition of 1M HCl. The precipitate was filtered, washed with water and air dried to give 740 mg of product. $^1$H NMR (400 MHz, d$_6$-DMSO): δ 7.89 (s, 1H), 7.63 (m, 2H), 7.56 (t, 1H), 7.50 (t, 1H), 7.24 (d, 1H), 7.07 (s, 1H); MS (EI) for $C_{15}H_9ClN_2O_3S$: 332 (MH$^+$).

Step 3

5-[6-(2-Chlorophenyl)-2-oxo-1,2-dihydropyrimidin-4-yl]thiophene-2-carboxamide 5-[6-(2-Chlorophenyl)-2-oxo-1,2-dihydropyrimidin-4-yl]thiophene-2-carboxylic acid (100 mg, 0.30 mmol) was suspended in 1 mL of formamide. The reaction mixture was stirred for 30 minutes at 200° C. After cooling, the precipitate was filtered, dissolved in 1 mL dimethylformamide and purified by reverse phase HPLC. 30 mg of product were isolated.

$^1$H NMR (400 MHz, d$_6$-DMSO): 12.22 (s, 1H), 8.14 (s, 1H), 8.08 (d, 1H), 7.78 (d, 1H), 7.65 (m, 3H), 7.59 (t, 1H), 7.52 (t, 1H), 7.17 (br s, 1H); MS (EI) for $C_{15}H_{10}ClN_3O_2S$: 331 (MH$^+$)

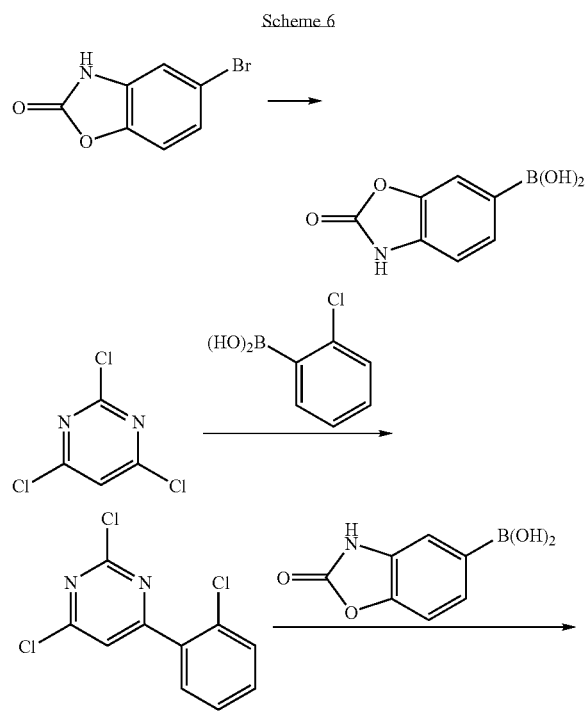

Scheme 6

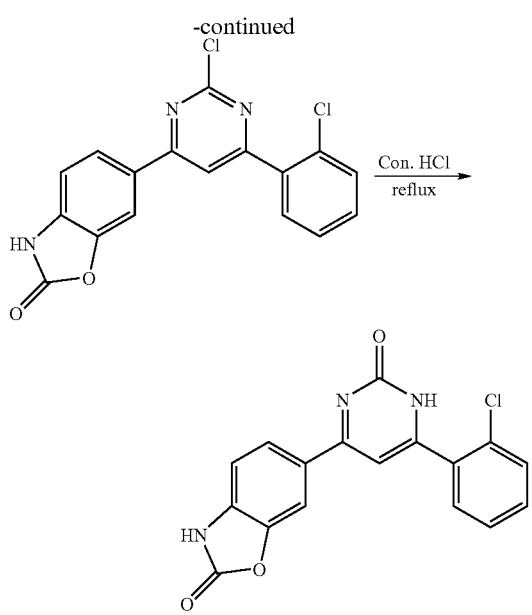

Example 15

6-[6-(2-chlorophenyl)-2-oxo-1,2-dihydropyrimidin-4-yl]-1,3-benzoxazol-2(3H)-one

Step 1

2-Oxo-2,3-dihydrobenzo[d]oxazol-6-ylboronic acid

To a solution of commercially available 5-bromo-3H-benzooxaol-2-one (1.0 g, 4.6 mmol) in dry THF (28 mL) at −78° C. under nitrogen was added BuLi (1.6 M in hexanes, 8.8 mL) dropwise, the reaction mixture was stirred −40° C. for 1 hour and trimethyl borate (2.13 mL) was added. The reaction mixture was allowed to warm up to rt and stirred overnight. 1N HCl (50 mL) was added and stirred for 30 min, then extracted with EtOAc. The organic layer was dried and concentrated to give 2-oxo-2,3-dihydrobenzo[d]oxazol-6-ylboronic acid as a solid, which was dried and used for the next step.

Step 2

2,4-Dichloro-6-(2-chlorophenyl)pyrimidine

To a solution of commercially available 2,4,6-trichloropyridine (5.16 g, 28.2 mmol) in THF (40 mL) was added commercially available 2-chlorophenylboronic acid (2.20 g, 14.1 mmol), Pd(OAc)$_2$ (282 mg), PPh$_3$ (660 mg), followed by Na$_2$CO$_3$ (28.2 mL, 1M). The reaction was heated to 60° C. for 3 hours and completed. The mixture was partitioned between EtOAc and water. The organic layer was washed with saturated brine, dried and concentrated. The residue was purified by chromatography to 2,4-dichloro-6-(2-chlorophenyl)pyrimidine (2.72 g, 75%) as a white solid.

Step 3

6-[6-(2-chlorophenyl)-2-oxo-1,2-dihydropyrimidin-4-yl]-1,3-benzoxazol-2(3H)-one A round flask was charged with 2,4-dichloro-6-(2-chlorophenyl)pyrimidine (150 mg), 2-oxo-2,3-dihydrobenzo[d]

oxazol-6-ylboronic acid (104 mg), Pd(dppf)Cl$_2$(15 mg), 1 M NaHCO$_3$ (0.5 mL) and THF (5 mL). The reaction mixture was stirred at 70° C. for 2 hours, then 4 mL of conc. HCl was added. The reaction was heated to 90° C. for 5 hours. The mixture was filtrated, concentrated and purified by prep-HPLC to give the product. $^1$H NMR (400 MHz, d6-DMSO): δ 11.00 (s, br, 2H), 7.81-7.75 (m, 2H), 7.62-7.43 (m, 3H), 7.12-7.00 (m, 3H). MS (EI) for C$_{17}$H$_{10}$ClN$_3$O$_3$: 339 (MH$^+$).

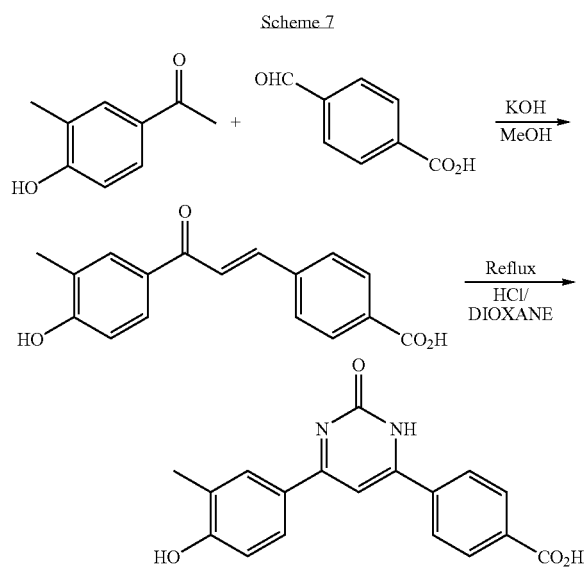

Example 16

4-(6-(4-Hydroxy-3-methylphenyl)-2-oxo-2,3-dihydropyrimidin-4-yl)benzoic acid

Step 1

(E)-4-(3-(4-Hydroxy-3-methylphenyl)-3-oxoprop-1-enyl)benzoic acid

Commercially available 4-formylbenzoic acid (15.0 g, 0.1 mol) and commercially available 4'-hydroxy-3'-methylacetophenone (15.0 g, 0.1 mol) were dissolved in 150 mL of methanol and 50 mL of water. The solution was cooled with an ice-water bath, to which was added potassium hydroxide (28.0 g, 0.5 mol). The reaction mixture was stirred overnight. The resulted mixture was poured on to 600 mL of ice-water, acidified to pH=4-5 with 1 M HCl, filtered, washed with water (200 mL), and dried in the air. 25 g (87%) of a yellowish solid was obtained.

$^1$H NMR (400 MHz, DMSO-d$_6$): δ 10.20 (br, 1H), 10.11 (s, 1H), 8.00-8.15 (m, 3H), 7.78 (m, 2H), 6.65 (m, 4H), 2.40 (s, 3H). MS (EI) for C$_{17}$H$_{14}$O$_4$: 283 (MH$^+$).

Step 2

4-(6-(4-Hydroxy-3-methylphenyl)-2-oxo-2,3-dihydropyrimidin-4-yl)benzoic acid (E)-4-(3-(4-Hydroxy-3-methylphenyl)-3-oxoprop-1-enyl)benzoic acid (14.7 g, 52.1 mmol) and urea (15.6 g, 0.26 mol) were suspended in 200 mL of 4N HCl solution in dioxane, and the reaction mixture was heated to reflux overnight, then cooled to room temperature. The resulted mixture was concentrated in vacuo to remove dioxane. The residues were suspended in 20 mL of methanol, filtered, washed with 50 mL of water, and dried in the air. 8.3 g (51%) of a yellowish powder was obtained.

$^1$H NMR (400 MHz, DMSO-d$_6$): δ 10.25 (s, 1H), 8.28 (m, 2H), 7.92-8.05 (m, 4H), 7.58 (s, 1H), 6.95 (m, 1H), 2.18 (s, 3H). MS (EI) for C$_{18}$H$_{14}$N$_2$O$_4$: 323 (MH$^+$).

Example 17

4-[6-(4-Hydroxy-3-methylphenyl)-2-oxo-2,3-dihydropyrimidin-4-yl]-N-(3-morpholin-4-ylpropyl)benzamide 4-(6-(4-Hydroxy-3-methylphenyl)-2-oxo-2,3-dihydropyrimidin-4-yl)benzoic acid (Compound 265, 15.5 mg, 48 umol) and 3-morpholinopropan-1-amine (5.8 mg, 40 umol) were dissolved in dichloroethane (1.25 mL) and N,N-dimethylformamide (0.79 mL). To this solution was added 1-hydroxybenzotriazole (6.8 mg, 50 umol) followed by 1-[3-(dimethylamino)propyl]-3-ethylcarbodiimide methiodide (17.8 mg, 60 umol). The reaction mixture was stirred at room temperature for 15 hours and was concentrated in vacuo. The reaction mixture was purified by reverse phase HPLC to give 5 mg of product. $^1$H-NMR (400 MHz, d6-DMSO): δ 8.64-8.69 (m, 1H), 8.19-8.27 (m, 3H), 7.94-8.01 (m, 3H), 7.86-7.91 (d, 1H), 7.50 (s, 1H), 6.88-6.95 (d, 1H), 3.54-3.60 (m, 4H), 3.27-3.36 (m, 4H), 2.29-2.41 (m, 4H), 2.21 (s, 3H), 1.65-1.77 (m, 2H). MS (EI): 449.5 (MH+).

Example 18

4-[6-(4-hydroxy-3-methylphenyl)-2-oxo-2,3-dihydropyrimidin-4-yl]-N-(3-pyrrolidin-1-ylpropyl)benzamide 4-[6-(4-hydroxy-3-methylphenyl)-2-oxo-2,3-dihydropyrimidin-4-yl]-N-(3-pyrrolidin-1-ylpropyl)benzamide was synthesized in a manner similar to Example 17, wherein 3-morpholinopropan-1-amine was substituted with commercially available 3-(pyrrolidin-1-yl)propan-1-amine.

$^1$H-NMR (400 MHz, d6-DMSO): δ 8.74 (m, 1H), 8.21-8.29 (m, 3H), 7.97-8.01 (m, 2H), 7.85-7.91 (d, 1H), 7.51 (s, 1H), 6.89-6.95 (d, 1H) 2.20 (s, 3H), 1.66-1.79 (m, 8H). MS (EI): 433.5 (MH+).

Example 19

6-[4-(1,4'-bipiperidin-1'-ylcarbonyl)phenyl]-4-(4-hydroxy-3-methylphenyl)pyrimidin-2(1H)-one 6-[4-(1,4'-bipiperidin-1'-ylcarbonyl)phenyl]-4-(4-hydroxy-3-methylphenyl)pyrimidin-2(1H)-one was synthesized in a manner similar to Example 17, wherein 3-morpholinopropan-1-amine was substituted with commercially available 1,4'-bipiperidine.

$^1$H-NMR (400 MHz, d6-DMSO): δ 8.25 (s, 1H), 8.16-8.21 (d, 1H), 7.98 (s, 1H), 7.84-7.90 (d, 1H), 7.51-7.57 (d, 2H), 7.46 (s, 1H), 6.88-6.94 (d, 1H), 4.47-4.59 (d, 2H), 2.96-3.11 (m, 2H), 2.68-2.85 (m, 2H), 2.43-2.50 (m, 1H), 2.21 (s, 3H), 1.76-1.89 (m, 1H), 1.61-1.73 (m, 1H), 1.32-1.53 (m, 8H). MS (EI): 473.6 (MH+).

Example 20

4-[6-(4-hydroxy-3-methylphenyl)-2-oxo-2,3-dihydropyrimidin-4-yl]-N-[2-(1-methylpyrrolidin-2-yl) ethyl]benzamide 4-[6-(4-hydroxy-3-methylphenyl)-2-oxo-2,3-dihydropyrimidin-4-yl]-N-[2-(1-methylpyrrolidin-2-yl)ethyl]benzamide was synthesized in a manner similar to Example 17, wherein 3-morpholinopropan-1-amine was substituted with commercially available 2-(1-methylpyrrolidin-2-yl)ethanamine.

$^1$H-NMR (400 MHz, d6-DMSO): δ 8.65-8.73 (m, 1H), 8.20-8.27 (m, 2H), 7.94-8.01 (m, 2H), 7.86-7.92 (d, 1H), 7.50 (s, 1H), 6.88-6.94 (d, 1H), 3.28-3.36 (m, 2H), 2.96-3.03 (m, 2H), 2.26 (s, 3H), 2.21 (s, 3H), 2.06-2.19 (m, 2H), 1.85-2.04 (m, 2H), 1.60-1.73 (m, 2H), 1.40-1.55 (m, 2H). MS (EI): 433.5 (MH+).

Example 21

4-[6-(4-hydroxy-3-methylphenyl)-2-oxo-2,3-dihydropyrimidin-4-yl]-N-(2-pyrrolidin-1-ylethyl)benzamide 4-[6-(4-hydroxy-3-methylphenyl)-2-oxo-2,3-dihydropyrimidin-4-yl]-N-(2-pyrrolidin-1-ylethyl)benzamide was synthesized in a manner similar to Example 17, wherein 3-morpholinopropan-1-amine was substituted with commercially available 2-(pyrrolidin-1-yl)ethanamine.

$^1$H-NMR (400 MHz, d6-DMSO): δ 8.64-8.70 (m, 1H), 8.20-8.29 (m, 3H), 7.95-8.02 (m, 3H), 7.85-7.91 (d, 1H), 7.50 (s, 1H), 6.89-6.94 (d, 1H), 3.38-3.48 (m, 4H), 2.60-2.67 (m, 2H), 2.52-2.58 (m, 2H), 2.21 (s, 3H), 1.68-1.73 (m, 4H). MS (EI): 419.5 (MH+).

Example 22

4-[6-(4-hydroxy-3-methylphenyl)-2-oxo-2,3-dihydropyrimidin-4-yl]-N-(2-piperidin-1-ylethyl)benzamide 4-[6-(4-hydroxy-3-methylphenyl)-2-oxo-2,3-dihydropyrimidin-4-yl]-N-(2-piperidin-1-ylethyl)benzamide was synthesized in a manner similar to Example 17, wherein 3-morpholinopropan-1-amine was substituted with commercially available 2-(piperidin-1-yl)ethanamine.

$^1$H-NMR (400 MHz, d6-DMSO): δ 8.56-8.63 (m, 1H), 8.19-8.27 (m, 3H), 7.93-8.00 (m, 3H), 7.85-7.91 (d, 1H), 7.50 (s, 1H), 6.88-6.94 (d, 1H), 3.36-3.45 (m, 4H), 2.34-2.48 (m, 3H), 2.20 (s, 3H), 1.46-1.55 (m, 4H), 1.34-1.43 (m, 31-1). MS (EI): 433.5 (MH+).

Example 23

4-[6-(4-hydroxy-3-methylphenyl)-2-oxo-2,3-dihydropyrimidin-4-yl]-N-methyl-N-(1-methylpyrrolidin-3-yl)benzamide 4-[6-(4-hydroxy-3-methylphenyl)-2-oxo-2,3-dihydropyrimidin-4-yl]-N-methyl-N-(1-methylpyrrolidin-3-yl)benzamide was synthesized in a manner similar to Example 17, wherein 3-morpholinopropan-1-amine was substituted with commercially available N,1-dimethylpyrrolidin-3-amine.

$^1$H-NMR (400 MHz, d6-DMSO): δ 8.15-8.26 (m, 3H), 7.98 (s, 1H), 7.84-7.91 (d, 1H), 7.42-7.54 (m, 2H), 6.86-6.94 (d, 1H), 4.16 (s, 1H), 2.63-3.03 (m, 4H), 2.27-2.45 (m, 4H), 2.20 (s, 3H), 1.76-2.02 (m, 3H). MS (EI): 419.5 (MH+).

Example 24

N-azetidin-3-yl-4-[6-(4-hydroxy-3-methylphenyl)-2-oxo-2,3-dihydropyrimidin-4-yl]benzamide N-azetidin-3-yl-4-[6-(4-hydroxy-3-methylphenyl)-2-oxo-2,3-dihydropyrimidin-4-yl]benzamide was synthesized in a manner similar to Example 17, wherein 3-morpholinopropan-1-amine was substituted with commercially available tert-butyl 3-aminoazetidine-1-carboxylate and then Boc deprotected under acidic conditions.

$^1$H NMR (400 MHz, d6-DMSO): δ 8.39 (s, 1H), 8.25 (d, 2H), 8.03-7.98 (m, 2H), 7.88 (d, 1H), 7.50 (s, 1H), 7.03-6.82 (m, 3H), 4.82-4.76 (m, 1H), 3.82-3.73 (m, 4H), 2.20 (s, 3H). MS (EI): 377 (MH+).

Example 25

6-(4-{[3-(aminomethyl)piperidin-1-yl] carbonyl}phenyl)-4-(4-hydroxy-3-methylphenyl) pyrimidin-2(1H)-one 6-(4-{[3-(aminomethyl)piperidin-1-yl]carbonyl}phenyl)-4-(4-hydroxy-3-methylphenyl)pyrimidin-2(1H)-one was synthesized in a manner similar to Example 8, wherein 3-morpholinopropan-1-amine was substituted with commercially available tert-butyl piperidin-3-ylmethylcarbamate and then Boc deprotected under acidic conditions.

$^1$H NMR (400 MHz, d6-DMSO): δ 8.39 (s, 1H), 8.20 (d, 2H), 7.97 (s, 1H), 7.87 (d, 1H), 7.52 (d, 2H), 7.46 (s, 1H), 6.91 (d, 1H), 3.12-2.82 (m, 4H), 2.68-2.62 (m, 2H), 2.20 (s, 3H), 1.88-1.24 (m, 5H). MS (EI): 419 (MH+).

Example 26

4-[6-(4-hydroxy-3-methylphenyl)-2-oxo-2,3-dihydropyrimidin-4-yl]-N-(piperidin-4-ylmethyl)benzamide 4-[6-(4-hydroxy-3-methylphenyl)-2-oxo-2,3-dihydropyrimidin-4-yl]-N-(piperidin-4-ylmethyl)benzamide was synthesized in a manner similar to Example 17, wherein 3-morpholinopropan-1-amine was substituted with commercially available tert-butyl 4-(aminomethyl)piperidine-1-carboxylate and then Boc deprotected under acidic conditions.

$^1$H NMR (400 MHz, d6-DMSO): δ 8.68 (t, 1H), 8.43 (s, 1H), 8.23 (d, 2H), 7.98 (d, 3H), 7.87 (dd, 1H), 7.49 (s, 1H), 6.91 (d, 1H), 3.20-3.18 (m, 2H), 3.10-3.06 (m, 4H), 2.64-2.54 (m, 1H), 2.20 (s, 3H), 1.74-1.66 (m, 2H), 1.24-1.14 (m, 2H). MS (EI): 419 (MH+).

Examples 27-79 below were made in a manner similar to Example 17, wherein the appropriate substitutions of commercially available reactants and/or reagents were made to arrive at these compounds. One skilled in the art would be readily able to ascertain which reactants and reagents need to be substituted. The skilled artisan would be readily able to commercially obtain these reactants and/or reagents that are necessary for making these compounds.

Example 27

6-{4-[(3-aminopiperidin-1-yl)carbonyl]phenyl}-4-(4-hydroxy-3-methylphenyl)pyrimidin-2(1H)-one

MS (EI): 405 (MH+).

Example 28

N-[(1-ethylpyrrolidin-2-yl)methyl]-4-[6-(4-hydroxy-3-methylphenyl)-2-oxo-2,3-dihydropyrimidin-4-yl]benzamide

MS (EI): 433 (MH+).

Example 29

4-[6-(4-hydroxy-3-methylphenyl)-2-oxo-2,3-dihydropyrimidin-4-yl]-N-[3-(1H-imidazol-1-yl)propyl]benzamide

MS (EI): 430 (MH+).

Example 30

4-(4-hydroxy-3-methylphenyl)-6-{4-[(4-methylpiperazin-1-yl)carbonyl]phenyl}pyrimidin-2(1H)-one

MS (EI): 405 (MH+).

Example 31

4-[6-(4-hydroxy-3-methylphenyl)-2-oxo-2,3-dihydropyrimidin-4-yl]-N-(2-morpholin-4-ylethyl)benzamide

MS (EI): 435 (MH+).

Example 32

6-(4-{[3-(diethylamino)pyrrolidin-1-yl]carbonyl}phenyl)-4-(4-hydroxy-3-methylphenyl)pyrimidin-2(1H)-one

MS (EI): 447 (MH+).

Example 33

4-[6-(4-hydroxy-3-methylphenyl)-2-oxo-2,3-dihydropyrimidin-4-yl]-N-(tetrahydrofuran-2-ylmethyl)benzamide

MS (EI): 406 (MH+).

Example 34

N-(2-cyanoethyl)-4-[6-(4-hydroxy-3-methylphenyl)-2-oxo-2,3-dihydropyrimidin-4-yl]benzamide

MS (EI): 375 (MH+).

Example 35

N-(furan-2-ylmethyl)-4-[6-(4-hydroxy-3-methylphenyl)-2-oxo-2,3-dihydropyrimidin-4-yl]benzamide

MS (ED: 402 (MH+).

Example 36

4-[6-(4-hydroxy-3-methylphenyl)-2-oxo-2,3-dihydropyrimidin-4-yl]-N-(pyridin-3-ylmethyl)benzamide

MS (ED: 413 (MH+).

Example 37

N-[(6-chloropyridin-3-yl)methyl]-4-[6-(4-hydroxy-3-methylphenyl)-2-oxo-2,3-dihydropyrimidin-4-yl]benzamide

MS (EI): 447 (MH+).

Example 38

N-(cyclopropylmethyl)-4-[6-(4-hydroxy-3-methylphenyl)-2-oxo-2,3-dihydropyrimidin-4-yl]benzamide

MS (EI): 376 (MH+).

Example 39

4-[6-(4-hydroxy-3-methylphenyl)-2-oxo-2,3-dihydropyrimidin-4-yl]-N-[(5-methylfuran-2-yl)methyl]benzamide

MS (ED: 416 (MH+).

Example 40

4-[6-(4-hydroxy-3-methylphenyl)-2-oxo-2,3-dihydropyrimidin-4-yl]-N-{[2-(methyloxy)phenyl]methyl}benzamide

MS (ED: 442 (MH+).

Example 41

N-(furan-2-ylmethyl)-4-[6-(4-hydroxy-3-methylphenyl)-2-oxo-2,3-dihydropyrimidin-4-yl]-N-methylbenzamide

MS (EI): 416 (MH+).

Example 42

4-[6-(4-hydroxy-3-methylphenyl)-2-oxo-2,3-dihydropyrimidin-4-yl]-N-(2-thienylmethyl)benzamide

MS (EI): 418 (MH+).

Example 43

4-[6-(4-hydroxy-3-methylphenyl)-2-oxo-2,3-dihydropyrimidin-4-yl]-N-pentylbenzamide

MS (EI): 392 (MH+).

Example 44

6-(4-{[4-(furan-2-ylcarbonyl)piperazin-1-yl]carbonyl}phenyl)-4-(4-hydroxy-3-methylphenyl)pyrimidin-2(1H)-one

MS (EI): 485 (MH+).

Example 45

4-[6-(4-hydroxy-3-methylphenyl)-2-oxo-2,3-dihydropyrimidin-4-yl]-N-(phenylmethyl)benzamide

MS (EI): 412 (MH+).

Example 46

4-[6-(4-hydroxy-3-methylphenyl)-2-oxo-2,3-dihydropyrimidin-4-yl]-N-[2-(phenyloxy)ethyl]benzamide

MS (EI): 442 (MH+).

Example 47

N-cyclopentyl-4-[6-(4-hydroxy-3-methylphenyl)-2-oxo-2,3-dihydropyrimidin-4-yl]benzamide

MS (EI): 390 (MH+).

Example 48

4-[6-(4-hydroxy-3-methylphenyl)-2-oxo-2,3-dihydropyrimidin-4-yl]-N-{[3-(methyloxy)phenyl]methyl}benzamide

MS (EI): 442 (MH+).

Example 49

4-(4-hydroxy-3-methylphenyl)-6-{4-[(4-pyrazin-2-ylpiperazin-1-yl)carbonyl]phenyl}pyrimidin-2(1H)-one

MS (EI): 469 (MH+).

Example 50

N-cyclopropyl-4-[6-(4-hydroxy-3-methylphenyl)-2-oxo-2,3-dihydropyrimidin-4-yl]benzamide

MS (EI): 362 (MH+).

Example 51

6-{4-[(4-acetylpiperazin-1-yl)carbonyl]phenyl}-4-(4-hydroxy-3-methylphenyl)pyrimidin-2(1H)-one

MS (EI): 433 (MH+).

Example 52

4-[6-(4-hydroxy-3-methylphenyl)-2-oxo-2,3-dihydropyrimidin-4-yl]-N-{[4-(methyloxy)phenyl]methyl}benzamide

MS (ED: 442 (MH+).

Example 53

N-[1-({4-[6-(4-hydroxy-3-methylphenyl)-2-oxo-2,3-dihydropyrimidin-4-yl]phenyl}carbonyl)pyrrolidin-3-yl]-N-methylacetamide

MS (EI): 447 (MH+).

Example 54

6-[4-({4-[2-(ethyloxy)ethyl]piperazin-1-yl}carbonyl)phenyl]-4-(4-hydroxy-3-methylphenyl)pyrimidin-2(1H)-one

MS (EI): 463 (MH+).

Example 55

4-(4-hydroxy-3-methylphenyl)-6-(4-{[4-(tetrahydrofuran-2-ylcarbonyl)piperazin-1-yl]carbonyl}phenyl)pyrimidin-2(1H)-one

MS (ED: 489 (MH+).

Example 56

N-cyclobutyl-4-[6-(4-hydroxy-3-methylphenyl)-2-oxo-2,3-dihydropyrimidin-4-yl]benzamide

MS (EI): 376 (MH+).

Example 57

4-(4-hydroxy-3-methylphenyl)-6-(4-{[4-(phenylmethyl)piperazin-1-yl]carbonyl}phenyl)pyrimidin-2(1H)-one

MS (EI): 481 (MH+).

Example 58

4-(4-hydroxy-3-methylphenyl)-6-[4-({4-[4-(methyloxy)phenyl]piperazin-1-yl}carbonyl)phenyl]pyrimidin-2(1H)-one

MS (EI): 497 (MH+).

Example 59

N-[(2,4-difluorophenyl)methyl]-4-[6-(4-hydroxy-3-methylphenyl)-2-oxo-2,3-dihydropyrimidin-4-yl]benzamide

MS (EI): 448 (MH+).

Example 60

4-[6-(4-hydroxy-3-methylphenyl)-2-oxo-2,3-dihydropyrimidin-4-yl]-N-methyl-N-(2-methylpropyl)benzamide

MS (EI): 392 (MH+).

Example 61

N-cyclohexyl-4-[6-(4-hydroxy-3-methylphenyl)-2-oxo-2,3-dihydropyrimidin-4-yl]benzamide

MS (EI): 404 (MH+).

Example 62

4-(4-hydroxy-3-methylphenyl)-6-{4-[(4-methylpiperidin-1-yl)carbonyl]phenyl}pyrimidin-2(1H)-one

MS (EI): 404 (MH+).

Example 63

N-[(3-chlorophenyl)methyl]-4-[6-(4-hydroxy-3-methylphenyl)-2-oxo-2,3-dihydropyrimidin-4-yl]benzamide

MS (EI): 446 (MH+).

Example 64

4-(4-hydroxy-3-methylphenyl)-6-{4-[(2-methylpyrrolidin-1-yl)carbonyl]phenyl}pyrimidin-2(1H)-one

MS (EI): 390 (MH+).

Example 65

4-(4-hydroxy-3-methylphenyl)-6-[4-(morpholin-4-ylcarbonyl)phenyl]pyrimidin-2(1H)-one

MS (EI): 392 (MH+).

Example 66

4-(4-hydroxy-3-methylphenyl)-6-[4-(pyrrolidin-1-ylcarbonyl)phenyl]pyrimidin-2(1H)-one

MS (EI): 376 (MH+).

Example 67 methyl 1-({4-[6-(4-hydroxy-3-methylphenyl)-2-oxo-2,3-dihydropyrimidin-4-yl]phenyl}-carbonyl)piperidine-4-carboxylate

MS (ED: 448 (MH+).

Example 68

4-(4-hydroxy-3-methylphenyl)-6-[4-(piperidin-1-ylcarbonyl)phenyl]pyrimidin-2(1H)-one

MS (EI): 390 (MH+).

Example 69

N-[(2-chlorophenyl)methyl]-4-[6-(4-hydroxy-3-methylphenyl)-2-oxo-2,3-dihydropyrimidin-4-yl]benzamide

MS (EI): 446 (MH+).

Example 70

N-[2-(2-fluorophenyl)ethyl]-4-[6-(4-hydroxy-3-methylphenyl)-2-oxo-2,3-dihydropyrimidin-4-yl]benzamide

MS (EI): 444 (MH+).

Example 71

6-[4-(azepan-1-ylcarbonyl)phenyl]-4-(4-hydroxy-3-methylphenyl)pyrimidin-2(1H)-one MS (EI) for C24 H25 N3 O3: 404 (MH+).

Example 72

4-[6-(4-hydroxy-3-methylphenyl)-2-oxo-2,3-dihydropyrimidin-4-yl]-N-(4-methylcyclohexyl)benzamide

MS (EI): 418 (MH+).

Example 73

N-cycloheptyl-4-[6-(4-hydroxy-3-methylphenyl)-2-oxo-2,3-dihydropyrimidin-4-yl]benzamide

MS (EI): 418 (MH+).

Example 74

N-[(4-chlorophenyl)methyl]-4-[6-(4-hydroxy-3-methylphenyl)-2-oxo-2,3-dihydropyrimidin-4-yl]benzamide

MS (EI): 446 (MH+).

Example 75

4-(4-hydroxy-3-methylphenyl)-6-(4-[(3-methylpiperidin-1-yl)carbonyl]phenyl)pyrimidin-2(1H)-one

MS (EI): 404 (MH+).

Example 76

4-(4-hydroxy-3-methylphenyl)-6-[4-({4-[3-(methyloxy)phenyl]piperazin-1-yl}carbonyl)phenyl]pyrimidin-2(1H)-one

MS (EI): 497 (MH+).

Example 77

N-(cyclohexylmethyl)-4-[6-(4-hydroxy-3-methylphenyl)-2-oxo-2,3-dihydropyrimidin-4-yl]benzamide MS (EI) for: 418 (MH+).

Example 78

4-(4-hydroxy-3-methylphenyl)-6-[4-({4-[2-(methyloxy)phenyl]piperazin-1-yl}carbonyl)phenyl]pyrimidin-2(1H)-one

MS (EI): 497 (MH+).

Example 79

6-{4-[(3,5-dimethylpiperidin-1-yl)carbonyl]phenyl}-4-(4-hydroxy-3-methylphenyl)pyrimidin-2(1H)-one

MS (ED: 418 (MH+).

Scheme 8

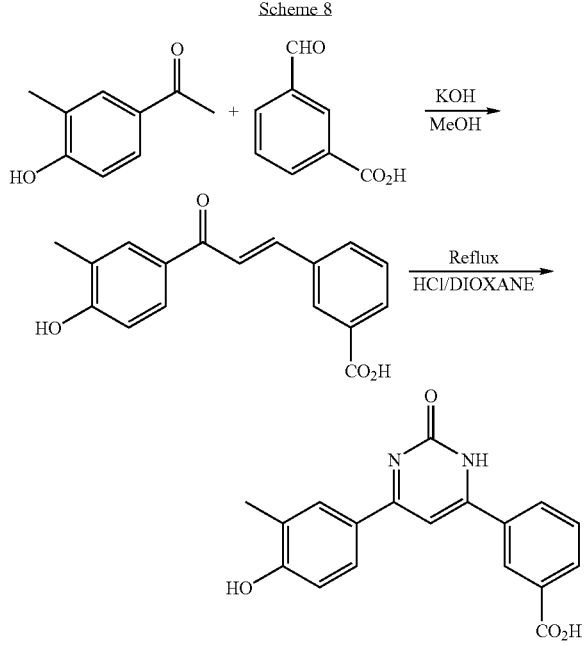

Example 80

3-(6-(4-Hydroxy-3-methylphenyl)-2-oxo-2,3-dihydropyrimidin-4-yl)benzoic acid

Step 1

(E)-3-(3-(4-Hydroxy-3-methylphenyl)-3-oxoprop-1-enyl)benzoic acid

Commercially available 3-formylbenzoic acid (15.0 g, 0.1 mol) and commercially available 4'-hydroxy-3'-methylacetophenone (15.0 g, 0.1 mol) were dissolved in 150 mL of methanol and 50 mL of water. The solution was cooled with an ice-water bath, to which was added potassium hydroxide (28.0 g, 0.5 mol). The reaction mixture was stirred overnight. The resulted mixture was poured on to 600 mL of ice-water, acidified to pH=4-5 with 1 N HCl, filtered, washed with water (200 mL), methanol (100 mL) and dried in the air. 19 g (67%) of a yellowish solid was obtained. $^1$H NMR (400 MHz, DMSO-$d_6$): δ 13.18 (br, 1H), 10.39 (s, 1H), 8.38 (s, 1H), 8.15 (m, 1H), 7.95 (m, 4H), 7.75 (d, 1H), 7.60 (m, 1H), 6.95 (d, 1H), 2.20 (s, 3H). MS (EI): 283 (MH$^+$).

Step 2

3-(6-(4-Hydroxy-3-methylphenyl)-2-oxo-2,3-dihydropyrimidin-4-yl)benzoic acid (E)-3-(3-(4-Hydroxy-3-methylphenyl)-3-oxoprop-1-enyl)benzoic acid (15.0 g, 53.0 mmol) and urea (16.0 g, 0.27 mol) was suspended in 200 mL of 4N HCl solution in dioxane, and the reaction mixture was heated to reflux overnight, then cooled to room temperature. The resulted mixture was concentrated in vacuo to remove dioxane. The residues were suspended in 150 mL of 2-propanol, filtered and washed with 50 mL of 2-propanol, dried in the air. 8.1 g (48%) of a yellowish powder was obtained. $^1$H NMR (400 MHz, DMSO-$d_6$): δ 10.40 (s, 1H), 8.60 (s, 1H), 8.35 (m, 1H), 8.18 (m, 1H), 8.00 (s, 1H), 7.90 (m, 1H), 7.65 (m, 1H), 7.55 (m, 1H), 6.95 (m, 1H), 2.18 (s, 3H). MS (EI): 323 (MH$^+$).

Example 81

3-[6-(4-hydroxy-3-methylphenyl)-2-oxo-2,3-dihydropyrimidin-4-yl]-N-(3-morpholin-4-ylpropyl)benzamide 3-[6-(4-hydroxy-3-methylphenyl)-2-oxo-2,3-dihydropyrimidin-4-yl]benzoic acid (Compound 289, 15.5 mg, 48 umol) and commercially available 3-morpholinopropan-1-amine (5.8 mg, 40 umol) were dissolved in dichloroethane (1.25 mL) and N,N-dimethylformamide (0.79 mL). To this solution was added commercially available 1-hydroxybenzotriazole (6.8 mg, 50 umol) followed by commercially available 1-[3-(dimethylamino)propyl]-3-ethylcarbodiimide methiodide (17.8 mg, 60 umol). The reaction mixture was stirred at room temperature for 15 hours and was concentrated in vacuo. The reaction mixture was purified by reverse phase HPLC to give 5 mg of product. $^1$H NMR (400 MHz, d6-DMSO): δ 8.65 (t, 1H), 8.51 (s, 1H), 8.28-8.23 (m, 2H), 8.02-7.96 (m, 2H), 7.87 (dd, 1H), 7.63 (t, 1H), 7.46 (s, 1H), 6.92 (d, 1H), 3.56 (t, 4H), 3.36-3.32 (m, 2H), 2.40-2.33 (m, 6H), 2.20 (s, 3H), 1.78-1.68 (m, 2H). MS (EI): 450 (MH+).

Example 82

3-[6-(4-hydroxy-3-methylphenyl)-2-oxo-2,3-dihydropyrimidin-4-yl]-N-(2-piperidin-1-ylethyl)benzamide 3-[6-(4-hydroxy-3-methylphenyl)-2-oxo-2,3-dihydropyrimidin-4-yl]-N-(2-piperidin-1-ylethyl)benzamide was synthesized in a manner similar to Example 81, wherein 3-morpholinopropan-1-amine was substituted with commercially available 2-(piperidin-1-yl)ethanamine.

$^1$H NMR (400 MHz, d6-DMSO): δ 8.60 (t, 1H), 8.51 (s, 1H), 8.26 (d, 2H), 8.00 (d, 1H), 7.96 (s, 1H), 7.87 (dd, 1H), 7.64 (t, 1H), 7.46 (s, 1H), 6.92 (d, 1H), 3.45-3.41 (m, 2H), 2.48-2.45 (m, 2H), 2.44-2.40 (m, 4H), 1.54-1.47 (m, 4H), 1.42-1.36 (m, 2H). MS (EI): 434 (MH+).

Example 83

6-{3-[(4-aminopiperidin-1-yl)carbonyl]phenyl}-4-(4-hydroxy-3-methylphenyl)pyrimidin-2(1H)-one 6-{3-[(4-aminopiperidin-1-yl)carbonyl]phenyl}-4-(4-hydroxy-3-methylphenyl)pyrimidin-2(1H)-one was synthesized in a manner similar to Example 81, wherein 3-morpholinopropan-1-amine was substituted with commercially available tert-butyl piperidin-4-ylcarbamate and then Boc deprotected under acidic conditions.

$^1$H NMR (400 MHz, d6-DMSO): δ 8.39 (s, 1H), 8.24 (d, 1H), 8.14 (s, 1H), 7.97 (s, 1H), 7.88 (dd, 1H), 7.62 (t, 1H), 7.54 (d, 1H), 7.49 (s, 1H), 6.91 (s, 1H), 6.91 (d, 1H), 4.46-4.37 (m, 1H), 3.15-2.93 (m, 4H), 2.20 (s, 3H), 1.96-1.73 (m, 2H), 1.41-1.28 (m, 2H). MS (EI): 405 (MH+).

Example 84

3-[6-(4-hydroxy-3-methylphenyl)-2-oxo-2,3-dihydropyrimidin-4-yl]-N-(2-pyrrolidin-1-ylethyl)benzamide 3-[6-(4-hydroxy-3-methylphenyl)-2-oxo-2,3-dihydropyrimidin-4-yl]-N-(2-pyrrolidin-1-ylethyl)benzamide was synthesized in a manner similar to Example 81, wherein 3-morpholinopropan-1-amine was substituted with commercially available 2-(pyrrolidin-1-yl)ethanamine.

$^1$H NMR (400 MHz, d6-DMSO): δ 8.66 (t, 1H), 8.52 (s, 1H), 8.26 (d, 2H), 8.02-7.96 (m, 2H), 7.87 (dd, 1H), 7.64 (t, 1H), 7.46 (s, 1H), 6.92 (d, 1H), 3.46-3.41 (m, 2H), 2.65 (t, 2H), 2.57-2.53 (m, 4H), 2.20 (s, 3H), 1.94-1.87 (m, 4H). MS (EI): 419 (MH+).

Example 85

3-[6-(4-hydroxy-3-methylphenyl)-2-oxo-2,3-dihydropyrimidin-4-yl]-N-(3-pyrrolidin-1-ylpropyl)benzamide 3-[6-(4-hydroxy-3-methylphenyl)-2-oxo-2,3-dihydropyrimidin-4-yl]-N-(3-pyrrolidin-1-ylpropyl)benzamide was synthesized in a manner similar to Example 81, wherein 3-morpholinopropan-1-amine was substituted with commercially available 3-(pyrrolidin-1-yl)propan-1-amine.

$^1$H NMR (400 MHz, d6-DMSO): δ 8.72 (t, 1H), 8.51 (s, 1H), 8.28 (d, 2H), 8.01-7.96 (m, 2H), 7.87 (dd, 1H), 7.63 (t, 1H), 7.47 (s, 1H), 6.92 (d, 1H), 3.38-3.32 (m, 2H), 2.58-2.50 (m, 6H), 2.20 (s, 3H), 1.78-1.68 (m, 6H). MS (EI): 434 (MH+).

Example 86

3-[6-(4-hydroxy-3-methylphenyl)-2-oxo-2,3-dihydropyrimidin-4-yl]-N-(2-morpholin-4-ylethyl)benzamide 3-[6-(4-hydroxy-3-methylphenyl)-2-oxo-2,3-dihydropyrimidin-4-yl]-N-(2-morpholin-4-ylethyl)benzamide was synthesized in a manner similar to Example 81, wherein 3-morpholinopropan-1-amine was substituted with commercially available 2-morpholinoethanamine.

$^1$H NMR (400 MHz, d6-DMSO): δ 8.60 (t, 1H), 8.51 (s, 1H), 8.28-8.25 (m, 2H), 8.01 (d, 1H), 7.96 (s, 1H), 7.87 (dd, 1H), 7.64 (t, 1H), 7.46 (s, 1H), 6.92 (d, 1H), 3.58 (t, 2H), 3.46-3.36 (m, 6H), 2.47-2.42 (m, 4H), 2.20 (s, 3H). MS (EI): 435 (MH+).

Example 87

6-(3-{[3-(aminomethyl)piperidin-1-yl]carbonyl}phenyl)-4-(4-hydroxy-3-methylphenyl)pyrimidin-2(1H)-one 6-(3-{[3-(aminomethyl)piperidin-1-yl]carbonyl}phenyl)-4-(4-hydroxy-3-methylphenyl)pyrimidin-2(1H)-one was synthesized in a manner similar to Example 81, wherein 3-morpholinopropan-1-amine was substituted with commercially available tert-butyl 3-(aminomethyl)piperidine-1-carboxylate and then Boc deprotected under acidic conditions.

$^1$H NMR (400 MHz, d6-DMSO): δ 8.39 (s, 1H), 8.23 (d, 1H), 8.14 (s, 1H), 7.97 (s, 1H), 7.88 (dd, 1H), 7.62-7.54 (m, 2H), 7.48 (s, 1H), 6.92 (d, 1H), 3.10-2.98 (m, 4H), 2.69-2.64 (m, 2H), 2.20 (s, 3H), 1.89-1.84 (m, 1H), 1.65-1.58 (m, 2H), 1.48-1.36 (m, 1H), 1.29-1.24 (m, 1H). MS (EI): 419 (MH+).

Example 88

3-[6-(4-hydroxy-3-methylphenyl)-2-oxo-2,3-dihydropyrimidin-4-yl]-N-[2-(1-methylpyrrolidin-2-yl)ethyl]benzamide 3-[6-(4-hydroxy-3-methylphenyl)-2-oxo-2,3-dihydropyrimidin-4-M-N12-(1-methylpyrrolidin-2-yl)ethyl]benzamide was synthesized in a manner similar to Example 81, wherein 3-morpholinopropan-1-amine was substituted with commercially available 2-(1-methylpyrrolidin-2-yl)ethanamine.

$^1$H NMR (400 MHz, d6-DMSO): δ 8.69 (t, 1H), 8.51 (s, 1H), 8.28-8.26 (m, 2H), 8.01-7.96 (m, 2H), 7.87 (dd, 1H), 7.64 (t, 1H), 7.46 (s, 1H), 6.93 (d, 1H), 3.36-3.33 (m, 2H), 3.02-2.98 (m, 1H), 2.27 (s, 3H), 2.20 (s, 3H), 2.18-2.10 (m, 2H), 2.04-1.89 (m, 2H), 1.70-1.62 (m, 2H), 1.56-1.44 (m, 2H). MS (EI): 434 (MH+).

Example 89

N-[(1-ethylpyrrolidin-2-yl)methyl]-3-[6-(4-hydroxy-3-methylphenyl)-2-oxo-2,3-dihydropyrimidin-4-yl]benzamide N-[(1-ethylpyrrolidin-2-yl)methyl]-3-[6-(4-hydroxy-3-methylphenyl)-2-oxo-2,3-dihydropyrimidin-4-yl]benzamide was synthesized in a manner similar to Example 81, wherein 3-morpholinopropan-1-amine was substituted with commercially available (1-ethylpyrrolidin-2-yl)methanamine.

$^1$H NMR (400 MHz, d6-DMSO): δ 8.64 (t, 1H), 8.51 (s, 1H), 8.29-8.24 (m, 2H), 8.01-7.96 (m, 2H), 7.88 (dd, 1H), 7.64 (t, 1H), 7.46 (s, 1H), 6.92 (d, 1H), 3.18-3.06 (m, 4H), 2.93-2.88 (m, 1H), 2.72-2.66 (m, 1H), 2.38-2.30 (m, 1H), 2.20 (s, 3H), 2.19-2.17 (m, 1H), 1.86-1.62 (m, 4H), 1.06 (t, 3H). MS (EI): 434 (MH+).

Example 90

6-{3-[(3-aminopyrrolidin-1-yl)carbonyl]phenyl}-4-(4-hydroxy-3-methylphenyl)pyrimidin-2(1H)-one 6-{3-[(3-aminopyrrolidin-1-yl)carbonyl]phenyl}-4-(4-hydroxy-3-methylphenyl)pyrimidin-2(1H)-one was synthesized in a manner similar to Example 81, wherein 3-morpholinopropan-1-amine was substituted with commercially available tert-butyl pyrrolidin-3-ylcarbamate and then Boc deprotected under acidic conditions.

$^1$H NMR (400 MHz, d6-DMSO): δ 8.31 (s, 1H), 8.26-8.22 (m, 2H), 7.97 (s, 1H), 7.88 (d, 1H), 7.68-7.59 (m, 2H), 7.48 (s, 1H), 6.92 (d, 1H), 3.68-3.57 (m, 4H), 3.19-3.14 (m, 1H), 2.20 (s, 3H), 2.08-1.98 (m, 1H), 1.78-1.69 (m, 1H). MS (EI): 391 (MH+).

Example 91

3-[6-(4-hydroxy-3-methylphenyl)-2-oxo-2,3-dihydropyrimidin-4-yl]-N-(piperidin-4-ylmethyl)benzamide 3-[6-(4-hydroxy-3-methylphenyl)-2-oxo-2,3-dihydropyrimidin-4-yl]-N-(piperidin-4-ylmethyl)benzamide was synthesized in a manner similar to Example 81, wherein 3-morpholinopropan-1-amine was substituted with commercially available tert-butyl 4-(aminomethyl)piperidine-1-carboxylate and then Boc deprotected under acidic conditions.

$^1$H NMR (400 MHz, d6-DMSO): δ 8.69 (t, 1H), 8.52 (s, 1H), 8.42 (s, 1H), 8.27 (d, 1H), 8.02 (d, 1H), 7.96 (d, 1H), 7.86 (dd, 1H), 7.63 (t, 1H), 7.45 (s, 1H), 6.92 (d, 1H), 3.20 (t, 2H), 3.11 (d, 2H), 2.63 (t, 2H), 2.20 (s, 3H), 1.78-1.72 (m, 3H), 1.28-1.18 (m, 2H). MS (EI): 419 (MH+).

Example 92

N-(4-aminocyclohexyl)-3-[6-(4-hydroxy-3-methylphenyl)-2-oxo-2,3-dihydropyrimidin-4-yl]benzamide N-(4-aminocyclohexyl)-3-[6-(4-hydroxy-3-methylphenyl)-2-oxo-2,3-dihydropyrimidin-4-yl]benzamide was synthesized in a manner similar to Example 81, wherein 3-morpholinopropan-1-amine was substituted with commercially available cyclohexane-1,4-diamine.

$^1$H NMR (400 MHz, d6-DMSO): δ 8.49-8.40 (m, 3H), 8.25 (d, 1H), 8.00-7.96 (m, 2H), 7.86 (dd, 1H), 7.62 (t, 1H), 7.44 (s, 1H), 6.92 (d, 1H), 3.81-3.73 (m, 1H), 2.84-2.76 (m, 1H), 2.20 (s, 3H), 1.96-1.88 (m, 4H), 1.44-1.28 (m, 4H). MS (EI): 419 (MH+).

Example 93

3-[6-(4-hydroxy-3-methylphenyl)-2-oxo-2,3-dihydropyrimidin-4-yl]-N-[2-(phenyloxy)ethyl]benzamide 3-[6-(4-hydroxy-3-methylphenyl)-2-oxo-2,3-dihydropyrimidin-4-yl]-N-[2-(phenyloxy)ethyl]benzamide was synthesized in a manner similar to Example 81, wherein 3-morpholinopropan-1-amine was substituted with commercially available 2-phenoxyethanamine.

$^1$H NMR (400 MHz, d6-DMSO): δ 8.90 (t, 1H), 8.55 (s, 1H), 8.48 (s, 1H), 8.28 (d, 1H), 8.03 (d, 1H), 7.96 (s, 1H), 7.86 (dd, 1H), 7.64 (t, 1H), 7.46 (s, 1H), 7.29-7.27 (m, 2H), 6.99-6.91 (m, 4H), 4.15 (t, 2H), 3.71-3.66 (m, 2H), 2.20 (s, 3H). MS (EI): 442 (MH+).

Examples 94-156 below were made in a manner similar to Example 81, wherein the appropriate substitutions of commercially available reactants and/or reagents were made to arrive at these compounds. One skilled in the art would be readily able to ascertain which reactants and reagents need to be substituted. The skilled artisan would be readily able to commercially obtain these reactants and/or reagents that are necessary for making these compounds.

Example 94

3-[6-(4-hydroxy-3-methylphenyl)-2-oxo-2,3-dihydropyrimidin-4-yl]-N-[3-(1H-imidazol-1-yl)propyl]benzamide

MS (EI): 430 (MH+).

Example 95

N-(2-cyanoethyl)-3-[6-(4-hydroxy-3-methylphenyl)-2-oxo-2,3-dihydropyrimidin-4-yl]benzamide

MS (EI): 375 (MH+).

Example 96

3-[6-(4-hydroxy-3-methylphenyl)-2-oxo-2,3-dihydropyrimidin-4-yl]-N-(tetrahydrofuran-2-ylmethyl)benzamide

MS (EI): 406 (MH+).

Example 97

N-[2-(2-fluorophenyl)ethyl]-3-[6-(4-hydroxy-3-methylphenyl)-2-oxo-2,3-dihydropyrimidin-4-yl]benzamide

MS (EI): 444 (MH+).

Example 98

3-[6-(4-hydroxy-3-methylphenyl)-2-oxo-2,3-dihydropyrimidin-4-yl]-N-(2-thienylmethyl)benzamide

MS (EI): 418 (MH+).

Example 99

3-[6-(4-hydroxy-3-methylphenyl)-2-oxo-2,3-dihydropyrimidin-4-yl]-N-[3-(4-methylpiperazin-1-yl)propyl]benzamide MS (EI) for C26 H31 N5 O3: 462 (MH+).

Example 100

3-[6-(4-hydroxy-3-methylphenyl)-2-oxo-2,3-dihydropyrimidin-4-yl]-N-(pyridin-3-ylmethyl)benzamide

MS (EI): 413 (MH+).

Example 101

N-cyclobutyl-3-[6-(4-hydroxy-3-methylphenyl)-2-oxo-2,3-dihydropyrimidin-4-yl]benzamide

MS (EI): 376 (MH+).

Example 102

N-[(6-chloropyridin-3-yl)methyl]-3-[6-(4-hydroxy-3-methylphenyl)-2-oxo-2,3-dihydropyrimidin-4-yl]benzamide

MS (EI): 447 (MH+).

Example 103

3-[6-(4-hydroxy-3-methylphenyl)-2-oxo-2,3-dihydropyrimidin-4-yl]-N-[(5-methylfuran-2-yl)methyl]benzamide

MS (EI): 416 (MH+).

Example 104

4-(4-hydroxy-3-methylphenyl)-6-{3-[(4-methylpiperidin-1-yl)carbonyl]phenyl}pyrimidin-2(1H)-one

MS (EI): 404 (MH+).

Example 105

N-[2-(dimethylamino)ethyl]-N-ethyl-3-[6-(4-hydroxy-3-methylphenyl)-2-oxo-2,3-dihydropyrimidin-4-yl]benzamide

MS (EI): 421 (MH+).

Example 106

4-(4-hydroxy-3-methylphenyl)-6-[3-(piperazin-1-ylcarbonyl)phenyl]pyrimidin-2(1H)-one

MS (EI): 391 (MH+).

Example 107

N-(furan-2-ylmethyl)-3-[6-(4-hydroxy-3-methylphenyl)-2-oxo-2,3-dihydropyrimidin-4-yl]benzamide

MS (EI): 402 (MH+).

Example 108

N-(furan-2-ylmethyl)-3-[6-(4-hydroxy-3-methylphenyl)-2-oxo-2,3-dihydropyrimidin-4-yl]-N-methylbenzamide

MS (EI): 416 (MH+).

Example 109

N-cyclopropyl-3-[6-(4-hydroxy-3-methylphenyl)-2-oxo-2,3-dihydropyrimidin-4-yl]benzamide

MS (EI): 362 (MH+).

Example 110

N-(cyclohexylmethyl)-3-[6-(4-hydroxy-3-methylphenyl)-2-oxo-2,3-dihydropyrimidin-4-yl]benzamide

MS (EI): 418 (MH+).

Example 111

6-{3-[(3-aminopiperidin-1-yl)carbonyl]phenyl}-4-(4-hydroxy-3-methylphenyl)pyrimidin-2(1H)-one

MS (EI): 405 (MH+).

Example 112

3-[6-(4-hydroxy-3-methylphenyl)-2-oxo-2,3-dihydropyrimidin-4-yl]-N-[3-(2-oxopyrrolidin-1-yl)propyl]benzamide

MS (EI): 447 (MH+).

Example 113

N-(cyclopropylmethyl)-3-[6-(4-hydroxy-3-methylphenyl)-2-oxo-2,3-dihydropyrimidin-4-yl]benzamide

MS (EI): 376 (MH+).

Example 114

3-[6-(4-hydroxy-3-methylphenyl)-2-oxo-2,3-dihydropyrimidin-4-yl]-N-(4-methylcyclohexyl)benzamide

MS (EI): 418 (MH+).

Example 115

3-[6-(4-hydroxy-3-methylphenyl)-2-oxo-2,3-dihydropyrimidin-4-yl]-N-(pyridin-4-ylmethyl)benzamide

MS (EI): 413 (MH+).

Example 116

3-[6-(4-hydroxy-3-methylphenyl)-2-oxo-2,3-dihydropyrimidin-4-yl]-N-{[4-(methyloxy)phenyl]methyl}benzamide

MS (EI): 442 (MH+).

Example 117

N-cyclopentyl-3-[6-(4-hydroxy-3-methylphenyl)-2-oxo-2,3-dihydropyrimidin-4-yl]benzamide

MS (EI): 390 (MH+).

Example 118

N-[2-(dimethylamino)ethyl]-3-[6-(4-hydroxy-3-methylphenyl)-2-oxo-2,3-dihydropyrimidin-4-yl]-N-methylbenzamide

MS (EI): 407 (MH+).

Example 119

N-butyl-3-[6-(4-hydroxy-3-methylphenyl)-2-oxo-2,3-dihydropyrimidin-4-yl]benzamide

MS (ED: 378 (MH+).

Example 120

N-[(3-chlorophenyl)methyl]-3-[6-(4-hydroxy-3-methylphenyl)-2-oxo-2,3-dihydropyrimidin-4-yl]benzamide

MS (EI): 446 (MH+).

Example 121

6-[3-(1,4'-bipiperidin-1'-ylcarbonyl)phenyl]-4-(4-hydroxy-3-methylphenyl)pyrimidin-2(1H)-one

MS (EI): 473 (MH+).

Example 122

N-[3-(dimethylamino)propyl]-3-[6-(4-hydroxy-3-methylphenyl)-2-oxo-2,3-dihydropyrimidin-4-yl]-N-methylbenzamide

MS (EI): 421 (MH+).

Example 123

4-(4-hydroxy-3-methylphenyl)-6-{3-[(4-pyrazin-2-ylpiperazin-1-yl)carbonyl]phenyl}pyrimidin-2(1H)-one

MS (EI): 469 (MH+).

Example 124

N-cycloheptyl-3-[6-(4-hydroxy-3-methylphenyl)-2-oxo-2,3-dihydropyrimidin-4-yl]benzamide

MS (EI): 418 (MH+).

Example 125

3-[6-(4-hydroxy-3-methylphenyl)-2-oxo-2,3-dihydropyrimidin-4-yl]-N-{[2-(methyloxy)phenyl]methyl}benzamide

MS (EI): 442 (MH+).

Example 126

6-(3-{[3-(diethylamino)pyrrolidin-1-yl]carbonyl}phenyl)-4-(4-hydroxy-3-methylphenyl)pyrimidin-2(1H)-one

MS (EI): 447 (MH+).

Example 127

N-cyclohexyl-3-[6-(4-hydroxy-3-methylphenyl)-2-oxo-2,3-dihydropyrimidin-4-yl]benzamide

MS (EI): 404 (MH+).

Example 128

N-[(2-fluorophenyl)methyl]-3-[6-(4-hydroxy-3-methylphenyl)-2-oxo-2,3-dihydropyrimidin-4-yl]-N-methylbenzamide

MS (EI): 444 (MH+).

Example 129

4-(4-hydroxy-3-methylphenyl)-6-(3-{[4-(phenylmethyl)piperazin-1-yl]carbonyl}phenyl)pyrimidin-2(1H)-one

MS (EI): 481 (MH+).

Example 130

4-(4-hydroxy-3-methylphenyl)-6-(3-{[4-(hydroxymethyl)piperidin-1-yl]carbonyl}phenyl)pyrimidin-2(1H)-one

MS (EI): 420 (MH+).

Example 131 ethyl 1-({3-[6-(4-hydroxy-3-methylphenyl)-2-oxo-2,3-dihydropyrimidin-4-yl]phenyl}carbonyl)piperidine-4-carboxylate

MS (EI): 462 (MH+).

Example 132

4-(4-hydroxy-3-methylphenyl)-6-{3-[(4-morpholin-4-ylpiperidin-1-yl)carbonyl]phenyl}pyrimidin-2(1H)-one

MS (EI): 475 (MH+).

Example 133

4-(4-hydroxy-3-methylphenyl)-6-[3-(pyrrolidin-1-ylcarbonyl)phenyl]pyrimidin-2(1H)-one

MS (EI): 376 (MH+).

Example 134

6-[3-({4-[2-(ethyloxy)ethyl]piperazin-1-yl}carbonyl)phenyl]-4-(4-hydroxy-3-methylphenyl)pyrimidin-2(1H)-one

MS (EI): 463 (MH+).

Example 135

3-[6-(4-hydroxy-3-methylphenyl)-2-oxo-2,3-dihydropyrimidin-4-yl]-N-methyl-N-(2-methylpropyl)benzamide

MS (ED: 392 (MH+).

Example 136

3-[6-(4-hydroxy-3-methylphenyl)-2-oxo-2,3-dihy-dropyrimidin-4-yl]-N,N-dipropyl-benzamide

MS (ED: 406 (MH+).

Example 137

6-[3-(azepan-1-ylcarbonyl)phenyl]-4-(4-hydroxy-3-methylphenyl)pyrimidin-2(1H)-one

MS (EI): 404 (MH+).

Example 138

4-(4-hydroxy-3-methylphenyl)-6-[3-({4-[2-(methy-loxy)ethyl]piperazin-1-yl}carbonyl)phenyl]pyrimi-din-2(1H)-one

MS (EI): 449 (MH+).

Example 139

4-(4-hydroxy-3-methylphenyl)-6-[3-(morpholin-4-ylcarbonyl)phenyl]pyrimidin-2(1H)-one

MS (EI): 392 (MH+).

Example 140

4-(4-hydroxy-3-methylphenyl)-6-{3-[(3-methylpip-eridin-1-yl)carbonyl]phenyl}pyrimidin-2(1H)-one

MS (EI): 404 (MH+).

Example 141

4-(4-hydroxy-3-methylphenyl)-6-[3-(piperidin-1-ylcarbonyl)phenyl]pyrimidin-2(1H)-one

MS (EI): 390 (MH+).

Example 142

6-{3-[(4-acetylpiperazin-1-yl)carbonyl]phenyl}-4-(4-hydroxy-3-methylphenyl)pyrimidin-2(1H)-one

MS (EI): 433 (MH+).

Example 143

N-[1-({3-[6-(4-hydroxy-3-methylphenyl)-2-oxo-2,3-dihydropyrimidin-4-yl]phenyl}-carbonyl)pyrrolidin-3-yl]-N-methylacetamide

MS (EI): 447 (MH+).

Example 144 methyl 1-({3-[6-(4-hydroxy-3-methylphenyl)-2-oxo-2,3-dihydropyrimidin-4-yl]phenyl}-carbonyl)piperi-dine-4-carboxylate

MS (EI): 448 (MH+).

Example 145

4-(4-hydroxy-3-methylphenyl)-6-{3-[(4-hydroxypip-eridin-1-yl)carbonyl]phenyl}-pyrimidin-2(1H)-one

MS (EI): 406 (MH+).

Example 146

6-{3-[(2-ethylpiperidin-1-yl)carbonyl]phenyl}-4-(4-hydroxy-3-methylphenyl)pyrimidin-2(1H)-one

MS (EI): 418 (MH+).

Example 147

4-(4-hydroxy-3-methylphenyl)-6-{3-[(4-methylpip-erazin-1-yl)carbonyl]phenyl}pyrimidin-2(1H)-one

MS (EI): 405 (MH+).

Example 148

N-butyl-3-[6-(4-hydroxy-3-methylphenyl)-2-oxo-2,3-dihydropyrimidin-4-yl]-N-methylbenzamide

MS (EI): 392 (MH+).

Example 149

4-(4-hydroxy-3-methylphenyl)-6-{3-[(2-methylpyr-rolidin-1-yl)carbonyl]phenyl}pyrimidin-2(1H)-one

MS (EI): 390 (MH+).

Example 150

4-(4-hydroxy-3-methylphenyl)-6-(3-{[4-(tetrahydro-furan-2-ylcarbonyl)piperazin-1-yl]carbonyl}phenyl) pyrimidin-2(1H)-one

MS (EI): 489 (MH+).

Example 151

4-(4-hydroxy-3-methylphenyl)-6-[3-({4-[2-(methy-loxy)phenyl]piperazin-1-yl}carbonyl)-phenyl]pyri-midin-2(1H)-one

MS (EI): 497 (MH+).

Example 152

3-[6-(4-hydroxy-3-methylphenyl)-2-oxo-2,3-dihy-dropyrimidin-4-yl]-N-{[3-(methyloxy)phenyl] methyl}benzamide

MS (ED: 442 (MH+).

Example 153

6-(3-{[4-(furan-2-ylcarbonyl)piperazin-1-yl] carbonyl}phenyl)-4-(4-hydroxy-3-methylphenyl) pyrimidin-2(1H)-one

MS (EI): 485 (MH+).

Example 154

4-(4-hydroxy-3-methylphenyl)-6-[3-({4-[3-(methyloxy)phenyl]piperazin-1-yl}carbonyl)phenyl]pyrimidin-2(1H)-one

MS (EI): 497 (MH+).

Example 155

4-(4-hydroxy-3-methylphenyl)-6-[3-({4-[4-(methyloxy)phenyl]piperazin-1-yl}carbonyl)phenyl]pyrimidin-2(1H)-one

MS (EI): 497 (MH+).

Example 156

3-[6-(4-hydroxy-3-methylphenyl)-2-oxo-2,3-dihydropyrimidin-4-yl]-N-methyl-N-(1-methylpiperidin-4-yl)benzamide

MS (EI): 433 (MH+).

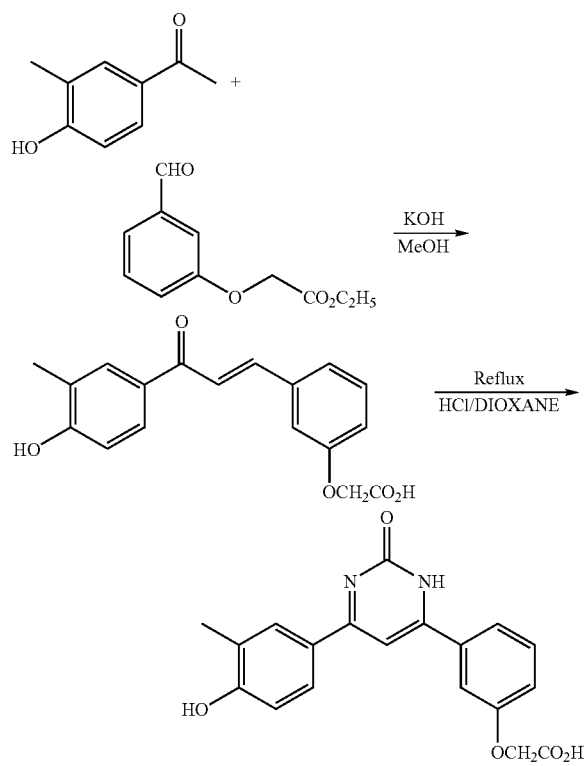

Scheme 9

Example 157

({3-[6-(4-Hydroxy-3-methylphenyl)-2-oxo-2,3-dihydropyrimidin-4-yl]phenyl}oxy)acetic acid

Step 1

(E)-2-(3-(3-(4-Hydroxy-3-methylphenyl)-3-oxoprop-1-enyl)phenoxy)acetic acid

Ethyl 2-(3-formylphenoxy)acetate (20.8 g, 0.1 mol) and 4'-hydroxy-3'-methylacetophenone (15.0 g, 0.1 mol) were dissolved in 150 mL of methanol and 50 mL of water. The solution was cooled with an ice-water bath, to which was added potassium hydroxide (21.0 g, 0.375 mol). The reaction mixture was stirred overnight. The resulted mixture was poured on to 600 mL of ice-water, acidified to pH=4-5 with 1 N HCl, and extracted with ethyl acetate (4×200 mL). The combined organic layers were washed with water and brine (200 mL each), dried over anhydrous sodium sulfate, filtered and concentrated in vacuo. The obtained yellow oil was dried under high-vacuum, 20 g (64%) of yellowish solid was obtained. $^1$H NMR (400 MHz, CDCl$_3$): δ 9.95 (s, 1H), 8.40 (br, 1H), 7.80 (s, 1H), 7.65 (m, 2H), 7.22-7.55 (m, 5H), 6.85 (d, 1H), 4.75 (s, 2H), 2.22 (s, 3H). MS (EI): 313 (MH$^+$).

Step 2

({3-[6-(4-Hydroxy-3-methylphenyl)-2-oxo-2,3-dihydropyrimidin-4-yl]phenyl}oxy)acetic acid (E)-2-(3-(3-(4-Hydroxy-3-methylphenyl)-3-oxoprop-1-enyl)phenoxy)acetic acid (15.0 g, 48.0 mmol) and urea (14.4 g, 0.24 mol) was suspended in 200 mL of 4N HCl solution in dioxane, and the reaction mixture was heated to reflux overnight, then cooled to room temperature. The resulted mixture was concentrated in vacuo to remove dioxane. The residues were suspended in 150 mL of 2-propanol and heated in a 90° C. oil bath for 10 minutes, then cooled down to room temperature by itself. The suspension was filtered, washed with 50 mL of 2-propanol and dried in the air. 9.2 g (54%) of yellow powder was obtained. $^1$H NMR (400 MHz, DMSO-d$_6$): δ 10.39 (s, 1H), 8.00 (s, 1H), 7.90 (m, 1H), 7.75 (m, 1H), 7.65 (s, 1H), 7.40-7.55 (m, 2H), 7.16 (m, 1H), 6.95 (m, 1H), 4.80 (s, 2H), 2.20 (s, 3H). MS (EI): 353 (MH$^+$).

Example 158

2-({3-[6-(4-hydroxy-3-methylphenyl)-2-oxo-2,3-dihydropyrimidin-4-yl]phenyl}oxy)-N-(3-morpholin-4-ylpropyl)acetamide ({3-[6-(4-Hydroxy-3-methylphenyl)-2-oxo-2,3-dihydropyrimidin-4-yl]phenyl}-oxy)acetic acid (Compound 222, 17 mg, 48 umol) and 3-morpholinopropan-1-amine (5.8 mg, 40 umol) were dissolved in dichloroethane (1.25 mL) and N,N-dimethylformamide (0.79 mL). To this solution was added 1-hydroxybenzotriazole (6.8 mg, 50 umol) followed by 1-[3-(dimethylamino)propyl]-3-ethylcarbodiimide methiodide (17.8 mg, 60 umol). The reaction mixture was stirred at room temperature for 15 hours and was concentrated in vacuo. The reaction mixture was purified by reverse phase HPLC to give 4 mg of product. $^1$H NMR (400 MHz, d6-DMSO): δ 8.31 (s, 1H), 8.17 (t, 1H), 7.96 (s, 1H), 7.87 (dd, 1H), 7.75 (d, 1H), 7.68 (s, 1H), 7.47 (t, 1H), 7.38 (s, 1H), 7.17 (dd, 1H), 6.92 (d, 1H), 4.61 (s, 2H), 3.61 (t, 4H), 3.21-3.16 (m, 2H), 2.30-2.22 (m, 6H), 2.20 (s, 3H), 1.63-1.57 (m, 2H). MS (EI): 480 (MH+).

Example 159

4-(4-hydroxy-3-methylphenyl)-6-{3-[(2-oxo-2-piperazin-1-ylethyl)oxy]phenyl}pyrimidin-2(1H)-one 4-(4-hydroxy-3-methylphenyl)-6-{3-[(2-oxo-2-piperazin-1-ylethyl)oxy]phenyl}-pyrimidin-2(1H)-one was synthesized in a manner similar to Example 158, wherein 3-morpholinopropan-1-amine was substituted with commercially available piperazine.

¹H NMR (400 MHz, d6-DMSO): δ 8.29 (s, 1H), 7.98 (s, 1H), 7.88 (dd, 1H), 7.72 (d, 1H), 7.65 (s, 1H), 7.47-7.40 (m, 2H), 7.12 (dd, 1H), 6.91 (d, 1H), 4.92 (s, 2H), 2.80 (t, 4H), 2.68 (t, 4H), 2.20 (s, 3H). MS (EI): 421 (MH+).

Example 160

N-(2-aminoethyl)-2-({3-[6-(4-hydroxy-3-methylphenyl)-2-oxo-2,3-dihydropyrimidin-4-yl]phenyl}oxy)acetamide N-(2-aminoethyl)-2-({3-[6-(4-hydroxy-3-methylphenyl)-2-oxo-2,3-dihydropyrimidin-4-yl]phenyl}oxy)acetamide was synthesized in a manner similar to Example 158, wherein 3-morpholinopropan-1-amine was substituted with commercially available ethane-1,2-diamine.

¹H NMR (400 MHz, d6-DMSO): δ 8.39 (s, 1H), 8.35 (t, 1H), 7.98 (s, 1H), 7.87 (dd, 1H), 7.76 (d, 1H), 7.69 (s, 1H), 7.48-7.42 (m, 2H), 7.16 (dd, 1H), 6.90 (d, 1H), 4.63 (s, 2H), 3.31-3.26 (m, 2H), 2.78 (t, 2H), 2.20 (s, 3H). MS (EI): 395 (MH+).

Example 161

N-(3-aminopropyl)-2-({3-[6-(4-hydroxy-3-methylphenyl)-2-oxo-2,3-dihydropyrimidin-4-yl]phenyl}oxy)acetamide N-(3-aminopropyl)-2-({3-[6-(4-hydroxy-3-methylphenyl)-2-oxo-2,3-dihydropyrimidin-4-yl]phenyl}oxy)acetamide was synthesized in a manner similar to Example 158, wherein 3-morpholinopropan-1-amine was substituted with commercially available propane-1,3-diamine.

¹H NMR (400 MHz, d6-DMSO): δ 8.41-8.37 (m, 2H), 7.93 (s, 1H), 7.84 (dd, 1H), 7.70 (d, 1H), 7.63 (s, 1H), 7.44 (t, 1H), 7.33 (s, 1H), 7.15 (dd, 1H), 6.90 (d, 1H), 4.59 (s, 2H), 3.26-3.21 (m, 2H), 2.83 (t, 2H), 2.20 (s, 3H), 1.75-1.68 (m, 2H). MS (EI): 409 (MH+).

Example 162

6-(3-{[2-(3-aminopiperidin-1-yl)-2-oxoethyl]oxy}phenyl)-4-(4-hydroxy-3-methylphenyl)-pyrimidin-2(1H)-one 6-(3-{[2-(3-aminopiperidin-1-yl)-2-oxoethyl]oxy}phenyl)-4-(4-hydroxy-3-methylphenyl)pyrimidin-2(1H)-one was synthesized in a manner similar to Example 158, wherein 3-morpholinopropan-1-amine was substituted with commercially available tert-butyl piperidin-3-ylcarbamate and then Boc deprotected under acidic conditions.

¹H NMR (400 MHz, d6-DMSO): δ 8.35 (s, 1H), 7.96 (s, 1H), 7.87 (dd, 1H), 7.71 (d, 1H), 7.63 (d, 1H), 7.44 (t, 1H), 7.38 (s, 1H), 7.12 (dd, 1H), 6.90 (d, 1H), 4.93 (s, 2H), 3.70-3.66 (m, 2H), 3.07-2.90 (m, 3H), 2.20 (s, 3H), 1.89-1.84 (m, 2H), 1.40-1.31 (m, 2H). MS (EI): 435 (MH+).

Example 163

N-[(1-ethylpyrrolidin-2-yl)methyl]-2-({3-[6-(4-hydroxy-3-methylphenyl)-2-oxo-2,3-dihydropyrimidin-4-yl]phenyl}oxy)acetamide N-[(1-ethylpyrrolidin-2-yl)methyl]-2-({3-[6-(4-hydroxy-3-methylphenyl)-2-oxo-2,3-dihydropyrimidin-4-yl]phenyl}oxy)acetamide was synthesized in a manner similar to Example 158, wherein 3-morpholinopropan-1-amine was substituted with commercially available (1-ethylpyrrolidin-2-yl)methanamine.

¹H NMR (400 MHz, d6-DMSO): δ 8.27 (s, 1H), 7.96-7.92 (m, 2H), 7.86 (dd, 1H), 7.74 (d, 1H), 7.68 (s, 1H), 7.47 (t, 1H), 7.38 (s, 1H), 7.16 (dd, 1H), 6.90 (d, 1H), 4.63 (s, 2H), 3.05-2.97 (m, 3H), 2.70-2.62 (m, 2H), 2.20 (s, 3H), 2.19-2.06 (m, 2H), 1.72-1.43 (m, 4H), 0.975 (t, 3H). MS (EI): 464 (MH+).

Example 164

2-({3-[6-(4-hydroxy-3-methylphenyl)-2-oxo-2,3-dihydropyrimidin-4-yl]phenyl}oxy)-N-(piperidin-4-ylmethyl)acetamide 2-({3-[6-(4-hydroxy-3-methylphenyl)-2-oxo-2,3-dihydropyrimidin-4-yl]phenyl}oxy)-N-(piperidin-4-ylmethyl)acetamide was synthesized in a manner similar to Example 158, wherein 3-morpholinopropan-1-amine was substituted with commercially available tert-butyl 4-(aminomethyl)piperidine-1-carboxylate and then Boc deprotected under acidic conditions.

¹H NMR (400 MHz, d6-DMSO): δ 8.41 (s, 1H), 8.24 (t, 1H), 7.95 (s, 1H), 7.86 (dd, 1H), 7.75 (d, 1H), 7.68 (s, 1H), 7.47 (t, 1H), 7.37 (s, 1H), 7.17 (dd, 1H), 6.91 (d, 1H), 4.63 (s, 2H), 3.11-3.03 (m, 4H), 2.58 (t, 2H), 2.20 (s, 3H), 1.62 (d, 3H), 1.20-1.11 (m, 2H). MS (EI): 450 (MH+).

Example 165

6-(3-{[2-(3-aminopyrrolidin-1-yl)-2-oxoethyl]oxy}phenyl)-4-(4-hydroxy-3-methylphenyl)pyrimidin-2(1H)-one 6-(3-{[2-(3-aminopyrrolidin-1-yl)-2-oxoethyl]oxy}phenyl)-4-(4-hydroxy-3-methylphenyl)pyrimidin-2(1H)-one was synthesized in a manner similar to Example 158, wherein 3-morpholinopropan-1-amine was substituted with commercially available tert-butyl pyrrolidin-3-ylcarbamate and then Boc deprotected under acidic conditions.

¹H NMR (400 MHz, d6-DMSO): δ 8.31 (s, 1H), 7.97 (s, 1H), 7.87 (dd, 1H), 7.72 (d, 1H), 7.64 (s, 1H), 7.45 (t, 1H), 7.37 (s, 1H), 7.12 (dd, 1H), 6.90 (d, 1H), 4.81 (s, 2H), 3.69-3.62 (m, 2H), 3.19-3.12 (m, 3H), 2.20 (s, 3H), 2.08-2.01 (m, 1H), 1.89-1.83 (m, 1H), 1.65-1.58 (m, 1H). MS (EI): 421 (MH+).

Example 166

N-[2-(dimethylamino)ethyl]-2-({3-[6-(4-hydroxy-3-methylphenyl)-2-oxo-2,3-dihydropyrimidin-4-yl]phenyl}oxy)acetamide N-[2-(dimethylamino)ethyl]-2-({3-[6-(4-hydroxy-3-methylphenyl)-2-oxo-2,3-dihydropyrimidin-4-yl]phenyl}oxy)acetamide was synthesized in a manner similar to Example 158, wherein 3-morpholinopropan-1-amine was substituted with commercially available N1,N1-dimethylethane-1,2-diamine.

¹NMR (400 MHz, d6-DMSO): δ 8.31 (s, 1H), 8.04 (t, 1H), 7.96 (s, 1H), 7.87 (d, 1H), 7.75 (d, 1H), 7.69 (s, 1H), 7.47 (t, 1H), 7.39 (s, 1H), 7.17 (dd, 1H), 6.91 (d, 1H), 4.61 (s, 2H), 3.28-3.21 (m, 2H), 2.32 (t, 2H), 2.21 (s, 3H), 2.13 (s, 3H). MS (EI): 423 (MH+).

Example 167

2-({3-[6-(4-hydroxy-3-methylphenyl)-2-oxo-2,3-dihydropyrimidin-4-yl]phenyl}oxy)-N-methyl-N-(2-methylpropyl)acetamide 2-({3-[6-(4-hydroxy-3-methylphenyl)-2-oxo-2,3-dihydropyrimidin-4-yl]phenyl}oxy)-N-methyl-N-(2-methylpropyl)acetamide was synthesized in a manner similar to Example 158, wherein 3-morpholinopropan-1-amine was substituted with commercially available N,2-dimethylpropan-1-amine.)

$^1$H NMR (400 MHz, d6-DMSO): 8.49 (s, 1H), 7.96 (s, 1H), 7.87 (dd, 1H), 7.69 (d, 1H), 7.56 (s, 1H), 7.46-7.41 (m, 1H), 7.35 (s, 1H), 7.12-7.08 (m, 1H) 6.90 (d, 1H), 4.96 (s, 2H), 3.18 (t, 2H), 3.02 (s, 3H), 2.20 (s, 3H), 1.91-1.86 (m, 1H), 0.92-0.79 (m, 6H). MS (EI): 422 (MH+).

Example 168

2-({3-[6-(4-hydroxy-3-methylphenyl)-2-oxo-2,3-dihydropyrimidin-4-yl]phenyl}oxy)-N-(2-pyrrolidin-1-ylethyl)acetamide 2-({3-[6-(4-hydroxy-3-methylphenyl)-2-oxo-2,3-dihydropyrimidin-4-yl]phenyl}oxy)-N-(2-pyrrolidin-1-ylethyl)acetamide was synthesized in a manner similar to Example 158, wherein 3-morpholinopropan-1-amine was substituted with commercially available 2-(pyrrolidin-1-yl)ethanamine.

$^1$H NMR (400 MHz, d6-DMSO): 8.29 (s, 1H), 8.10 (t, 1H), 7.96 (s, 1H), 7.87 (dd, 1H), 7.75 (d, 1H), 7.69 (1H), 7.47 (t, 1H), 7.38 (s, 1H), 7.17 (dd, 1H), 6.92 (d, 1H), 4.61 (s, 2H), 3.30-3.24 (m, 4H), 2.48-2.41 (m, 4H), 2.20 (s, 3H), 1.65-1.62 (m, 4H). MS (EI): 450 (MH+).

Example 169

N-[2-(diethylamino)ethyl]-2-({3-[6-(4-hydroxy-3-methylphenyl)-2-oxo-2,3-dihydropyrimidin-4-yl]phenyl}oxy)acetamide N-[2-(diethylamino)ethyl]-2-({3-[6-(4-hydroxy-3-methylphenyl)-2-oxo-2,3-dihydropyrimidin-4-yl]phenyl}oxy)acetamide was synthesized in a manner similar to Example 158, wherein 3-morpholinopropan-1-amine was substituted with commercially available N1,N1-diethylethane-1,2-diamine $^1$H NMR (400 MHz, d6-DMSO): 8.31 (s, 1H), 8.01-7.97 (m, 2H), 7.87 (d, 1H), 7.75 (d, 1H), 7.69 (s, 1H), 7.47 (t, 1H), 7.39 (s, 1H), 7.17 (d, 1H), 6.91 (d, 1H), 4.61 (s, 2H), 3.23-3.18 (m, 4H), 2.48-2.42 (m, 4H), 2.20 (s, 3H), 0.92 (t, 6H). MS (EI): 452 (MH+).

Example 170

2-({3-[6-(4-hydroxy-3-methylphenyl)-2-oxo-2,3-dihydropyrimidin-4-yl]phenyl}oxy)-N-(2-piperidin-1-ylethyl)acetamide 2-({3-[6-(4-hydroxy-3-methylphenyl)-2-oxo-2,3-dihydropyrimidin-4-yl]phenyl}oxy)-N-(2-piperidin-1-ylethyl)acetamide was synthesized in a manner similar to Example 158, wherein 3-morpholinopropan-1-amine was substituted with commercially available 2-(piperidin-1-yl)ethanamine.

$^1$H NMR (400 MHz, d6-DMSO): δ 8.30 (s, 1H), 8.00 (t, 1H), 7.96 (s, 1H), 7.87 (dd, 1H), 7.75 (d, 1H), 7.69 (s, 1H), 7.47 (t, 1H), 7.38 (s, 1H), 7.17 (dd, 1H), 6.91 (d, 1H), 4.61 (s, 2H), 3.28-3.22 (m, 2H), 2.38-2.29 (m, 6H), 2.20 (s, 3H), 1.48-1.42 (m, 4H), 1.37-1.31 (m, 2H). MS (EI): 464 (MH+).

Example 171

2-({3-[6-(4-hydroxy-3-methylphenyl)-2-oxo-2,3-dihydropyrimidin-4-yl]phenyl}oxy)-N-(3-pyrrolidin-1-ylpropyl)acetamide 2-({3-[6-(4-hydroxy-3-methylphenyl)-2-oxo-2,3-dihydropyrimidin-4-yl]phenyl}oxy)-N-(3-pyrrolidin-1-ylpropyl)acetamide was synthesized in a manner similar to Example 158, wherein 3-morpholinopropan-1-amine was substituted with commercially available 2-(piperidin-1-yl)ethanamine.

$^1$H NMR (400 MHz, d6-DMSO): δ 8.28 (s, 1H), 8.24 (t, 1H), 7.95 (s, 1H), 7.87 (dd, 1H), 7.74 (d, 1H), 7.67 (s, 1H), 7.47 (t, 1H), 7.38 (s, 1H), 7.16 (dd, 1H), 6.90 (d, 1H), 4.61 (s, 2H), 3.22-2.16 (m, 2H), 2.45-2.38 (m, 6H), 2.20 (s, 3H), 1.68-1.58 (m, 6H). MS (EI): 464 (MH+).

Example 172

2-({3-[6-(4-hydroxy-3-methylphenyl)-2-oxo-2,3-dihydropyrimidin-4-yl]phenyl}oxy)-N-{2-[(1-methylethyl)oxy]ethyl}acetamide 2-({3-[6-(4-hydroxy-3-methylphenyl)-2-oxo-2,3-dihydropyrimidin-4-yl]phenyl}oxy)-N-{2-[(1-methylethyl)oxy]ethyl}acetamide was synthesized in a manner similar to Example 158, wherein 3-morpholinopropan-1-amine was substituted with commercially available 2-isopropoxyethanamine.

$^1$H NMR (400 MHz, d6-DMSO): δ 8.51 (s, 1H), 8.12 (t, 1H), 7.95 (s, 1H), 7.86 (d, 1H), 7.74 (d, 1H), 7.69 (s, 1H), 7.47 (t, 1H), 7.37 (s, 1H), 7.16 (d, 1H), 6.91 (dd, 1H), 4.61 (s, 2H), 3.58-3.48 (m, 2H), 3.36-3.23 (m, 3H), 2.20 (s, 3H), 1.09-1.05 (m, 6H). MS (EI): 438 (MH+).

Example 173

2-({3-[6-(4-hydroxy-3-methylphenyl)-2-oxo-2,3-dihydropyrimidin-4-yl]phenyl}oxy)-N-[2-(1-methylpyrrolidin-2-yl)ethyl]acetamide 2-({3-[6-(4-hydroxy-3-methylphenyl)-2-oxo-2,3-dihydropyrimidin-4-yl]phenyl}oxy)-N-[2-(1-methylpyrrolidin-2-yl)ethyl]acetamide was synthesized in a manner similar to Example 158, wherein 3-morpholinopropan-1-amine was substituted with commercially available 2-(1-methylpyrrolidin-2-yl)ethanamine.

$^1$H NMR (400 MHz, d6-DMSO): δ 8.30 (s, 1H), 8.25 (t, 1H), 7.96 (s, 1H), 7.87 (dd, 1H), 7.75 (d, 1H), 7.68 (s, 1H), 7.47 (t, 1H), 7.39 (s, 1H), 7.17 (dd, 1H), 6.92 (d, 1H), 4.61 (s, 2H), 3.22-3.18 (m, 2H), 2.20 (s, 3H), 2.17 (s, 3H), 2.05-1.97 (m, 3H), 1.88-1.73 (m, 2H), 1.61-1.53 (m, 2H), 1.42-1.34 (m, 2H). MS (EI): 464 (MH+).

Example 174

N-[3-(dimethylamino)propyl]-2-({3-[6-(4-hydroxy-3-methylphenyl)-2-oxo-2,3-dihydropyrimidin-4-yl]phenyl}oxy)acetamide N-[3-(dimethylamino)propyl]-2-({3-[6-(4-hydroxy-3-methylphenyl)-2-oxo-2,3-dihydropyrimidin-4-yl]phenyl}oxy)acetamide was synthesized in a manner similar to Example 158, wherein 3-morpholinopropan-1-amine was substituted with commercially available N1,N1-dimethylpropane-1,3-diamine.

¹H NMR (400 MHz, d6-DMSO): δ 8.30 (s, 1H), 8.26 (t, 1H), 7.96 (s, 1H), 7.87 (dd, 1H), 7.74 (d, 1H), 7.68 (s, 1H), 7.47 (t, 1H), 7.38 (s, 1H), 7.17 (dd, 1H), 6.91 (d, 1H), 4.61 (s, 2H) 3.21-3.16 (m, 2H), 2.28-2.21 (m, 2H), 2.20 (s, 3H), 2.10 (s, 6H), 1.61-1.53 (m, 2H). MS (EI): 438 (MH+).

Example 175

6-[3-({2-[3-(diethylamino)pyrrolidin-1-yl]-2-oxoethyl}oxy)phenyl]-4-(4-hydroxy-3-methylphenyl)pyrimidin-2(1H)-one 6-[3-({2-[3-(diethylamino)pyrrolidin-1-yl]-2-oxoethyl}oxy)phenyl]-4-(4-hydroxy-3-methylphenyl)pyrimidin-2(1H)-one was synthesized in a manner similar to Example 158, wherein 3-morpholinopropan-1-amine was substituted with commercially available N,N-diethylpyrrolidin-3-amine.

¹H NMR (400 MHz, d6-DMSO): δ 8.36 (s, 1H), 7.97 (s, 1H), 7.88 (d, 1H), 7.71 (d, 1H), 7.63 (s, 1H), 7.44 (t, 1H), 7.37 (s, 1H), 7.12 (d, 1H), 6.91 (d, 1H), 4.86 (s, 2H), 3.82-3.62 (m, 3H), 3.25-3.17 (m, 2H), 2.59-2.53 (m, 4H), 2.20 (s, 3H), 2.08-1.98 (m, 1H), 1.82-1.74 (m, 1H), 0.98-0.91 (m, 6H). MS (EI): 478 (MH+).

Example 176

2-({3-[6-(4-hydroxy-3-methylphenyl)-2-oxo-2,3-dihydropyrimidin-4-yl]phenyl}oxy)-N-methyl-N-(1-methylpyrrolidin-3-yl)acetamide 2-({3-[6-(4-hydroxy-3-methylphenyl)-2-oxo-2,3-dihydropyrimidin-4-yl]phenyl}oxy)-N-methyl-N-(1-methylpyrrolidin-3-yl)acetamide was synthesized in a manner similar to Example 158, wherein 3-morpholinopropan-1-amine was substituted with commercially available N,1-dimethylpyrrolidin-3-amine.

¹H NMR (400 MHz, d6-DMSO): δ 8.30 (s, 1H), 7.96 (s, 1H), 7.88 (d, 1H), 7.70 (d, 1H), 7.61 (s, 1H), 7.47-7.42 (m, 1H), 7.36 (s, 1H), 7.13-7.09 (m, 1H), 6.90 (d, 1H), 4.94 (d, 2H), 4.54-4.98 (m, 1H), 2.90 (s, 3H), 2.78-2.54 (m, 2H), 2.38-2.32 (m, 1H), 2.22 (s, 3H), 2.20 (s, 3H), 2.18-2.02 (m, 2H), 1.78-1.64 (m, 1H). MS (EI): 450 (MH+).

Example 177

4-(4-hydroxy-3-methylphenyl)-6-(3-{[2-(4-methyl-1,4-diazepan-1-yl)-2-oxoethyl]oxy}-phenyl)pyrimidin-2(1H)-one 4-(4-hydroxy-3-methylphenyl)-6-(3-{[2-(4-methyl-1,4-diazepan-1-yl)-2-oxoethyl]oxy}phenyl)pyrimidin-2(1H)-one was synthesized in a manner similar to Example 158, wherein 3-morpholinopropan-1-amine was substituted with commercially available 1-methyl-1,4-diazepane.

¹H NMR (400 MHz, d6-DMSO): δ 8.28 (s, 1H), 7.97 (s, 1H), 7.87 (d, 1H), 7.70 (d, 1H), 7.61 (d, 1H), 7.44 (t, 1H), 7.38 (d, 1H), 7.11 (d, 1H), 6.90 (d, 1H), 4.95 (d, 2H), 3.58-3.47 (m, 4H), 2.70-2.64 (m, 2H), 2.58-2.56 (m, 1H), 2.51-2.48 (m, 1H), 2.22 (s, 3H), 2.20 (s, 3H), 1.94-1.88 (m, 1H), 1.81-1.74 (m, 1H). MS (EI): 450 (MH+).

Example 178

2-({3-[6-(4-hydroxy-3-methylphenyl)-2-oxo-2,3-dihydropyrimidin-4-yl]phenyl}oxy)-N-[3-(1H-imidazol-1-yl)propyl]acetamide 2-({3-[6-(4-hydroxy-3-methylphenyl)-2-oxo-2,3-dihydropyrimidin-4-yl]phenyl}oxy)-N-[3-(1H-imidazol-1-yl)propyl]acetamide was synthesized in a manner similar to Example 158, wherein 3-morpholinopropan-1-amine was substituted with commercially available 3-(1H-imidazol-1-yl)propan-1-amine.

¹H NMR (400 MHz, d6-DMSO): δ 8.44 (s, 1H), 8.25 (t, 1H), 7.95 (s, 1H), 7.86 (d, 1H), 7.76 (d, 1H), 7.72 (s, 1H), 7.59 (s, 1H), 7.48 (t, 1H), 7.39 (s, 1H), 7.19 (dd, 1H), 7.15 (s, 1H), 6.91 (d, 1H), 6.86 (s, 1H), 4.61 (s, 2H), 3.96 (t, 2H), 3.16-3.12 (m, 2H), 2.20 (s, 3H), 1.92-1.86 (m, 2H). MS (EI): 461 (MH+).

Example 179

N-[2-(dimethylamino)ethyl]-2-({3-[6-(4-hydroxy-3-methylphenyl)-2-oxo-2,3-dihydropyrimidin-4-yl]phenyl}oxy)-N-methylacetamide N-[2-(dimethylamino)ethyl]-2-({3-[6-(4-hydroxy-3-methylphenyl)-2-oxo-2,3-dihydropyrimidin-4-yl]phenyl}oxy)-N-methylacetamide was synthesized in a manner similar to Example 158, wherein 3-morpholinopropan-1-amine was substituted with commercially available N1,N1,N2-trimethylethane-1,2-diamine.

¹H NMR (400 MHz, d6-DMSO): δ 8.30 (s, 1H), 7.96 (s, 1H), 7.87 (d, 1H), 7.68 (d, 1H), 7.61 (d, 1H), 7.46-7.41 (m, 1H), 7.36 (s, 1H), 7.13-7.09 (m, 1H), 6.90 (d, 1H), 4.96 (s, 2H), 2.95 (s, 3H), 2.48-2.40 (m, 2H), 2.34-2.31 (m, 2H), 2.20 (s, 6H), 2.11 (s, 3H). MS (EI): 438 (MH+).

Example 180

2-({3-[6-(4-hydroxy-3-methylphenyl)-2-oxo-2,3-dihydropyrimidin-4-yl]phenyl}oxy)-N-methyl-N-(1-methylpiperidin-4-yl)acetamide 2-({3-[6-(4-hydroxy-3-methylphenyl)-2-oxo-2,3-dihydropyrimidin-4-yl]phenyl}oxy)-N-methyl-N-(1-methylpiperidin-4-yl)acetamide was synthesized in a manner similar to Example 158, wherein 3-morpholinopropan-1-amine was substituted with commercially available N,1-dimethylpiperidin-4-amine.

¹H NMR (400 MHz, d6-DMSO): δ 8.27 (s, 1H), 7.96 (s, 1H), 7.86 (d, 1H), 7.70 (d, 1H), 7.61 (s, 1H), 7.46-7.41 (m, 1H), 7.36 (d, 1H), 7.10 (d, 1H), 6.90 (d, 1H), 4.96 (d, 2H), 4.23-4.16 (m, 1H), 2.82 (m, 5H), 2.20 (s, 3H), 2.18 (s, 3H), 2.01-1.88 (m, 2H), 1.84-1.63 (m, 3H), 1.47-1.44 (m, 1H). MS (EI): 464 (MH+).

Example 181

N-[3-(dimethylamino)propyl]-2-({3-[6-(4-hydroxy-3-methylphenyl)-2-oxo-2,3-dihydropyrimidin-4-yl]phenyl}oxy)-N-methylacetamide N-[3-(dimethylamino)propyl]-2-({3-[6-(4-hydroxy-3-methylphenyl)-2-oxo-2,3-dihydropyrimidin-4-yl]

phenyl}oxy)-N-methylacetamide was synthesized in a manner similar to Example 158, wherein 3-morpholinopropan-1-amine was substituted with commercially available N1,N1,N3-trimethylpropane-1,3-diamine.

$^1$H NMR (400 MHz, d6-DMSO): δ 8.31 (s, 1H), 7.96 (s, 1H), 7.87 (dd, 1H), 7.01 (t, 1H), 7.62 (d, 1H), 7.46-7.37 (m, 2H), 7.12-7.08 (m, 1H), 6.90 (d, 1H), 4.96 (d, 2H), 3.46-3.38 (m, 2H), 2.92 (s, 3H), 2.27 (t, 1H), 2.20 (s, 3H), 2.19-2.17 (m, 1H), 2.14 (s, 3H), 2.10 (s, 3H), 1.88-1.82 (m, 1H), 1.62-1.58 (m, 1H). MS (EI): 452 (MH+).

Example 182

6-(3-{[2-(4-ethylpiperazin-1-yl)-2-oxoethyl]oxy}phenyl)-4-(4-hydroxy-3-methylphenyl)-pyrimidin-2(1H)-one 6-(3-{[2-(4-ethylpiperazin-1-yl)-2-oxoethyl]oxy}phenyl)-4-(4-hydroxy-3-methylphenyl)pyrimidin-2(1H)-one was synthesized in a manner similar to Example 158, wherein 3-morpholinopropan-1-amine was substituted with commercially available 1-ethyl piperazine.

$^1$H NMR (400 MHz, d6-DMSO): δ 8.37 (s, 1H), 7.96 (s, 1H), 7.87 (dd, 1H), 7.70 (d, 1H), 7.62 (s, 1H), 7.44 (t, 1H), 7.37 (s, 1H), 7.12 (dd, 1H), 6.90 (d, 1H), 4.96 (s, 2H), 3.51-3.46 (m, 4H), 2.46-2.40 (m, 2H), 2.38-2.32 (m, 4H), 2.20 (s, 3H), 0.99 (t, 3H). MS (EI): 450 (MH+).

Example 183

N-[2-(dimethylamino)ethyl]-N-ethyl-2-({3-[6-(4-hydroxy-3-methylphenyl)-2-oxo-2,3-dihydropyrimidin-4-yl]phenyl}oxy)acetamide N-[2-(dimethylamino)ethyl]-N-ethyl-2-({3-[6-(4-hydroxy-3-methylphenyl)-2-oxo-2,3-dihydropyrimidin-4-yl]phenyl}oxy)acetamide was synthesized in a manner similar to Example 158, wherein 3-morpholinopropan-1-amine was substituted with commercially available N1-ethyl-N2,N2-dimethylethane-1,2-diamine.

$^1$H NMR (400 MHz, d6-DMSO): δ 8.32 (s, 1H), 7.96 (s, 1H), 7.86 (d, 1H), 7.69 (d, 1H), 7.60 (d, 1H), 7.44 (t, 1H), 7.35 (s, 1H), 7.12-7.08 (m, 1H), 6.90 (d, 1H), 4.94 (d, 2H), 3.34-3.30 (m, 2H), 2.50-2.32 (m, 4H), 2.20 (s, 6H), 2.11 (s, 3H), 1.21-1.02 (m, 3H). MS (EI): 452 (MH+).

Example 184

6-(3-{[2-(1,4'-bipiperidin-1'-yl)-2-oxoethyl]oxy}phenyl)-4-(4-hydroxy-3-methylphenyl)-pyrimidin-2(1H)-one 6-(3-{[2-(1,4'-bipiperidin-1'-yl)-2-oxoethyl]oxy}phenyl)-4-(4-hydroxy-3-methylphenyl)pyrimidin-2(1H)-one was synthesized in a manner similar to Example 158, wherein 3-morpholinopropan-1-amine was substituted with commercially available 1,4'-bipiperidine.

$^1$H NMR (400 MHz, d6-DMSO): δ 8.29 (s, 1H), 7.97 (s, 1H), 7.87 (dd, 1H), 7.69 (d, 1H), 7.61 (s, 1H), 7.44 (t, 1H), 7.37 (s, 1H), 7.12 (dd, 1H), 6.90 (d, 1H), 5.01-4.89 (m, 2H), 4.35 (d, 1H), 3.91 (d, 1H), 3.03 (t, 2H), 2.58 (t, 1H), 2.42-2.38 (m, 4H), 2.20 (s, 3H), 1.74 (t, 2H), 1.46-1.24 (m, 8H). MS (EI): 504 (MH+).

Example 185

6-[3-({2-[3-(aminomethyl)piperidin-1-yl]-2-oxoethyl}oxy)phenyl]-4-(4-hydroxy-3-methylphenyl)pyrimidin-2(1H)-one 6-[3-({2-[3-(aminomethyl)piperidin-1-yl]-2-oxoethyl}oxy)phenyl]-4-(4-hydroxy-3-methylphenyl)pyrimidin-2(1H)-one was synthesized in a manner similar to Example 158, wherein 3-morpholinopropan-1-amine was substituted with commercially available tert-butyl piperidin-3-ylmethylcarbamate and then Boc deprotected under acidic conditions.

$^1$H NMR (400 MHz, d6-DMSO): δ 8.39 (s, 1H), 7.49 (s, 1H), 7.85 (dd, 1H), 7.74-7.58 (m, 2H), 7.44-7.35 (m, 2H), 7.09 (dd, 1H), 6.90 (d, 1H), 5.01-4.91 (m, 2H), 3.98-3.78 (m, 2H), 3.10-2.95 (m, 2H), 2.70-2.62 (m, 2H), 2.20 (s, 3H), 1.88-1.32 (m, 5H). MS (EI): 450 (MH+).

Example 186

2-({3-[6-(4-hydroxy-3-methylphenyl)-2-oxo-2,3-dihydropyrimidin-4-yl]phenyl}oxy)-N-(2-morpholin-4-ylethyl)acetamide 2-({3-[6-(4-hydroxy-3-methylphenyl)-2-oxo-2,3-dihydropyrimidin-4-yl]phenyl}oxy)-N-(2-morpholin-4-ylethyl)acetamide was synthesized in a manner similar to Example 158, wherein 3-morpholinopropan-1-amine was substituted with commercially available 2-morpholinoethanamine.

$^1$H NMR (400 MHz, d6-DMSO): δ 8.35 (s, 1H), 8.04 (t, 1H), 7.96 (s, 1H), 7.87 (dd, 1H), 7.75 (d, 1H), 7.69 (s, 1H), 7.47 (t, 1H), 7.39 (s, 1H), 7.18 (dd, 1H), 6.91 (d, 1H), 4.61 (s, 2H), 3.52 (t, 4H), 3.30-3.24 (m, 2H), 2.40-2.32 (m, 6H), 2.20 (s, 3H). MS (EI): 466 (MH+).

Example 187

N-butyl-2-({3-[6-(4-hydroxy-3-methylphenyl)-2-oxo-2,3-dihydropyrimidin-4-yl]phenyl}oxy)-N-methylacetamide N-butyl-2-({3-[6-(4-hydroxy-3-methylphenyl)-2-oxo-2,3-dihydropyrimidin-4-yl]phenyl}oxy)-N-methylacetamide was synthesized in a manner similar to Example 158, wherein 3-morpholinopropan-1-amine was substituted with commercially available N-methylbutan-1-amine.

$^1$H NMR (400 MHz, d6-DMSO): δ 8.44 (s, 1H), 7.96 (s, 1H), 7.87 (dd, 1H), 7.69 (d, 1H), 7.60 (d, 1H), 7.46-7.41 (m, 1H), 7.36 (s, 1H), 7.10 (d, 1H), 6.90 (d, 1H), 4.92 (s, 2H), 3.32-3.25 (m, 2H), 2.92 (s, 3H), 2.20 (s, 3H), 1.62-1.40 (m, 2H), 1.38-1.16 (m, 2H), 0.94-0.80 (m, 3H). MS (EI): 422 (MH+).

Example 188

N-(4-aminocyclohexyl)-2-({3-[6-(4-hydroxy-3-methylphenyl)-2-oxo-2,3-dihydropyrimidin-4-yl]phenyl}oxy)acetamide N-(4-aminocyclohexyl)-2-({3-[6-(4-hydroxy-3-methylphenyl)-2-oxo-2,3-dihydropyrimidin-4-yl]phenyl}oxy)acetamide was synthesized in a manner similar to Example 158, wherein 3-morpholinopropan-1-amine was substituted with commercially available cyclohexane-1,4-diamine.

$^1$H NMR (400 MHz, d6-DMSO): δ 8.44 (s, 1H), 8.01 (d, 1H), 7.95 (d, 1H), 7.85 (dd, 1H), 7.74 (d, 1H), 7.68 (s, 1H), 7.46 (t, 1H), 7.36 (s, 1H), 7.16 (dd, 1H), 6.92 (d, 1H), 4.59 (s, 2H), 3.60-3.56 (m, 1H), 2.78-2.72 (m, 1H), 2.20 (s, 3H), 1.87-1.77 (m, 4H), 1.46-1.37 (m, 4H). MS (EI): 450 (MH+).

Example 189

4-(4-hydroxy-3-methylphenyl)-6-(3-{[2-(4-methylpiperazin-1-yl)-2-oxoethyl]oxy}-phenyl)pyrimidin-2(1H)-one 4-(4-hydroxy-3-methylphenyl)-6-(3-{[2-(4-methylpiperazin-1-yl)-2-oxoethyl]oxy}phenyl)pyrimidin-2(1H)-one was synthesized in a manner similar to Example 158, wherein 3-morpholinopropan-1-amine was substituted with commercially available 1-methyl piperazine.

$^1$H NMR (400 MHz, d6-DMSO): δ 8.19 (s, 1H), 7.97 (s, 1H), 7.88 (dd, 1H), 7.70 (d, 1H), 7.62 (s, 1H), 7.45 (t, 1H), 7.37 (s, 1H), 7.12 (dd, 1H), 6.90 (d, 1H), 4.96 (s, 2H), 3.50-3.44 (m, 4H), 2.38-2.36 (m, 2H), 2.30-2.28 (m, 2H), 2.20 (s, 3H), 2.18 (s, 3H). MS (ED: 435 (MH+).

Examples 190-244 below were made in a manner similar to Example 17, wherein the appropriate substitutions of commercially available reactants and/or reagents were made to arrive at these compounds. One skilled in the art would be readily able to ascertain which reactants and reagents need to be substituted. The skilled artisan would be readily able to commercially obtain these reactants and/or reagents that are necessary for making these compounds.

Example 190

N-(2-cyanoethyl)-2-({3-[6-(4-hydroxy-3-methylphenyl)-2-oxo-2,3-dihydropyrimidin-4-yl]phenyl}oxy)acetamide

MS (EI): 405 (MH+).

Example 191

2-({3-[6-(4-hydroxy-3-methylphenyl)-2-oxo-2,3-dihydropyrimidin-4-yl]phenyl}oxy)-N-[3-(methyloxy)propyl]acetamide

MS (EI): 424 (MH+).

Example 192

2-({3-[6-(4-hydroxy-3-methylphenyl)-2-oxo-2,3-dihydropyrimidin-4-yl]phenyl}oxy)-N-[(5-methylfuran-2-yl)methyl]acetamide

MS (EI): 446 (MH+).

Example 193

N-[(6-chloropyridin-3-yl)methyl]-2-({3-[6-(4-hydroxy-3-methylphenyl)-2-oxo-2,3-dihydropyrimidin-4-yl]phenyl}oxy)acetamide

MS (EI): 477 (MH+).

Example 194

N-butyl-2-({3-[6-(4-hydroxy-3-methylphenyl)-2-oxo-2,3-dihydropyrimidin-4-yl]phenyl}oxy)acetamide

MS (EI): 408 (MH+).

Example 195

4-(4-hydroxy-3-methylphenyl)-6-(3-{[2-(3-methylpiperidin-1-yl)-2-oxoethyl]oxy}-phenyl)pyrimidin-2(1H)-one

MS (EI): 434 (MH+).

Example 196

N-[(2-fluorophenyl)methyl]-2-({3-[6-(4-hydroxy-3-methylphenyl)-2-oxo-2,3-dihydropyrimidin-4-yl]phenyl}oxy)-N-methylacetamide

MS (EI): 474 (MH+).

Example 197

2-({3-[6-(4-hydroxy-3-methylphenyl)-2-oxo-2,3-dihydropyrimidin-4-yl]phenyl}oxy)-N-[2-(phenyloxy)ethyl]acetamide

MS (EI): 472 (MH+).

Example 198

2-({3-[6-(4-hydroxy-3-methylphenyl)-2-oxo-2,3-dihydropyrimidin-4-yl]phenyl}oxy)-N-(pyridin-3-ylmethyl)acetamide

MS (EI): 443 (MH+).

Example 199

N-(cyclopropylmethyl)-2-({3-[6-(4-hydroxy-3-methylphenyl)-2-oxo-2,3-dihydropyrimidin-4-yl]phenyl}oxy)acetamide

MS (EI): 406 (MH+).

Example 200

2-({3-[6-(4-hydroxy-3-methylphenyl)-2-oxo-2,3-dihydropyrimidin-4-yl]phenyl}oxy)-N-(2-methylpropyl)acetamide

MS (EI): 408 (MH+).

Example 201

2-({3-[6-(4-hydroxy-3-methylphenyl)-2-oxo-2,3-dihydropyrimidin-4-yl]phenyl}oxy)-N-pentylacetamide

MS (EI): 422 (MH+).

Example 202

2-({3-[6-(4-hydroxy-3-methylphenyl)-2-oxo-2,3-dihydropyrimidin-4-yl]phenyl}oxy)-N-(pyridin-4-ylmethyl)acetamide

MS (EI): 443 (MH+).

Example 203

N-cyclopentyl-2-({3-[6-(4-hydroxy-3-methylphenyl)-2-oxo-2,3-dihydropyrimidin-4-yl]phenyl}oxy)acetamide

MS (EI): 420 (MH+).

Example 204

N-[(3-chlorophenyl)methyl]-2-({3-[6-(4-hydroxy-3-methylphenyl)-2-oxo-2,3-dihydropyrimidin-4-yl]phenyl}oxy)acetamide

MS (EI): 476 (MH+).

Example 205

N-[2-(2-fluorophenyl)ethyl]-2-({3-[6-(4-hydroxy-3-methylphenyl)-2-oxo-2,3-dihydropyrimidin-4-yl]phenyl}oxy)acetamide

MS (EI): 474 (MH+).

Example 206

N-(furan-2-ylmethyl)-2-({3-[6-(4-hydroxy-3-methylphenyl)-2-oxo-2,3-dihydropyrimidin-4-yl]phenyl}oxy)-N-methylacetamide

MS (EI): 446 (MH+).

Example 207

N-(furan-2-ylmethyl)-2-({3-[6-(4-hydroxy-3-methylphenyl)-2-oxo-2,3-dihydropyrimidin-4-yl]phenyl}oxy)acetamide

MS (EI): 432 (MH+).

Example 208

4-(4-hydroxy-3-methylphenyl)-6-(3-{[2-(4-morpholin-4-ylpiperidin-1-yl)-2-oxoethyl]oxy}-phenyl)pyrimidin-2(1H)-one

MS (EI): 505 (MH+).

Example 209

N-cyclopropyl-2-({3-[6-(4-hydroxy-3-methylphenyl)-2-oxo-2,3-dihydropyrimidin-4-yl]phenyl}oxy)acetamide

MS (EI): 392 (MH+).

Example 210

2-({3-[6-(4-hydroxy-3-methylphenyl)-2-oxo-2,3-dihydropyrimidin-4-yl]phenyl}oxy)-N-propylacetamide

MS (EI): 394 (MH+).

Example 211

4-(4-hydroxy-3-methylphenyl)-6-{3-[(2-{4-[2-(methyloxy)ethyl]piperazin-1-yl}-2-oxoethyl)oxy]phenyl}pyrimidin-2(1H)-one

MS (EI): 479 (MH+).

Example 212 methyl 1-[({3-[6-(4-hydroxy-3-methylphenyl)-2-oxo-2,3-dihydropyrimidin-4-yl]phenyl}oxy)acetyl]piperidine-4-carboxylate

MS (EI): 478 (MH+).

Example 213

4-(4-hydroxy-3-methylphenyl)-6-[3-({2-oxo-2-[4-(tetrahydrofuran-2-ylcarbonyl)piperazin-1-yl]ethyl}oxy)phenyl]pyrimidin-2(1H)-one

MS (EI): 519 (MH+).

Example 214

6-(3-{[2-(4-acetylpiperazin-1-yl)-2-oxoethyl]oxy}phenyl)-4-(4-hydroxy-3-methylphenyl)pyrimidin-2(1H)-one

MS (EI): 463 (MH+).

Example 215

6-{3-[(2-{4-[2-(ethyloxy)ethyl]piperazin-1-yl}-2-oxoethyl)oxy]phenyl}-4-(4-hydroxy-3-methylphenyl)pyrimidin-2(1H)-one

MS (EI): 493 (MH+).

Example 216

N-(cyclohexylmethyl)-2-({3-[6-(4-hydroxy-3-methylphenyl)-2-oxo-2,3-dihydropyrimidin-4-yl]phenyl}oxy)acetamide

MS (EI): 448 (MH+).

Example 217

2-({3-[6-(4-hydroxy-3-methylphenyl)-2-oxo-2,3-dihydropyrimidin-4-yl]phenyl}oxy)-N-{[2-(methyloxy)phenyl]methyl}acetamide

MS (EI): 472 (MH+).

Example 218

N-cyclobutyl-2-({3-[6-(4-hydroxy-3-methylphenyl)-2-oxo-2,3-dihydropyrimidin-4-yl]phenyl}oxy)acetamide

MS (EI): 406 (MH+).

Example 219

4-(4-hydroxy-3-methylphenyl)-6-(3-{[2-(2-methylpyrrolidin-1-yl)-2-oxoethyl]oxy}-phenyl)pyrimidin-2(1H)-one

MS (EI): 420 (MH+).

Example 220

4-(4-hydroxy-3-methylphenyl)-6-[3-({2-oxo-2-[4-(phenylmethyl)piperazin-1-yl]ethyl}oxy)phenyl]pyrimidin-2(1H)-one

MS (EI): 511 (MH+).

Example 221

4-(4-hydroxy-3-methylphenyl)-6-[3-({2-[4-(hydroxymethyl)piperidin-1-yl]-2-oxoethyl}oxy)phenyl]pyrimidin-2(1H)-one

MS (EI): 450 (MH+).

Example 222

N-[(2-chlorophenyl)methyl]-2-({3-[6-(4-hydroxy-3-methylphenyl)-2-oxo-2,3-dihydropyrimidin-4-yl]phenyl}oxy)acetamide

MS (EI): 476 (MH+).

Example 223

4-(4-hydroxy-3-methylphenyl)-6-(3-{[2-oxo-2-(4-pyrazin-2-ylpiperazin-1-yl)ethyl]oxy}phenyl)pyrimidin-2(1H)-one

MS (EI): 499 (MH+).

Example 224

4-(4-hydroxy-3-methylphenyl)-6-(3-{[2-(4-methylpiperidin-1-yl)-2-oxoethyl]oxy}phenyl)-pyrimidin-2(1H)-one

MS (EI): 434 (MH+).

Example 225

6-[3-({2-[4-(furan-2-ylcarbonyl)piperazin-1-yl]-2-oxoethyl}oxy)phenyl]-4-(4-hydroxy-3-methylphenyl)pyrimidin-2(1H)-one

MS (EI): 515 (MH+).

Example 226

N-[(2,4-difluorophenyl)methyl]-2-({3-[6-(4-hydroxy-3-methylphenyl)-2-oxo-2,3-dihydropyrimidin-4-yl]phenyl}oxy)acetamide

MS (EI): 478 (MH+).

Example 227

N-{1-[({3-[6-(4-hydroxy-3-methylphenyl)-2-oxo-2,3-dihydropyrimidin-4-yl]phenyl}oxy)acetyl]pyrrolidin-3-yl}-N-methylacetamide

MS (EI): 477 (MH+).

Example 228 ethyl 1-[({3-[6-(4-hydroxy-3-methylphenyl)-2-oxo-2,3-dihydropyrimidin-4-yl]phenyl}oxy)acetyl]piperidine-4-carboxylate

MS (EI): 492 (MH+).

Example 229

N-cycloheptyl-2-({3-[6-(4-hydroxy-3-methylphenyl)-2-oxo-2,3-dihydropyrimidin-4-yl]phenyl}oxy)acetamide

MS (EI): 448 (MH+).

Example 230

6-{3-[(2-azepan-1-yl-2-oxoethyl)oxy]phenyl}-4-(4-hydroxy-3-methylphenyl)pyrimidin-2(1H)-one

MS (EI): 434 (MH+).

Example 231

4-(4-hydroxy-3-methylphenyl)-6-{3-[(2-oxo-2-piperidin-1-ylethyl)oxy]phenyl}pyrimidin-2(1H)-one

MS (EI): 420 (MH+).

Example 232

2-({3-[6-(4-hydroxy-3-methylphenyl)-2-oxo-2,3-dihydropyrimidin-4-yl]phenyl}oxy)-N-{[3-(methyloxy)phenyl]methyl}acetamide

MS (EI): 472 (MH+).

Example 233

2-({3-[6-(4-hydroxy-3-methylphenyl)-2-oxo-2,3-dihydropyrimidin-4-yl]phenyl}oxy)-N-{[4-(methyloxy)phenyl]methyl}acetamide

MS (EI): 472 (MH+).

Example 234

2-({3-[6-(4-hydroxy-3-methylphenyl)-2-oxo-2,3-dihydropyrimidin-4-yl]phenyl}oxy)-N,N-dipropylacetamide

MS (EI): 436 (MH+).

Example 235

4-(4-hydroxy-3-methylphenyl)-6-{3-[(2-{4-[3-(methyloxy)phenyl]piperazin-1-yl}-2-oxoethyl)oxy]phenyl}pyrimidin-2(1H)-one

MS (EI): 527 (MH+).

Example 236

2-({3-[6-(4-hydroxy-3-methylphenyl)-2-oxo-2,3-dihydropyrimidin-4-yl]phenyl}oxy)-N-(tetrahydrofuran-2-ylmethyl)acetamide

MS (EI): 436 (MH+).

Example 237

2-({3-[6-(4-hydroxy-3-methylphenyl)-2-oxo-2,3-dihydropyrimidin-4-yl]phenyl}oxy)-N-(4-methylcyclohexyl)acetamide

MS (EI): 448 (MH+).

Example 238

4-(4-hydroxy-3-methylphenyl)-6-{3-[(2-{4-[4-(methyloxy)phenyl]piperazin-1-yl}-2-oxoethyl)oxy]phenyl}pyrimidin-2(1H)-one

MS (EI): 527 (MH+).

Example 239

4-(4-hydroxy-3-methylphenyl)-6-(3-{[2-(4-hydroxypiperidin-1-yl)-2-oxoethyl]oxy}-phenyl)pyrimidin-2(1H)-one

MS (EI): 436 (MH+).

Example 240

N-cyclohexyl-2-({3-[6-(4-hydroxy-3-methylphenyl)-2-oxo-2,3-dihydropyrimidin-4-yl]phenyl}oxy)acetamide

MS (EI): 434 (MH+).

Example 241

4-(4-hydroxy-3-methylphenyl)-6-(3-{[2-(2-methylpiperidin-1-yl)-2-oxoethyl]oxy}-phenyl)-pyrimidin-2(1H)-one

MS (EI): 434 (MH+).

Example 242

6-(3-{[2-(2-ethylpiperidin-1-yl)-2-oxoethyl]oxy}phenyl)-4-(4-hydroxy-3-methylphenyl)-pyrimidin-2(1H)-one

MS (EI): 448 (MH+).

Example 243

N-[(4-chlorophenyl)methyl]-2-({3-[6-(4-hydroxy-3-methylphenyl)-2-oxo-2,3-dihydropyrimidin-4-yl]phenyl}oxy)acetamide

MS (EI): 476 (MH+).

Example 244

4-(4-hydroxy-3-methylphenyl)-6-{3-[(2-{4-[2-(methyloxy)phenyl]piperazin-1-yl}-2-oxoethyl)oxy]phenyl}pyrimidin-2(1H)-one

MS (EI): 527 (MH+).

Scheme 10

Example 245

({4-[6-(4-Hydroxy-3-methylphenyl)-2-oxo-2,3-dihydropyrimidin-4-yl]phenyl}oxy)acetic acid Step 1

(E)-2-(4-[3-(4-Hydroxy-3-methylphenyl)-3-oxoprop-1-enyl]phenoxy)acetic acid

Commercially available ethyl 2-(4-formylphenoxy)acetate (20.0 g, 0.1 mol) and commercially available 4'-hydroxy-3'- methylacetophenone (15.0 g, 0.1 mol) were dissolved in 200 mL of methanol and 50 mL of water. The solution was cooled with an ice-water bath, to which was added potassium hydroxide (22.0 g, 0.392 mol). The reaction mixture was stirred overnight. The resulted mixture was poured on to 600 mL of ice-water, acidified to pH=4-5 with 1 N HCl, and extracted with ethyl acetate (4×200 mL). The combined organic layers were washed with water and brine (200 mL each), dried over anhydrous sodium sulfate, filtered and concentrated in vacuo. The obtained yellow oil was dried under high-vacuum, 10 g (33%) of yellowish solid was obtained. MS (EI): 313 (MH$^+$).

Step 2

({4-[6-(4-Hydroxy-3-methylphenyl)-2-oxo-2,3-dihydropyrimidin-4-yl]phenyl}oxy)acetic acid (E)-2-(4-[3-(4-Hydroxy-3-methylphenyl)-3-oxoprop-1-enyl]phenoxy)acetic acid (10.0 g, 32.0 mmol) and urea (5.9 g, 0.10 mol) was suspended in 150 mL of 4N HCl solution in dioxane, and the reaction mixture was heated to reflux overnight, then cooled to room temperature. The resulted mixture was concentrated in vacuo to remove dioxane. The residues were suspended in 100 mL of 2-propanol and heated in a 90° C. oil bath for 10 minutes, then let it cooled down to room temperature by itself. The suspension was filtered, washed with 50 mL of 2-propanol and dried in the air. 4.0 g (35%) of yellow powder was obtained. $^1$H NMR (400 MHz, DMSO-d$_6$): δ 10.76 (s, 1H), 8.15 (s, 1H), 8.04 (s, 1H), 7.94 (d, 1H), 7.46 (s, 1H), 7.13 (d, 2H), 7.03 (d, 1H), 7.03 (d, 1H), 4.86 (s, 2H), 2.21 (s, 3H). MS (EI): 353 (MH+).

Example 246

2-({4-[6-(4-hydroxy-3-methylphenyl)-2-oxo-2,3-dihydropyrimidin-4-yl]phenyl}oxy)-N-(2-piperidin-1-ylethyl)acetamide ({4-[6-(4-hydroxy-3-methylphenyl)-2-oxo-2,3-dihydro-pyrimidin-4-yl]phenyl}oxy)-acetic acid (Compound 266, 17 mg, 48 umol) and 2-morpholinoethanamine (5.2 mg, 40 umol) were dissolved in dichloroethane (1.25 mL) and N,N-dimethylformamide (0.79 mL). To this solution was added 1-hydroxybenzotriazole (6.8 mg, 50 umol) followed by 1-[3-(dimethylamino)propyl]-3-ethylcarbodiimide methiodide (17.8 mg, 60 umol). The reaction mixture was stirred at room temperature for 15 hours and was concentrated in vacuo. The reaction mixture was purified by reverse phase HPLC to give 5 mg of product. $^1$H NMR (400 MHz, d6-DMSO): δ 8.23 (s, 1H), 8.14 (d, 2H), 8.03 (t, 1H), 7.94 (s, 1H), 7.85 (d, 1H), 7.33 (s, 1H), 7.09 (dd, 2H), 6.90 (d, 1H), 4.59 (s, 2H), 3.27-3.24 (m, 2H), 2.37-2.33 (m, 6H), 2.20 (s, 3H), 1.49-1.44 (m, 4H), 1.38-1.34 (m, 2H). MS (EI): 464 (MH+).

Example 247

2-({4-[6-(4-hydroxy-3-methylphenyl)-2-oxo-2,3-dihydropyrimidin-4-yl]phenyl}oxy)-N-piperidin-4-ylacetamide 2-({4-[6-(4-hydroxy-3-methylphenyl)-2-oxo-2,3-dihydropyrimidin-4-yl]phenyl}-oxy)-N-piperidin-4-ylacetamide was synthesized in a manner similar to Example 246, wherein 2-morpholinoethanamine was substituted with commercially available tert-butyl 4-aminopiperidine-1-carboxylate and then Boc deprotected under acidic conditions.

$^1$H-NMR (400 MHz, d6-DMSO): δ 8.10 (d, 2H), 8.02 (d, 1H), 7.97 (s, 1H), 7.83 (dd, 1H), 7.31 (s, 1H), 7.08 (d, 2H), 6.96 (d, 1H), 4.57 (s, 2H), 3.62 (m, 2H), 2.63 (m, 4H), 2.2 (m, 4H), 1.72 (m, 2H), 1.55 (m, 2H). MS (EI): 465.2 (MH+).

Example 248

2-({4-[6-(4-hydroxy-3-methylphenyl)-2-oxo-2,3-dihydropyrimidin-4-yl]phenyl}oxy)-N-(1-methylpiperidin-4-yl)acetamide 2-({4-[6-(4-hydroxy-3-methylphenyl)-2-oxo-2,3-dihydropyrimidin-4-yl]phenyl}oxy)-N-(1-methylpiperidin-4-yl) acetamide was synthesized in a manner similar to Example 246, wherein 2-morpholinoethanamine was substituted with commercially available 1-methyl piperazine.

$^1$H-NMR (400 MHz, d6-DMSO): δ 8.12 (d, 2H), 8.03 (d, 1H), 7.93 (s, 1H), 7.86 (dd, 1H), 7.35 (s, 1H), 7.09 (d, 2H), 6.90 (d, 1H), 5.0 (s, 1H), 4.57 (s, 2H), 3.57 (m, 1H), 2.62 (m, 4H), 2.20 (s, 3H), 2.02 (s, 3H), 1.75 (m, 2H), 1.59 (m, 2H). MS (EI): 449.2 (MH+).

Example 249

N-(1-ethylpiperidin-4-yl)-2-({4-[6-(4-hydroxy-3-methylphenyl)-2-oxo-2,3-dihydro-pyrimidin-4-yl]phenyl}oxy)acetamide N-(1-ethylpiperidin-4-yl)-2-({4-[6-(4-hydroxy-3-methylphenyl)-2-oxo-2,3-dihydropyrimidin-4-yl]phenyl}oxy)acetamide was synthesized in a manner similar to Example 246, wherein 2-morpholinoethanamine was substituted with commercially available 1-ethyl piperazine.

$^1$H-NMR (400 MHz, d6-DMSO): δ 8.13 (d, 2H), 8.05 (d, 1H), 7.94 (s, 1H), 7.84 (dd, 1H), 7.33 (s, 1H), 7.08 (d, 2H), 6.91 (d, 1H), 4.58 (s, 2H), 2.81 (s, 2H), 2.29 (m, 2H), 2.20 (s, 2H), 1.88 (m, 6H), 1.70 (m, 2H), 1.49 (m, 2H), 0.98 (t, 2H). MS (EI): 463.2 (MH+).

Examples 250 below was made in a manner similar to Example 246, wherein the appropriate substitutions of commercially available reactants and/or reagents were made to arrive at this compound. One skilled in the art would be readily able to ascertain which reactants and reagents need to be substituted. The skilled artisan would be readily able to commercially obtain these reactants and/or reagents that are necessary for making this compound.

Example 250

4-(4-hydroxy-3-methylphenyl)-6-{4-[(2-oxo-2-piperazin-1-ylethyl)oxy]phenyl}pyrimidin-2(1H)-one

MS (EI): 421 (MH+).

Example 251

N-[2-(diethylamino)ethyl]-2-({4-[6-(4-hydroxy-3-methylphenyl)-2-oxo-2,3-dihydropyrimidin-4-yl]phenyl}oxy)acetamide N-[2-(diethylamino)ethyl]-2-({4-[6-(4-hydroxy-3-methylphenyl)-2-oxo-2,3-dihydropyrimidin-4-yl]phenyl}oxy)acetamide was synthesized in a manner similar to Example 246, wherein 2-morpholinoethanamine was substituted with commercially available N1,N1-diethyl-N2-methylethane-1,2-diamine.

$^1$H NMR (400 MHz, d6-DMSO): δ 8.28 (s, 1H), 8.14 (d, 2H), 8.01 (s, 1H), 7.95 (s, 1H), 7.84 (d, 1H), 7.34 (s, 1H), 7.09

(dd, 2H), 6.91 (dd, 1H), 4.59 (s, 2H), 3.28-3.18 (m, 4H), 2.48-2.46 (m, 4H), 2.20 (s, 3H), 0.97-0.93 (m, 6H). MS (EI): 452 (MH+).

Example 252

6-[4-({2-[3-(diethylamino)pyrrolidin-1-yl]-2-oxoethyl}oxy)phenyl]-4-(4-hydroxy-3-methylphenyl)pyrimidin-2(1H)-one 6-[4-({2-[3-(diethylamino)pyrrolidin-1-yl]-2-oxoethyl}oxy)phenyl]-4-(4-hydroxy-3-methylphenyl)pyrimidin-2(1H)-one was synthesized in a manner similar to Example 246, wherein 2-morpholinoethanamine was substituted with commercially available N,N-diethylpyrrolidin-3-amine.
$^{1}$H NMR (400 MHz, d6-DMSO): δ 8.35 (s, 1H), 8.10 (d, 2H), 7.95 (s, 1H), 7.84 (d, 1H), 7.31 (s, 1H), 7.06 (d, 2H), 6.90 (d, 1H), 4.86 (d, 2H), 3.78-3.68 (m, 3H), 3.04-2.98 (m, 2H), 2.62-2.54 (m, 4H), 2.20 (s, 3H), 2.06-1.98 (m, 1H), 1.68-1.56 (m, 1H), 0.98-0.92 (m, 6H). MS (EI): 478 (MH+).

Example 253

6-(4-{[2-(1,4'-bipiperidin-1'-yl)-2-oxoethyl]oxy}phenyl)-4-(4-hydroxy-3-methylphenyl)-pyrimidin-2(1H)-one 6-(4-{[2-(1,4'-bipiperidin-1'-yl)-2-oxoethyl]oxy}phenyl)-4-(4-hydroxy-3-methylphenyl)pyrimidin-2(1H)-one was synthesized in a manner similar to Example 246, wherein 2-morpholinoethanamine was substituted with commercially available 1,4'-bipiperidine.
$^{1}$H NMR (400 MHz, d6-DMSO): δ 8.25 (s, 1H), 8.10 (d, 2H), 7.94 (s, 1H), 7.85 (d, 1H), 7.31 (s, 1H), 7.05 (d, 2H), 6.90 (d, 1H), 4.96 (d, 2H), 4.38 (d, 1H), 3.88 (d, 2H), 3.09-3.01 (m, 2H), 2.48-2.42 (m, 4H), 2.20 (s, 3H), 1.78-1.72 (m, 2H), 1.52-1.32 (m, 8H). MS (EI): 504 (MH+).

Example 254

N-[2-(dimethylamino)ethyl]-2-({4-[6-(4-hydroxy-3-methylphenyl)-2-oxo-2,3-dihydropyrimidin-4-yl]phenyl}oxy)acetamide N-[2-(dimethylamino)ethyl]-2-({4-[6-(4-hydroxy-3-methylphenyl)-2-oxo-2,3-dihydropyrimidin-4-yl]phenyl}oxy)acetamide was synthesized in a manner similar to Example 246, wherein 2-morpholinoethanamine was substituted with commercially available N1,N1-dimethylethane-1,2-diamine.
$^{1}$H NMR (400 MHz, d6-DMSO): δ 8.24 (s, 1H), 8.13 (d, 2H), 8.07 (t, 1H), 7.94 (s, 1H), 7.85 (d, 1H), 7.33 (s, 1H), 7.13-7.08 (m, 2H), 6.90 (d, 1H), 4.61 (s, 2H), 3.26-3.22 (m, 2H), 2.34 (t, 2H), 2.20 (s, 3H), 2.16 (s, 6H). MS (EI): 423 (MH+).

Example 255 below was made in a manner similar to Example 254, wherein the appropriate substitutions of commercially available reactants and/or reagents were made to arrive at this compound. One skilled in the art would be readily able to ascertain which reactants and reagents need to be substituted. The skilled artisan would be readily able to commercially obtain these reactants and/or reagents that are necessary for making this compound.

Example 255

N-(2-aminoethyl)-2-({4-[6-(4-hydroxy-3-methylphenyl)-2-oxo-2,3-dihydropyrimidin-4-yl]phenyl}oxy)acetamide

MS (EI): 395 (MH+).

Example 256

N-[3-(dimethylamino)propyl]-2-({4-[6-(4-hydroxy-3-methylphenyl)-2-oxo-2,3-dihydropyrimidin-4-yl]phenyl}oxy)acetamide N-[3-(dimethylamino)propyl]-2-({4-[6-(4-hydroxy-3-methylphenyl)-2-oxo-2,3-dihydropyrimidin-4-yl]phenyl}oxy)acetamide was synthesized in a manner similar to Example 246, wherein 2-morpholinoethanamine was substituted with commercially available N1,N1-dimethylpropane-1,3-diamine.
$^{1}$H NMR (400 MHz, d6-DMSO): δ 8.28-8.24 (m, 2H), 8.13 (d, 2H), 7.93 (s, 1H), 7.84 (d, 1H), 7.33 (s, 1H), 7.09 (d, 2H), 6.90 (d, 1H), 4.59 (s, 2H), 3.22-3.18 (m, 2H), 2.24 (t, 2H), 2.20 (s, 3H), 2.18 (s, 6H), 1.62-1.56 (m, 2H). MS (EI): 438 (MH+).

Example 257

N-[2-(dimethylamino)ethyl]-N-ethyl-2-({4-[6-(4-hydroxy-3-methylphenyl)-2-oxo-2,3-dihydropyrimidin-4-yl]phenyl}oxy)acetamide N-[2-(dimethylamino)ethyl]-N-ethyl-2-({4-[6-(4-hydroxy-3-methylphenyl)-2-oxo-2,3-dihydropyrimidin-4-yl]phenyl}oxy)acetamide was synthesized in a manner similar to Example 246, wherein 2-morpholinoethanamine was substituted with commercially available N1-ethyl-N2,N2-dimethylethane-1,2-diamine.
$^{1}$H NMR (400 MHz, d6-DMSO): δ 8.30 (s, 1H), 8.10 (d, 2H), 7.94 (s, 1H), 7.84 (d, 1H), 7.31 (s, 1H), 7.06-7.03 (m, 2H), 6.90 (d, 1H), 4.96 (d, 2H), 3.34-3.30 (m, 2H), 2.50-2.32 (m, 4H), 2.22 (s, 3H), 2.20 (s, 3H), 2.18 (s, 3H), 1.20-1.02 (m, 3H). MS (EI): 452 (MH+).

Examples 258-333 below were made in a manner similar to Example 246, wherein the appropriate substitutions of commercially available reactants and/or reagents were made to arrive at these compounds. One skilled in the art would be readily able to ascertain which reactants and reagents need to be substituted. The skilled artisan would be readily able to commercially obtain these reactants and/or reagents that are necessary for making these compounds.

Example 258

N-(3-aminopropyl)-2-({4-[6-(4-hydroxy-3-methylphenyl)-2-oxo-2,3-dihydropyrimidin-4-yl]phenyl}oxy)acetamide

MS (EI): 409 (MH+).

Example 259

2-({4-[6-(4-hydroxy-3-methylphenyl)-2-oxo-2,3-dihydropyrimidin-4-yl]phenyl}oxy)-N-(2-morpholin-4-ylethyl)acetamide

MS (EI): 465 (MH+).

Example 260

2-({4-[6-(4-hydroxy-3-methylphenyl)-2-oxo-2,3-dihydropyrimidin-4-yl]phenyl}oxy)-N-methyl-N-(1-methylpiperidin-4-yl)acetamide

MS (EI): 463 (MH+).

Example 261

6-[4-({2-[3-(aminomethyl)piperidin-1-yl]-2-oxoethyl}oxy)phenyl]-4-(4-hydroxy-3-methylphenyl)pyrimidin-2(1H)-one

MS (EI): 449 (MH+),

Example 262

N-[3-(dimethylamino)propyl]-2-({4-[6-(4-hydroxy-3-methylphenyl)-2-oxo-2,3-dihydropyrimidin-4-yl]phenyl}oxy)-N-methylacetamide

MS (EI): 451 (MH+).

Example 263

2-({4-[6-(4-hydroxy-3-methylphenyl)-2-oxo-2,3-dihydropyrimidin-4-yl]phenyl}oxy)-N-methyl-N-(1-methylpyrrolidin-3-yl)acetamide

MS (ED: 449 (MH+).

Example 264

2-({4-[6-(4-hydroxy-3-methylphenyl)-2-oxo-2,3-dihydropyrimidin-4-yl]phenyl}oxy)-N-(3-pyrrolidin-1-ylpropyl)acetamide

MS (EI): 463 (MH+).

Example 265

N-[2-(dimethylamino)ethyl]-2-({4-[6-(4-hydroxy-3-methylphenyl)-2-oxo-2,3-dihydropyrimidin-4-yl]phenyl}oxy)-N-methylacetamide

MS (EI): 437 (MH+).

Example 266

4-(4-hydroxy-3-methylphenyl)-6-(4-{[2-(4-methyl-1,4-diazepan-1-yl)-2-oxoethyl]oxy}-phenyl)pyrimidin-2(1H)-one

MS (EI): 449 (MH+).

Example 267

6-(4-{[2-(4-ethylpiperazin-1-yl)-2-oxoethyl]oxy}phenyl)-4-(4-hydroxy-3-methylphenyl)-pyrimidin-2(1H)-one

MS (EI): 449 (MH+).

Example 268

2-({4-[6-(4-hydroxy-3-methylphenyl)-2-oxo-2,3-dihydropyrimidin-4-yl]phenyl}oxy)-N-[3-(1H-imidazol-1-yl)propyl]acetamide

MS (EI): 460 (MH+).

Example 269

4-(4-hydroxy-3-methylphenyl)-6-(4-{[2-(4-methylpiperazin-1-yl)-2-oxoethyl]oxy}-phenyl)pyrimidin-2(1H)-one

MS (EI): 435 (MH+).

Example 270

2-({4-[6-(4-hydroxy-3-methylphenyl)-2-oxo-2,3-dihydropyrimidin-4-yl]phenyl}oxy)-N-(tetrahydrofuran-2-ylmethyl)acetamide

MS (EI): 436 (MH+).

Example 271

2-({4-[6-(4-hydroxy-3-methylphenyl)-2-oxo-2,3-dihydropyrimidin-4-yl]phenyl}oxy)-N-[2-(phenyloxy)ethyl]acetamide

MS (EI): 472 (MH+).

Example 272

6-{4-[(2-{4-[2-(ethyloxy)ethyl]piperazin-1-yl}-2-oxoethyl)oxy]phenyl}-4-(4-hydroxy-3-methylphenyl)pyrimidin-2(1H)-one

MS (EI): 493 (MH+).

Example 273

2-({4-[6-(4-hydroxy-3-methylphenyl)-2-oxo-2,3-dihydropyrimidin-4-yl]phenyl}oxy)-N-[(5-methylfuran-2-yl)methyl]acetamide

MS (EI): 446 (MH+).

Example 274

N-(cyclohexylmethyl)-2-({4-[6-(4-hydroxy-3-methylphenyl)-2-oxo-2,3-dihydropyrimidin-4-yl]phenyl}oxy)acetamide

MS (EI): 448 (MH+).

Example 275

N-[(6-chloropyridin-3-yl)methyl]-2-({4-[6-(4-hydroxy-3-methylphenyl)-2-oxo-2,3-dihydro-pyrimidin-4-yl]phenyl}oxy)acetamide

MS (EI): 477 (MH+).

Example 276

2-({4-[6-(4-hydroxy-3-methylphenyl)-2-oxo-2,3-dihydropyrimidin-4-yl]phenyl}oxy)-N-[2-(methyloxy)ethyl]acetamide

MS (EI): 410 (MH+).

Example 277

N-(cyclopropylmethyl)-2-({4-[6-(4-hydroxy-3-methylphenyl)-2-oxo-2,3-dihydropyrimidin-4-yl]phenyl}oxy)acetamide

MS (EI): 406 (MH+).

Example 278

N-{1-[({4-[6-(4-hydroxy-3-methylphenyl)-2-oxo-2,3-dihydropyrimidin-4-yl]phenyl}oxy)-acetyl]pyrrolidin-3-yl}-N-methylacetamide

MS (EI): 477 (MH+).

Example 279

6-(4-{[2-(4-acetylpiperazin-1-yl)-2-oxoethyl]oxy}phenyl)-4-(4-hydroxy-3-methylphenyl)-pyrimidin-2(1H)-one

MS (EI): 463 (MH+).

Example 280

4-(4-hydroxy-3-methylphenyl)-6-{4-[(2-{4-[4-(methyloxy)phenyl]piperazin-1-yl}-2-oxoethyl)oxy]phenyl}pyrimidin-2(1H)-one

MS (EI): 527 (MH+).

Example 281

6-[4-({2-[4-(furan-2-ylcarbonyl)piperazin-1-yl]-2-oxoethyl}oxy)phenyl]-4-(4-hydroxy-3-methylphenyl)pyrimidin-2(1H)-one

MS (EI): 515 (MH+).

Example 282

N-(furan-2-ylmethyl)-2-({4-[6-(4-hydroxy-3-methylphenyl)-2-oxo-2,3-dihydropyrimidin-4-yl]phenyl}oxy)acetamide

MS (EI): 432 (MH+).

Example 283

4-(4-hydroxy-3-methylphenyl)-6-{4-[(2-oxo-2-pyrrolidin-1-ylethyl)oxy]phenyl}pyrimidin-2(1H)-one

MS (EI): 406 (MH+).

Example 284

2-({4-[6-(4-hydroxy-3-methylphenyl)-2-oxo-2,3-dihydropyrimidin-4-yl]phenyl}oxy)-N-(3-morpholin-4-ylpropyl)acetamide

MS (EI): 479 (MH+).

Example 285

4-(4-hydroxy-3-methylphenyl)-6-(4-{[2-(4-morpholin-4-ylpiperidin-1-yl)-2-oxoethyl]oxy}-phenyl)pyrimidin-2(1H)-one

MS (EI): 505 (MH+).

Example 286

4-(4-hydroxy-3-methylphenyl)-6-[4-({2-oxo-2-[4-(tetrahydrofuran-2-ylcarbonyl)piperazin-1-yl]ethyl}oxy)phenyl]pyrimidin-2(1H)-one

MS (EI): 519 (MH+).

Example 287

2-({4-[6-(4-hydroxy-3-methylphenyl)-2-oxo-2,3-dihydropyrimidin-4-yl]phenyl}oxy)-N-{[3-(methyloxy)phenyl]methyl}acetamide

MS (ED: 472 (MH+).

Example 288

4-(4-hydroxy-3-methylphenyl)-6-(4-{[2-(4-methylpiperidin-1-yl)-2-oxoethyl]oxy}phenyl)-pyrimidin-2(1H)-one

MS (EI): 434 (MH+).

Example 289

2-({4-[6-(4-hydroxy-3-methylphenyl)-2-oxo-2,3-dihydropyrimidin-4-yl]phenyl}oxy)-N-(pyridin-3-ylmethyl)acetamide

MS (EI): 443 (MH+).

Example 290

4-(4-hydroxy-3-methylphenyl)-6-{4-[(2-{4-[2-(methyloxy)ethyl]piperazin-1-yl}-2-oxoethyl)oxy]phenyl}pyrimidin-2(1H)-one

MS (EI): 479 (MH+).

Example 291

2-({4-[6-(4-hydroxy-3-methylphenyl)-2-oxo-2,3-dihydropyrimidin-4-yl]phenyl}oxy)-N-{2-[(1-methylethyl)oxy]ethyl}acetamide

MS (EI): 438 (MH+).

Example 292

2-({-4-[6-(4-hydroxy-3-methylphenyl)-2-oxo-2,3-dihydropyrimidin-4-yl]phenyl}oxy)-N-[3-(4-methylpiperazin-1-yl)propyl]acetamide

MS (EI): 492 (MH+).

Example 293

2-({4-[6-(4-hydroxy-3-methylphenyl)-2-oxo-2,3-dihydropyrimidin-4-yl]phenyl}oxy)-N-pentylacetamide

MS (EI): 422 (MH+).

Example 294

4-(4-hydroxy-3-methylphenyl)-6-(4-{[2-(2-methylpyrrolidin-1-yl)-2-oxoethyl]oxy}phenyl)-pyrimidin-2(1H)-one

MS (EI): 420 (MH+).

Example 295

4-(4-hydroxy-3-methylphenyl)-6-{4-[(2-morpholin-4-yl-2-oxoethyl)oxy]phenyl}pyrimidin-2(1H)-one

MS (EI): 422 (MH+).

Example 296

6-{4-[(2-azepan-1-yl-2-oxoethyl)oxy]phenyl}-4-(4-hydroxy-3-methylphenyl)pyrimidin-2(1H)-one

MS (EI): 434 (MH+).

Example 297

2-({4-[6-(4-hydroxy-3-methylphenyl)-2-oxo-2,3-dihydropyrimidin-4-yl]phenyl}oxy)-N-(2-thienylmethyl)acetamide

MS (EI): 448 (MH+).

Example 298

N-cyclopropyl-2-({4-[6-(4-hydroxy-3-methylphenyl)-2-oxo-2,3-dihydropyrimidin-4-yl]phenyl}oxy)acetamide

MS (EI): 392 (MH+).

Example 299

N-(2-cyanoethyl)-2-({4-[6-(4-hydroxy-3-methylphenyl)-2-oxo-2,3-dihydropyrimidin-4-yl]phenyl}oxy)acetamide

MS (EI): 405 (MH+).

Example 300

N-[(3-chlorophenyl)methyl]-2-({4-[6-(4-hydroxy-3-methylphenyl)-2-oxo-2,3-dihydropyrimidin-4-yl]phenyl}oxy)acetamide

MS (EI): 476 (MH+).

Example 301

2-({4-[6-(4-hydroxy-3-methylphenyl)-2-oxo-2,3-dihydropyrimidin-4-yl]phenyl}oxy)-N-(2-methylpropyl)acetamide

MS (EI): 408 (MH+).

Example 302

4-(4-hydroxy-3-methylphenyl)-6-{4-[(2-{4-[2-(methyloxy)phenyl]piperazin-1-yl}-2-oxoethyl)oxy]phenyl}pyrimidin-2(1H)-one

MS (EI): 527 (MH+).

Example 303

2-({4-[6-(4-hydroxy-3-methylphenyl)-2-oxo-2,3-dihydropyrimidin-4-yl]phenyl}oxy)-N-methyl-N-(2-methylpropyl)acetamide

MS (EI): 422 (MH+).

Example 304 methyl 1-[({4-[6-(4-hydroxy-3-methylphenyl)-2-oxo-2,3-dihydropyrimidin-4-yl]phenyl}oxy)acetyl]piperidine-4-carboxylate

MS (EI): 478 (MH+).

Example 305

4-(4-hydroxy-3-methylphenyl)-6-(4-{[2-oxo-2-(4-pyrazin-2-ylpiperazin-1-yl)ethyl]oxy}-phenyl)pyrimidin-2(1H)-one

MS (EI): 499 (MH+).

Example 306

N-[(2,4-difluorophenyl)methyl]-2-({4-[6-(4-hydroxy-3-methylphenyl)-2-oxo-2,3-dihydropyrimidin-4-yl]phenyl}oxy)acetamide

MS (EI): 478 (MH+).

Example 307

4-(4-hydroxy-3-methylphenyl)-6-{4-[(2-oxo-2-piperidin-1-ylethyl)oxy]phenyl}pyrimidin-2(1H)-one

MS (EI): 420 (MH+).

Example 308

4-(4-hydroxy-3-methylphenyl)-6-[4-({2-[4-(hydroxymethyl)piperidin-1-yl]-2-oxoethyl}-oxy)phenyl]pyrimidin-2(1H)-one

MS (EI): 450 (MH+).

Example 309

N-(furan-2-ylmethyl)-2-({4-[6-(4-hydroxy-3-methylphenyl)-2-oxo-2,3-dihydropyrimidin-4-yl]phenyl}oxy)-N-methylacetamide

MS (EI): 446 (MH+).

Example 310

2-({4-[6-(4-hydroxy-3-methylphenyl)-2-oxo-2,3-dihydropyrimidin-4-yl]phenyl}oxy)-N-[3-(2-oxopyrrolidin-1-yl)propyl]acetamide

MS (EI): 477 (MH+).

Example 311

4-(4-hydroxy-3-methylphenyl)-6-(4-([2-(4-hydroxypiperidin-1-yl)-2-oxoethyl]oxy)-phenyl)pyrimidin-2(1H)-one

MS (EI): 436 (MH+).

Example 312 ethyl 1-[({4-[6-(4-hydroxy-3-methylphenyl)-2-oxo-2,3-dihydropyrimidin-4-yl]phenyl}oxy-)acetyl]piperidine-4-carboxylate

MS (EI): 492 (MH+).

Example 313

N-butyl-2-({4-[6-(4-hydroxy-3-methylphenyl)-2-oxo-2,3-dihydropyrimidin-4-yl]phenyl}oxy)-N-methylacetamide

MS (EI): 422 (MH+).

Example 314

4-(4-hydroxy-3-methylphenyl)-6-[4-({2-oxo-2-[4-(phenylmethyl)piperazin-1-yl]ethyl}oxy)phenyl]pyrimidin-2(1H)-one

MS (EI): 511 (MH+).

Example 315

N-cyclohexyl-2-({4-[6-(4-hydroxy-3-methylphenyl)-2-oxo-2,3-dihydropyrimidin-4-yl]phenyl}oxy)acetamide

MS (EI): 434 (MH+).

Example 316

2-({4-[6-(4-hydroxy-3-methylphenyl)-2-oxo-2,3-dihydropyrimidin-4-yl]phenyl}oxy)-N-{[4-(methyloxy)phenyl]methyl}acetamide

MS (EI): 472 (MH+).

Example 317

2-({4-[6-(4-hydroxy-3-methylphenyl)-2-oxo-2,3-dihydropyrimidin-4-yl]phenyl}oxy)-N-(pyridin-4-ylmethyl)acetamide

MS (EI): 443 (MH+).

Example 318

2-({4-[6-(4-hydroxy-3-methylphenyl)-2-oxo-2,3-dihydropyrimidin-4-yl]phenyl}oxy)-N-{[2-(methyloxy)phenyl]methyl}acetamide

MS (EI): 472 (MH+).

Example 319

N-butyl-2-({4-[6-(4-hydroxy-3-methylphenyl)-2-oxo-2,3-dihydropyrimidin-4-yl]phenyl}-oxy)acetamide

MS (EI): 408 (MH+).

Example 320

N-[(2-fluorophenyl)methyl]-2-({4-[6-(4-hydroxy-3-methylphenyl)-2-oxo-2,3-dihydropyrimidin-4-yl]phenyl}oxy)-N-methylacetamide

MS (EI): 474 (MH+).

Example 321

N-[2-(2-fluorophenyl)ethyl]-2-({4-[6-(4-hydroxy-3-methylphenyl)-2-oxo-2,3-dihydropyrimidin-4-yl]phenyl}oxy)acetamide

MS (EI): 474 (MH+).

Example 322

N-cyclobutyl-2-({4-[6-(4-hydroxy-3-methylphenyl)-2-oxo-2,3-dihydropyrimidin-4-yl]phenyl}oxy)acetamide

MS (EI): 406 (MH+).

Example 323

2-({4-[6-(4-hydroxy-3-methylphenyl)-2-oxo-2,3-dihydropyrimidin-4-yl]phenyl}oxy)-N,N-dipropylacetamide

MS (EI): 436 (MH+).

Example 324

2-({4-[6-(4-hydroxy-3-methylphenyl)-2-oxo-2,3-dihydropyrimidin-4-yl]phenyl}oxy)-N-[3-(methyloxy)propyl]acetamide

MS (EI): 424 (MH+).

Example 325

2-({4-[6-(4-hydroxy-3-methylphenyl)-2-oxo-2,3-dihydropyrimidin-4-yl]phenyl}oxy)-N-propylacetamide

MS (EI): 394 (MH+).

Example 326

N-cyclopentyl-2-({4-[6-(4-hydroxy-3-methylphenyl)-2-oxo-2,3-dihydropyrimidin-4-yl]phenyl}oxy)acetamide

MS (EI): 420 (MH+).

Example 327

6-(4-{[2-(2-ethylpiperidin-1-yl)-2-oxoethyl]oxy}phenyl)-4-(4-hydroxy-3-methylphenyl)-pyrimidin-2(1H)-one

MS (EI): 448 (MH+).

Example 328

4-(4-hydroxy-3-methylphenyl)-6-(4-{[2-(3-methylpiperidin-1-yl)-2-oxoethyl]oxy}phenyl)-pyrimidin-2(1H)-one

MS (EI): 434 (MH+).

Example 329

N-cycloheptyl-2-({4-[6-(4-hydroxy-3-methylphenyl)-2-oxo-2,3-dihydropyrimidin-4-yl]phenyl}oxy)acetamide

MS (EI): 448 (MH+).

Example 330

6-(4-{[2-(3,5-dimethylpiperidin-1-yl)-2-oxoethyl]oxy}phenyl)-4-(4-hydroxy-3-methylphenyl)pyrimidin-2(1H)-one

MS (EI): 448 (MH+).

Example 331

2-({4-[6-(4-hydroxy-3-methylphenyl)-2-oxo-2,3-dihydropyrimidin-4-yl]phenyl}oxy)-N-(4-methylcyclohexyl)acetamide

MS (EI): 448 (MH+).

Example 332

4-(4-hydroxy-3-methylphenyl)-6-{4-{(2-{4-[3-(methyloxy)phenyl]piperazin-1-yl}-2-oxoethyl)oxy}phenyl}pyrimidin-2(1H)-one

MS (EI): 527 (MH+).

Example 333

N-[(2-chlorophenyl)methyl]-2-({4-[6-(4-hydroxy-3-methylphenyl)-2-oxo-2,3-dihydropyrimidin-4-yl]phenyl}oxy)acetamide

MS (ED: 476 (MH+).

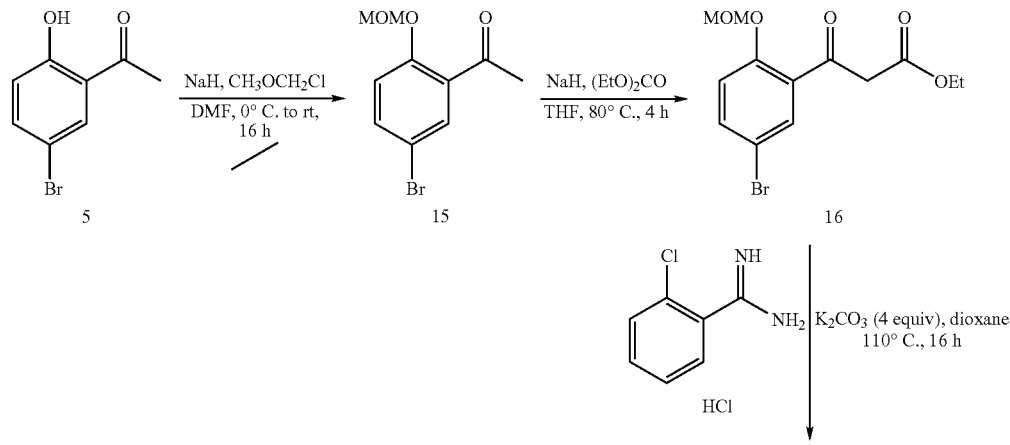

Scheme 11

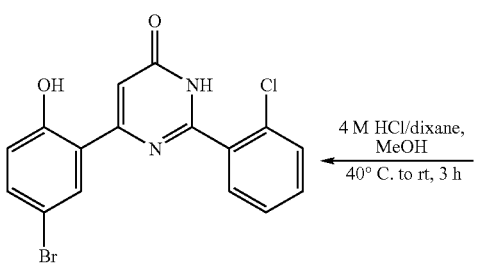 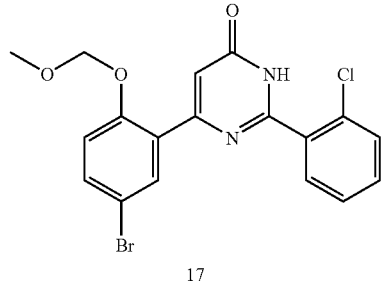

Example 334

6-(5-Bromo-2-hydroxyphenyl)-2-(2-chlorophenyl)pyrimidin-4(3H)-one

Step 1

1-(5-Bromo-2-(methoxymethoxy)phenyl)ethanone (15)

To a slurry of sodium hydride (60% oily dispersion; 1.125 g, 28 mmol) in anhydrous DMF (80 mL), 1-(5-bromo-2-hydroxyphenyl)ethanone (4.67 g, 21.7 mmol) was added at 0° C. under a nitrogen atmosphere. After stirring for 1 h at the same temperature, methyl chloromethyl ether (tech, 90%; 2.35 g, 26 mmol) was added dropwise. The reaction mixture was allowed to gradually warm to room temperature and was stirred for 4 h. The reaction mixture was then quenched by pouring it onto saturated $NH_4Cl$ (aq) (100 mL). The reaction mixture was then extracted with 8:1 $Et_2O$/EtOAc (2×150 mL). The combined organic layers were washed with water (4×80 mL), brine (60 mL), and dried over $MgSO_4$. After purification by flash chromatography (9:1 hexane/EtOAc), the title compound (15) was obtained as colorless oil (4.44 g, 79% yield).

$^1$H NMR (400 MHz, $CDCl_3$) δ 7.80 (d, 1H), 7.50 (dd, 1H), 7.09 (d, 1H), 5.27 (s, 2H), 3.51 (s, 3H), 2.62 (s, 3H); $^{13}$C NMR (100 MHz, $CDCl_3$) δ 198.5, 155.6, 136.2, 133.0, 130.6, 117.0, 114.5, 94.8, 56.7, 31.9. MS (GC-MS) for $C_8H_7BrO_2$: 214, 216 ($MH^+$).

Step 2

1-(5-Bromo-2-(methoxymethoxy)phenyl)-4-methoxybutane-1,3-dione (16)

To a slurry of sodium hydride (60% oily dispersion; 1.49 g, 37 mmol) and diethylcarbonate (6.0 mL, 49 mmol) in anhydrous THF (70 mL), a solution of 1-(5-bromo-2-(methoxymethoxy)phenyl)ethanone (15, 4.435 g, 17.1 mmol) in anhydrous THF (30 mL) was added in one portion at rt under a nitrogen atmosphere. The mixture was stirred at 80° C. for 5 h. As the reaction was deemed complete by LC-MS, the mixture was cooled to room temperature and quenched by pouring it onto 1:1 ice/1N $NaHSO_4$ (100 mL). Extractions with $Et_2O$ (2×150 mL) followed. The combined organic layers were washed with water (80 mL), brine (60 mL), and then dried over $MgSO_4$. After purification by flash chromatography (9:1 to 8:2 hexane/EtOAc), the title compound (16) was obtained as colorless oil (4.403 g, 78% yield).

$^1$H NMR (400 MHz, $CDCl_3$) δ 12.7 (s, 1H, enol), 7.94 (m, 1H), 7.55 (dd, 1H), 7.43 (d, 1H, enol), 7.12 (d, 1H), 7.09 (d, 1H, enol), 5.96 (s, 1H, enol), 5.25 (s, 2H), 4.26 (q, 2H, enol), 4.18 (q, 2H), 4.11 (q, 2H, enol), 3.97 (s, 2H), 3.50 (s, 3H), 1.35 (t, 3H, enol), 1.25 (t, 3H); $^{13}$C NMR (100 MHz, $CDCl_3$) δ 192.0, 173.6 (enol), 167.9, 167.4 (enol), 156.0, 154.9 (enol), 137.2, 134.5 (enol), 133.6, 132.2 (enol), 128.6 (enol), 125.2 (enol), 117.1 (enol), 116.9, 114.8 (enol), 114.5 (enol), 94.9, 61.4, 60.7 (enol), 60.6, 56.8, 56.6 (enol), 50.6, 21.3, 14.5 (enol), 14.4 (enol), 14.3. MS (LC-MS, ESI) for $C_{13}H_5BrO_5$: 330, 332 ($MH^+$).

Step 3

6-(5-Bromo-2-(methoxymethoxy)phenyl)-2-(2-chlorophenyl)pyrimidin-4(3H)-one (17)

A 100-mL round bottom flask was charged with 1-(5-bromo-2-(methoxymethoxy)phenyl)-4-methoxybutane-1,3-dione (16, 780 mg, 2.36 mmol), benzamidine hydrochloride (457 mg, 2.39 mmol), potassium carbonate (705 mg, 5.10 mmol) and anhydrous dioxane (16 mL). The mixture was stirred at 110° C. for 16 h under a nitrogen atmosphere. As the reaction was deemed complete by LC-MS, the mixture was cooled to room temperature and poured onto 1N $NaHSO_4$ (50 mL). Extractions with EtOAc (2×80 mL) followed. The combined organic layers were washed with water (40 mL), brine (30 mL), and then dried over $MgSO_4$. After purification by flash chromatography (96:4 $CH_2Cl_2$/$CH_3OH$), the title compound (17) was obtained as colorless oil (574 mg, 57% yield).

$^1$H NMR (400 MHz, $d_6$-DMSO) δ 12.98 (br s, 1H), 8.05 (dd, 1H), 7.56-7.73 (m, 3H), 7.50 (dt, 1H), 7.24 (d, 1H), 7.00 (br s, 1H) 5.35 (s, 2H), 3.42 (s, 3H); MS (GC-MS) for $C_{18}H_{14}BrClN_2O_3$: 420, 422 ($MH^+$).

Step 4

6-(5-Bromo-2-hydroxyphenyl)-2-(2-chlorophenyl)pyrimidin-4(3H)-one (344)

6-(5-Bromo-2-(methoxymethoxy)phenyl)-2-(2-chlorophenyl)pyrimidin-4(3H)-one (17, 158 mg, 0.37 mmol) in methanol (5 mL) was treated with a solution 4 M HCl in dioxane (0.8 mL, 3.2 mmol) at 40° C. for 3 h. The title product (344) precipitated out of solution as a white solid (109 mg, 78% yield), which was isolated by filtration and rinsed with hot methanol.

$^1$H NMR (400 MHz, $d_6$-DMSO) δ 11.7 (br s, 1H), 8.13 (d, 1H), 7.73 (dd, 1H), 7.66 (d, 1H), 7.60 (dt, 1H), 7.53 (dt, 1H), 7.47 (dd, 1H), 7.22 (s, 1H), 6.91 (d, 1H); MS (GC-MS) for $C_{16}H_{10}BrClN_2O_2$: 376, 378 ($MH^+$).

Scheme 12

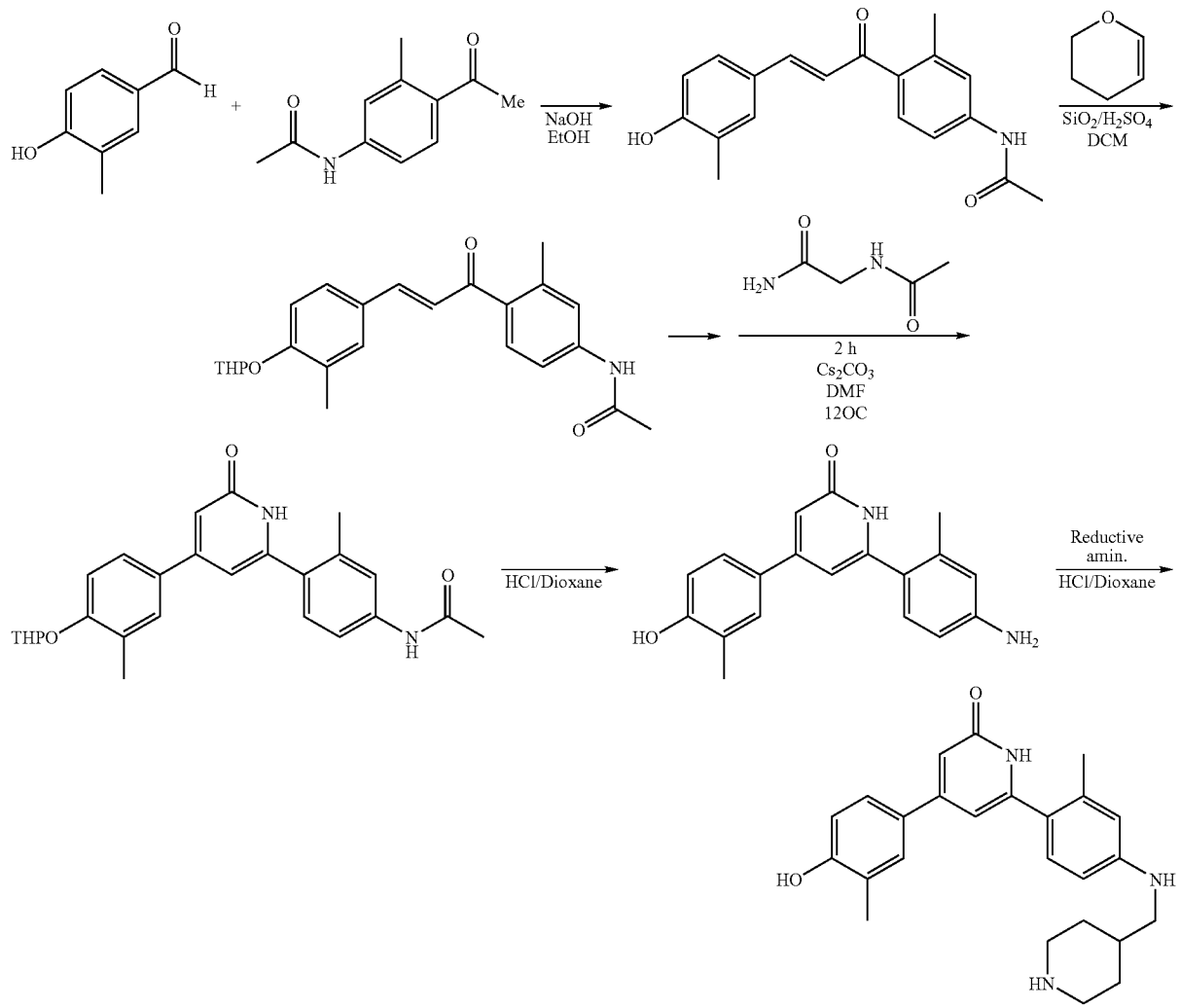

Example 335

4-(4-hydroxy-3-methylphenyl)-6-{2-methyl-4-[(piperidin-4-ylmethyl)amino]phenyl}-pyridin-2(1H)-one (E)-N-(4-(3-(4-hydroxy-3-methylphenyl)acryloyl)-3-methylphenyl)acetamide.

To a mixture of N-(4-acetyl-3-methylphenyl)acetamide (1.3 g, 7.0 mmol) and NaOH (1.4 g, 36 mmol) in 25 mL of absolute EtOH was added 4-hydroxy-3-methylbenzaldehyde (1.0 g, 7.3 mmol). The reaction mixture was stirred at room temperature for 18 hr. 5 mL of water was added and the reaction mixture was acidified with concentrated HCl to pH 5-6. The aqueous layer was extracted with two 25 mL portions of EOAc, and the layers were separated. The organic layer was dried with $Na_2SO_4$, filtered and concentrated under reduced pressure. The resulting product was submitted to the next step without further purification.

MS (EI) for $C_{19}H_{19}NO_3$: 310 (MH+).

Step 2

(E)-N-(3-methyl-4-(3-(3-methyl-4-(tetrahydro-2H-pyran-2-yloxy)phenyl)acryloyl)-phenyl)acetamide To a solution of (E)-N-(4-(3-(4-hydroxy-3-methylphenyl)acryloyl)-3-methylphenyl)acetamide (100 mg, 0.32 mmol) in DCM was added 300 mg of $H_2SO_4/SiO_2$ (cat. amount), and 3,4-dihydro-2H-pyran (500 mg, 5.9 mmol). The reaction mixture was stirred for 1 h at room temperature. The resulting slurry was filtered, concentrated under reduced pressure, and the product was purified by column chromatography (EtOAc/Hex, 10% to 50% gradient), resulting in 80 mg (78%) of the title compound. MS (EI) for $C_{24}H_{27}NO_4$: 394 (MH+).

Step 3

6-(4-amino-2-methylphenyl)-4-(4-hydroxy-3-methylphenyl)pyridin-2(1H)-one

In a round bottom flask was added (E)-N-(3-methyl-4-(3-(3-methyl-4-(tetrahydro-2H-pyran-2-yloxy)phenyl)acryloyl)phenyl)acetamide (100 mg, 0.25 mmol), DMF (2.0 mL), $Cs_2CO_3$ (200 mg), and 2-acetamidoacetamide (180 mg, 1.55 mmol). The reaction mixture was heated to 140° C. for 1 h, cooled down to room temperature, filtered, and concentrated down under reduced pressure.

The resulting oil was then dissolved in 4N HCl/dioxane (5.0 mL) and 1 mL of DMF, and heated to 90° C. for 12 h. The resulting mixture was allowed to cool down to room temperature and concentrated under reduced pressure. The resulting product was submitted to the next step without further purification. MS (EI) for $C_{19}H_{18}N_2O_2$: 307 (MH$^+$).

Step 4

4-(4-hydroxy-3-methylphenyl)-6-{2-methyl-4-[(piperidin-4-ylmethyl)amino]-phenyl}pyridin-2(1H)-one In a round bottom flask was added 6-(4-amino-2-methylphenyl)-4-(4-hydroxy-3-methylphenyl)pyridin-2(1H)-one (76 mg, 0.25 mmol), 1,2 Dichloroethane (5.0 mL), acetic acid (0.1 mL), and N-Boc-4-Formyl piperidine (0.65 mg, 0.30 mmol). The reaction was stirred at room temperature for 15 minutes before adding sodium triacetoxy borohydride (85 mg, 0.40 mmol). Stirring was continued at room temperature for 10 min. The reaction was then concentrated down under reduced pressure. The resulting oil was then dissolved in 4N HCl/dioxane (5.0 mL) and stirred at 45° C. for 1 h. The resulting slurry was cooled down to room temperature and the precipitate was filtered off. The resulting solid was then dissolved in MeOH and purified by preparatory HPLC (15-40% gradient of $NH_4OAc/ACN$) to give 4-(4-hydroxy-3-methylphenyl)-6-{2-methyl-4-[(piperidin-4-ylmethyl)amino]phenyl}pyridin-2(1H)-one as the acetate salt (16 mg, 14% yield over 2 steps). $^1$H NMR (400 MHz, d6-DMSO) δ 7.47 (s, 1H), 7.39 (dd, 1H), 7.06 (d, 1H), 6.85 (d, 1H), 6.45 (m, 2H), 6.36 (s, 1H), 6.27 (s, 1H), 5.95 (t, 1H), 2.98 (m, 2H), 2.91 (t, 1H), 2.48 (m, 2H), 2.22 (s, 3H), 2.16 (s, 3H), 1.72 (m, 4H), 1.09 (m, 1H); MS (EI) for $C_{25}H_{29}N_3O_2$: 404 (MH$^+$).

Example 336

6-(2-chlorophenyl)-4-(4-hydroxy-3-methylphenyl) pyridin-2(1H)-one 6-(2-chlorophenyl)-4-(4-hydroxy-3-methylphenyl)pyridin-2(1H)-one was prepared by a procedure analogous to Example 345 in which commercially available 1-(2-chlorophenyl)ethanone was substituted for N-(4-acetyl-3-methylphenyl)acetamide. $^1$H NMR (400 MHz, d6-DMSO): δ 9.85 (br s, 1H), 7.60-7.42 (m, 7H), 6.84 (d, 1H), 6.56 (br s, 2H), 2.16 (s, 3H). MS (EI) for $C_{18}H_{14}ClNO_2$: 312 (MH+).

Example 337

6-(3-bromophenyl)-2-(2-chlorophenyl)pyrimidin-4 (3H)-one 6-(3-bromophenyl)-2-(2-chlorophenyl)pyrimidin-4(3H)-one was synthesized in a manner similar to Example 334.

$^1$H NMR (400 MHz, d6-DMSO): δ 13.01 (br.s, 1H), 8.24 (s, 1H), 8.09 (d, 1H), 7.72-7.69 (m, 2H), 7.65-7.56 (m, 2H), 7.53-7.43 (m, 2H), 7.04 (s, 1H). MS (EI): 363 (MH+).

Example 338

2-(2-chlorophenyl)-6-(4-hydroxy-3-methylphenyl) pyrimidin-4(3H)-one 2-(2-chlorophenyl)-6-(4-hydroxy-3-methylphenyl)pyrimidin-4(3H)-one was synthesized in a manner similar to Example 334.

$^1$H NMR (400 MHz, CDCl$_3$): δ 7.9 (m, 2H), 7.8 (dd, 1H), 7.5 (m, 3H), 6.9 (d, 1H), 6.8 (s, 1H). MS (EI): 313 (MH+).

Compounds are active against PIM (wherein PIM refers to PIM-1, PIM-2, and/or PIM-3 throughout this application) kinase activity. Accordingly, compounds of the invention can also be useful for treating proliferative disorders associated with PIM kinase activity.

PIM Assay Protocol

PIM kinase activity can be measured by monitoring peptide substrate dependent hydrolysis of ATP via quantitation of remaining ATP with luciferase based chemiluminescence. For compound evaluation, 0.5 ul compound dissolved in DMSO is added to 10 ul of PIM-1, PIM-2 and/or PIM-3 dissolved in assay buffer (20 mM HEPES pH 7.5, 10 mM MgCl2, 0.03% Triton and 1 mM DTT). After preincubation for about 30 minutes at about room temperature, the reaction is initiated by addition of 10 ul of ATP and substrate peptide AKRRRLSA in assay buffer. The reaction mixture is incubated for about 120 min at room temperature, and the reaction progress can be quantitated by addition of 10 ul Kinase-Glo (Promega) and measuring chemiluminescence in a Victor reader (Perkin Elmer). A reaction in which compound is omitted is used to determine maximum reaction progress. Omission of compound and enzyme from the reaction can be used to determine zero reaction progress.

The compounds in Tables 1 and 2 have been tested for their PIM (either PIM-1, PIM-2 and/or PIM-3) inhibitory activity (IC$_{50}$ values), and these compounds have PIM IC$_{50}$ values of less than 5000 nM. A preferred group of compounds of Tables 1 and 2 have PIM-1 IC$_{50}$ values of less than 5000 nM. Another preferred group of compounds of Tables 1 and 2 have PIM-1 IC$_{50}$ values of less than 2000 nM. Another preferred group of compounds of Tables 1 and 2 have PIM-1 IC$_{50}$ values of less than 1000 nM. Another preferred group of compounds of Tables 1 and 2 have PIM-1 IC$_{50}$ values of less than 500 nM. Another preferred group of compounds of Tables 1 and 2 have PIM-1 IC$_{50}$ values of less than 200 nM. Another preferred group of compounds of Tables 1 and 2 have PIM-1 IC$_{50}$ values of less than 100 nM. Another preferred group of compounds of Tables 1 and 2 have PIM-1 IC$_{50}$ values of less than 50 nM. Another preferred group of compounds of Tables 1 and 2 have PIM-1 IC$_{50}$ values of less than 25 nM. Another preferred group of compounds of Tables 1 and 2 have PIM-3 IC$_{50}$ values of less than 5000 nM. Another preferred group of compounds of Tables 1 and 2 have PIM-3 IC$_{50}$ values of less than 2000 nM. Another preferred group of compounds of Tables 1 and 2 have PIM-3 IC$_{50}$ values of less than 1000 nM. Another preferred group of compounds of Tables 1 and 2 have PIM-3 IC$_{50}$ values of less than 500 nM. Another preferred group of compounds of Tables 1 and 2 have PIM-3 IC$_{50}$ values of less than 200 nM. Another preferred group of compounds of Tables 1 and 2 have PIM-3 IC$_{50}$ values of less than 100 nM. Another preferred group of compounds of Tables 1 and 2 have PIM-3 IC$_{50}$ values of less than 50 nM. Another preferred group of compounds of Tables 1 and 2 have PIM-3 IC$_{50}$ values of less than 25 nM. Another preferred group of compounds of Tables 1 and 2 have PIM-2 IC$_{50}$ values of less than 5000 nM. Another preferred group of compounds of Tables 1 and 2 have PIM-2 IC$_{50}$ values of less than 2000 nM. Another preferred group of compounds of Tables 1 and 2 have PIM-2 IC$_{50}$ values of less than 1000 nM. Another preferred group of compounds of Tables 1 and 2 have PIM-2 IC$_{50}$ values of less than 500 nM. Another preferred group of compounds of Tables 1 and 2 have PIM-2 IC$_{50}$ values of less than 200 nM. Another preferred group of compounds of Tables 1 and 2 have PIM-2 IC$_{50}$ values of less than 100 nM.

Some of the compounds in Tables 1 and 2 can also be active against CK2 kinase activity. The inhibitory effect of the compounds in Tables 1 and 2 against CK2 kinase activity can be measured by the following assays:

Biological Assay

For a biochemical measurement of CK2 inhibitory activity, the compounds of the invention were screened in a luciferase-coupled chemiluminescence assay that detects consumption of ATP by the CK2 enzyme. The assay was performed using two different constructs of the enzyme, CK2 holoenzyme and CK2 alpha subunit. The assay buffer is composed of 20 mM Tris, pH 7.5, 10 mM MgCl$_2$, 0.03% Triton-X-1000, 1 mM DTT and 0.1 mM NaVO$_3$.

For the CK2 alpha subunit assay, the assay is performed as follows: 0.5 µl of test compound is added to a microtiter plate, followed by the addition of 10 µl substrate containing CK2 peptide (RRRDDDSDDD) and ATP and 10 µl of alpha subunit of the CK2 enzyme. The concentration of CK2 peptide is 9 µM, ATP is 2 µM and CK2-alpha subunit is 10 nM.

For the CK2 holoenzyme assay, the assay is performed as follows: 0.5 µl of test compound is added to a microtiter plate, followed by the addition of 10 µl substrate containing casein and ATP and 10 µl of CK2 holoenzyme. The concentration of casein is 2 µM, ATP is 2 µM and CK2 holoenzyme is 6 nM.

For both assays, the mixture is shaken briefly and incubated for 120 min at room temperature. At the end of the incubation, 10 µl of Kinase Glo (luciferase) is added and the signal is detected in a luminescence reader (Victor, Perkin Elmer).

Biological Assay

For a biochemical measurement of CK2 inhibitory activity, compounds of the invention were screened in a luciferase-coupled chemiluminescence assay that detects consumption of ATP by the CK2 enzyme. The assay was performed using two different constructs of the enzyme, CK2 holoenzyme and CK2 alpha subunit. The assay buffer is composed of 20 mM Tris, pH 7.5, 10 mM MgCl$_2$, 0.03% Triton-X-1000, 1 mM DTT and 0.1 mM NaVO$_3$.

For the CK2 alpha subunit assay, the assay is performed as follows: 0.5 µl of test compound is added to a microtiter plate, followed by the addition of 10 µl substrate containing CK2 peptide (RRRDDDSDDD) and ATP and 10 µl of alpha subunit of the CK2 enzyme. The concentration of CK2 peptide is 9 µM, ATP is 2 µM and CK2-alpha subunit is 10 nM.

For the CK2 holoenzyme assay, the assay is performed as follows: 0.5 µl of test compound is added to a microtiter plate, followed by the addition of 10 µl substrate containing casein and ATP and 10 µl of CK2 holoenzyme. The concentration of casein is 2 µM, ATP is 2 µM and CK2 holoenzyme is 6 nM.

For both assays, the mixture is shaken briefly and incubated for 120 min at room temperature. At the end of the incubation, 10 µl of Kinase Glo (luciferase) is added and the signal is detected in a luminescence reader (Victor, Perkin Elmer).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A compound of Formula I:

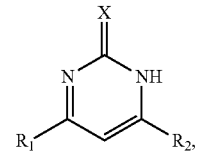

or a pharmaceutically acceptable salt thereof, wherein:

X is O or S;

$R_1$ is —($C_6$-$C_{10}$)aryl, —($C_6$-$C_{10}$)aryl-($C_1$-$C_6$)alkyl, 1,3-benzoxazol-2(3H)-one, methylisoxazolyl, or isoxazoyl, wherein each of the —($C_6$-$C_{10}$)aryl or —($C_6$-$C_{10}$)aryl-($C_1$-$C_6$)alkyl is substituted with 1, 2, or 3 groups independently selected from —NHR$^8$, —NR$^8$R$^9$, —OR$^{10}$, -(4-10 membered)heterocycloalkyl, —C(O)-(4-10 membered)heterocycloalkyl, —C(O)—N(E1)($C_1$-$C_6$)alkyl-R$^6$, —C(O)N(E7)(4-10 membered)heterocycloalkyl, —C(O)—N(E9)($C_3$-$C_{10}$)cycloalkyl, —C(O)—N(E10)($C_1$-$C_6$)alkyl-O—($C_6$-$C_{10}$)aryl, —O—($C_1$-$C_6$)alkyl-C(O)—N(E11)($C_1$-$C_6$)alkyl-O—($C_6$-$C_{10}$)aryl, —C(O)—N(E12)($C_1$-$C_6$)alkyl-CN, —O—($C_1$-$C_6$)alkyl-C(O)—OH, and —C(O)—OH, and wherein each of the 1,3-benzoxazol-2(3H)-one or isoxazolyl is substituted with 1, 2, or 3 groups independently selected from —NHR$^8$, —NR$^8$R$^9$, —OR$^{10}$, -(4-10 membered)heterocycloalkyl, —C(O)-(4-10 membered)heterocycloalkyl, —C(O)—N(E1)($C_1$-$C_6$)alkyl-R$^6$, —C(O)N(E7)(4-10 membered)heterocycloalkyl, —C(O)—N(E8)($C_1$-$C_6$)alkyl, —C(O)—N(E9)($C_3$-$C_{10}$)cycloalkyl, —C(O)—N(E10)($C_1$-$C_6$)alkyl-O—($C_6$-$C_{10}$)aryl, —O—($C_1$-$C_6$)alkyl-C(O)—N(E11)($C_1$-$C_6$)alkyl-O—($C_6$-$C_{10}$)aryl, —C(O)—N(E12)($C_1$-$C_6$)alkyl-CN, —O—($C_1$-$C_6$)alkyl-C(O)—OH, and —C(O)—OH;

$R_2$ is phenyl optionally substituted with 1, 2 or 3 substituents selected from hydrogen, halo, —OH, and —($C_1$-$C_6$)alkyl;

$R^3$ is —($C_3$-$C_{10}$)cycloalkyl or -(4-10 membered)heterocycloalkyl;

$R^4$ is -(4-10 membered)heterocycloalkyl, -(5-10 membered)heteroaryl, or —($C_3$-$C_{10}$)cycloalkyl;

$R^5$ is H or NH$_2$;

$R^6$ is -(4-10 membered)heterocycloalkyl optionally substituted with oxo, -(5-10 membered)heteroaryl, or —($C_3$-$C_{10}$)cycloalkyl;

$R^7$ is -(4-10 membered)heterocycloalkyl optionally substituted with oxo, -(5-10 membered)heteroaryl, or —($C_3$-$C_{10}$)cycloalkyl;

$R^8$ is —($C_1$-$C_6$)alkyl-N(H)(4-10 membered)heterocycloalkyl, —($C_1$-$C_6$)alkyl-(4-10 membered)heterocycloalkyl, —($C_1$-$C_6$)alkyl-NH$_2$, —($C_1$-$C_6$)alkyl-(5-6 membered)heteroaryl, or -(4-10 membered)heterocycloalkyl;

$R^9$ is —($C_1$-$C_3$)alkyl;

$R^{10}$ is —($C_1$-$C_6$)alkyl-C(O)—R$^3$, —($C_1$-$C_6$)alkyl-C(O)—N(E14)R$^4$, —($C_1$-$C_6$)alkyl-C(O)—N(E2)($C_1$-$C_6$)alkyl-R$^5$, —($C_1$-$C_6$)alkyl-C(O)—N(E3)($C_1$-$C_6$)alkyl-N($C_1$-$C_6$)alkyl]$_2$, —($C_1$-$C_6$)alkyl-C(O)N(E4)($C_1$-$C_6$)alkyl-R$^7$, ($C_1$-$C_6$)alkyl-C(O)—N(E5)($C_1$-$C_6$)alkyl-($C_1$-$C_6$)alkoxy, —($C_1$-$C_6$)alkyl-C(O)—N(E6)($C_1$-$C_6$)alkyl-CN, or —($C_1$-$C_6$)alkyl-C(O)—N[($C_1$-$C_6$)alkyl]$_2$;

wherein each of said -(4-10 membered)heterocycloalkyl, -(5-10 membered)heteroaryl, —($C_3$-$C_{10}$)cycloalkyl, and —($C_6$-$C_{10}$)aryl within each of $R^1$, $R^3$, $R^4$, $R^6$ or $R^7$ is unsubstituted or independently substituted at any ring position with 1, 2 or 3 substituents independently selected from —($C_1$-$C_6$)alkyl, —$NH_2$, -(4-10 membered)heterocycloalkyl optionally substituted with —($C_1$-$C_3$)alkyl, —N[($C_1$-$C_6$)alkyl]$_2$, —($C_1$-$C_6$)alkyl-$NH_2$, —($C_1$-$C_6$)alkyl-($C_1$-$C_6$)alkoxy, —N(E13)C(O)—($C_1$-$C_6$)alkyl, —($C_6$-$C_{10}$)aryl optionally substituted with —($C_1$-$C_3$)alkoxy, halo, —C(O)—($C_1$-$C_6$)alkyl, —C(O)-(5-10 membered)heteroaryl, —($C_1$-$C_6$)alkyl-OH, —OH, —C(O)O—($C_1$-$C_6$)alkyl, —C(O)-(4-10 membered)heterocycloalkyl, —($C_1$-$C_3$)alkyl-($C_6$-$C_{10}$)aryl, —($C_1$-$C_6$)alkoxy, and -(5-10 membered)heteroaryl, and wherein the substitutuents for each of the -(4-10 membered)heterocycloalkyl, -(5-10 membered)heteroaryl, —($C_3$-$C_{10}$)cycloalkyl, and —($C_6$-$C_{10}$)aryl can be the same or different for any one of $R^1$, $R^3$, $R^4$, $R^6$ or $R^7$;

each of E1, E2, E3, E4, E5, E6, E7, E9, E10, E11, E12, E13 and E14, which can be the same or different, is hydrogen or —($C_1$-$C_3$)alkyl.

2. The compound according to claim 1, wherein the compound is of Formula I; $R_1$ is phenyl or methylphenyl, wherein the phenyl or methylphenyl is substituted with —C(O)-(4-10 membered)heterocycloalkyl optionally substituted at any ring position of the —C(O)-(4-10 membered)heterocycloalkyl with 1, 2 or 3 groups independently selected from —($C_1$-$C_3$)alkyl, —($C_6$-$C_{10}$)aryl-O—($C_1$-$C_3$)alkyl, —O—($C_1$-$C_6$)alkyl, -(5-10 membered)heteroaryl, —C(O)-(5-10 membered)heteroaryl, -(4-10 membered)heterocycloalkyl, —C(O)-(4-10 membered)heterocycloalkyl, —OH, —C(O)O—($C_1$-$C_3$)alkyl, —N(H)C(O)—($C_1$-$C_3$)alkyl, —C(O)—($C_1$-$C_3$)alkyl, —($C_1$-$C_3$)alkyl-($C_6$-$C_{10}$)aryl, —($C_1$-$C_6$)alkyl-O—($C_1$-$C_6$)alkyl, —($C_1$-$C_6$)alkyl-OH, —$NH_2$, and —($C_1$-$C_6$)alkyl-$NH_2$;

$R_2$ is

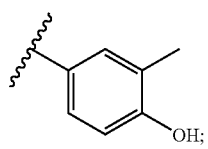

and

X is O.

3. The compound according to claim 1, wherein the compound is of Formula I; $R_1$ is phenyl or methylphenyl, wherein the phenyl or methylphenyl is substituted with —C(O)N(H)($C_1$-$C_6$)alkyl-($C_3$-$C_6$)cycloalkyl;

$R_2$ is

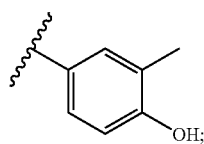

and

X is O.

4. The compound according to claim 1, wherein the compound is of Formula I;

$R_1$ is phenyl or methylphenyl, wherein the phenyl or methylphenyl is substituted with —(O)-alkyl-C(O)-(4-10 membered)heterocycloalkyl optionally substituted at any ring position of the —(O)-alkyl-C(O)-(4-10 membered)heterocycloalkyl group with 1, 2 or 3 groups independently selected from —N(H)C(O)—($C_1$-$C_6$)alkyl, —N[($C_1$-$C_6$)alkyl]-C(O)—($C_1$-$C_6$)alkyl, —C(O)-(5-10 membered)heteroaryl, —($C_1$-$C_6$)alkyl-($C_6$-$C_{10}$)aryl, —($C_1$-$C_6$)alkyl-O—($C_1$-$C_6$)alkyl, —C(O)—($C_1$-$C_6$)alkyl, —OH, -(4-10 membered)heterocycloalkyl, —($C_1$-$C_6$)alkyl-OH, -(5-10 membered)heteroaryl, —C(O)—O—($C_1$-$C_6$)alkyl, —C(O)-(4-10 membered)heterocycloalkyl, —($C_6$-$C_{10}$)aryl optionally substituted with —O—($C_1$-$C_3$)alkyl and —($C_1$-$C_6$)alkyl;

$R_2$ is

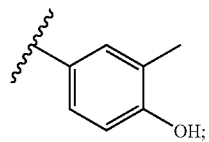

and

X is O.

5. The compound according to claim 1, wherein the compound is of Formula I;

$R_1$ is phenyl or methylphenyl, wherein the phenyl or methylphenyl is substituted with —O— ($C_1$-$C_6$)alkyl-C(O)—N(H)($C_1$-$C_6$)alkyl;

$R_2$ is

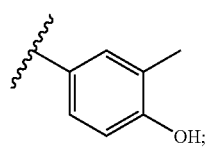

and

X is O.

6. The compound according to claim 1, wherein the compound is of Formula I;

$R_1$ is phenyl or methylphenyl, wherein the phenyl or methylphenyl is substituted with —O— ($C_1$-$C_6$)alkyl-C(O)—N(H)($C_1$-$C_6$)alkyl-(4-10 membered)heterocycloalkyl or —O— ($C_1$-$C_6$)alkyl-C(O)—N[($C_1$-$C_6$)alkyl]-($C_1$-$C_6$)alkyl-(4-10 membered)heterocycloalkyl, wherein the -(4-10 membered)heterocycloalkyl portion of the —O—($C_1$-$C_6$)alkyl-C(O)—N(H)($C_1$-$C_6$)alkyl-(4-10 membered)heterocycloalkyl or —O—($C_1$-$C_6$)alkyl-C(O)—N[($C_1$-$C_6$)alkyl]-($C_1$-$C_6$)alkyl-(4-10 membered)heterocycloalkyl group is optionally substituted with 1, 2 or 3 groups independently selected from oxo, —($C_1$-$C_6$)alkyl-phenyl, —O—($C_1$-$C_6$)alkyl and —($C_1$-$C_6$)alkyl;

R₂ is

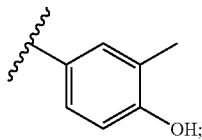

and
X is O.

7. The compound according to claim 1, wherein the compound is of Formula I;

R₁ is phenyl or methylphenyl, wherein the phenyl or methylphenyl is substituted with —C(O)—N(H)(C₁-C₆)alkyl-(4-10 membered)heterocycloalkyl, wherein the -(4-10 membered)heterocycloalkyl portion of the —C(O)—N(H)(C₁-C₆)alkyl-(4-10 membered)heterocycloalkyl group is optionally substituted with 1, 2 or 3-(C₁-C₆)alkyl groups;

R₂ is

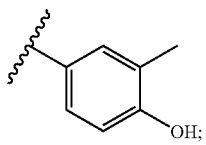

and
X is O.

8. The compound according to claim 1, wherein the compound is of Formula I;

R₁ is phenyl or methylphenyl, wherein the phenyl or methylphenyl is substituted with —O— (C₁-C₆)alkyl-C(O)—N(H)(C₁-C₆)alkyl-(C₃-C₁₀)cycloalkyl;

R₂ is

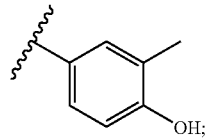

and
X is O.

9. The compound according to claim 1, wherein the compound is of Formula I;

R₁ is phenyl or methylphenyl substituted with —O—(C₁-C₆)alkyl-C(O)—N(H)(C₁-C₆)alkyl-NR₁₃R₁₄, wherein R₁₃ and R₁₄ are each selected from H and —(C₁-C₆)alkyl;

R₂ is

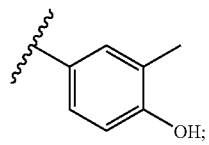

and
X is O.

10. The compound selected from:

4-(4-hydroxy-3-methylphenyl)-6-(3-{[2-(3-methylpiperidin-1-yl)-2-oxoethyl]oxy}phenyl)pyrimidin-2(1H)-one;
4-(4-hydroxy-3-methylphenyl)-6-(4-{[2-(2-methylpyrrolidin-1-yl)-2-oxoethyl]oxy}phenyl)pyrimidin-2(1H)-one;
4-(4-hydroxy-3-methylphenyl)-6-{4-[(2-morpholin-4-yl-2-oxoethyl)oxy]phenyl}pyrimidin-2(1H)-one;
N-[(2-fluorophenyl)methyl]-2-({3-[6-(4-hydroxy-3-methylphenyl)-2-oxo-2,3-dihydropyrimidin-4-yl]phenyl}oxy)-N-methylacetamide;
2-({3-[6-(4-hydroxy-3-methylphenyl)-2-oxo-2,3-dihydropyrimidin-4-yl]phenyl}oxy)-N-[2-(phenyloxy)ethyl]acetamide;
2-({3-[6-(4-hydroxy-3-methylphenyl)-2-oxo-2,3-dihydropyrimidin-4-yl]phenyl}oxy)-N-(pyridin-3-ylmethyl)acetamide;
N-[(6-chloropyridin-3-yl)methyl]-3-[6-(4-hydroxy-3-methylphenyl)-2-oxo-2,3-dihydropyrimidin-4-yl]benzamide;
6-{4-[(2-azepan-1-yl-2-oxoethyl)oxy]phenyl}-4-(4-hydroxy-3-methylphenyl)pyrimidin-2(1H)-one;
3-[6-(4-hydroxy-3-methylphenyl)-2-oxo-2,3-dihydropyrimidin-4-yl]-N-[(5-methylfuran-2-yl)methyl]benzamide;
N-(cyclopropylmethyl)-2-({3-[6-(4-hydroxy-3-methylphenyl)-2-oxo-2,3-dihydropyrimidin-4-yl]phenyl}oxy)acetamide;
2-({4-[6-(4-hydroxy-3-methylphenyl)-2-oxo-2,3-dihydropyrimidin-4-yl]phenyl}oxy)-N-(2-thienylmethyl)acetamide;
N-(2-cyanoethyl)-4-[6-(4-hydroxy-3-methylphenyl)-2-oxo-2,3-dihydropyrimidin-4-yl]benzamide;
N-cyclopropyl-2-({4-[6-(4-hydroxy-3-methylphenyl)-2-oxo-2,3-dihydropyrimidin-4-yl]phenyl}oxy)acetamide;
4-(4-hydroxy-3-methylphenyl)-6-{3-[(4-methylpiperidin-1-yl)carbonyl]phenyl}pyrimidin-2(1H)-one;
2-({3-[6-(4-hydroxy-3-methylphenyl)-2-oxo-2,3-dihydropyrimidin-4-yl]phenyl}oxy)-N-(2-methylpropyl)acetamide;
2-({3-[6-(4-hydroxy-3-methylphenyl)-2-oxo-2,3-dihydropyrimidin-4-yl]phenyl}oxy)-N-methyl-N-(2-methylpropyl)acetamide;
4-(4-hydroxy-3-methylphenyl)-6-[2-methyl-4-(4-methylpiperazin-1-yl)phenyl]pyrimidin-2(1H)-one;
2-({4-[6-(4-hydroxy-3-methylphenyl)-2-oxo-2,3-dihydropyrimidin-4-yl]phenyl}oxy)-N-(1-methylpiperidin-4-yl)acetamide;

3-[6-(4-hydroxy-3-methylphenyl)-2-oxo-2,3-dihydropyrimidin-4-yl]-N-(2-piperidin-1-ylethyl)benzamide;
4-(4-hydroxy-3-methylphenyl)-6-(4-{[2-(3-methylpiperidin-1-yl)-2-oxoethyl]oxy}phenyl)pyrimidin-2(1H)-one;
2-({3-[6-(4-hydroxy-3-methylphenyl)-2-oxo-2,3-dihydropyrimidin-4-yl]phenyl}oxy)-N-(tetrahydrofuran-2-ylmethyl)acetamide;
N-cycloheptyl-2-({4-[6-(4-hydroxy-3-methylphenyl)-2-oxo-2,3-dihydropyrimidin-4-yl]phenyl}oxy)acetamide;
4-[6-(4-hydroxy-3-methylphenyl)-2-oxo-2,3-dihydropyrimidin-4-yl]-N-methyl-N-(2-methylpropyl)benzamide;
2-({3-[6-(4-hydroxy-3-methylphenyl)-2-oxo-2,3-dihydropyrimidin-4-yl]phenyl}oxy)-N-(4-methylcyclohexyl)acetamide;
N-cyclohexyl-4-[6-(4-hydroxy-3-methylphenyl)-2-oxo-2,3-dihydropyrimidin-4-yl]benzamide;
N-[(3-chlorophenyl)methyl]-3-[6-(4-hydroxy-3-methylphenyl)-2-oxo-2,3-dihydropyrimidin-4-yl]benzamide;
6-[3-(1,4'-bipiperidin-1'-ylcarbonyl)phenyl]-4-(4-hydroxy-3-methylphenyl)pyrimidin-2(1H)-one;
4-[6-(4-hydroxy-3-methylphenyl)-2-oxo-2,3-dihydropyrimidin-4-yl]benzoic acid;
({4-[6-(4-hydroxy-3-methylphenyl)-2-oxo-2,3-dihydropyrimidin-4-yl]phenyl}oxy)acetic acid;
4-(4-hydroxy-3-methylphenyl)-6-{3-[(2-{4-[4-(methyloxy)phenyl]piperazin-1-yl}-2-oxoethyl)oxy]phenyl}pyrimidin-2(1H)-one;
4-(4-hydroxy-3-methylphenyl)-6-{4-[(4-methylpiperidin-1-yl)carbonyl]phenyl}pyrimidin-2(1H)-one;
6-(4-{[2-(3,5-dimethylpiperidin-1-yl)-2-oxoethyl]oxy}phenyl)-4-(4-hydroxy-3-methylphenyl)pyrimidin-2(1H)-one;
N-[3-(dimethylamino)propyl]-3-[6-(4-hydroxy-3-methylphenyl)-2-oxo-2,3-dihydropyrimidin-4-yl]-N-; methylbenzamide;
N-[(3-chlorophenyl)methyl]-4-[6-(4-hydroxy-3-methylphenyl)-2-oxo-2,3-dihydropyrimidin-4-yl]benzamide;
2-({3-[6-(4-hydroxy-3-methylphenyl)-2-oxo-2,3-dihydropyrimidin-4-yl]phenyl}oxy)-N-(3-morpholin-4-ylpropyl)acetamide;
2-({3-[6-(4-hydroxy-3-methylphenyl)-2-oxo-2,3-dihydropyrimidin-4-yl]phenyl}oxy)-N-[2-(1-methylpyrrolidin-2-yl)ethyl]acetamide;
N-[3-(dimethylamino)propyl]-2-({3-[6-(4-hydroxy-3-methylphenyl)-2-oxo-2,3-dihydropyrimidin-4-yl]phenyl}oxy)acetamide;
3-[6-(4-hydroxy-3-methylphenyl)-2-oxo-2,3-dihydropyrimidin-4-yl]-N-(2-morpholin-4-ylethyl)benzamide;
6-[3-({2-[3-(diethylamino)pyrrolidin-1-yl]-2-oxoethyl}oxy)phenyl]-4-(4-hydroxy-3-methylphenyl)pyrimidin-2(1H)-one;
2-({3-[6-(4-hydroxy-3-methylphenyl)-2-oxo-2,3-dihydropyrimidin-4-yl]phenyl}oxy)-N-methyl-N-(1-methylpyrrolidin-3-yl)acetamide;
6-[4-({2-[(1-ethylpiperidin-4-yl)amino]ethyl}amino)-2-methylphenyl]-4-(4-hydroxy-3-methylphenyl)pyrimidin-2(1H)-one;
4-(4-hydroxy-3-methy)phenyl)-6-{2-methyl-4-[(piperidin-4-ylmethyl)amino]phenyl}pyrimidin-2(1H)-one;
4-(4-hydroxy-3-methylphenyl)-6-{2-methyl-4-[(piperidin-3-ylmethyl)amino]phenyl}pyrimidin-2(1H)-one;
6-{4-[(3-aminopropyl)amino]-2-methylphenyl}-4-(4-hydroxy-3-methylphenyl)pyrimidin-2(1H)-one;
2-({4-[6-(4-hydroxy-3-methylphenyl)-2-oxo-2,3-dihydropyrimidin-4-yl]phenyl}oxy)-N-piperidin-4-ylacetamide;
N-(2-aminoethyl)-2-({3-[6-(4-hydroxy-3-methylphenyl)-2-oxo-2,3-dihydropyrimidin-4-yl]phenyl}oxy)acetamide;
4-(4-hydroxy-3-methylphenyl)-6-(2-methyl-4-{[(2-methyl-1H-imidazol-4-yl)methyl]amino}phenyl)pyrimidin-2(1H)-one;
N-(3-aminopropyl)-2-({3-[6-(4-hydroxy-3-methylphenyl)-2-oxo-2,3-dihydropyrimidin-4-yl]phenyl}oxy)acetamide;
6-{4-[(2-aminoethyl)amino]-2-methylphenyl}-4-(4-hydroxy-3-methylphenyl)pyrimidin-2(1H)-one;
6-(3-{[2-(3-aminopiperidin-1-yl)-2-oxoethyl]oxy}phenyl)-4-(4-hydroxy-3-methylphenyl)pyrimidin-2(1H)-one;
N-[(1-ethylpyrrolidin-2-yl)methyl]-2-({3-[6-(4-hydroxy-3-methylphenyl)-2-oxo-2,3-dihydropyrimidin-4-yl]phenyl}oxy)acetamide;
4-(4-hydroxy-3-methylphenyl)-6-{4-[(1H-imidazol-4-ylmethyl)amino]-2-methylphenyl}pyrimidin-2(1H)-one;
2-({3-[6-(4-hydroxy-3-methylphenyl)-2-oxo-2,3-dihydropyrimidin-4-yl]phenyl}oxy)-N-(piperidin-4-ylmethyl)acetamide;
6-(3-{[2-(3-aminopyrrolidin-1-yl)-2-oxoethyl]oxy}phenyl)-4-(4-hydroxy-3-methylphenyl)pyrimidin-2(1H)-one;
N-[2-(dimethylamino)ethyl]-2-({3-[6-(4-hydroxy-3-methylphenyl)-2-oxo-2,3-dihydropyrimidin-4-yl]phenyl}oxy)acetamide;
N-[2-(diethylamino)ethyl]-2-({4-[6-(4-hydroxy-3-methylphenyl)-2-oxo-2,3-dihydropyrimidin-4-yl]phenyl}oxy)acetamide;
4-[6-(4-hydroxy-3-methylphenyl)-2-oxo-2,3-dihydropyrimidin-4-yl]-N-[2-(1-methylpyrrolidin-2-yl)ethyl]benzamide;
6-(3-{[3-(aminomethyl)piperidin-1-yl]carbonyl}phenyl)-4-(4-hydroxy-3-methylphenyl)pyrimidin-2(1H)-one;

N-{1-[({4-[6-(4-hydroxy-3-methylphenyl)-2-oxo-2,3-dihydropyrimidin-4-yl]phenyl}oxy)acetyl]pyrrolidin-3-yl}-N-methylacetamide;
6-(4-{[2-(4-acetylpiperazin-1-yl)-2-oxoethyl]oxy}phenyl)-4-(4-hydroxy-3-methylphenyl)pyrimidin-2(1H)-one;
4-[6-(4-hydroxy-3-methylphenyl)-2-oxo-2,3-dihydropyrimidin-4-yl]-N-(2-morpholin-4-ylethyl)benzamide;
4-(4-hydroxy-3-methylphenyl)-6-{4-[(2-{4-[4-(methyloxy)phenyl]piperazin-1-yl}-2-oxoethyl)oxy]phenyl}pyrimidin-2(1H)-one;
6-(4-{[3-(diethylamino)pyrrolidin-1-yl]carbonyl}phenyl)-4-(4-hydroxy-3-methylphenyl)pyrimidin-2(1H)-one;
N-[(6-chloropyridin-3-yl)methyl]-2-({3-[6-(4-hydroxy-3-methylphenyl)-2-oxo-2,3-dihydropyrimidin-4-yl]phenyl}oxy)acetamide;
6-[4-({2-[4-(furan-2-ylcarbonyl)piperazin-1-yl]-2-oxoethyl}oxy)phenyl]-4-(4-hydroxy-3-methylphenyl)pyrimidin-2(1H)-one;
N-(furan-2-ylmethyl)-2-({4-[6-(4-hydroxy-3-methylphenyl)-2-oxo-2,3-dihydropyrimidin-4-yl]phenyl}oxy)acetamide;
4-(4-hydroxy-3-methylphenyl)-6-{4-[(2-oxo-2-pyrrolidin-1-ylethyl)oxy]phenyl}pyrimidin-2(1H)-one;
2-({4-[6-(4-hydroxy-3-methylphenyl)-2-oxo-2,3-dihydropyrimidin-4-yl]phenyl}oxy)-N-(3-morpholin-4-ylpropyl)acetamide;
4-(4-hydroxy-3-methylphenyl)-6-(4-{[2-(4-morpholin-4-ylpiperidin-1-yl)-2-oxoethyl]oxy}phenyl)pyrimidin-2(1H)-one;
4-(4-hydroxy-3-methylphenyl)-6-[4-({2-oxo-2-[4-(tetrahydrofuran-2-ylcarbonyl)piperazin-1-yl]ethyl}oxy)phenyl]pyrimidin-2(1H)-one;
3-[6-(4-hydroxy-3-methylphenyl)-2-oxo-2,3-dihydropyrimidin-4-yl]-N-[3-(4-methylpiperazin-1-yl)propyl]benzamide;
2-({4-[6-(4-hydroxy-3-methylphenyl)-2-oxo-2,3-dihydropyrimidin-4-yl]phenyl}oxy)-N-{[3-(methyloxy)phenyl]methyl}acetamide;
4-(4-hydroxy-3-methylphenyl)-6-(4-{[2-(4-methylpiperidin-1-yl)-2-oxoethyl]oxy}phenyl)pyrimidin-2(1H)-one;
4-[6-(4-hydroxy-3-methylphenyl)-2-oxo-2,3-dihydropyrimidin-4-yl]-N-(tetrahydrofuran-2-ylmethyl)benzamide;
N-[3-(dimethylamino)propyl]-2-({3-[6-(4-hydroxy-3-methylphenyl)-2-oxo-2,3-dihydropyrimidin-4-yl]phenyl}oxy)-N-methylacetamide;
4-[6-(4-hydroxy-3-methylphenyl)-2-oxo-2,3-dihydropyrimidin-4-yl]-N-(2-piperidin-1-ylethyl)benzamide;
6-(3-{[2-(4-ethylpiperazin-1-yl)-2-oxoethyl]oxy}phenyl)-4-(4-hydroxy-3-methylphenyl)pyrimidin-2(1H)-one;
N-[3-(dimethylamino)propyl]-2-({4-[6-(4-hydroxy-3-methylphenyl)-2-oxo-2,3-dihydropyrimidin-4-yl]phenyl}oxy)acetamide;
N-[2-(dimethylamino)ethyl]-N-ethyl-2-({3-[6-(4-hydroxy-3-methylphenyl)-2-oxo-2,3-dihydropyrimidin-4-yl]phenyl}oxy)acetamide;
6-(3-{[2-(1,4'-bipiperidin-1'-yl)-2-oxoethyl]oxy}phenyl)-4-(4-hydroxy-3-methylphenyl)pyrimidin-2(1H)-one;
6-[3-({2-[3-(aminomethyl)piperidin-1-yl]-2-oxoethyl}oxy)phenyl]-4-(4-hydroxy-3-methylphenyl)pyrimidin-2(1H)-one;
N-[2-(dimethylamino)ethyl]-N-ethyl-2-({4-[6-(4-hydroxy-3-methylphenyl)-2-oxo-2,3-dihydropyrimidin-4-yl]phenyl}oxy)acetamide;
2-({3-[6-(4-hydroxy-3-methylphenyl)-2-oxo-2,3-dihydropyrimidin-4-yl]phenyl}oxy)-N-(2-morpholin-4-ylethyl)acetamide;
N-butyl-2-({3-[6-(4-hydroxy-3-methylphenyl)-2-oxo-2,3-dihydropyrimidin-4-yl]phenyl}oxy)-N-methylacetamide;
4-[6-(4-hydroxy-3-methylphenyl)-2-oxo-2,3-dihydropyrimidin-4-yl]-N-(3-morpholin-4-ylpropyl)benzamide;
6-(4-{[3-(aminomethyl)piperidin-1-yl]carbonyl}phenyl)-4-(4-hydroxy-3-methylphenyl)pyrimidin-2(1H)-one;
N-(4-aminocyclohexyl)-3-[6-(4-hydroxy-3-methylphenyl)-2-oxo-2,3-dihydropyrimidin-4-yl]benzamide;
4-[6-(4-hydroxy-3-methylphenyl)-2-oxo-2,3-dihydropyrimidin-4-yl]-N-(piperidin-4-ylmethyl)benzamide;
3-[6-(4-hydroxy-3-methylphenyl)-2-oxo-2,3-dihydropyrimidin-4-yl]-N-[2-(phenyloxy)ethyl]benzamide;
N-(4-aminocyclohexyl)-2-({3-[6-(4-hydroxy-3-methylphenyl)-2-oxo-2,3-dihydropyrimidin-4-yl]phenyl}oxy)acetamide;
4-[6-(4-hydroxy-3-methylphenyl)-2-oxo-2,3-dihydropyrimidin-4-yl]-N-methyl-N-(1-methylpyrrolidin-3-yl)benzamide;
N-(3-aminopropyl)-2-({4-[6-(4-hydroxy-3-methylphenyl)-2-oxo-2,3-dihydropyrimidin-4-yl]phenyl}oxy)acetamide;
4-(4-hydroxy-3-methylphenyl)-6-(3-{[2-(4-methylpiperazin-1-yl)-2-oxoethyl]oxy}phenyl)pyrimidin-2(1H)-one;
2-({4-[6-(4-hydroxy-3-methylphenyl)-2-oxo-2,3-dihydropyrimidin-4-yl]phenyl}oxy)-N-methyl-N-(1-methylpiperidin-4-yl)acetamide;
N-(2-cyanoethyl)-2-({3-[6-(4-hydroxy-3-methylphenyl)-2-oxo-2,3-dihydropyrimidin-4-yl]phenyl}oxy)acetamide;
3-[6-(4-hydroxy-3-methylphenyl)-2-oxo-2,3-dihydropyrimidin-4-yl]-N-[3-(1H-imidazol-1-yl)propyl]benzamide;
6-[4-({2-[3-(aminomethyl)piperidin-1-yl]-2-oxoethyl}oxy)phenyl]-4-(4-hydroxy-3-methylphenyl)pyrimidin-2(1H)-one;
N-[(1-ethylpyrrolidin-2-yl)methyl]-4-[6-(4-hydroxy-3-methylphenyl)-2-oxo-2,3-dihydropyrimidin-4-yl]benzamide;

4-[6-(4-hydroxy-3-methylphenyl)-2-oxo-2,3-dihydropyrimidin-4-yl]-N-[3-(1H-imidazol-1-yl)propyl]benzamide;
N-[3-(dimethylamino)propyl]-2-({4-[6-(4-hydroxy-3-methylphenyl)-2-oxo-2,3-dihydropyrimidin-4-yl]phenyl}oxy)-N-methylacetamide;
2-({4-[6-(4-hydroxy-3-methylphenyl)-2-oxo-2,3-dihydropyrimidin-4-yl]phenyl}oxy)-N-(2-morpholin-4-ylethyl)acetamide;
2-({4-[6-(4-hydroxy-3-methylphenyl)-2-oxo-2,3-dihydropyrimidin-4-yl]phenyl}oxy)-N-methyl-N-(1-methylpyrrolidin-3-yl)acetamide;
2-({4-[6-(4-hydroxy-3-methylphenyl)-2-oxo-2,3-dihydropyrimidin-4-yl]phenyl}oxy)-N-(3-pyrrolidin-1-ylpropyl)acetamide;
N-(2-cyanoethyl)-3-[6-(4-hydroxy-3-methylphenyl)-2-oxo-2,3-dihydropyrimidin-4-yl]benzamide;
N-[2-(dimethylamino)ethyl]-2-({4-[6-(4-hydroxy-3-methylphenyl)-2-oxo-2,3-dihydropyrimidin-4-yl]phenyl}oxy)-N-methylacetamide;
4-(4-hydroxy-3-methylphenyl)-6-(4-{[2-(4-methyl-1,4-diazepan-1-yl)-2-oxoethyl]oxy}phenyl)pyrimidin-2(1H)-one;
6-(4-{[2-(4-ethylpiperazin-1-yl)-2-oxoethyl]oxy}phenyl)-4-(4-hydroxy-3-methylpheny])pyrimidin-2(1H)-one;
3-[6-(4-hydroxy-3-methylphenyl)-2-oxo-2,3-dihydropyrimidin-4-yl]-N-(tetrahydrofuran-2-ylmethyl)benzamide;
N-[2-(2-fluorophenyl)ethyl]-3-[6-(4-hydroxy-3-methylphenyl)-2-oxo-2,3-dihydropyrimidin-4-yl]benzamide;
2-({4-[6-(4-hydroxy-3-methylphenyl)-2-oxo-2,3-dihydropyrimidin-4-yl]phenyl}oxy)-N-[3-(1H-imidazol-1-yl)propyl]acetamide;
4-(4-hydroxy-3-methylphenyl)-6-{4-[(4-methylpiperazin-1-yl)carbonyl]phenyl}pyrimidin-2(1H)-one;
4-(4-hydroxy-3-methylphenyl)-6-(4-{[2-(4-methylpiperazin-1-yl)-2-oxoethyl]oxy}phenyl)pyrimidin-2(1H)-one;
2-({4-[6-(4-hydroxy-3-methylphenyl)-2-oxo-2,3-dihydropyrimidin-4-yl]phenyl}oxy)-N-(tetrahydrofuran-2-ylmethyl)acetamide;
2-({3-[6-(4-hydroxy-3-methylphenyl)-2-oxo-2,3-dihydropyrimidin-4-yl]phenyl}oxy)-N-[3-(methyloxy)propyl]acetamide;
2-({4-[6-(4-hydroxy-3-methylphenyl)-2-oxo-2,3-dihydropyrimidin-4-yl]phenyl}oxy)-N-[2-(phenyloxy)ethyl]acetamide;
6-{4-[(2-{4-[2-(ethyloxy)ethyl]piperazin-1-yl}-2-oxoethyl)oxy]phenyl}-4-(4-hydroxy-3-methylphenyl)pyrimidin-2(1H)-one;
2-({4-[6-(4-hydroxy-3-methylphenyl)-2-oxo-2,3-dihydropyrimidin-4-yl]phenyl}oxy)-N-[(5-methylfuran-2-yl)methyl]acetamide;
N-(cyclohexylmethyl)-2-({4-[6-(4-hydroxy-3-methylphenyl)-2-oxo-2,3-dihydropyrimidin-4-yl]phenyl}oxy)acetamide;
3-[6-(4-hydroxy-3-methylphenyl)-2-oxo-2,3-dihydropyrimidin-4-yl]-N-(2-thienylmethyl)benzamide;
N-[(6-chloropyridin-3-yl)methyl]-2-({4-[6-(4-hydroxy-3-methylphenyl)-2-oxo-2,3-dihydropyrimidin-4-yl]phenyl}oxy)acetamide;
2-({4-[6-(4-hydroxy-3-methylphenyl)-2-oxo-2,3-dihydropyrimidin-4-yl]phenyl}oxy)-N-[2-(methyloxy)ethyl]acetamide;
N-(cyclopropylmethyl)-2-({4-[6-(4-hydroxy-3-methylphenyl)-2-oxo-2,3-dihydropyrimidin-4-yl]phenyl}oxy)acetamide;
2-({3-[6-(4-hydroxy-3-methylphenyl)-2-oxo-2,3-dihydropyrimidin-4-yl]phenyl}oxy)-N-[(5-methylfuran-2-yl)methyl]acetamide;
3-[6-(4-hydroxy-3-methylphenyl)-2-oxo-2,3-dihydropyrimidin-4-yl]-N-(pyridin-3-ylmethyl)benzamide;
2-({4-[6-(4-hydroxy-3-methylphenyl)-2-oxo-2,3-dihydropyrimidin-4-yl]phenyl}oxy)-N-(pyridin-3-ylmethyl)acetamide;
4-(4-hydroxy-3-methylphenyl)-6-{4-[(2-{4-[2-(methyloxy)ethyl]piperazin-1-yl}-2-oxoethyl)oxy]phenyl}pyrimidin-2(1H)-one;
N-butyl-2-({3-[6-(4-hydroxy-3-methylphenyl)-2-oxo-2,3-dihydropyrimidin-4-yl]phenyl}oxy)acetamide;
2-({4-[6-(4-hydroxy-3-methylphenyl)-2-oxo-2,3-dihydropyrimidin-4-yl]phenyl}oxy)-N-{2-[(1-methylethyl)oxy]ethyl}acetamide;
2-({4-[6-(4-hydroxy-3-methylphenyl)-2-oxo-2,3-dihydropyrimidin-4-yl]phenyl}oxy)-N-[3-(4-methylpiperazin-1-yl)propyl]acetamide;
N-cyclobutyl-3-[6-(4-hydroxy-3-methylphenyl)-2-oxo-2,3-dihydropyrimidin-4-yl]benzamide;
4-(4-hydroxy-3-methylphenyl)-6-{2-methyl-4-[(tetrahydro-2H-pyran-4-ylmethyl)amino]phenyl}pyrimidin-2(1H)-one;
2-({4-[6-(4-hydroxy-3-methylphenyl)-2-oxo-2,3-dihydropyrimidin-4-yl]phenyl}oxy)-N-pentylacetamide;
N-[2-(2-fluorophenyl)ethyl]-4-[6-(4-hydroxy-3-methylphenyl)-2-oxo-2,3-dihydropyrimidin-4-yl]benzamide;
N-cyclohexyl-3-[6-(4-hydroxy-3-methylphenyl)-2-oxo-2,3-dihydropyrimidin-4-yl]benzamide;
N-[(2-fluorophenyl)methyl]-3-[6-(4-hydroxy-3-methylphenyl)-2-oxo-2,3-dihydropyrimidin-4-yl]-N-methylbenzamide;
3-[6-(4-hydroxy-3-methylphenyl)-2-oxo-2,3-dihydropyrimidin-4-yl]benzoic acid;
4-(4-hydroxy-3-methylphenyl)-6-(3-{[2-(2-methylpiperidin-1-yl)-2-oxoethyl]oxy}phenyl)pyrimidin-2(1H)-one;
6-[4-(azepan-1-ylcarbonyl)phenyl]-4-(4-hydroxy-3-methylpheny))pyrimidin-2(1H)-one;

4-(4-hydroxy-3-methylphenyl)-6-(3-{[4-(phenylmethyl)piperazin-1-yl]carbonyl}phenyl)pyrimidin-2(1H)-one;
4-[6-(4-hydroxy-3-methylphenyl)-2-oxo-2,3-dihydropyrimidin-4-yl]-N-(4-methylcyclohexyl)benzamide;
6-(3-{[2-(2-ethylpiperidin-1-yl)-2-oxoethyl]oxy}phenyl)-4-(4-hydroxy-3-methylphenyl)pyrimidin-2(1H)-one;
N-[(4-chlorophenyl)methyl]-2-({3-[6-(4-hydroxy-3-methylphenyl)-2-oxo-2,3-dihydropyrimidin-4-yl]phenyl}oxy)acetamide;
N-cycloheptyl-4-[6-(4-hydroxy-3-methylphenyl)-2-oxo-2,3-dihydropyrimidin-4-yl]benzamide;
4-(4-hydroxy-3-methylphenyl)-6-(3-{[4-(hydroxymethyl)piperidin-1-yl]carbonyl}phenyl)pyrimidin-2(1H)-one;
N-[(4-chlorophenyl)methyl]-4-[6-(4-hydroxy-3-methylphenyl)-2-oxo-2,3-dihydropyrimidin-4-yl]benzamide;
4-(4-hydroxy-3-methylphenyl)-6-{4-[(3-methylpiperidin-1-yl)carbonyl]phenyl}pyrimidin-2(1H)-one;
4-(4-hydroxy-3-methylphenyl)-6-{3-[(2-{4-[2-(methyloxy)phenyl]piperazin-1-yl}-2-oxoethyl)oxy]phenyl}pyrimidin-2(1H)-one;
ethyl 1-({3-[6-(4-hydroxy-3-methylphenyl)-2-oxo-2,3-dihydropyrimidin-4-yl]phenyl}carbonyl)piperidine-4-carboxylate;
N-[(3-chlorophenyl)methyl]-2-({4-[6-(4-hydroxy-3-methylphenyl)-2-oxo-2,3-dihydropyrimidin-4-yl]phenyl}oxy)acetamide;
2-({3-[6-(4-hydroxy-3-methylphenyl)-2-oxo-2,3-dihydropyrimidin-4-yl]phenyl}oxy)-N-pentylacetamide;
2-({3-[6-(4-hydroxy-3-methylphenyl)-2-oxo-2,3-dihydropyrimidin-4-yl]phenyl}oxy)-N-(pyridin-4-ylmethyl)acetamide;
N-cyclopentyl-2-({3-[6-(4-hydroxy-3-methylphenyl)-2-oxo-2,3-dihydropyrimidin-4-yl]phenyl}oxy)acetamide;
N-[(3-chlorophenyl)methyl]-2-({3-[6-(4-hydroxy-3-methylphenyl)-2-oxo-2,3-dihydropyrimidin-4-yl]phenyl}oxy)acetamide;
2-({4-[6-(4-hydroxy-3-methylphenyl)-2-oxo-2,3-dihydropyrimidin-4-yl]phenyl}oxy)-N-(2-methylpropyl)acetamide;
4-(4-hydroxy-3-methylphenyl)-6-{4-[(2-{4-[2-(methyloxy)phenyl]piperazin-1-yl}-2-oxoethyl)oxy]phenyl}pyrimidin-2(1H)-one;
2-({4-[6-(4-hydroxy-3-methylphenyl)-2-oxo-2,3-dihydropyrimidin-4-yl]phenyl}oxy)-N-methyl-N-(2-methylpropyl)acetamide;
N-[2-(2-fluorophenyl)ethyl]-2-({3-[6-(4-hydroxy-3-methylphenyl)-2-oxo-2,3-dihydropyrimidin-4-yl]phenyl}oxy)acetamide;
methyl 1-[({4-[6-(4-hydroxy-3-methylphenyl)-2-oxo-2,3-dihydropyrimidin-4-yl]phenyl}oxy)acetyl]piperidine-4-carboxylate;
N-(furan-2-ylmethyl)-2-({3-[6-(4-hydroxy-3-methylphenyl)-2-oxo-2,3-dihydropyrimidin-4-yl]phenyl}oxy)-N-methylacetamide;
4-(4-hydroxy-3-methylphenyl)-6-(4-{[2-oxo-2-(4-pyrazin-2-ylpiperazin-1-yl)ethyl]oxy}phenyl)pyrimidin-2(1H)-one;
N-[(2,4-difluorophenyl)methyl]-2-({4-[6-(4-hydroxy-3-methylphenyl)-2-oxo-2,3-dihydropyrimidin-4-yl]phenyl}oxy)acetamide;
4-(4-hydroxy-3-methylphenyl)-6-{4-[(2-oxo-2-piperidin-1-ylethyl)oxy]phenyl}pyrimidin-2(1H)-one;
4-(4-hydroxy-3-methylphenyl)-6-[4-({2-[4-(hydroxymethyl)piperidin-1-yl]-2-oxoethyl}oxy)phenyl]pyrimidin-2(1H)-one;
N-(furan-2-ylmethyl)-2-({4-[6-(4-hydroxy-3-methylphenyl)-2-oxo-2,3-dihydropyrimidin-4-yl]phenyl}oxy)-N-methylacetamide;
N-(furan-2-ylmethyl)-2-({3-[6-(4-hydroxy-3-methylphenyl)-2-oxo-2,3-dihydropyrimidin-4-yl]phenyl}oxy)acetamide;
4-(4-hydroxy-3-methylphenyl)-6-[3-(piperazin-1-ylcarbonyl)phenyl]pyrimidin-2(1H)-one;
N-(furan-2-ylmethyl)-3-[6-(4-hydroxy-3-methylphenyl)-2-oxo-2,3-dihydropyrimidin-4-yl]benzamide;
4-(4-hydroxy-3-methylphenyl)-6-(3-{[2-(4-morpholin-4-ylpiperidin-1-yl)-2-oxoethyl]oxy}phenyl)pyrimidin-2(1H)-one;
N-cyclopropyl-2-({3-[6-(4-hydroxy-3-methylphenyl)-2-oxo-2,3-dihydropyrimidin-4-yl]phenyl}oxy)acetamide;
N-(furan-2-ylmethyl)-3-[6-(4-hydroxy-3-methylphenyl)-2-oxo-2,3-dihydropyrimidin-4-yl]-N-methylbenzamide;
2-({4-[6-(4-hydroxy-3-methylphenyl)-2-oxo-2,3-dihydropyrimidin-4-yl]phenyl}oxy)-N-[3-(2-oxopyrrolidin-1-yl)propyl]acetamide;
N-cyclopropyl-3-[6-(4-hydroxy-3-methylphenyl)-2-oxo-2,3-dihydropyrimidin-4-yl]benzamide;
N-(cyclohexylmethyl)-3-[6-(4-hydroxy-3-methylphenyl)-2-oxo-2,3-dihydropyrimidin-4-yl]benzamide;
5-[6-(2-Chlorophenyl)-2-oxo-1,2-dihydropyrimidin-4-yl]thiophene-2-carboxamide;
4-(4-hydroxy-3-methylphenyl)-6-(4-{[2-(4-hydroxypiperidin-1-yl)-2-oxoethyl]oxy}phenyl)pyrimidin-2(1H)-one;
6-{3-[(3-aminopiperidin-1-yl)carbonyl]phenyl}-4-(4-hydroxy-3-methylphenyl)pyrimidin-2(1H)-one;
ethyl 1-[({4-[6-(4-hydroxy-3-methylphenyl)-2-oxo-2,3-dihydropyrimidin-4-yl]phenyl}oxy)acetyl]piperidine-4-carboxylate;
N-butyl-2-({4-[6-(4-hydroxy-3-methylphenyl)-2-oxo-2,3-dihydropyrimidin-4-yl]phenyl}oxy)-N-methylacetamide;

4-(4-hydroxy-3-methylphenyl)-6-[4-({2-oxo-2-[4-(phenylmethyl)piperazin-1-yl]ethyl}oxy)phenyl]pyrimidin-2(1H)-one;
N-cyclohexyl-2-({4-[6-(4-hydroxy-3-methylphenyl)-2-oxo-2,3-dihydropyrimidin-4-yl]phenyl}oxy)acetamide;
2-({4-[6-(4-hydroxy-3-methylphenyl)-2-oxo-2,3-dihydropyrimidin-4-yl]phenyl}oxy)-N-{[4-(methyloxy)phenyl]methyl}acetamide;
2-({3-[6-(4-hydroxy-3-methylphenyl)-2-oxo-2,3-dihydropyrimidin-4-yl]phenyl}oxy)-N-propylacetamide;
2-({4-[6-(4-hydroxy-3-methylphenyl)-2-oxo-2,3-dihydropyrimidin-4-yl]phenyl}oxy)-N-(pyridin-4-ylmethyl)acetamide;
2-({4-[6-(4-hydroxy-3-methylphenyl)-2-oxo-2,3-dihydropyrimidin-4-yl]phenyl}oxy)-N-{[2-(methyloxy)phenyl]methy])acetamide;
N-butyl-2-({4-[6-(4-hydroxy-3-methylphenyl)-2-oxo-2,3-dihydropyrimidin-4-yl]phenyl}oxy)acetamide;
4-(4-hydroxy-3-methylphenyl)-6-{3-[(2-{4-[2-(methyloxy)ethyl]piperazin-1-yl}-2-oxoethyl)oxy]phenyl}pyrimidin-2(1H)-one;
3-[6-(4-hydroxy-3-methylphenyl)-2-oxo-2,3-dihydropyrimidin-4-yl]-N-[3-(2-oxopyrrolidin-1-yl)propyl]benzamide;
methyl 1-[({3-[6-(4-hydroxy-3-methylphenyl)-2-oxo-2,3-dihydropyrimidin-4-yl]phenyl}oxy)acetyl]piperidine-4-carboxylate;
4-(4-hydroxy-3-methylphenyl)-6-[3-({2-oxo-2-[4-(tetrahydrofuran-2-ylcarbonyl)piperazin-1-yl]ethyl}oxy)phenyl]pyrimidin-2(1H)-one;
N-[(2-fluorophenyl)methyl]-2-({4-[6-(4-hydroxy-3-methylphenyl)-2-oxo-2,3-dihydropyrimidin-4-yl]phenyl}oxy)-N-methylacetamide;
N-[2-(2-fluorophenyl)ethyl]-2-({4-[6-(4-hydroxy-3-methylphenyl)-2-oxo-2,3-dihydropyrimidin-4-yl]phenyl}oxy)acetamide;
6-(3-{[2-(4-acetylpiperazin-1-yl)-2-oxoethyl]oxy}phenyl)-4-(4-hydroxy-3-methylphenyl)pyrimidin-2(1H)-one;
N-(furan-2-ylmethyl)-4-[6-(4-hydroxy-3-methylphenyl)-2-oxo-2,3-dihydropyrimidin-4-yl]benzamide;
4-[6-(4-hydroxy-3-methylphenyl)-2-oxo-2,3-dihydropyrimidin-4-yl]-N-(pyridin-3-ylmethyl)benzamide;
6-{3-[(2-{4-[2-(ethyloxy)ethyl]piperazin-1-yl}-2-oxoethyl)oxy]phenyl}-4-(4-hydroxy-3-methylphenyl)pyrimidin-2(1H)-one;
N-[(6-chloropyridin-3-yl)methyl]-4-[6-(4-hydroxy-3-methylphenyl)-2-oxo-2,3-dihydropyrimidin-4-yl]benzamide;
N-cyclobutyl-2-({4-[6-(4-hydroxy-3-methylphenyl)-2-oxo-2,3-dihydropyrimidin-4-yl]phenyl}oxy)acetamide;
N-(cyclohexylmethyl)-2-({3-[6-(4-hydroxy-3-methylphenyl)-2-oxo-2,3-dihydropyrimidin-4-yl]phenyl}oxy)acetamide;
N-(cyclopropylmethyl)-3-[6-(4-hydroxy-3-methylphenyl)-2-oxo-2,3-dihydropyrimidin-4-yl]benzamide;
N-(cyclopropylmethyl)-4-[6-(4-hydroxy-3-methylphenyl)-2-oxo-2,3-dihydropyrimidin-4-yl]benzamide;
4-[6-(4-hydroxy-3-methylphenyl)-2-oxo-2,3-dihydropyrimidin-4-yl]-N-[(5-methylfuran-2-yl)methyl]benzamide;
2-({4-[6-(4-hydroxy-3-methylphenyl)-2-oxo-2,3-dihydropyrimidin-4-yl]phenyl}oxy)-N,N-dipropylacetamide;
3-[6-(4-hydroxy-3-methylphenyl)-2-oxo-2,3-dihydropyrimidin-4-yl]-N-(4-methylcyclohexyl)benzamide;
2-({3-[6-(4-hydroxy-3-methylphenyl)-2-oxo-2,3-dihydropyrimidin-4-yl]phenyl}oxy)-N-{[2-(methyloxy)phenyl]methyl}acetamide;
N-cyclobutyl-2-({3-[6-(4-hydroxy-3-methylphenyl)-2-oxo-2,3-dihydropyrimidin-4-yl]phenyl}oxy)acetamide;
4-(4-hydroxy-3-methylphenyl)-6-(3-{[2-(2-methylpyrrolidin-1-yl)-2-oxoethyl]oxy}phenyl)pyrimidin-2(1H)-one;
4-(4-hydroxy-3-methylphenyl)-6-[3-({2-oxo-2-[4-(phenylmethyl)piperazin-1-yl]ethyl}oxy)phenyl]pyrimidin-2(1H)-one;
4-[6-(4-hydroxy-3-methylphenyl)-2-oxo-2,3-dihydropyrimidin-4-yl]-N-{[2-(methyloxy)phenyl]methyl}benzamide;
2-({4-[6-(4-hydroxy-3-methylphenyl)-2-oxo-2,3-dihydropyrimidin-4-yl]phenyl}oxy)-N-[3-(methyloxy)propyl]acetamide;
N-(furan-2-ylmethyl)-4-[6-(4-hydroxy-3-methylphenyl)-2-oxo-2,3-dihydropyrimidin-4-yl]-N-methylbenzamide;
3-[6-(4-hydroxy-3-methylphenyl)-2-oxo-2,3-dihydropyrimidin-4-yl]-N-(pyridin-4-ylmethyl)benzamide;
4-(4-hydroxy-3-methylphenyl)-6-[3-({2-[4-(hydroxymethyl)piperidin-1-yl]-2-oxoethyl}oxy)phenyl]pyrimidin-2(1H)-one;
4-[6-(4-hydroxy-3-methylphenyl)-2-oxo-2,3-dihydropyrimidin-4-yl]-N-(2-thienylmethyl)benzamide;
2-({4-[6-(4-hydroxy-3-methylphenyl)-2-oxo-2,3-dihydropyrimidin-4-yl]phenyl}oxy)-N-propylacetamide;
N-[(2-chlorophenyl)methyl]-2-({3-[6-(4-hydroxy-3-methylphenyl)-2-oxo-2,3-dihydropyrimidin-4-yl]phenyl}oxy)acetamide;
4-(4-hydroxy-3-methylphenyl)-6-(3-{[2-oxo-2-(4-pyrazin-2-ylpiperazin-1-yl)ethyl]oxy}phenyl)pyrimidin-2(1H)-one;
({3-[6-(4-hydroxy-3-methylphenyl)-2-oxo-2,3-dihydropyrimidin-4-yl]phenyl}oxy)acetic acid;
3-[6-(4-hydroxy-3-methylphenyl)-2-oxo-2,3-dihydropyrimidin-4-yl]-N-{[4-(methyloxy)phenyl]methyl}benzamide;

6-(4-{[4-(furan-2-ylcarbonyl)piperazin-1-yl]carbonyl}phenyl)-4-(4-hydroxy-3-methylphenyl)pyrimidin-2(1H)-one;
4-[6-(4-hydroxy-3-methylphenyl)-2-oxo-2,3-dihydropyrimidin-4-yl]-N-(phenylmethyl)benzamide;
4-(4-hydroxy-3-methylphenyl)-6-(3-{[2-(4-methylpiperidin-1-yl)-2-oxoethyl]oxy}phenyl)pyrimidin-2(1H)-one;
6-[3-({2-[4-(furan-2-ylcarbonyl)piperazin-1-yl]-2-oxoethyl}oxy)phenyl]-4-(4-hydroxy-3-methylphenyl)pyrimidin-2(1H)-one;
N-[(2,4-difluorophenyl)methyl]-2-({3-[6-(4-hydroxy-3-methylphenyl)-2-oxo-2,3-dihydropyrimidin-4-yl]phenyl}oxy)acetamide;
N-{1-[({3-[6-(4-hydroxy-3-methylphenyl)-2-oxo-2,3-dihydropyrimidin-4-yl]phenyl}oxy)acetyl]pyrrolidin-3-yl}-N-methylacetamide;
ethyl 1-[({3-[6-(4-hydroxy-3-methylphenyl)-2-oxo-2,3-dihydropyrimidin-4-yl]phenyl}oxy)acetyl]piperidine-4-carboxylate;
4-[6-(4-hydroxy-3-methylphenyl)-2-oxo-2,3-dihydropyrimidin-4-yl]-N-[2-(phenyloxy)ethyl]benzamide;
N-cycloheptyl-2-({3-[6-(4-hydroxy-3-methylphenyl)-2-oxo-2,3-dihydropyrimidin-4-yl]phenyl}oxy)acetamide;
N-cyclopentyl-4-[6-(4-hydroxy-3-methylphenyl)-2-oxo-2,3-dihydropyrimidin-4-yl]benzamide;
4-[6-(4-hydroxy-3-methylphenyl)-2-oxo-2,3-dihydropyrimidin-4-yl]-N-{[3-(methyloxy)phenyl]methyl}benzamide;
6-{3-[(2-azepan-1-yl-2-oxoethyl)oxy]phenyl}-4-(4-hydroxy-3-methylphenyl)pyrimidin-2(1H)-one;
4-(4-hydroxy-3-methylphenyl)-6-{3-[(2-oxo-2-piperidin-1-ylethyl)oxy]phenyl}pyrimidin-2(1H)-one;
N-cyclopentyl-2-({4-[6-(4-hydroxy-3-methylphenyl)-2-oxo-2,3-dihydropyrimidin-4-yl]phenyl}oxy)acetamide;
4-(4-hydroxy-3-methylphenyl)-6-{4-[(4-pyrazin-2-ylpiperazin-1-yl)carbonyl]phenyl}pyrimidin-2(1H)-one;
2-({3-[6-(4-hydroxy-3-methylphenyl)-2-oxo-2,3-dihydropyrimidin-4-yl]phenyl}oxy)-N-{[3-(methyloxy)phenyl]methyl}acetamide;
N-cyclopropyl-4-[6-(4-hydroxy-3-methylphenyl)-2-oxo-2,3-dihydropyrimidin-4-yl]benzamide;
6-{4-[(4-acetylpiperazin-1-yl)carbonyl]phenyl}-4-(4-hydroxy-3-methylphenyl)pyrimidin-2(1H)-one;
4-[6-(4-hydroxy-3-methylphenyl)-2-oxo-2,3-dihydropyrimidin-4-yl]-N-{[4-(methyloxy)phenyl]methyl}benzamide;
N-cyclopentyl-3-[6-(4-hydroxy-3-methylphenyl)-2-oxo-2,3-dihydropyrimidin-4-yl]benzamide;
N-[1-({4-[6-(4-hydroxy-3-methylphenyl)-2-oxo-2,3-dihydropyrimidin-4-yl]phenyl}carbonyl)pyrrolidin-3-yl]-N-methylacetamide;
6-(4-{[2-(2-ethylpiperidin-1-yl)-2-oxoethyl]oxy}phenyl)-4-(4-hydroxy-3-methylphenyl)pyrimidin-2(1H)-one;
2-({3-[6-(4-hydroxy-3-methylphenyl)-2-oxo-2,3-dihydropyrimidin-4-yl]phenyl}oxy)-N-{[4-(methyloxy)phenyl]methyl}acetamide;
6-[4-({4-[2-(ethyloxy)ethyl]piperazin-1-yl}carbonyl)phenyl]-4-(4-hydroxy-3-methylphenyl)pyrimidin-2(1H)-one;
4-(4-hydroxy-3-methylphenyl)-6-(4-{[4-(tetrahydrofuran-2-ylcarbonyl)piperazin-1-yl]carbonyl}phenyl)pyrimidin-2(1H)-one;
N-cyclobutyl-4-[6-(4-hydroxy-3-methylphenyl)-2-oxo-2,3-dihydropyrimidin-4-yl]benzamide;
2-({3-[6-(4-hydroxy-3-methylphenyl)-2-oxo-2,3-dihydropyrimidin-4-yl]phenyl}oxy)-N,N-dipropylacetamide;
4-(4-hydroxy-3-methylphenyl)-6-(4-{[4-(phenylmethyl)piperazin-1-yl]carbonyl}phenyl)pyrimidin-2(1H)-one;
4-(4-hydroxy-3-methylphenyl)-6-[4-({4-[4-(methyloxy)phenyl]piperazin-1-yl}carbonyl)phenyl]pyrimidin-2(1H)-one;
4-(4-hydroxy-3-methylphenyl)-6-{3-[(2-{4-[3-(methyloxy)phenyl]piperazin-1-yl}-2-oxoethyl)oxy]phenyl}pyrimidin-2(1H)-one;
N-[(2,4-difluorophenyl)methyl]-4-[6-(4-hydroxy-3-methylphenyl)-2-oxo-2,3-dihydropyrimidin-4-yl]benzamide;
4-(4-hydroxy-3-methylphenyl)-6-(3-{[2-(4-methyl-1,4-diazepan-1-yl)-2-oxoethyl]oxy}phenyl)pyrimidin-2(1H)-one;
3-[6-(4-hydroxy-3-methylphenyl)-2-oxo-2,3-dihydropyrimidin-4-yl]-N-[2-(1-methylpyrrolidin-2-yl)ethyl]benzamide;
N-azetidin-3-yl-4-[6-(4-hydroxy-3-methylphenyl)-2-oxo-2,3-dihydropyrimidin-4-yl]benzamide;
N-[(1-ethylpyrrolidin-2-yl)methyl]-3-[6-(4-hydroxy-3-methylphenyl)-2-oxo-2,3-dihydropyrimidin-4-yl]benzamide;
6-{3-[(3-aminopyrrolidin-1-yl)carbonyl]phenyl}-4-(4-hydroxy-3-methylphenyl)pyrimidin-2(1H)-one;
2-({3-[6-(4-hydroxy-3-methylphenyl)-2-oxo-2,3-dihydropyrimidin-4-yl]phenyl}oxy)-N-[3-(1H-imidazol-1-yl)propyl]acetamide;
6-(4-({2-[3-(diethylamino)pyrrolidin-1-yl]-2-oxoethyl}oxy)phenyl)-4-(4-hydroxy-3-methylphenyl)pyrimidin-2(1H)-one;
6-(4-{[2-(1,4'-bipiperidin-1'-yl)-2-oxoethyl]oxy}phenyl)-4-(4-hydroxy-3-methylphenyl)pyrimidin-2(1H)-one;

N-[2-(dimethylamino)ethyl]-2-({3-[6-(4-hydroxy-3-methylphenyl)-2-oxo-2,3-dihydropyrimidin-4-yl]phenyl}oxy)-N-methylacetamide
4-[6-(4-hydroxy-3-methylphenyl)-2-oxo-2,3-dihydropyrimidin-4-yl]-N-(2-pyrrolidin-1-ylethyl)benzamide;
N-[2-(dimethylamino)ethyl]-2-({4-[6-(4-hydroxy-3-methylphenyl)-2-oxo-2,3-dihydropyrimidin-4-yl]phenyl}oxy)acetamide;
2-({3-[6-(4-hydroxy-3-methylphenyl)-2-oxo-2,3-dihydropyrimidin-4-yl]phenyl}oxy)-N-methyl-N-(1-methylpiperidin-4-yl)acetamide;
2-({4-[6-(4-hydroxy-3-methylphenyl)-2-oxo-2,3-dihydropyrimidin-4-yl]phenyl}oxy)-N-(2-piperidin-1-ylethyl)acetamide;
N-(2-aminoethyl))-2-({4-[6-(4-hydroxy-3-methylphenyl)-2-oxo-2,3-dihydropyrimidin-4-yl]phenyl}oxy)acetamide;
3-[6-(4-hydroxy-3-methylphenyl)-2-oxo-2,3-dihydropyrimidin-4-yl]-N-(piperidin-4-ylmethyl)benzamide;
3-[6-(4-hydroxy-3-methylphenyl)-2-oxo-2,3-dihydropyrimidin-4-yl]-N-(3-morpholin-4-ylpropyl)benzamide;
4-(4-hydroxy-3-methylphenyl)-6-(3-{[2-(4-hydroxypiperidin-1-yl)-2-oxoethyl]oxy}phenyl)pyrimidin-2(1H)-one;
4-(4-hydroxy-3-methylphenyl)-6-{3-[(4-pyrazin-2-ylpiperazin-1-yl)carbonyl]phenyl}pyrimidin-2(1H)-one;
2-({4-[6-(4-hydroxy-3-methylphenyl)-2-oxo-2,3-dihydropyrimidin-4-yl]phenyl}oxy)-N-(4-methylcyclohexyl)acetamide;
4-(4-hydroxy-3-methylphenyl)-6-{4-[(2-methylpyrrolidin-1-yl)carbonyl]phenyl}pyrimidin-2(1H)-one;
4-(4-hydroxy-3-methylphenyl)-6-[4-(morpholin-4-ylcarbonyl)phenyl]pyrimidin-2(1H)-one;
N-cycloheptyl-3-[6-(4-hydroxy-3-methylphenyl)-2-oxo-2,3-dihydropyrimidin-4-yl]benzamide;
4-(4-hydroxy-3-methylphenyl)-6-{4-[(2-{4-[3-(methyloxy)phenyl]piperazin-1-yl}-2-oxoethyl)oxy]phenyl}pyrimidin-2(1H)-one;
N-cyclohexyl-2-({3-[6-(4-hydroxy-3-methylphenyl)-2-oxo-2,3-dihydropyrimidin-4-yl]phenyl}oxy)acetamide;
3-[6-(4-hydroxy-3-methylphenyl)-2-oxo-2,3-dihydropyrimidin-4-yl]-N-{[2-(methyloxy)phenyl]methyl}benzamide;
4-(4-hydroxy-3-methylphenyl)-6-[4-(pyrrolidin-1-ylcarbonyl)phenyl]pyrimidin-2(1H)-one;
6-(3-{[3-(diethylamino)pyrrolidin-1-yl]carbonyl}phenyl)-4-(4-hydroxy-3-methylphenyl)pyrimidin-2(1H)-one;
methyl 1-({4-[6-(4-hydroxy-3-methylphenyl)-2-oxo-2,3-dihydropyrimidin-4-yl]phenyl}carbonyl)piperidine-4-carboxylate;
4-(4-hydroxy-3-methylphenyl)-6-[4-(piperidin-1-ylcarbonyl)phenyl]pyrimidin-2(1H)-one;
N-[(2-chlorophenyl)methyl]-4-[6-(4-hydroxy-3-methylphenyl)-2-oxo-2,3-dihydropyrimidin-4-yl]benzamide;
2-({3-[6-(4-hydroxy-3-methylphenyl)-2-oxo-2,3-dihydropyrimidin-4-yl]phenyl}oxy)-N-(2-pyrrolidin-1-ylethyl)acetamide;
N-[2-(diethylamino)ethyl]-2-({3-[6-(4-hydroxy-3-methylphenyl)-2-oxo-2,3-dihydropyrimidin-4-yl]phenyl}oxy)acetamide;
6-{4-[(1-ethylpiperidin-4-yl)amino]-2-methylphenyl}-4-(4-hydroxy-3-methylphenyl)pyrimidin-2(1H)-one;
2-({3-[6-(4-hydroxy-3-methylphenyl)-2-oxo-2,3-dihydropyrimidin-4-yl]phenyl}oxy)-N-(2-piperidin-1-ylethyl)acetamide;
4-(4-hydroxy-3-methylphenyl)-6-{2-methyl-4-[(piperidin-4-ylmethyl)oxy]phenyl}pyrimidin-2(1H)-one;
2-({3-[6-(4-hydroxy-3-methylphenyl)-2-oxo-2,3-dihydropyrimidin-4-yl]phenyl}oxy)-N-(3-pyrrolidin-1-ylpropyl)acetamide;
6-{4-[(3-aminopiperidin-1-yl)carbonyl]phenyl}-4-(4-hydroxy-3-methylphenyl)pyrimidin-2(1H)-one;
6-{3-[(4-aminopiperidin-1-yl)carbonyl]phenyl}-4-(4-hydroxy-3-methylphenyl)pyrimidin-2(1H)-one;
4-[6-(4-hydroxy-3-methylphenyl)-2-oxo-2,3-dihydropyrimidin-4-yl]-N-(3-pyrrolidin-1-ylpropyl)benzamide;
3-[6-(4-hydroxy-3-methylphenyl)-2-oxo-2,3-dihydropyrimidin-4-yl]-N-(2-pyrrolidin-1-ylethyl)benzamide;
N-(1-ethylpiperidin-4-yl)-2-({4-[6-(4-hydroxy-3-methylphenyl)-2-oxo-2,3-dihydropyrimidin-4-yl]phenyl}oxy)acetamide;
6-[4-(1,4'-bipiperidin-1'-ylcarbonyl)phenyl]-4-(4-hydroxy-3-methylphenyl)pyrimidin-2(1H)-one;
2-({3-[6-(4-hydroxy-3-methylphenyl)-2-oxo-2,3-dihydropyrimidin-4-yl]phenyl}oxy)-N-{2-[(1-methylethyl)oxy]ethyl}acetamide;
3-[6-(4-hydroxy-3-methylphenyl)-2-oxo-2,3-dihydropyrimidin-4-yl]-N-(3-pyrrolidin-1-ylpropyl)benzamide;
4-(4-hydroxy-3-methylphenyl)-6-(2-methyl-4-{[(1-methyl-1H-imidazol-2-yl)methyl]amino}phenyl)pyrimidin-2(1H)-one;
4-(4-hydroxy-3-methylphenyl)-6-{4-[(2-oxo-2-piperazin-1-ylethyl)oxy]phenyl}pyrimidin-2(1H)-one;
4-(4-hydroxy-3-methylphenyl)-6-[4-({4-[3-(methyloxy)phenyl]piperazin-1-yl}carbonyl)phenyl]pyrimidin-2(1H)-one;
4-(4-hydroxy-3-methylphenyl)-6-{3-[(4-morpholin-4-ylpiperidin-1-yl)carbonyl]phenyl}pyrimidin-2(1H)-one;

-continued 4-(4-hydroxy-3-methylphenyl)-6-[3-(pyrrolidin-1-ylcarbonyl)phenyl]pyrimidin-2(1H)-one;
N-(cyclohexylmethyl)-4-[6-(4-hydroxy-3-methylphenyl)-2-oxo-2,3-dihydropyrimidin-4-yl]benzamide;
6-[3-({4-[2-(ethyloxy)ethyl]piperazin-1-yl}carbonyl)phenyl]-4-(4-hydroxy-3-methylphenyl)pyrimidin-2(1H)-one;
4-(4-hydroxy-3-methylphenyl)-6-[4-({4-[2-(methyloxy)phenyl]piperazin-1-yl}carbonyl)phenyl]pyrimidin-2(1H)-one;
6-{4-[(3,5-dimethylpiperidin-1-yl)carbonyl]phenyl}-4-(4-hydroxy-3-methylphenyl)pyrimidin-2(1H)-one;
6-[3-(azepan-1-ylcarbonyl)phenyl]-4-(4-hydroxy-3-methylphenyl)pyrimidin-2(1H)-one;
4-(4-hydroxy-3-methylphenyl)-6-[3-({4-[2-(methyloxy)ethyl]piperazin-1-yl}carbonyl)phenyl]pyrimidin-2(1H)-one;
4-(4-hydroxy-3-methylphenyl)-6-[3-(morpholin-4-ylcarbonyl)phenyl]pyrimidin-2(1H)-one;
4-(4-hydroxy-3-methylphenyl)-6-{3-[(3-methylpiperidin-1-yl)carbonyl]phenyl}pyrimidin-2(1H)-one;
4-(4-hydroxy-3-methylphenyl)-6-[3-(piperidin-1-ylcarbonyl)phenyl]pyrimidin-2(1H)-one;
6-{3-[(4-acetylpiperazin-1-yl)carbonyl]phenyl}-4-(4-hydroxy-3-methylphenyl)pyrimidin-2(1H)-one;
N-[1-({3-[6-(4-hydroxy-3-methylphenyl)-2-oxo-2,3-dihydropyrimidin-4-yl]phenyl}carbonyl)pyrrolidin-3-yl]-N-methylacetamide;
methyl 1-({3-[6-(4-hydroxy-3-methylphenyl)-2-oxo-2,3-dihydropyrimidin-4-yl]phenyl}carbonyl)piperidine-4-carboxylate;
4-(4-hydroxy-3-methylphenyl)-6-{3-[(4-hydroxypiperidin-1-yl)carbonyl]phenyl}pyrimidin-2(1H)-one;
6-{3-[(2-ethylpiperidin-1-yl)carbonyl]phenyl}-4-(4-hydroxy-3-methylphenyl)pyrimidin-2(1H)-one;
4-(4-hydroxy-3-methylphenyl)-6-{3-[(4-methylpiperazin-1-yl)carbonyl]phenyl}pyrimidin-2(1H)-one;
4-(4-hydroxy-3-methylphenyl)-6-{3-[(2-methylpyrrolidin-1-yl)carbonyl]phenyl}pyrimidin-2(1H)-one;
4-(4-hydroxy-3-methylphenyl)-6-(3-{[4-(tetrahydrofuran-2-ylcarbonyl)piperazin-1-yl]carbonyl}phenyl)pyrimidin-2(1H)-one;
4-(4-hydroxy-3-methylphenyl)-6-[3-({4-[2-(methyloxy)phenyl]piperazin-1-yl}carbonyl)phenyl]pyrimidin-2(1H)-one;
3-[6-(4-hydroxy-3-methylphenyl)-2-oxo-2,3-dihydropyrimidin-4-yl]-N-{[3-(methyloxy)phenyl]methyl}benzamide;
6-(3-{[4-(furan-2-ylcarbonyl)piperazin-1-yl]carbonyl}phenyl)-4-(4-hydroxy-3-methylphenyl)pyrimidin-2(1H)-one;
4-(4-hydroxy-3-methylphenyl)-6-[3-({4-[3-(methyloxy)phenyl]piperazin-1-yl}carbonyl)phenyl]pyrimidin-2(1H)-one;
4-(4-hydroxy-3-methylphenyl)-6-[3-({4-[4-(methyloxy)phenyl]piperazin-1-yl}carbonyl)phenyl]pyrimidin-2(1H)-one;
3-[6-(4-hydroxy-3-methylphenyl)-2-oxo-2,3-dihydropyrimidin-4-yl]-N-methyl-N-(1-methylpiperidin-4-yl)benzamide;
N-[(2-chlorophenyl)methyl]-2-({4-[6-(4-hydroxy-3-methylphenyl)-2-oxo-2,3-dihydropyrimidin-4-yl]phenyl}oxy)acetamide;
4-(4-hydroxy-3-methylphenyl)-6-{3-[(2-oxo-2-piperazin-1-ylethyl)oxy]phenyl}pyrimidin-2(1H)-one;
6-[6-(2-chlorophenyl)-2-oxo-1,2-dihydropyrimidin-4-yl]-1,3-benzoxazol-2(3H)-one;
4-(4-hydroxy-3-methylphenyl)-6-(5-methylisoxazol-3-yl)pyrimidin-2(1H)-one;
6-(5-Bromo-2-hydroxyphenyl)-2-(2-chlorophenyl)pyrimidin-4(3H)-one;
4-(4-hydroxy-3-methylphenyl)-6-{2-methyl-4-[(piperidin-4-ylmethyl)amino]phenyl}pyridin-2(1H)-one;
6-(2-chlorophenyl)-4-(4-hydroxy-3-methylphenyl)pyridin-2(1H)-one;
6-(3-bromophenyl)-2-(2-chlorophenyl)pyrimidin-4(3H)-one; and
2-(2-chlorophenyl)-6-(4-hydroxy-3-methylphenyl)pyrimidin-4(3H)-one.

11. A compound selected from one of the following compounds:
- N-butyl-3-[6-(4-hydroxy-3-methylphenyl)-2-oxo-2,3-dihydropyrimidin-4-yl]-N-methylbenzamide;
- 3-[6-(4-hydroxy-3-methylphenyl)-2-oxo-2,3-dihydropyrimidin-4-yl]-N-methyl-N-(2-methylpropyl)benzamide;
- 3-[6-(4-hydroxy-3-methylphenyl)-2-oxo-2,3-dihydropyrimidin-4-yl]-N,N-dipropylbenzamide;
- 4-[6-(4-hydroxy-3-methylphenyl)-2-oxo-2,3-dihydropyrimidin-4-yl]-N-pentylbenzamide; and
- N-butyl-3-[6-(4-hydroxy-3-methylphenyl)-2-oxo-2,3-dihydropyrimidin-4-yl]benzamide.

12. A pharmaceutical composition comprising the compound according to claim 1 and a pharmaceutically acceptable carrier, excipient, or diluent.

* * * * *

UNITED STATES PATENT AND TRADEMARK OFFICE
CERTIFICATE OF CORRECTION

PATENT NO. : 8,242,129 B2  
APPLICATION NO. : 12/597275  
DATED : August 14, 2012  
INVENTOR(S) : Amy L. Tsuhako et al.

Page 1 of 1

It is certified that error appears in the above-identified patent and that said Letters Patent is hereby corrected as shown below:

In the Claims

Claim 1, Column 282, lines 15-16: please delete "1,3-benzoxazol-2(3H)-one" and insert --1,3-benzoxazol-2(3H)-only--;

Claim 1, Column 282, line 16: please delete "isoxazoyl" and insert --isoxazolyl--;

Claim 1, Column 282, line 29: please delete "1,3-benzoxazol-2(3H)-one" and insert --1,3-benzoxazol-2(3H)-only--;

Claim 1, Column 282, line 42: please delete "substitutuents" and insert --substituents--;

Claim 1, Column 283, line 17: please delete "substitutuents" and insert --substituents--.

Signed and Sealed this
Sixteenth Day of April, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,242,129 B2  
APPLICATION NO. : 12/597275  
DATED : August 14, 2012  
INVENTOR(S) : Amy L. Tsuhako et al.

Page 1 of 1

It is certified that error appears in the above-identified patent and that said Letters Patent is hereby corrected as shown below:

In the Claims

Claim 1, Column 282, lines 15-16: please delete "1,3-benzoxazol-2(3H)-one" and insert --1,3-benzoxazol-2(3H)-onyl--;

Claim 1, Column 282, line 16: please delete "isoxazoyl" and insert --isoxazolyl--;

Claim 1, Column 282, line 29: please delete "1,3-benzoxazol-2(3H)-one" and insert --1,3-benzoxazol-2(3H)-onyl--;

Claim 1, Column 282, line 42: please delete "substitutuents" and insert --substituents--;

Claim 1, Column 283, line 17: please delete "substitutuents" and insert --substituents--.

This certificate supersedes the Certificate of Correction issued April 16, 2013.

Signed and Sealed this  
Sixteenth Day of July, 2013

Teresa Stanek Rea  
*Acting Director of the United States Patent and Trademark Office*